US012612449B2

(12) United States Patent
Purcell et al.

(10) Patent No.: US 12,612,449 B2
(45) Date of Patent: Apr. 28, 2026

(54) HIV-1 ANTIBODIES

(71) Applicant: The University of Melbourne, Victoria (AU)

(72) Inventors: Damian Purcell, Victoria (AU); Behnaz Heydarchi, Victoria (AU)

(73) Assignee: The University of Melbourne, Victoria (AU)

( * ) Notice: Subject to any disclaimer, the term of this patent is extended or adjusted under 35 U.S.C. 154(b) by 657 days.

(21) Appl. No.: 18/007,859

(22) PCT Filed: Jun. 10, 2021

(86) PCT No.: PCT/AU2021/050593

§ 371 (c)(1),
(2) Date: Dec. 2, 2022

(87) PCT Pub. No.: WO2021/248198

PCT Pub. Date: Dec. 16, 2021

(65) Prior Publication Data

US 2023/0272048 A1 Aug. 31, 2023

(30) Foreign Application Priority Data

Jun. 10, 2020 (AU) ................................ 2020901907
Apr. 13, 2021 (AU) ................................ 2021901071

(51) Int. Cl.
*C07K 16/081* (2026.01)
*A61P 31/18* (2006.01)
*C12N 15/63* (2006.01)

(52) U.S. Cl.
CPC ............ *C07K 16/081* (2013.01); *A61P 31/18* (2018.01); *C12N 15/63* (2013.01); *C07K 2317/565* (2013.01); *C07K 2317/567* (2013.01); *C07K 2317/76* (2013.01); *C07K 2317/92* (2013.01)

(58) Field of Classification Search
CPC .................................................... C07K 16/081
USPC ...................................................... 424/147.1
See application file for complete search history.

(56) References Cited

U.S. PATENT DOCUMENTS

2020/0172601 A1 6/2020 Sajadi et al.

FOREIGN PATENT DOCUMENTS

| | | | |
|---|---|---|---|
| CN | 110483636 | A | 11/2019 |
| WO | WO 2011/123900 | A1 | 10/2011 |
| WO | WO 2016/149695 | A1 | 9/2016 |
| WO | WO 2019/014405 | A1 | 1/2019 |

OTHER PUBLICATIONS

Teh et al (Plant Biotechnology Journal, 2014, 12: 300-311).*
Sun et al (Arch Virol, 2016, 161: 2449-2455).*
Mayer et al (PLOS Medicine, 2017, 14(110: e1002435).*
Liu et al (Journal of Virology, 2016, 90(21): 9712-9724).*
Derking, et al., "Comprehensive Antigenic Map of a Cleaved Soluble HIV-1 Envelope Trimer," PLOS Pathogens, vol. 11, No. 3:e1004767 <doi: 10.1371/journal.ppat. 1004767>, 22 pages, 2015.
Heydarchi, et al., "Repeated Vaccination of Cows with HIV Env gp140 during Subsequent Pregnancies Elicits and Sustains an Enduring Strong Env-Binding and Neutralising Antibody Response," PLOS One, vol. 11, No. 6, e0157353, <doi:10.1371/journal.pone. 0157353>, 2016, 16 pages.
International Search Report & Written Opinion, PCT Application No. PCT/AU2021/050593, dated Aug. 30, 2021, 8 pages.
Purcell, et al., "HIV-1 Env Trimers Eliciting Antibody With Neutralising and Cellular-dependent Functions in Vaccinated Cows," AIDS Research and Human Retroviruses, vol. 34, Supplement 1, p. 130, Abstract No. P01.33, 2018.
Zhang, et al., "Understanding the molecular mechanism of the broad and potent neutralization of HIV-1 by antibody VRC01 from the perspective of molecular dynamics simulation and binding free energy calculations," J Mol Model, vol. 18, pp. 4517-4527, 2012.
Greenspan NS et al. (1999) "Defining epitopes: It's not as easy as it seems", Nat Biotechnol. Oct;17(10):936-7. doi: 10.1038/13590.
Kumar R et al. (2018) "Broadly neutralising antibodies in HIV-1 treatment and prevention", Therapeutic Advances in Vaccines and Immunology, 2018; 6(4):61-68.
Heydarchi et al. (2017) "Trimeric gp120-specific bovine monoclonal antibodies require cysteine and aromatic residues in CDRH3 for high affinity binding to HIV Env", Mabs, 9:550-566.
Sok et al. (2017) "Rapid elicitation of broadly neutralizing antibodies to HIV by immunization in cows", Nature, 548:108-111.
Heydarchi et al. (2022) "Broad and ultra-potent cross-clade neutralization of HIV-1 by a vaccine-induced CD4 binding site bovine antibody", Cell Rep Med, May 17;3(5):100635.
Li et al., "Construction and Immunization of HIV-1 Envelope Glycoprotein Trimer gp140 Vaccine", National Center for AIDS/STD Control and Prevention, Chinese Center for Disease Control and Prevention, p. 1-5. (2014).

* cited by examiner

*Primary Examiner* — Sean E Aeder
(74) *Attorney, Agent, or Firm* — Morgan, Lewis & Bockius LLP

(57) ABSTRACT

The invention relates to antigen binding sites, antibodies and fragments thereof, as well as compositions, kits and uses thereof for the treatment, attenuation and/or prevention of human immunodeficiency virus type 1 (HIV-1).

10 Claims, 42 Drawing Sheets

Specification includes a Sequence Listing.

FIGURE 3B
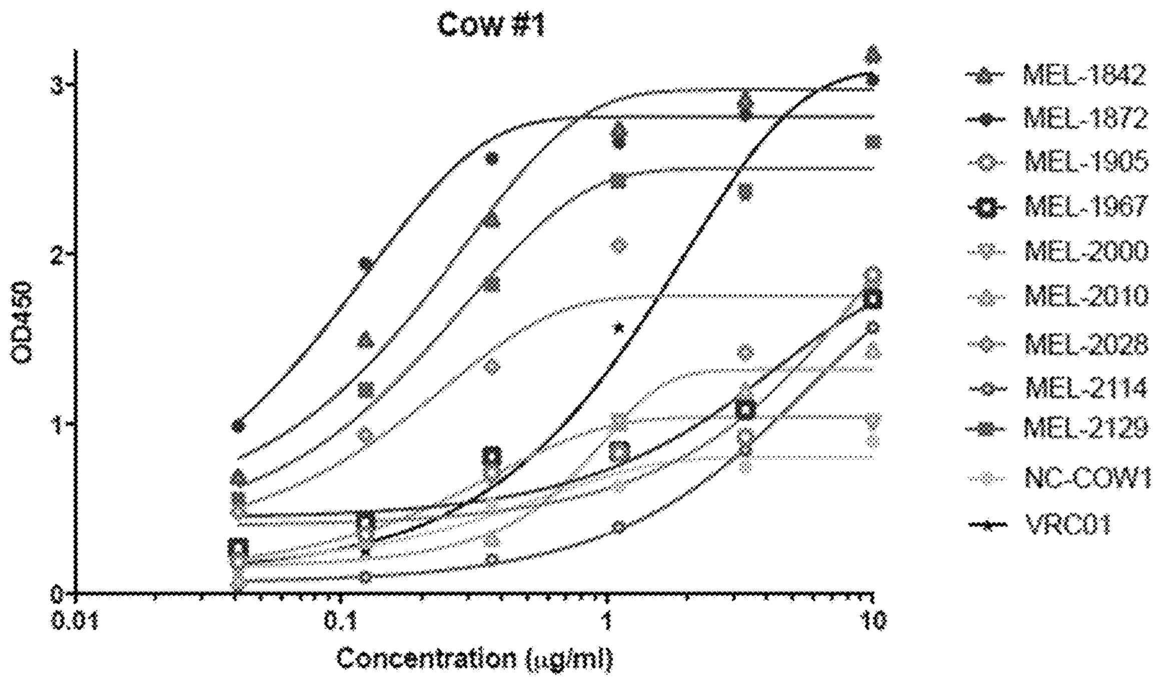
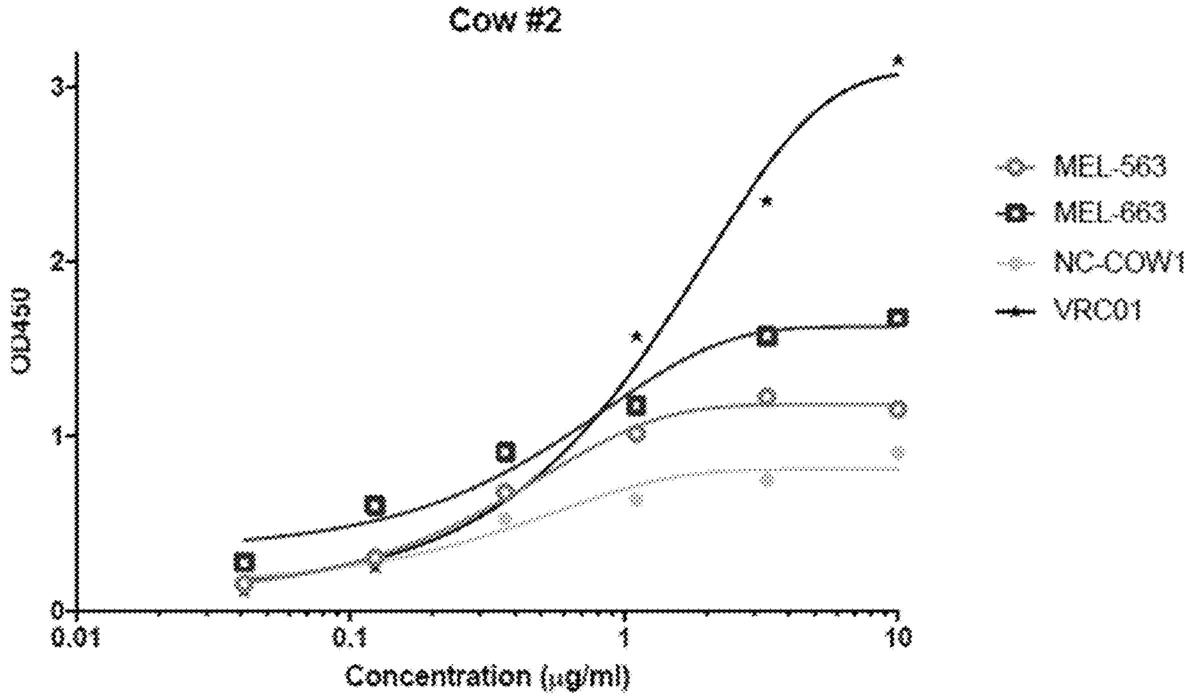

FIGURE 3C
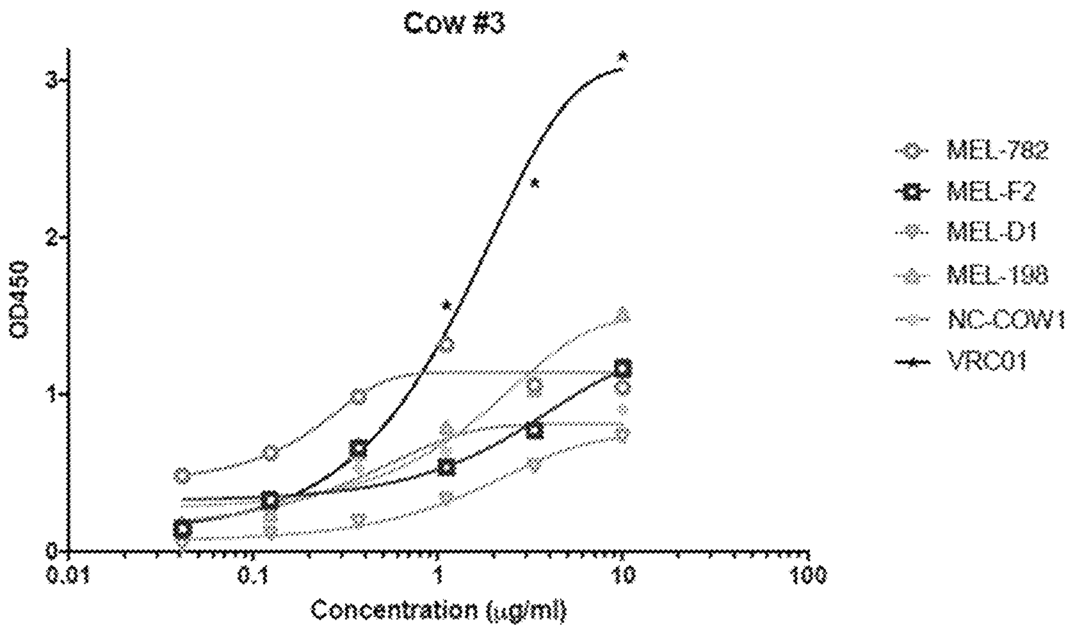
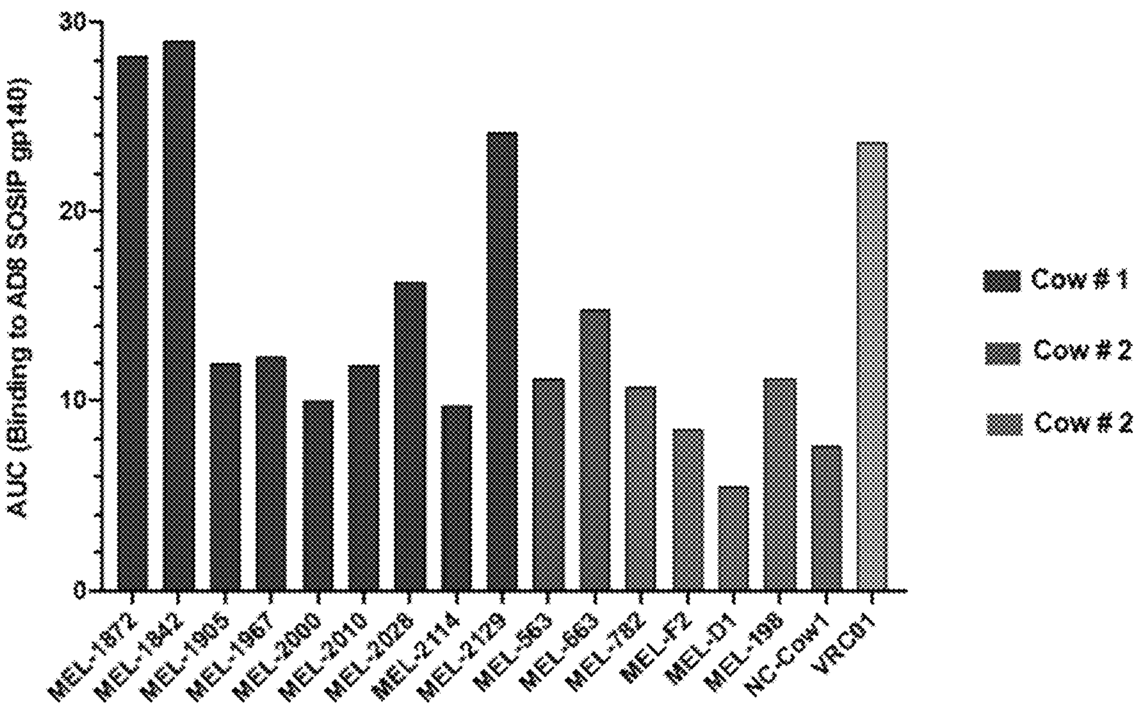

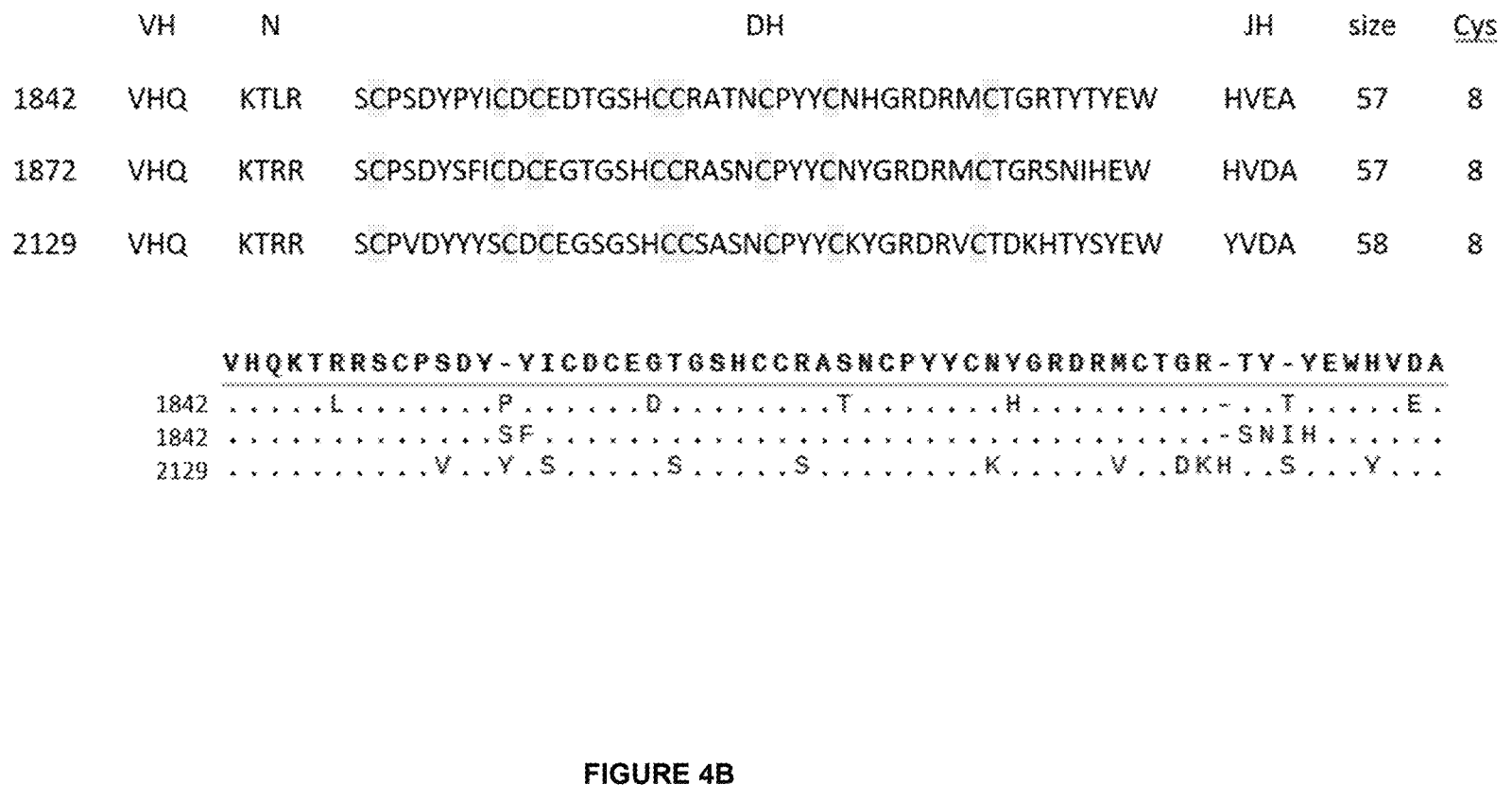

| | VH | N | DH | JH | size | Cys |
|---|---|---|---|---|---|---|
| 1842 | VHQ | KTLR | SCPSDYPYICDCEDTGSHCCRATNCPYYCNHGRDRMCTGRTYTYEW | HVEA | 57 | 8 |
| 1872 | VHQ | KTRR | SCPSDYSFICDCEGTGSHCCRASNCPYYCNYGRDRMCTGRSNIHEW | HVDA | 57 | 8 |
| 2129 | VHQ | KTRR | SCPVDYYYSCDCEGSGSHCCSASNCPYYCKYGRDRVCTDKHTYSYEW | YVDA | 58 | 8 |

```
     VHQKTRRSCPSDY-YICDCEGTGSHCCRASNCPYYCNYGRDRMCTGR-TY-YEWHVDA
1842 .....L.......P......D........T.......H.........~..T.....E.
1842 .............SF................................-SNIH......
2129 ..........V..Y.S.....S.....S........K.....V..DKH..S...Y...
```

FIGURE 4B

Figure 5A:
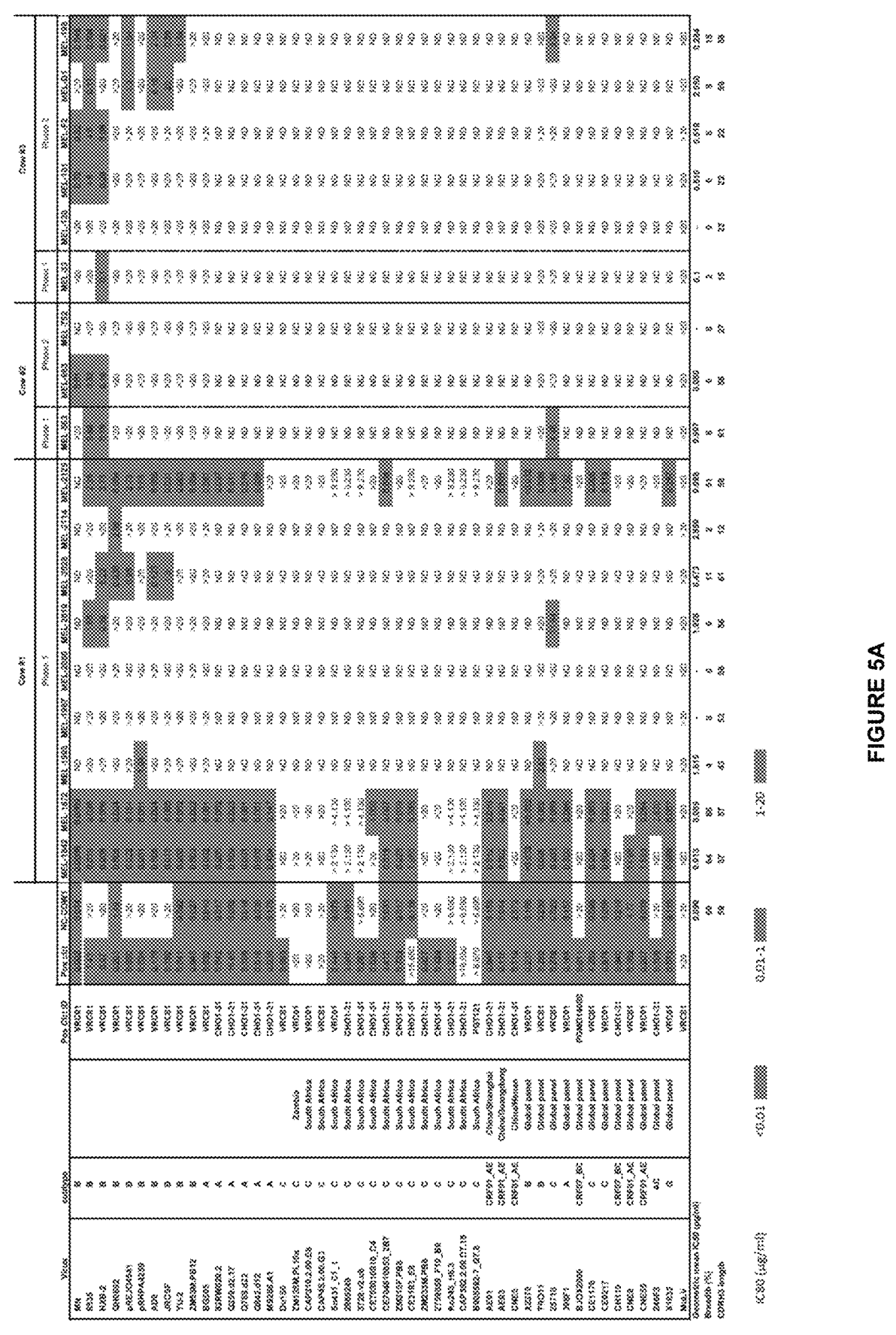

| | | | | | | Cow #1 | | | | | | | | | Cow #2 | | | Cow #3 | | | | | |
|---|---|---|---|---|---|---|---|---|---|---|---|---|---|---|---|---|---|---|---|---|---|---|---|
| | | | | | | Phase 1 | | | | | | | | | Phase 1 | Phase 2 | | Phase 1 | Phase 2 | | | | |
| Virus | subtype | | Pos Ctrl ID | Pos ctrl | NC-COW1 | MEL-1842 | MEL-1672 | MEL-1908 | MEL-1987 | MEL-2050 | MEL-2819 | MEL-2028 | MEL-2114 | MEL-2129 | MEL-563 | MEL-685 | MEL-752 | MEL-33 | MEL-120 | MEL-101 | MEL-F2 | MEL-D1 | MEL-198 |
| MN | B | | VRC01 | [illegible] | [illegible] | [illegible] | [illegible] | ND | ND | ND | ND | ND | ND | ND | >20 | [illegible] | ND | >20 | >20 | [illegible] | [illegible] | >20 | [illegible] |
| 6535 | B | | VRC01 | [illegible] | >20 | [illegible] | [illegible] | >20 | >20 | >20 | [illegible] | >20 | >20 | [illegible] | [illegible] | [illegible] | >20 | >20 | >20 | [illegible] | [illegible] | [illegible] | [illegible] |
| HXB-2 | B | | VRC01 | [illegible] | >20 | [illegible] | [illegible] | >20 | >20 | >20 | [illegible] | [illegible] | >20 | [illegible] | [illegible] | [illegible] | >20 | [illegible] | >20 | [illegible] | [illegible] | >20 | [illegible] |
| QH0692 | B | | VRC01 | [illegible] | [illegible] | [illegible] | [illegible] | >20 | >20 | >20 | >20 | [illegible] | [illegible] | [illegible] | >20 | >20 | >20 | >20 | >20 | >20 | >20 | >20 | >20 |
| pREJO4541 | B | | VRC01 | [illegible] | >20 | [illegible] | [illegible] | >20 | >20 | >20 | >20 | [illegible] | >20 | [illegible] | >20 | >20 | >20 | >20 | >20 | >20 | >20 | [illegible] | [illegible] |
| pRHPA4259 | B | | VRC01 | [illegible] | >20 | [illegible] | [illegible] | [illegible] | >20 | >20 | >20 | >20 | >20 | [illegible] | >20 | >20 | >20 | >20 | >20 | >20 | >20 | >20 | >20 |
| AD8 | B | | VRC01 | [illegible] | >20 | [illegible] | [illegible] | >20 | >20 | >20 | >20 | [illegible] | >20 | [illegible] | >20 | >20 | >20 | >20 | >20 | >20 | >20 | [illegible] | [illegible] |
| JRCSF | B | | VRC01 | [illegible] | >20 | [illegible] | [illegible] | >20 | >20 | >20 | >20 | [illegible] | >20 | [illegible] | >20 | >20 | >20 | >20 | >20 | >20 | >20 | [illegible] | [illegible] |
| YU-2 | B | | VRC01 | [illegible] | [illegible] | [illegible] | [illegible] | >20 | >20 | >20 | >20 | >20 | >20 | [illegible] | >20 | >20 | >20 | >20 | >20 | >20 | >20 | >20 | [illegible] |
| ZM53M.PB12 | B | | VRC01 | [illegible] | [illegible] | [illegible] | [illegible] | >20 | >20 | >20 | >20 | >20 | >20 | [illegible] | >20 | >20 | >20 | >20 | >20 | >20 | >20 | >20 | >20 |
| BG505 | A | | VRC01 | [illegible] | [illegible] | [illegible] | [illegible] | >20 | >20 | >20 | >20 | >20 | >20 | [illegible] | >20 | >20 | >20 | >20 | >20 | >20 | >20 | >20 | >20 |
| 92RW020.2 | A | | CH01-31 | [illegible] | [illegible] | [illegible] | [illegible] | ND | ND | ND | ND | ND | ND | [illegible] | ND | ND | ND | ND | ND | ND | ND | ND | ND |
| Q259.d2.17 | A | | CH01-21 | [illegible] | [illegible] | [illegible] | [illegible] | ND | ND | ND | ND | ND | ND | [illegible] | ND | ND | ND | ND | ND | ND | ND | ND | ND |
| Q769.d22 | A | | CH01-31 | [illegible] | [illegible] | [illegible] | [illegible] | ND | ND | ND | ND | ND | ND | [illegible] | ND | ND | ND | ND | ND | ND | ND | ND | ND |
| Q842.d12 | A | | CH01-31 | [illegible] | [illegible] | [illegible] | [illegible] | ND | ND | ND | ND | ND | ND | [illegible] | ND | ND | ND | ND | ND | ND | ND | ND | ND |
| M9286.A1 | A | | CH01-21 | [illegible] | [illegible] | [illegible] | [illegible] | ND | ND | ND | ND | ND | ND | >20 | ND | ND | ND | ND | ND | ND | ND | ND | ND |
| Du156 | C | | VRC01 | [illegible] | >20 | >20 | >20 | ND | ND | ND | ND | ND | ND | >20 | ND | ND | ND | ND | ND | ND | ND | ND | ND |
| ZM135M.PL10a | C | Zambia | VRC01 | >20 | >20 | >20 | >20 | ND | ND | ND | ND | ND | ND | >20 | ND | ND | ND | ND | ND | ND | ND | ND | ND |
| CAP210.2.00.E8 | C | South Africa | VRC01 | >20 | >20 | >20 | >20 | ND | ND | ND | ND | ND | ND | >20 | ND | ND | ND | ND | ND | ND | ND | ND | ND |
| CAP45.2.00.G3 | C | South Africa | VRC01 | >20 | >20 | >20 | >20 | ND | ND | ND | ND | ND | ND | >20 | ND | ND | ND | ND | ND | ND | ND | ND | ND |
| Sn431_C1_1 | C | South Africa | VRC01 | [illegible] | [illegible] | >2.130 | >4.130 | ND | ND | ND | ND | ND | ND | >9.230 | ND | ND | ND | ND | ND | ND | ND | ND | ND |
| 2865249 | C | South Africa | CH01-21 | [illegible] | [illegible] | >2.130 | >4.130 | ND | ND | ND | ND | ND | ND | >9.230 | ND | ND | ND | ND | ND | ND | ND | ND | ND |
| 3728.v2.c6 | C | South Africa | CH01-31 | [illegible] | >6.690 | >2.130 | >4.130 | ND | ND | ND | ND | ND | ND | >9.230 | ND | ND | ND | ND | ND | ND | ND | ND | ND |
| CE703010210_C4 | C | South Africa | CH01-31 | [illegible] | >20 | >20 | [illegible] | ND | ND | ND | ND | ND | ND | >20 | ND | ND | ND | ND | ND | ND | ND | ND | ND |
| CE704810053_2B7 | C | South Africa | CH01-21 | [illegible] | [illegible] | [illegible] | [illegible] | ND | ND | ND | ND | ND | ND | [illegible] | ND | ND | ND | ND | ND | ND | ND | ND | ND |
| ZM215F.PB8 | C | South Africa | CH01-31 | [illegible] | [illegible] | [illegible] | [illegible] | ND | ND | ND | ND | ND | ND | >20 | ND | ND | ND | ND | ND | ND | ND | ND | ND |
| CE2182_E2 | C | South Africa | CH01-31 | >15.650 | [illegible] | [illegible] | [illegible] | ND | ND | ND | ND | ND | ND | >9.230 | ND | ND | ND | ND | ND | ND | ND | ND | ND |
| ZM233M.PB6 | C | South Africa | CH01-21 | [illegible] | >20 | >20 | >20 | ND | ND | ND | ND | ND | ND | >20 | ND | ND | ND | ND | ND | ND | ND | ND | ND |
| 2750859_F19_B9 | C | South Africa | CH01-31 | [illegible] | >20 | >20 | >20 | ND | ND | ND | ND | ND | ND | >20 | ND | ND | ND | ND | ND | ND | ND | ND | ND |
| Ko243_H6.3 | C | South Africa | CH01-21 | [illegible] | >6.690 | >2.130 | >4.130 | ND | ND | ND | ND | ND | ND | >9.230 | ND | ND | ND | ND | ND | ND | ND | ND | ND |
| CAP382.2.09.D7.15 | C | South Africa | CH01-21 | >15.650 | >6.690 | >2.130 | >4.130 | ND | ND | ND | ND | ND | ND | >9.230 | ND | ND | ND | ND | ND | ND | ND | ND | ND |
| B905592-7_Q7.8 | C | South Africa | PGT121 | >8.870 | >6.690 | >2.130 | >4.130 | ND | ND | ND | ND | ND | ND | >9.230 | ND | ND | ND | ND | ND | ND | ND | ND | ND |
| AE01 | CRF01_AE | China/Shanghai | CH01-21 | [illegible] | [illegible] | [illegible] | [illegible] | ND | ND | ND | ND | ND | ND | >20 | ND | ND | ND | ND | ND | ND | ND | ND | ND |
| AE03 | CRF01_AE | China/Guangdong | CH01-21 | [illegible] | [illegible] | [illegible] | [illegible] | ND | ND | ND | ND | ND | ND | [illegible] | ND | ND | ND | ND | ND | ND | ND | ND | ND |
| CNE5 | CRF01_AE | China/Henan | CH01-31 | [illegible] | [illegible] | >20 | >20 | ND | ND | ND | ND | ND | ND | >20 | ND | ND | ND | ND | ND | ND | ND | ND | ND |
| X2278 | B | Global panel | VRC01 | [illegible] | [illegible] | [illegible] | [illegible] | ND | ND | ND | ND | ND | ND | [illegible] | ND | ND | ND | ND | ND | ND | ND | ND | ND |
| TRO11 | B | Global panel | VRC01 | [illegible] | [illegible] | [illegible] | [illegible] | [illegible] | >20 | >20 | >20 | >20 | >20 | [illegible] | >20 | >20 | >20 | >20 | >20 | >20 | >20 | >20 | >20 |
| 25710 | C | Global panel | VRC01 | [illegible] | [illegible] | [illegible] | [illegible] | >20 | >20 | >20 | [illegible] | >20 | >20 | [illegible] | [illegible] | >20 | >20 | >20 | >20 | >20 | >20 | >20 | [illegible] |
| 398F1 | A | Global panel | VRC01 | [illegible] | [illegible] | [illegible] | [illegible] | ND | ND | ND | ND | ND | ND | [illegible] | ND | ND | ND | ND | ND | ND | ND | ND | ND |
| BJOX2000 | CRF07_BC | Global panel | PGMD1400 | [illegible] | >20 | >20 | >20 | ND | ND | ND | ND | ND | ND | >20 | ND | ND | ND | ND | ND | ND | ND | ND | ND |
| CE1176 | C | Global panel | VRC01 | [illegible] | [illegible] | [illegible] | [illegible] | ND | ND | ND | ND | ND | ND | [illegible] | ND | ND | ND | ND | ND | ND | ND | ND | ND |
| CE0217 | C | Global panel | VRC01 | [illegible] | [illegible] | [illegible] | [illegible] | ND | ND | ND | ND | ND | ND | [illegible] | ND | ND | ND | ND | ND | ND | ND | ND | ND |
| CH119 | CRF07_BC | Global panel | CH01-21 | [illegible] | [illegible] | >20 | >20 | ND | ND | ND | ND | ND | ND | >20 | ND | ND | ND | ND | ND | ND | ND | ND | ND |
| CNE8 | CRF01_AE | Global panel | VRC01 | [illegible] | [illegible] | [illegible] | >20 | ND | ND | ND | ND | ND | ND | >20 | ND | ND | ND | ND | ND | ND | ND | ND | ND |
| CNE55 | CRF01_AE | Global panel | VRC01 | [illegible] | [illegible] | [illegible] | [illegible] | ND | ND | ND | ND | ND | ND | >20 | ND | ND | ND | ND | ND | ND | ND | ND | ND |
| 246F3 | AC | Global panel | CH01-21 | [illegible] | >20 | >20 | [illegible] | ND | ND | ND | ND | ND | ND | >20 | ND | ND | ND | ND | ND | ND | ND | ND | ND |
| X1632 | G | Global panel | VRC01 | [illegible] | [illegible] | [illegible] | [illegible] | ND | ND | ND | ND | ND | ND | [illegible] | ND | ND | ND | ND | ND | ND | ND | ND | ND |
| MuLV | | | VRC01 | >20 | >20 | >20 | >20 | >20 | >20 | >20 | >20 | >20 | >20 | >20 | >20 | >20 | >20 | >20 | >20 | >20 | >20 | >20 | >20 |
| Geometric mean IC50 (µg/ml) | | | | | 0.090 | 0.013 | 0.069 | 1.619 | - | - | 1.028 | 0.473 | 2.559 | 0.028 | 0.907 | 0.080 | - | 0.1 | - | 0.510 | 0.518 | 2.050 | 0.224 |
| Breadth (%) | | | | | 60 | 64 | 88 | 4 | 8 | 6 | 6 | 11 | 2 | 51 | 8 | 6 | 8 | 2 | 9 | 6 | 5 | 8 | 15 |
| CDRH3 length | | | | | 58 | 87 | 57 | 45 | 52 | 58 | 56 | 61 | 12 | 58 | 61 | 56 | 27 | 15 | 22 | 52 | 22 | 58 | 58 |

Figure 5B:
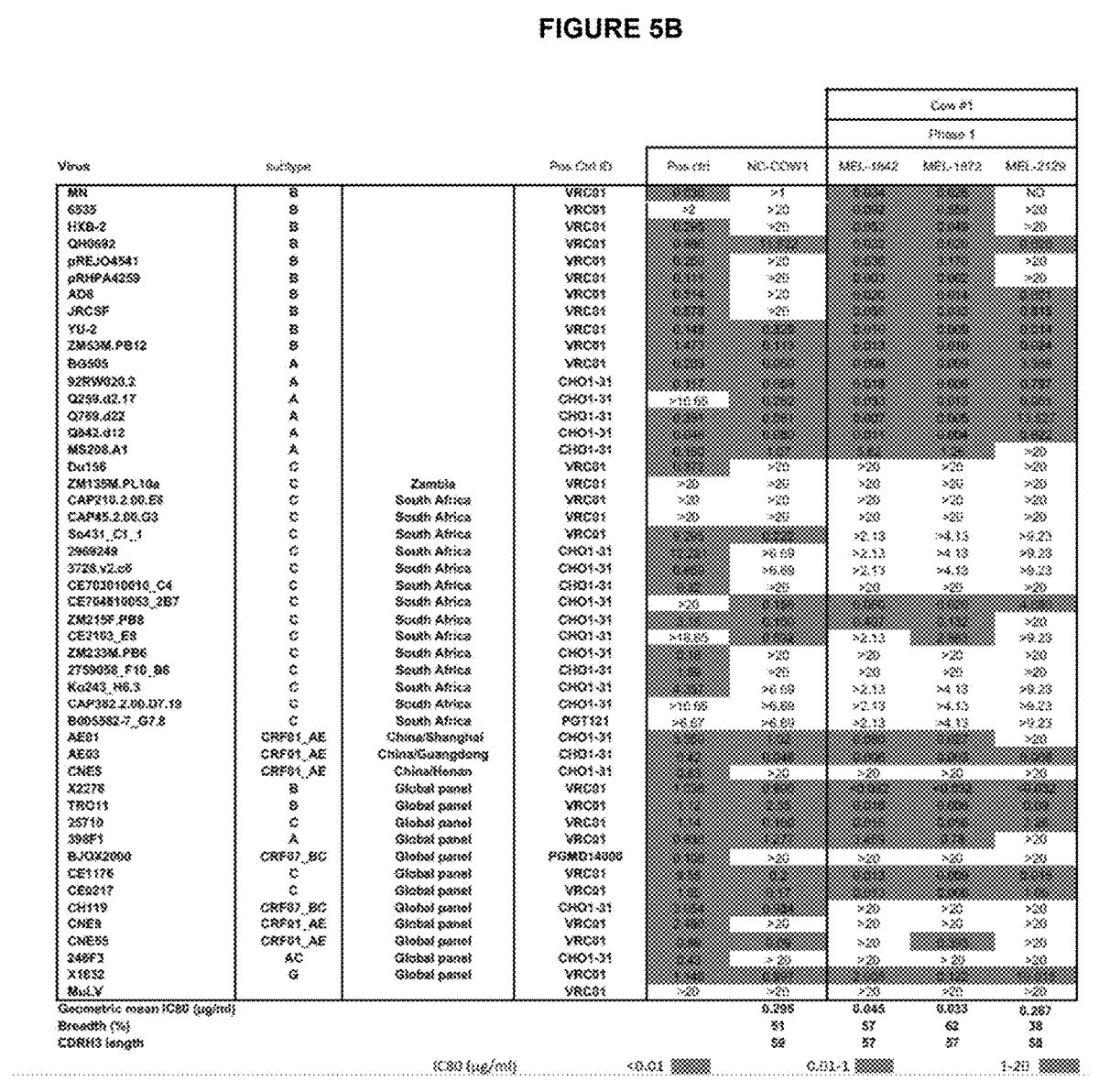

| | | | | | | Cow #1 | | |
|---|---|---|---|---|---|---|---|---|
| | | | | | | Phase 1 | | |
| Virus | Subtype | | Pos Ctrl ID | Pos ctrl | NC-COW1 | MEL-1842 | MEL-1872 | MEL-2129 |
| MN | B | | VRC01 | [illegible] | >1 | [illegible] | [illegible] | ND |
| 6535 | B | | VRC01 | >2 | >20 | [illegible] | [illegible] | >20 |
| HXB-2 | B | | VRC01 | [illegible] | >20 | [illegible] | [illegible] | >20 |
| QH0692 | B | | VRC01 | [illegible] | [illegible] | [illegible] | [illegible] | [illegible] |
| pREJO4541 | B | | VRC01 | [illegible] | >20 | [illegible] | [illegible] | >20 |
| pRHPA4259 | B | | VRC01 | [illegible] | >20 | [illegible] | [illegible] | >20 |
| AD8 | B | | VRC01 | [illegible] | >20 | [illegible] | [illegible] | [illegible] |
| JRCSF | B | | VRC01 | [illegible] | >20 | [illegible] | [illegible] | [illegible] |
| YU-2 | B | | VRC01 | [illegible] | [illegible] | [illegible] | [illegible] | [illegible] |
| ZM53M.PB12 | B | | VRC01 | 1.47 | [illegible] | [illegible] | [illegible] | [illegible] |
| BG505 | A | | VRC01 | [illegible] | [illegible] | [illegible] | [illegible] | [illegible] |
| 92RW020.2 | A | | CHO1-31 | [illegible] | [illegible] | [illegible] | [illegible] | [illegible] |
| Q259.d2.17 | A | | CHO1-31 | >10.66 | [illegible] | [illegible] | [illegible] | [illegible] |
| Q769.d22 | A | | CHO1-31 | [illegible] | [illegible] | [illegible] | [illegible] | [illegible] |
| Q842.d12 | A | | CHO1-31 | [illegible] | [illegible] | [illegible] | [illegible] | [illegible] |
| MS208.A1 | A | | CHO1-31 | [illegible] | [illegible] | [illegible] | [illegible] | >20 |
| Du156 | C | | VRC01 | [illegible] | >20 | >20 | >20 | >20 |
| ZM135M.PL10a | C | Zambia | VRC01 | >20 | >20 | >20 | >20 | >20 |
| CAP210.2.00.E8 | C | South Africa | VRC01 | >20 | >20 | >20 | >20 | >20 |
| CAP45.2.00.G3 | C | South Africa | VRC01 | >20 | >20 | >20 | >20 | >20 |
| So431_C1_1 | C | South Africa | VRC01 | [illegible] | [illegible] | >2.13 | >4.13 | >9.23 |
| 2966249 | C | South Africa | CHO1-31 | [illegible] | >6.69 | >2.13 | >4.13 | >9.23 |
| 3728.v2.c8 | C | South Africa | CHO1-31 | [illegible] | >6.69 | >2.13 | >4.13 | >9.23 |
| CE703010010_C4 | C | South Africa | CHO1-31 | [illegible] | >20 | >20 | >20 | >20 |
| CE704810053_2B7 | C | South Africa | CHO1-31 | >20 | [illegible] | [illegible] | [illegible] | [illegible] |
| ZM215F.PB8 | C | South Africa | CHO1-31 | [illegible] | [illegible] | [illegible] | [illegible] | >20 |
| CE2103_E8 | C | South Africa | CHO1-31 | >10.65 | [illegible] | >2.13 | [illegible] | >9.23 |
| ZM233M.PB6 | C | South Africa | CHO1-31 | [illegible] | >20 | >20 | >20 | >20 |
| 2759058_F10_B6 | C | South Africa | CHO1-31 | [illegible] | >20 | >20 | >20 | >20 |
| Ko243_H6.3 | C | South Africa | CHO1-31 | [illegible] | >6.69 | >2.13 | >4.13 | >9.23 |
| CAP382.2.00.D7.19 | C | South Africa | CHO1-31 | >10.66 | >6.69 | >2.13 | >4.13 | >9.23 |
| B005582-7_G7.8 | C | South Africa | PGT121 | >6.67 | >6.69 | >2.13 | >4.13 | >9.23 |
| AE01 | CRF01_AE | China/Shanghai | CHO1-31 | [illegible] | [illegible] | [illegible] | [illegible] | >20 |
| AE03 | CRF01_AE | China/Guangdong | CHO1-31 | [illegible] | [illegible] | [illegible] | [illegible] | [illegible] |
| CNE5 | CRF01_AE | China/Henan | CHO1-31 | [illegible] | >20 | >20 | >20 | >20 |
| X2278 | B | Global panel | VRC01 | [illegible] | [illegible] | [illegible] | [illegible] | [illegible] |
| TRO11 | B | Global panel | VRC01 | [illegible] | [illegible] | [illegible] | [illegible] | [illegible] |
| 25710 | C | Global panel | VRC01 | [illegible] | [illegible] | [illegible] | [illegible] | [illegible] |
| 398F1 | A | Global panel | VRC01 | [illegible] | [illegible] | [illegible] | [illegible] | >20 |
| BJOX2000 | CRF07_BC | Global panel | PGMD14000 | [illegible] | >20 | >20 | >20 | >20 |
| CE1176 | C | Global panel | VRC01 | [illegible] | [illegible] | [illegible] | [illegible] | [illegible] |
| CE0217 | C | Global panel | VRC01 | [illegible] | [illegible] | [illegible] | [illegible] | [illegible] |
| CH119 | CRF07_BC | Global panel | CHO1-31 | [illegible] | [illegible] | >20 | >20 | >20 |
| CNE8 | CRF01_AE | Global panel | VRC01 | [illegible] | >20 | >20 | >20 | >20 |
| CNE55 | CRF01_AE | Global panel | VRC01 | [illegible] | [illegible] | >20 | [illegible] | >20 |
| 246F3 | AC | Global panel | CHO1-31 | [illegible] | > 20 | >20 | > 20 | >20 |
| X1632 | G | Global panel | VRC01 | [illegible] | [illegible] | [illegible] | [illegible] | [illegible] |
| MuLV | | | VRC01 | >20 | >20 | >20 | >20 | >20 |
| Geometric mean IC80 (μg/ml) | | | | | 0.295 | 0.045 | 0.033 | 0.267 |
| Breadth (%) | | | | | 51 | 57 | 62 | 38 |
| CDRH3 length | | | | | 59 | 57 | 57 | 58 |

IC80 (μg/ml) <0.01 0.01-1 1-20

Geometric mean IC50

| Clade | n | VRC01 | | NC-Cow1 | | MEL-1842 | | MEL-1872 | | MEL-2129 | |
|---|---|---|---|---|---|---|---|---|---|---|---|
| | | Breadth | IC50 | Breadth | IC50 | Breadth | IC50 | Breadth | IC50 | Breadth | IC50 |
| A | 7 | NA | NA | 100% | 0.040 | 100% | 0.011 | 100% | 0.005 | 86% | 0.215 |
| B | 12 | 100% | 0.0117 | 50% | 0.094 | 100% | 0.004 | 100% | 0.004 | 100% * | 0.072 |
| C | 19 | NA | NA | 42% | 0.081 | 32% | 0.018 | 37% | 0.021 | 21% | 0.087 |
| AE | 5 | NA | NA | 100% | 0.216 | 80% | 0.154 | 60% | 0.008 | 20% | 0.001 |
| BC | 2 | NA | NA | 50% | 0.219 | 0% | - | 0% | - | 0% | - |
| AC | 1 | NA | NA | 0% | - | 0% | - | 100% | 2.530 | 0% | - |
| G | 1 | 100% | 0.073 | 100% | 0.116 | 100% | 0.069 | 100% | 0.007 | 100% | 0.257 |
| | 47 | | | | | | | | | | |

IC50 (μg/ml) <0.01 0.01-1 1-20

* 11 clade B tested.

Geometric mean IC80

| Clade | n | VRC01 | | NC-Cow1 | | MEL-1842 | | MEL-1872 | | MEL-2129 | |
|---|---|---|---|---|---|---|---|---|---|---|---|
| | | Breadth | IC80 | Breadth | IC80 | Breadth | IC80 | Breadth | IC80 | Breadth | IC80 |
| A | 7 | NA | NA | 100% | 0.185 | 100% | 0.070 | 100% | 0.025 | 71% | 1.030 |
| B | 12 | 92% | 0.346 | 42% | 1.029 | 100% | 0.030 | 100% | 0.031 | 64% * | 0.047 |
| C | 19 | NA | NA | 37% | 0.181 | 26% | 0.035 | 32% | 0.053 | 21% | 0.710 |
| AE | 5 | NA | NA | 60% | 0.164 | 40% | 0.022 | 60% | 0.032 | 20% | 0.006 |
| BC | 2 | NA | NA | 50% | 0.934 | 0% | - | 0% | - | 0% | - |
| AC | 1 | NA | NA | 0% | - | 0% | - | 0% | - | 0% | - |
| G | 1 | 100% | 1.146 | 100% | 0.997 | 100% | 2.005 | 100% | 0.122 | 100% | 10.015 |
| | 47 | | | | | | | | | | |

IC80 (μg/ml) <0.01 0.01-1 1-20

* 11 clade B tested.

FIGURE 5C

| | | 1967 | 2000 | 2114 | 1905 | 2010 | 2028 | 2129 | 1872 | 1842 | 33 | 130 | F2 | D1 | 198 | 563 | 782 |
|---|---|---|---|---|---|---|---|---|---|---|---|---|---|---|---|---|---|
| | **Self** | 68 | 69 | 46 | 63 | 67 | 63 | 63 | 80 | 85 | 72 | 63 | 74 | 57 | 63 | 81 | 95 |
| CD4bs | **b12** | -47 | -46 | -1 | -33 | -8 | -47 | 56 | 84 | 84 | 6 | 11 | 9 | -14 | 5 | 14 | 0 |
| | **VRC01** | 0 | 12 | 1 | 2 | -1 | -8 | 45 | 76 | 87 | 3 | 3 | -2 | 7 | 13 | 4 | 0 |
| | **HJ16** | 23 | 11 | 13 | 10 | 4 | -14 | 26 | 73 | 75 | 6 | 9 | 4 | -1 | -4 | 2 | 12 |
| | **3BNC117** | 12 | 19 | 1 | 4 | 4 | -3 | 54 | 74 | 69 | 0 | -2 | -1 | 1 | 16 | -4 | 2 |
| V3- glycan | **PGT121** | 3 | 11 | -6 | -5 | -3 | -5 | 0 | 10 | 4 | -12 | -3 | -5 | -5 | -8 | -7 | -3 |
| | **10-1074** | 6 | 7 | -2 | -2 | -2 | -15 | 0 | 14 | 11 | -8 | -3 | 2 | -12 | -13 | -4 | -8 |
| V2-apex | **PGT145** | 11 | 26 | 4 | 3 | -5 | -6 | 15 | -2 | -11 | -6 | 3 | -3 | -8 | -13 | -2 | -3 |
| Interface | **PGT151** | 49 | 33 | 9 | 31 | 0 | 23 | 8 | 15 | 27 | -4 | 1 | 2 | -15 | -18 | -1 | -6 |

FIGURE 6A

FIGURE 7A
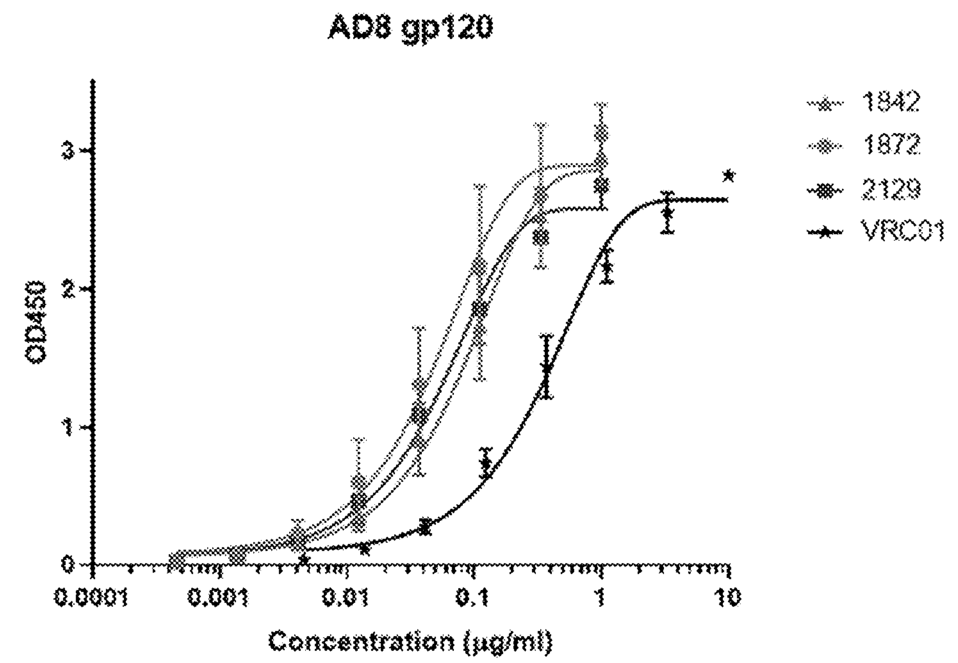
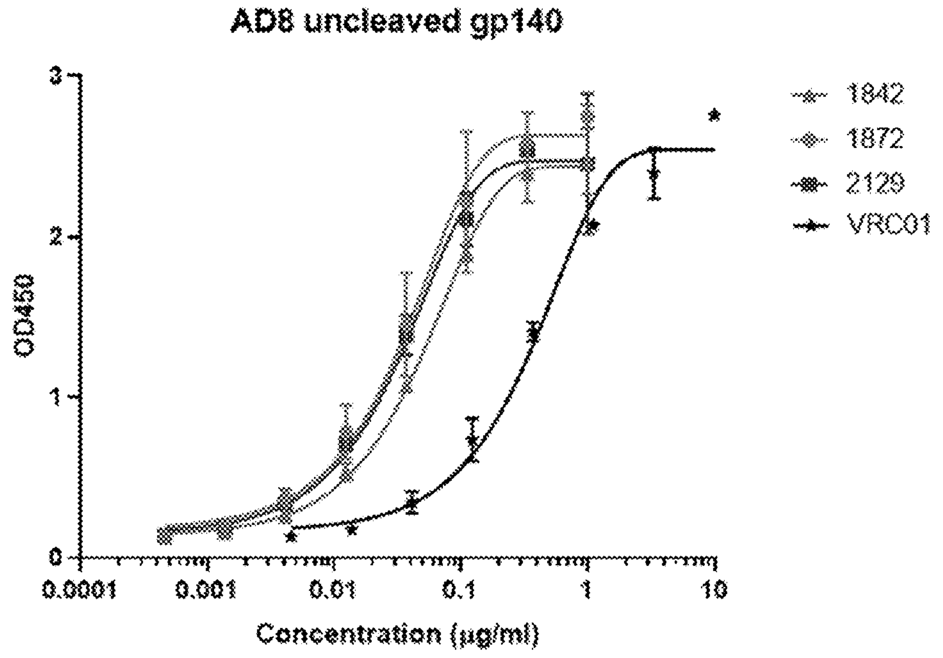

FIGURE 7B
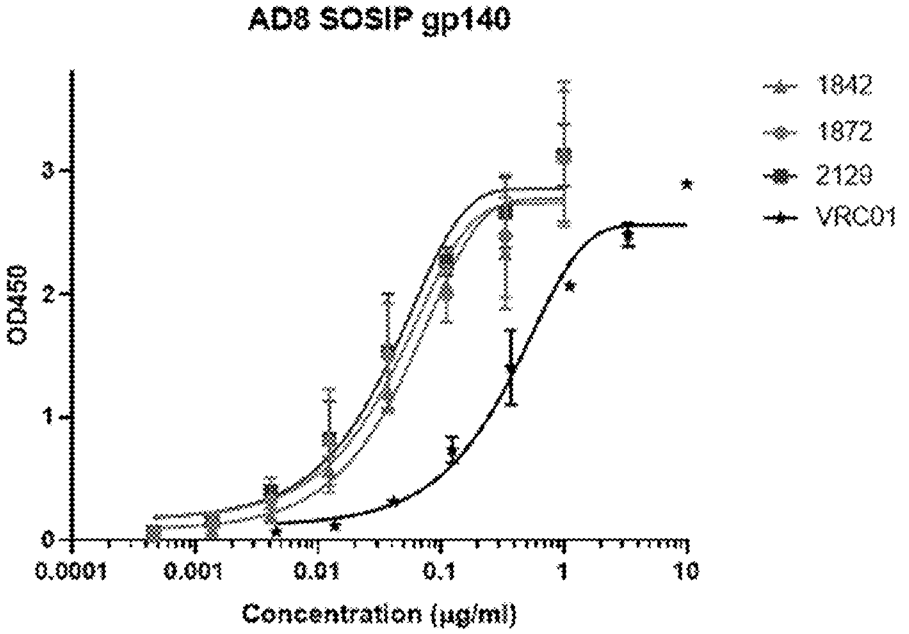
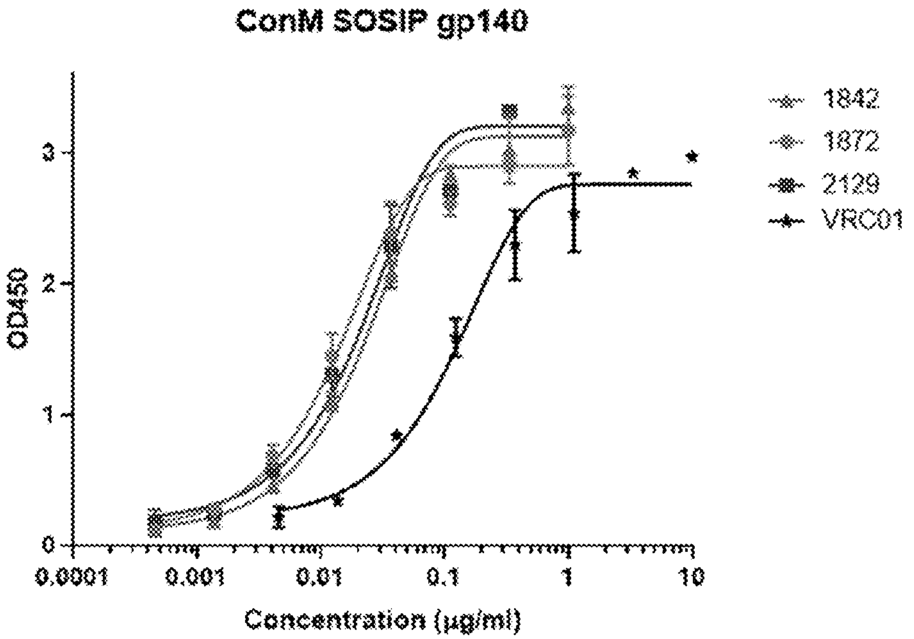
| Antibody | AD8 gp120 | AD8 gp140 | AD8 SOSIP | ConM SOSIP |
|---|---|---|---|---|
| **1842** | 0.06 µg/ml | 0.03 µg/ml | 0.05 µg/ml | 0.02 µg/ml |
| **1872** | 0.03 µg/ml | 0.02 µg/ml | 0.04 µg/ml | 0.02 µg/ml |
| **2129** | 0.04 µg/ml | 0.02 µg/ml | 0.01 µg/ml | 0.01 µg/ml |
| **VRC01** | 0.29 µg/ml | 0.14 µg/ml | 0.11 µg/ml | 0.08 µg/ml |

| | MEL-1842 | MEL-1872 | MEL-2129 | MEL-198 | MEL-2028 | VRC01 | b12 | PGT121 |
|---|---|---|---|---|---|---|---|---|
| WT | 0.004 | 0.004 | 0.005 | 2.572 | 0.117 | 0.193 | 0.263 | 0.016 |
| E87A | 0.006 | 0.005 | 0.009 | > 10 | 0.153 | 0.429 | 0.469 | 0.020 |
| K121A | 0.003 | 0.004 | 0.005 | 1.417 | 0.139 | 0.272 | 0.212 | 0.014 |
| L179A | 0.003 | 0.003 | 0.005 | 0.050 | 0.061 | 0.099 | 0.192 | 0.007 |
| D185A | 0.003 | 0.002 | 0.004 | 2.581 | 0.084 | 0.132 | 0.294 | 0.006 |
| N197A | 0.003 | 0.002 | 0.003 | 0.393 | 0.109 | 0.082 | 0.030 | 0.014 |
| N262A | 0.005 | 0.003 | 0.004 | 0.865 | 0.105 | 0.119 | 0.189 | 0.010 |
| N276A | 0.005 | 0.004 | 0.005 | 2.117 | 0.097 | 0.035 | 0.238 | 0.017 |
| D279A | 0.002 | 0.003 | 0.011 | 1.798 | 0.091 | > 4 | 0.628 | 0.012 |
| K282A | 0.002 | 0.003 | 0.002 | 5.816 | 0.125 | 0.114 | 0.176 | 0.011 |
| N283A | 0.005 | 0.005 | 0.011 | 2.428 | 0.096 | 0.196 | 0.171 | 0.018 |
| P313A | 0.004 | 0.004 | 0.005 | 3.150 | 0.093 | 0.173 | 0.243 | 0.016 |
| N332T | 0.005 | 0.004 | 0.005 | 1.045 | 0.076 | 0.132 | 0.465 | 0.110 |
| Q363A | 0.004 | 0.003 | 0.007 | 4.258 | 0.097 | 0.161 | 0.386 | 0.013 |
| S364A | 0.004 | 0.003 | 0.018 | 1.233 | 0.057 | 0.063 | 0.070 | 0.012 |
| G366A | 0.014 | 0.029 | 0.015 | 0.969 | 0.137 | 0.129 | 1.285 | 0.010 |
| E370A | 0.005 | 0.003 | 0.005 | > 10 | 0.222 | 0.183 | 0.446 | 0.066 |
| I371A | 0.008 | 0.293 | 3.520 | 4.632 | 0.063 | 0.187 | 0.225 | 0.011 |
| V372A | 0.004 | 0.003 | 0.006 | > 10 | 0.099 | 0.218 | 2.460 | 0.014 |
| M373A | 0.004 | 0.003 | 0.005 | 2.654 | 0.090 | 0.231 | 0.183 | 0.016 |
| R419A | 0.003 | 0.003 | 0.005 | 1.142 | 0.109 | 0.152 | 0.268 | 0.009 |
| T455A | 0.005 | 0.004 | 0.105 | 6.626 | 0.130 | 0.125 | 0.143 | 0.009 |
| G471A | > 4 | > 4 | > 4 | > 10 | 0.363 | 0.657 | 1.004 | 0.039 |
| G472A | 0.002 | 0.002 | 0.004 | > 10 | 0.144 | 0.173 | 0.369 | 0.013 |
| G473A | 0.003 | 0.002 | 0.007 | 0.295 | 0.079 | 0.104 | 0.158 | 0.009 |
| D474A | 0.009 | 0.003 | 0.055 | > 10 | 0.101 | 0.302 | 0.366 | 0.014 |
| M475A | 0.004 | 0.004 | 0.006 | > 10 | 0.080 | 0.196 | 0.242 | 0.024 |
| R476A | 0.003 | 0.001 | 0.002 | > 10 | 0.043 | 0.101 | 0.186 | 0.017 |

| | MEL-1842 | MEL-1872 | MEL-2129 | MEL-2026 | VRC01 | b12 | PGT121 |
|---|---|---|---|---|---|---|---|
| WT | 0.020 | 0.014 | 0.021 | 0.484 | 0.514 | 0.919 | 0.060 |
| E87A | 0.017 | 0.015 | 0.024 | 0.787 | 1.642 | 3.234 | 0.063 |
| K121A | 0.013 | 0.013 | 0.020 | 0.644 | 0.702 | 0.744 | 0.058 |
| L179A | 0.009 | 0.007 | 0.014 | 0.362 | 0.429 | 2.020 | 0.022 |
| D185A | 0.007 | 0.008 | 0.013 | 0.514 | 0.570 | 1.303 | 0.030 |
| N197A | 0.007 | 0.006 | 0.008 | 0.674 | 0.250 | 0.165 | 0.035 |
| N262A | 0.012 | 0.007 | 0.013 | 0.664 | 0.586 | 0.498 | 0.024 |
| N276A | 0.012 | 0.012 | 0.023 | 0.472 | 0.107 | 0.732 | 0.044 |
| D279A | 0.006 | 0.007 | 0.058 | 0.479 | > 4 | 1.477 | 0.054 |
| K282A | 0.009 | 0.004 | 0.010 | 0.397 | 0.297 | 0.594 | 0.027 |
| N283A | 0.013 | 0.016 | 0.048 | 0.267 | 0.527 | 0.672 | 0.064 |
| P313A | 0.012 | 0.011 | 0.024 | 0.351 | 0.599 | 0.733 | 0.042 |
| N332T | 0.016 | 0.011 | 0.016 | 0.445 | 0.482 | 0.722 | 1.840 |
| Q363A | 0.018 | 0.009 | 0.028 | 0.504 | 0.414 | 1.681 | 0.075 |
| S364A | 0.015 | 0.012 | 0.069 | 0.282 | 0.185 | 0.215 | 0.034 |
| G366A | 0.054 | 0.117 | 0.071 | 0.388 | 0.331 | > 4 | 0.028 |
| E370A | 0.037 | 0.015 | 0.027 | 0.859 | 0.932 | 0.717 | 0.033 |
| I371A | 0.057 | > 4 | > 4 | 0.180 | 0.751 | 0.954 | 0.039 |
| V372A | 0.014 | 0.010 | 0.021 | 0.445 | 0.584 | > 4 | 0.054 |
| M373A | 0.013 | 0.011 | 0.020 | 0.377 | 0.712 | 0.582 | 0.044 |
| R419A | 0.010 | 0.009 | 0.023 | 0.571 | 0.451 | 1.817 | 0.032 |
| T455A | 0.031 | 0.100 | 1.201 | 0.607 | 0.344 | 0.688 | 0.040 |
| G471A | > 4 | > 4 | > 4 | 1.751 | > 4 | > 4 | 0.115 |
| G472A | 0.007 | 0.004 | 0.012 | 0.867 | 0.423 | > 4 | 0.038 |
| G473A | 0.011 | 0.009 | 0.037 | 0.418 | 0.603 | 0.741 | 0.028 |
| D474A | 0.060 | 0.027 | 0.829 | 0.927 | 2.630 | 2.910 | 0.045 |
| M475A | 0.011 | 0.009 | 0.018 | 0.440 | 0.619 | 0.643 | 0.094 |
| R476A | 0.028 | 0.014 | 0.013 | 0.435 | 0.427 | 1.289 | 0.059 |

NC-COW1 H

NSQVQLRESGPSLMKPSQTLSLTCTVSGSSLNDKSVGWVRQAPGKALQWLGSV
DTSGNTDYNPGLKSRLSITKDNSKSRISLTVTGMTTEDSATYYCITAHQKTNKKECPEDY
TYNPRCPQQYGWSDCDCMGDRFGGYCRQDGCSNYIHRSTYEWYVSAWGQGLLVTVSS

NC-COW1 L

NSHSYELTQPSSVSGSLGQRVSVTCSGSSSNVGNGYVSWYQLIPGSAPRTIIYGDT
SRASGVPERFSGSRSGNTATLTISSLQAEDEADFFCASPDDSSSNAVFGSGTTLTVL

Alignment of VL genes and VH genes

```
Consensus      ----LTQPSSVSGSLGQRVS-TCSGSSSNVGNGYVSWYQLIPGSAPRT-IYGDTSRASGVP-RFSGSRSGNT-TLTISSLQAEDEAD-FC
NC-Cow1        HSYE................V...........................I............E..........A..............F.. 90
2129           -QAV................T...........................L............D..........V..............Y.. 89
Consensus      AS--D-SSNAVFG-GTTLTV-
NC-Cow1        ..PD.S.......S......L 111
2129           ..AE.G.......R......V 110
2129 _Copy     ..AE.G.......R......V 110
NC-C_Copy      ..PD.S.......S......L 111
```

```
Consensus      KVQLRESGPSLVKPSQTLSLTCTASGFSLSDKAVGWVRQAPG-ALEWLGSIDT-GNA-YNPGLKSRLSITKDNSKSQVSLSVSSVTTEDS
1842           ....Q.....................................Q..........G...D...............A..............G. 90
1872           ..........................................QP.....T...T...V.......................L........ 90
2129           ..........................................K..........G...G.............G.................. 90
NC-COW1        Q..........M...........V..S..N..S.........K..Q....V..S..TD..................RI..T.TGM..... 90

Consensus      ATYYCSTVHQKT--RSCP-DY-Y------------CDCEG-G-SHCCRA-NCPYYC--GRDR-CT------YEW-V-AWGQGLLVTVSS
1842           ............-L....S..P.I-----------...DT.-......T.....NH...M..GR-TYT..H.E............ 165
1872           ...H........-R....S..SFI-----------....T.-......S.....NY...M..GR-SNIH..H.D............ 165
2129           ............-R....V..Y.S------------....S.-....S.S.....KY...V..DKHTYS...Y.D............ 166
NC-COW1        .....I.A....NKKE..E..T.NPRCPQQYGWSD...M.DRFGGY..QDG.SN.IH-----------RST...Y.S............ 168
```

| Virus | Clade | Activity | MEL-1842 | MEL-1872 | MEL-2129 | NC-Cow1 | Pos Ctrl | Pos Ctrl ID |
|---|---|---|---|---|---|---|---|---|
| MuLV | | Neg Ctrl | >64 | >124 | >280 | >201 | >50 | CH01-31 |
| TRO.11 | B | Global Panel | 0.005 | 0.002 | 0.008 | 0.239 | 0.282 | VRC01 |
| TRO.11.N279A | B | CD4 bnAb KO | 0.002 | 0.006 | 0.424 | 78 | >50 | VRC01 |
| 25710 | C | Global Panel | 0.003 | 0.009 | 0.158 | 0.029 | 0.278 | VRC01 |
| 25710.N280D | C | CD4 bnAb KO | >64 | 94 | >280 | 0.017 | >50 | VRC01 |
| Ce1176 | C | Global Panel | 0.004 | 0.003 | 0.005 | 0.065 | 4.289 | VRC01 |
| Ce1176.G458Y | C | CD4 bnAb KO | 0.006 | 0.003 | 0.036 | 0.065 | >50 | VRC01 |
| CE0217 | C | Global Panel | 0.004 | 0.002 | 0.119 | 0.059 | 0.874 | VRC01 |
| CE0217.N280D | C | CD4 bnAb KO | 53.65 | 72 | 263.13 | 0.019 | 3.474 | VRC01 |
| X1632 | G | Global Panel | 0.069 | 0.007 | 0.257 | 0.118 | 0.073 | VRC01 |
| X1632.G458Y | G | CD4 bnAb KO | 0.107 | 0.019 | 29 | 0.070 | >50 | VRC01 |
| CNE55 | CRF01_AE | Global Panel, China/Yunnan | 1.563 | 0.054 | >280 | 0.019 | 0.207 | VRC01 |
| CNE55.N280D | CRF01_AE | CD4 bnAb KO | >64 | >124 | >280 | 0.084 | 1.014 | VRC01 |

IC80 (µg/ml)

| Virus | Clade | Activity | MEL-1842 | MEL-1872 | MEL-2129 | NC-Cow1 | Pos Ctrl | Pos Ctrl ID |
|---|---|---|---|---|---|---|---|---|
| MLV | | Neg Ctrl | >64 | >124 | >280 | >201 | >50 | CH01-31 |
| TRO.11 | B | Global Panel | 0.016 | 0.006 | 0.029 | 2.55 | 1.12 | VRC01 |
| TRO.11.N279A | B | CD4 bnAb KO | 0.0072 | 0.022 | 1.83 | >201 | >50 | VRC01 |
| 25710 | C | Global Panel | 0.015 | 0.056 | 3.28 | 0.1 | 1.14 | VRC01 |
| 25710.N280D | C | CD4 bnAb KO | >64 | >124 | >280 | 0.081 | >50 | VRC01 |
| Ce1176 | C | Global Panel | 0.013 | 0.009 | 0.015 | 0.2 | 9.55 | VRC01 |
| Ce1176.G458Y | C | CD4 bnAb KO | 0.016 | 0.011 | 0.224 | 0.25 | >50 | VRC01 |
| CE0217 | C | Global Panel | 0.013 | 0.006 | 1.06 | 0.17 | 1.65 | VRC01 |
| CE0217.N280D | C | CD4 bnAb KO | >64 | >124 | >280 | 0.06 | 31.48 | VRC01 |
| X1632 | G | Global Panel | 2.005 | 0.122 | 10.015 | 0.997 | 1.146 | VRC01 |
| X1632.G458Y | G | CD4 bnAb KO | 1.68 | 0.114 | 170 | 0.730 | >50 | VRC01 |
| CNE55 | CRF01_AE | Global Panel, China/Yunnan | >64 | 0.393 | >280 | 0.09 | 0.89 | VRC01 |
| CNE55.N280D | CRF01_AE | CD4 bnAb KO | >64 | >124 | >280 | 0.63 | 11.45 | VRC01 |

HIV-1 ANTIBODIES

FIELD OF THE INVENTION

The invention relates to antigen binding sites, antibodies and fragments thereof, as well as compositions, kits and uses thereof for the treatment, attenuation and/or prevention of human immunodeficiency virus type 1 (HIV-1).

RELATED APPLICATIONS

The present application is the US national stage of International Patent Application No. PCT/AU2021/050593, filed Jun. 10, 2021, which claims the benefit of and priority to Australian provisional applications AU 2020901907, filed Jun. 10, 2020, and AU 2021901071, filed Apr. 13, 2020, the contents of each which are hereby incorporated by reference in their entireties.

SEQUENCE LISTING

The instant application contains a Sequence Listing which has been submitted in ASCII format via EFS-Web and is hereby incorporated by reference in its entirety. The ASCII copy, created on Jun. 10, 2020, is 91,000 bytes in size and is named "SequenceListing_ST25.txt".

BACKGROUND OF THE INVENTION

Human immunodeficiency virus type 1 (HIV-1) continues to be a major global health problem, with more than 35 million individuals, including about 1.8 million children living with HIV infection in 2016, with a global HIV prevalence of 0.8% among adults in 2015.

Despite an improved understanding of the pathogenesis of HIV-1 including how HIV-1 manipulates a host's machinery in order to favor its own replication and transmission, a functional cure or protective vaccine remains elusive.

Antiretroviral therapy (ART) has reduced the incidence of infection and improved the quality of life of those infected; however, treatment must continue for life because viral rebound has been demonstrated upon treatment interruption. Further, ART targets infectious replicating viruses and is largely unable to access virus that remains dormant in viral reservoirs as provirus that can propagate by cell division. Thus, although current ART is essential in reduction of disease incidence, it alone is not sufficient in reducing HIV-1 incidence and/or providing a functional cure.

In the sera of human immunodeficiency virus type 1 (HIV-1) infected patients, antivirus antibodies can be detected over a certain period after infection without any clinical manifestations of the acquired immunodeficiency syndrome (AIDS). At this state of active immune response, high numbers of antigen-specific B-cells are expected in the circulation. These B-cells are used as fusion partners for the generation of human monoclonal anti-HIV-1 antibodies. One major drawback in identification of a vaccine composition suitable for more reliable prevention of human individuals from HIV-1 infection and/or for more successful therapeutic treatment of infected patients is the ability of the HIV-1 virus to escape antibody capture by genetic variation. Such escape mutants may be characterized by a change of only one or several of the amino acids within one of the targeted antigenic determinants and may occur, for example, as a result of spontaneous or induced mutation of the HIV-1 virus. In addition to genetic variation, certain other properties of the HIV-1 envelope glycoprotein, such as high levels of glycosylation, makes it difficult to elicit neutralizing antibodies.

HIV-1 is among the most genetically diverse viral pathogens. Of the three main branches of the HIV-1 phylogenetic tree, the M (main), N (new), and 0 (outlier) groups, group M viruses are the most widespread, accounting for over 99% of global infections. This group is presently divided into nine distinct genetic subtypes, or clades (A through K), based on full-length sequences. Env is the most variable HIV-1 gene, with up to 35% sequence diversity between clades, 20% sequence diversity within clades, and up to 10% sequence diversity in a single infected person. Clade B is dominant in Europe, the Americas, and Australia. Clade C is common in southern Africa, China, and India and presently infects more people worldwide than any other cade. Clades A and D are prominent in central and eastern Africa.

The HIV-1 Env protein, which inserts into the HIV-1 viral envelope, is however the only viral protein accessible to antibody-directed immunity on infectious virions and infected cells. Antibody is a dominant mechanism for clearing viral infections mediating direct neutralisation of virion infectivity and antibody-directed cellular immunity and possesses several benefits over the chemical-based treatments, including improved specificity and safety. Previous attempts at vaccination against the HIV-1 Env protein in human and animal models have however yielded little or no active neutralising Abs.

Given the above limitations, there remains a need for improved therapies for the treatment, attenuation and/or prevention of HIV-1 infection.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention provides an antigen binding site that binds to or specifically binds to human immunodeficiency virus type 1 (HIV-1). Preferably, the antigen binding site comprises an antigen binding domain of an antibody, wherein the antigen binding domain binds to or specifically binds to HIV-1. In an aspect of the invention, the antigen binding site is capable of neutralising or inhibiting HIV-1 infection.

In any aspect of the invention, the antigen binding site binds to or specifically binds to a HIV-1 viral envelope protein, preferably the HIV-1 viral envelope protein is gp120. In an embodiment, the antigen binding site is capable of binding to or specifically binding to one or more of a monomeric HIV-1 gp120, uncleaved gp140 (gp160), SOSIP gp140, and a trimer forms of HIV-1 viral envelope glycoproteins, preferably ConM SOSIP. In one embodiment, the antigen binding site is capable of binding to or specifically binding to viral envelope proteins according to any one, two, three, four or five of SEQ ID NOs: 65-69. In this aspect, the antigen binding site may be capable of binding to any of the above viral envelope proteins more effectively than an antibody comprising a VH and VL of antibody VRC01 according to SEQ ID NO: 70 and 71 respectively. In an embodiment, the antigen binding site is capable of binding 2, 4, 6, 8, 10, 20, 30, 40, 50, 60, 70, 80, 90 or 100-fold more effectively than an antibody comprising a VH and VL of antibody VRC01 according to SEQ ID NO: 70 and 71 respectively.

In any aspect of the invention, the antigen binding site binds to the outer domain of a HIV-1 viral envelope protein, preferably gp120, preferably within the CD4 binding site of gp120. Preferably, the antigen binding site binds to C2, V3, C3, C4 and/or C5 domains of gp120. In one embodiment, the antigen binding site binds to or specifically binds to Loop D of the C2 domain of gp120, the Tip or Base regions of the V3 domain of gp120, the CD4binding site (CD4bs) of the C3 domain of gp120, the β23 domain of the C4 domain of gp120 and/or the β24-α5 connection of the C5 domain of gp120. In a preferred aspect, the antigen binding site binds within the CD4bs of the C3 domain of gp120, the β23 domain of the C4 gp120 protein and/or β24-α5 connection of the C5 domain of gp120.

In any aspect of the invention, the antigen binding site binds to one or more of residues 262, 276, 279, 282, 283 of the C2 domain of gp120, preferably residue 262 of the C2 domain of gp120. In another aspect, the antigen binding site binds to one or more of residues 313, 329 and 332 of the V3 domain of gp120, preferably residue 329 of the V3 domain of gp120. In another aspect, the antigen binding site binds to one or more of residues 363, 364, 365, 366, 367, 368, 369, 370, 371, 372 and 373 of the C3 domain of gp120, preferably residues 366, 367, 368 and 371 of the C3 domain of gp120. In another aspect, the antigen binding site binds to one or more of residues 419, 455 and 457 of the C4 domain of gp120, preferably residues 455 and 457 of the C4 domain of the gp120 protein. In another aspect, the antigen binding site binds to one or more of residues 471, 472, 473, 474, 475 and 476 of the C5 domain of the gp120 protein, preferably residues 471, 472, 473 and 474 of the C5 domain of the gp120 protein, more preferably residue 471 of the gp120 protein.

In another aspect, the antigen binding site binds to at least one of, or all of, residues 366, 371, 457 and 471 of gp120. In yet another aspect, the antigen binding site binds to residues 366 and 471 of the gp120 protein.

In another aspect, the antigen binding site may exhibit 30% or less binding to a gp120 protein mutated at any one of residues G366, I371, D457 and G471 compared to binding to an unmutated gp120 protein. In one embodiment, the antigen binding site may exhibit 30% or less binding to a gp120 protein mutated at any one or more residues N262, D279, T455, G472, G473 and D474 compared to binding to an unmutated gp120 protein. In a preferred embodiment, the gp120 protein has a sequence as set forth in SEQ ID NO: 65.

In any aspect of the invention, any antigen binding site described herein is capable of competing for binding with human broadly neutralising antibodies (BrNAbs) selected from the list consisting of b12, HJ16, 3BNC117 or the VRC01 antibody comprising VH and VL sequences according to SEQ ID NO: 70 and 71 respectively. In this aspect, the antigen binding sites described herein are capable of inhibiting human BrNAb binding by at least 20%, at least, 30%, at least 40%, at least 50%, at least 60%, at least 70%, at least 80%, at least 90% or more.

In one aspect of the invention, there is provided any antigen binding site that binds to HIV-1 and competitively inhibits binding of 1842, 1872 and 2129 antibody as described herein (i.e. comprising a VH comprising a sequence set forth in SEQ ID NO: 15 and a VL comprising a sequence set forth in SEQ ID NO: 63; comprising a VH comprising a sequence set forth in SEQ ID NO: 15 and a VL comprising a sequence set forth in SEQ ID NO: 73; comprising a VH comprising a sequence set forth in SEQ ID NO: 31 and a VL comprising a sequence set forth in SEQ ID NO: 63; comprising a VH comprising a sequence set forth in SEQ ID NO: 31 and a VL comprising a sequence set forth in SEQ ID NO: 73; comprising a VH comprising a sequence set forth in SEQ ID NO: 61 and a VL comprising a sequence set forth in SEQ ID NO: 63; or comprising a VH comprising a sequence set forth in SEQ ID NO: 61 and a VL comprising a sequence set forth in SEQ ID NO: 73).

In another aspect of the invention, there is provided an antigen binding site that binds to the same epitope on HIV-1 as an antibody that comprises a VH domain comprising the amino acid sequence as set forth in any one of SEQ ID NOs: 15, 31 and 61, and a VL domain comprising the amino acid sequence as set forth in SEQ ID NO: 63 or 73.

In any aspect of the invention, the antigen binding site may bind to HIV-1 and does not detectably bind to or bind significantly to HIV-2. The binding of an antigen binding site to HIV-1 and HIV-2 may be determined by any method described herein or known in the art.

In any aspect of the invention, any antigen binding site of the invention may bind to HIV-1 and exhibit neutralization of HIV-1 at an $IC_{50}$ of less than 0.5 μg/ml, less than 0.4 μg/ml, less than 0.3 μg/ml, less than 0.2 μg/ml, less than 0.1 μg/ml, less than 0.08 μg/ml, less than 0.06 μg/ml, less than 0.05 μg/ml, less than 0.03 μg/ml, less than 0.01 μg/ml, less than 0.008 μg/ml, less than 0.006 μg/ml, less than 0.005 μg/ml, less than 0.003 μg/ml or less than 0.001 μg/ml. Preferably, the $IC_{50}$ of the antigen binding site is less than 0.2 μg/ml or less than 0.01 μg/ml. The $IC_{50}$ value may be determined by any means in the art including the methods described herein. In an aspect, the neutralization of HIV-1 relates to neutralization of HIV-1 infection at a dose of 50% tissue culture infectious doses (200 TCID-50).

In another aspect, an antigen binding site of the invention comprises a VH comprising a sequence set forth in SEQ ID NO: 15 and a VL comprising a sequence set forth in SEQ ID NO: 63; or comprises a VH comprising a sequence set forth in SEQ ID NO: 15 and a VL comprising a sequence set forth in SEQ ID NO: 73 and exhibits binding to HIV-1 AD8 gp120 with an $EC_{50}$ of about 0.06 μg/ml, binding to HIV-1 AD8 gp140 with an $EC_{50}$ of about 0.03 μg/ml, binding to HIV-1 AD8 SOSIP with an $EC_{50}$ of about 0.05 μg/ml, and/or binding to HIV-1 ConM SOSIP with an $EC_{50}$ of about 0.02 μg/ml. In another aspect the antigen binding site having these $IC_{50}$ values is antibody 1842 as described herein.

In another aspect, an antigen binding site of the invention comprises a VH comprising a sequence set forth in SEQ ID NO: 31 and a VL comprising a sequence set forth in SEQ ID NO: 63; or comprises a VH comprising a sequence set forth in SEQ ID NO: 31 and a VL comprising a sequence set forth in SEQ ID NO: 73 and exhibits binding to HIV-1 AD8 gp120 with an $EC_{50}$ of about 0.03 μg/ml, binding to HIV-1 AD8 gp140 with an $EC_{50}$ of about 0.02 μg/ml, binding to HIV-1 AD8 SOSIP with an $EC_{50}$ of about 0.04 μg/ml, and/or binding to HIV-1 ConM SOSIP with an $EC_{50}$ of about 0.02 μg/ml. In another aspect the antigen binding site having these $IC_{50}$ values is antibody 1872 as described herein.

In another aspect, an antigen binding site of the invention comprises a VH comprising a sequence set forth in SEQ ID NO: 61 and a VL comprising a sequence set forth in SEQ ID NO: 63; or comprises a VH comprising a sequence set forth in SEQ ID NO: 61 and a VL comprising a sequence set forth in SEQ ID NO: 73 and exhibits binding to HIV-1 AD8 gp120 with an $EC_{50}$ of about 0.04 μg/ml for, binding to HIV-1 AD8 gp140 with an $EC_{50}$ of about 0.02 μg/ml, binding to HIV-1 AD8 SOSIP with an $EC_{50}$ of about 0.01 μg/ml, and/or binding to HIV-1 ConM SOSIP with an $EC_{50}$ of about 0.01 μg/ml. In another aspect the antigen binding site having these $IC_{50}$ values is antibody 2129 as described herein.

In any aspect of the invention, the antigen binding site comprises an amino acid sequence of any one of SEQ ID NOs: 3, 19, 35, 82, 89, 103, 117 or 130.

In any aspect, the antigen binding site comprises:

a heavy chain complementarity determining region 1 (CDRH1) having an amino acid sequence of SEQ ID NO: 1;

a heavy chain complementarity determining region 2 (CDRH2) having an amino acid sequence of any one of SEQ ID NOs: 2, 18, 34, or 81;

a heavy chain complementarity determining region 3 (CDRH3) having an amino acid sequence of any one of SEQ ID NOs: 3, 19, 35, or 82; and complementarity determining regions of a light chain variable region.

In any aspect, the antigen binding site comprises:

a heavy chain complementarity determining region 1 (CDRH1) having an amino acid sequence of SEQ ID NO: 87;

a heavy chain complementarity determining region 2 (CDRH2) having an amino acid sequence of any one of SEQ ID NOs: 88, 102, 116 or 129;

a heavy chain complementarity determining region 3 (CDRH3) having an amino acid sequence of any one of SEQ ID NOs: 89, 103, 117 or 130; and complementarity determining regions of a light chain variable region.

In this aspect it will be understood that the complementarity determining regions of the light chain variable region are not essential for antigen binding, which is predominantly driven by the heavy chain complementarity determining regions. In this aspect, any suitable light chain variable region may be used. Preferably, the antigen binding site comprises CDRH1, CDRH2 and CDRH3 in a heavy chain variable region paired with a light chain variable region. Preferably, the light chain is encoded by a Vλ1 gene, more preferably encoded by a Vλ1x, Vλ1d and Vλ1e gene.

In one aspect, the light chain variable region comprises a light chain complementarity determining region 1 (CDRL1) according to SEQ ID NO: 83 a light chain complementarity determining region 2 (CDRL2) according to SEQ ID NO: 84 and a light chain complementarity determining region 3 (CDRL3) according to SEQ ID NO: 85.

In another aspect, the light chain variable region comprises a light chain complementarity determining region 1 (CDRL1) according to SEQ ID NO: 39 or 74 a light chain complementarity determining region 2 (CDRL2) according to SEQ ID NO: 40 or 75 and a light chain complementarity determining region 3 (CDRL3) according to SEQ ID NO: 41 or 76.

In another aspect, the light chain variable region comprises a light chain complementarity determining region 1 (CDRL1) according to SEQ ID NO: 131 a light chain complementarity determining region 2 (CDRL2) according to SEQ ID NO: 132 and a light chain complementarity determining region 3 (CDRL3) according to SEQ ID NO: 133.

In an embodiment of the invention, any antigen binding site described herein comprises a human constant region and bovine variable regions that are capable of neutralising human immunodeficiency virus type 1 (HIV-1). It will be understood that the present invention therefore provides broadly neutralising antibodies (BrNAbs).

The invention provides antigen binding site for binding to HIV-1, the antigen binding site comprising:

FR1-CDR1-FR2-CDR2-FR3-CDR3-FR4, and

FR1a-CDR1a-FR2a-CDR2a-FR3a-CDR3a-FR4a wherein:

FR1, FR2, FR3 and FR4 are each framework regions;

CDR1, CDR2 and CDR3 are each complementarity determining regions;

FR1a, FR2a, FR3a and FR4a are each framework regions;

CDR1a, CDR2a and CDR3a are each complementarity determining regions;

wherein the sequence of any of the framework regions or complementarity determining regions are as described herein.

The invention provides an antigen binding site for binding to HIV-1, the antigen binding site including:

FR1-CDR1-FR2-CDR2-FR3-CDR3-FR4-linker-FR1a-CDR1a-FR2a-CDR2a-FR3a-CDR3a-FR4a wherein:

FR1, FR2, FR3 and FR4 are each framework regions;

CDR1, CDR2 and CDR3 are each complementarity determining regions;

FR1a, FR2a, FR3a and FR4a are each framework regions;

CDR1a, CDR2a and CDR3a are each complementarity determining regions;

wherein the sequence of any of the complementarity determining regions have an amino acid sequence as described in Table 1 below (e.g. CDRH1, CDRH2, CDRH3, CDRL1, CDRL2, CDRL3). Preferably, the framework regions have an amino acid sequence also as described in Table 1 below, including amino acid variation at particular residues which can be determined by aligning the various framework regions derived from each antibody. The invention also includes where CDR1, CDR2 and CDR3 are sequences from the VH, CDR1a, CDR2a and CDR3a are sequences from VL, or where CDR1, CDR2 and CDR3 are sequences from the VL, CDR1a, CDR2a and CDR3a are sequences from VH.

As defined herein, the linker may be a chemical, one or more amino acids (including a polypeptide), or a disulphide bond formed between two cysteine residues.

In another aspect, the antigen binding site comprises a heavy chain complementarity determining region 1 (CDRH1) according to any one of SEQ ID NOs: 1, 17 or 33, a CDRH2 according to any one of SEQ ID NOs: 2, 18 or 34 and a CDRH3 according to any one of SEQ ID NOs: 3, 19 or 35. In another aspect, the antigen binding site comprises a CDRH1 comprising a sequence at least about 80%, at least 85%, at least 90%, at least 92%, at least 95%, at least 97%, at least 99% identical to a sequence set forth in any one of SEQ ID NO: 1, 17 or 33, a CDRH2 comprising a sequence at least about 80%, at least 85%, at least 90%, at least 92%, at least 95%, at least 97%, at least 99% identical to a sequence set forth in any one of SEQ ID NOs: 2, 18 or 34; and a CDRH3 comprising a sequence at least about 80%, at least 85%, at least 90%, at least 92%, at least 95%, at least 97%, at least 99% identical to a sequence set forth in SEQ ID NO: NOs: 3, 19 or 35.

In another aspect, the antigen binding site comprises the heavy chain variable region of any one of SEQ ID NOs: 15, 31 or 61. In a further aspect, the antigen binding site comprises a sequence at least about 80%, at least 85%, at least 90%, at least 92%, at least 95%, at least 97%, at least 99% identical to the heavy chain variable regions set forth in any one of SEQ ID NOs: 15, 31 or 61.

In any aspect, the antigen binding site comprises a light chain complementarity determining region 1 (CDRL1) according to SEQ ID NOs: 39 or 74, a CDRL2 according to SEQ ID NOs: 40 or 75 and a CDRL3 according to SEQ ID NOs: 41 or 76. In another aspect, the antigen binding site comprises a CDRL1 comprising a sequence at least about 80%, at least 85%, at least 90%, at least 92%, at least 95%, at least 97%, at least 99% identical to a sequence set forth in SEQ ID NOs: 39 or 74, a CDRL2 comprising a sequence at least about 80%, at least 85%, at least 90%, at least 92%, at least 95%, at least 97%, at least 99% identical to a sequence set forth in SEQ ID NOs:40 or 75 and a CDRL3 comprising a sequence at least about 80%, at least 85%, at least 90%, at least 92%, at least 95%, at least 97%, at least 99% identical to a sequence set forth in SEQ ID NO: 41 or 76.

In another aspect, the antigen binding site comprises the light chain variable region of SEQ ID NOs: 63 or 73. In a further aspect, the antigen binding site comprises a sequence at least about 80%, at least 85%, at least 90%, at least 92%, at least 95%, at least 97%, at least 99% identical to the light chain variable region set forth in SEQ ID NOs: 63 or 73.

In an aspect, the antigen binding site comprises, consists essentially of or consists of an amino acid sequence of (in order of N to C terminus or C to N terminus) SEQ ID NO: 15 and 63 or SEQ ID NO: 15 and 73.

In an aspect, the antigen binding site comprises, consists essentially of or consists of an amino acids sequence of (in order of N to C terminus or C to N terminus) SEQ ID NO: 31 and 63 or SEQ ID NO: 31 and 73.

In an aspect, the antigen binding site comprises, consists essentially of or consists of an amino acids sequence of (in order of N to C terminus or C to N terminus) SEQ ID NO: 61 and 63 or SEQ ID NO: 61 and 73.

The present invention also provides an antigen binding site comprising an antigen binding domain of an antibody, wherein the antigen binding domain binds to or specifically binds to HIV-1, wherein the antigen binding domain comprises at least one of:

(i) a VH comprising a complementarity determining region (CDR) 1 comprising a sequence at least about 80%, at least 85%, at least 90%, at least 92%, at least 95%, at least 97%, at least 99% identical to a sequence set forth in SEQ ID NO: 1, a CDR2 comprising a sequence at least about 80%, at least 85%, at least 90%, at least 92%, at least 95%, at least 97%, at least 99% identical to a sequence set forth in SEQ ID NO: 2 and a CDR3 comprising a sequence at least about 80%, at least 85%, at least 90%, at least 92%, at least 95%, at least 97%, at least 99% identical to a sequence set forth in SEQ ID NO: 3;

(ii) a VH comprising a sequence at least about 95% or 96% or 97% or 98% or 99% identical to a sequence set forth in SEQ ID NO: 15;

(iii) a VL comprising a CDR1 comprising a sequence at least about 80%, at least 85%, at least 90%, at least 92%, at least 95%, at least 97%, at least 99% identical to a sequence set forth in any one of SEQ ID NOs: 39, 74 or 83, a CDR2 comprising a sequence at least about 80%, at least 85%, at least 90%, at least 92%, at least 95%, at least 97%, at least 99% identical to a sequence set forth in any one of SEQ ID NOs: 40, 75 or 84 and a CDR3 comprising a sequence at least about 80%, at least 85%, at least 90%, at least 92%, at least 95%, at least 97%, at least 99% identical to a sequence set forth in any one of SEQ ID NOs: 41, 76 or 85;

(iv) a VL comprising a sequence at least about 95% identical to a sequence set forth in SEQ ID NO: 63 or 73;

(v) a VH comprising a CDR1 comprising a sequence set forth in SEQ ID NO: 1, a CDR2 comprising a sequence set forth in SEQ ID NO: 2 and a CDR3 comprising a sequence set forth in SEQ ID NO: 3;

(vi) a VH comprising a sequence set forth in SEQ ID NO: 15;

(vii) a VL comprising a CDR1 comprising a sequence set forth in any one of SEQ ID NOs: 39, 74 or 83, a CDR2 comprising a sequence set forth in any one of SEQ ID NOs: 40, 75 or 84 and a CDR3 comprising a sequence set forth in any one of SEQ ID NOs: 41, 76 or 85;

(viii) a VL comprising a sequence set forth in SEQ ID NOs: 63 or 73;

(ix) a VH comprising a CDR1 comprising a sequence set forth in SEQ ID NO: 1, a CDR2 comprising a sequence set forth in SEQ ID NO: 2 and a CDR3 comprising a sequence set forth in SEQ ID NO: 3; and a VL comprising a CDR1 comprising a sequence set forth in any one of SEQ ID NOs: 39, 74 or 83, a CDR2 comprising a sequence set forth in any one of SEQ ID NOs: 40, 75 or 84 and a CDR3 comprising a sequence set forth in any one of SEQ ID NOs: 41, 76 or 85; or (x) a VH comprising a sequence set forth in SEQ ID NO: 15 and a VL comprising a sequence set forth in SEQ ID NO: 63 or 73.

In any aspect of the invention, the antigen binding domain further comprises at least one of:

(i) a VH comprising a framework region (FR) 1 comprising a sequence at least about 80%, at least 85%, at least 90%, at least 92%, at least 95%, at least 97%, at least 99% identical to a sequence set forth in SEQ ID NO: 7, a FR2 comprising a sequence at least about 80%, at least 85%, at least 90%, at least 92%, at least 95%, at least 97%, at least 99% identical to a sequence set forth in SEQ ID NO: 8, a FR3 comprising a sequence at least about 80%, at least 85%, at least 90%, at least 92%, at least 95%, at least 97%, at least 99% identical to a sequence set forth in SEQ ID NO: 9, and a FR4 comprising a sequence at least about 80%, at least 85%, at least 90%, at least 92%, at least 95%, at least 97%, at least 99% identical to a sequence set forth in SEQ ID NO: 10;

(ii) a VL comprising a FR1 comprising a sequence at least about 80%, at least 85%, at least 90%, at least 92%, at least 95%, at least 97%, at least 99% identical to a sequence set forth in SEQ ID NO: 53 or 77, a FR2 comprising a sequence at least about 80%, at least 85%, at least 90%, at least 92%, at least 95%, at least 97%, at least 99% identical to a sequence set forth in SEQ ID NO: 54 or 78, a FR3 comprising a sequence at least about 80%, at least 85%, at least 90%, at least 92%, at least 95%, at least 97%, at least 99% identical to a sequence set forth in SEQ ID NO: 55 or 79, and a FR4 comprising a sequence at least about 80%, at least 85%, at least 90%, at least 92%, at least 95%, at least 97%, at least 99% identical to a sequence set forth in SEQ ID NO: 56 or 80;

(iii) a VH comprising a FR1 comprising a sequence set forth in SEQ ID NO: 7, a FR2 comprising a sequence set forth in SEQ ID NO: 8, a FR3 comprising a sequence set forth in SEQ ID NO: 9, and a FR4 comprising a sequence set forth in SEQ ID NO: 10;

(iv) a VL comprising a FR1 comprising a sequence set forth in SEQ ID NO: 53 or 77, a FR2 comprising a sequence set forth in SEQ ID NO: 54 or 78, a FR3 comprising a sequence set forth in SEQ ID NO: 55 or 79, and a FR4 comprising a sequence set forth in SEQ ID NO: 56 or 80; or (v) a VH comprising a FR1 comprising a sequence set forth in SEQ ID NO: 7, a FR2 comprising a sequence set forth in SEQ ID NO: 8, a FR3 comprising a sequence set forth in SEQ ID NO: 9, and a FR4 comprising a sequence set forth in SEQ ID NO: 10; and a VL comprising a FR1 comprising a sequence set forth in SEQ ID NO: 53 or 77, a FR2 comprising a sequence set forth in SEQ ID NO: 54 or 78, a FR3 comprising a sequence set forth in SEQ ID NO: 55 or 79, and a FR4 comprising a sequence set forth in SEQ ID NO: 56 or 80.

The present invention also provides an antigen binding site comprising an antigen binding domain of an antibody, wherein the antigen binding domain binds to or specifically binds to human immunodeficiency virus type 1 (HIV-1), wherein the antigen binding domain comprises at least one of:

(i) a VH comprising a complementarity determining region 1 (CDRH1) comprising a sequence at least about 80%, at least 85%, at least 90%, at least 92%, at least 95%, at least 97%, at least 99% identical to a sequence set forth in SEQ ID NO: 17, a CDRH2 comprising a sequence at least about 80%, at least 85%, at least 90%, at least 92%, at least 95%, at least 97%, at least 99% identical to a sequence set forth in SEQ ID NO: 18 and a CDRH3 comprising a sequence at least about 80%, at least 85%, at least 90%, at least 92%, at least 95%, at least 97%, at least 99% identical to a sequence set forth in SEQ ID NO: 19;

(ii) a VH comprising a sequence at least about 95% or 96% or 97% or 98% or 99% identical to a sequence set forth in SEQ ID NO: 31;

(iii) a VL comprising a CDR1 comprising a sequence at least about 80%, at least 85%, at least 90%, at least 92%, at least 95%, at least 97%, at least 99% identical to a sequence set forth in any one of SEQ ID NOs: 39, 74 or 83, a CDR2 comprising a sequence at least about 80%, at least 85%, at least 90%, at least 92%, at least 95%, at least 97%, at least 99% identical to a sequence set forth in any one of SEQ ID NOs: 40, 75 or 84 and a CDR3 comprising a sequence at least about 80%, at least 85%, at least 90%, at least 92%, at least 95%, at least 97%, at least 99% identical to a sequence set forth in any one of SEQ ID NOs: 41, 76 or 85;

(iv) a VL comprising a sequence at least about 95% identical to a sequence set forth in SEQ ID NO: 63 or 73;

(v) a VH comprising a CDR1 comprising a sequence set forth in SEQ ID NO: 17, a CDR2 comprising a sequence set forth in SEQ ID NO: 18 and a CDR3 comprising a sequence set forth in SEQ ID NO: 19;

(vi) a VH comprising a sequence set forth in SEQ ID NO: 31;

(vii) a VL comprising a CDR1 comprising a sequence set forth in any one of SEQ ID NOs: 39, 74 or 83, a CDR2 comprising a sequence set forth in any one of SEQ ID NOs: 40, 75 or 84 and a CDR3 comprising a sequence set forth in any one of SEQ ID NOs: 41, 76 or 85;

(viii) a VL comprising a sequence set forth in SEQ ID NOs: 63 or 73;

(ix) a VH comprising a CDR1 comprising a sequence set forth in SEQ ID NO: 17, a CDR2 comprising a sequence set forth in SEQ ID NO: 18 and a CDR3 comprising a sequence set forth in SEQ ID NO: 19; and a VL comprising a CDR1 comprising a sequence set forth in any one of SEQ ID NOs: 39, 74 or 83, a CDR2 comprising a sequence set forth in any one of SEQ ID NOs: 40, 75 or 84 and a CDR3 comprising a sequence set forth in any one of SEQ ID NOs: 41, 75 or 85; or (x) a VH comprising a sequence set forth in SEQ ID NO: 31 and a VL comprising a sequence set forth in SEQ ID NOs: 63 or 73.

In any aspect of the invention, the antigen binding domain further comprises at least one of:

(i) a VH comprising a framework region (FR) 1 comprising a sequence at least about 80%, at least 85%, at least 90%, at least 92%, at least 95%, at least 97%, at least 99% identical to a sequence set forth in SEQ ID NO: 23, a FR2 comprising a sequence at least about 80%, at least 85%, at least 90%, at least 92%, at least 95%, at least 97%, at least 99% identical to a sequence set forth in SEQ ID NO: 24, a FR3 comprising a sequence at least about 80%, at least 85%, at least 90%, at least 92%, at least 95%, at least 97%, at least 99% identical to a sequence set forth in SEQ ID NO: 25, and a FR4 comprising a sequence at least about 80%, at least 85%, at least 90%, at least 92%, at least 95%, at least 97%, at least 99% identical to a sequence set forth in SEQ ID NO: 26;

(ii) a VL comprising a FR1 comprising a sequence at least about 80%, at least 85%, at least 90%, at least 92%, at least 95%, at least 97%, at least 99% identical to a sequence set forth in SEQ ID NO: 53 or 77, a FR2 comprising a sequence at least about 80%, at least 85%, at least 90%, at least 92%, at least 95%, at least 97%, at least 99% identical to a sequence set forth in SEQ ID NO: 54 or 78, a FR3 comprising a sequence at least about 80%, at least 85%, at least 90%, at least 92%, at least 95%, at least 97%, at least 99% identical to a sequence set forth in SEQ ID NO: 55 or 79, and a FR4 comprising a sequence at least about 80%, at least 85%, at least 90%, at least 92%, at least 95%, at least 97%, at least 99% identical to a sequence set forth in SEQ ID NO: 56 or 80;

(iii) a VH comprising a FR1 comprising a sequence set forth in SEQ ID NO: 23, a FR2 comprising a sequence set forth in SEQ ID NO: 24, a FR3 comprising a sequence set forth in SEQ ID NO: 25, and a FR4 comprising a sequence set forth in SEQ ID NO: 26;

(iv) a VL comprising a FR1 comprising a sequence set forth in SEQ ID NO: 53 or 77, a FR2 comprising a sequence set forth in SEQ ID NO: 54 or 78, a FR3 comprising a sequence set forth in SEQ ID NO: 55 or 79, and a FR4 comprising a sequence set forth in SEQ ID NO: 56 or 80; or (v) a VH comprising a FR1 comprising a sequence set forth in SEQ ID NO: 23, a FR2 comprising a sequence set forth in SEQ ID NO: 24, a FR3 comprising a sequence set forth in SEQ ID NO: 25, and a FR4 comprising a sequence set forth in SEQ ID NO: 26; and a VL comprising a FR1 comprising a sequence set forth in SEQ ID NO: 53 or 77, a FR2 comprising a sequence set forth in SEQ ID NO: 54 or 78, a FR3 comprising a sequence set forth in SEQ ID NO: 55 or 79, and a FR4 comprising a sequence set forth in SEQ ID NO: 56 or 80.

The present invention also provides an antigen binding site comprising an antigen binding domain of an antibody, wherein the antigen binding domain binds to or specifically binds to human immunodeficiency virus type 1 (HIV-1), wherein the antigen binding domain comprises at least one of:

- (i) a VH comprising a complementarity determining region (CDR) 1 comprising a sequence at least about 80%, at least 85%, at least 90%, at least 92%, at least 95%, at least 97%, at least 99% identical to a sequence set forth in SEQ ID NO: 33, a CDR2 comprising a sequence at least about 80%, at least 85%, at least 90%, at least 92%, at least 95%, at least 97%, at least 99% identical to a sequence set forth in SEQ ID NO: 34 and a CDR3 comprising a sequence at least about 80%, at least 85%, at least 90%, at least 92%, at least 95%, at least 97%, at least 99% identical to a sequence set forth in SEQ ID NO: 35;
- (ii) a VH comprising a sequence at least about 95% or 96% or 97% or 98% or 99% identical to a sequence set forth in SEQ ID NO: 61;
- (iii) a VL comprising a CDR1 comprising a sequence at least about 80%, at least 85%, at least 90%, at least 92%, at least 95%, at least 97%, at least 99% identical to a sequence set forth in any one of SEQ ID NOs: 39, 74 or 83, a CDR2 comprising a sequence at least about 80%, at least 85%, at least 90%, at least 92%, at least 95%, at least 97%, at least 99% identical to a sequence set forth in any one of SEQ ID NOs: 40, 75 or 84 and a CDR3 comprising a sequence at least about 80%, at least 85%, at least 90%, at least 92%, at least 95%, at least 97%, at least 99% identical to a sequence set forth in any one of SEQ ID NOs: 41, 76 or 85;
- (iv) a VL comprising a sequence at least about 95% identical to a sequence set forth in SEQ ID NOs: 63 or 73;
- (v) a VH comprising a CDR1 comprising a sequence set forth in SEQ ID NO: 33, a CDR2 comprising a sequence set forth in SEQ ID NO: 34 and a CDR3 comprising a sequence set forth in SEQ ID NO: 35;
- (vi) a VH comprising a sequence set forth in SEQ ID NO: 61;
- (vii) a VL comprising a CDR1 comprising a sequence set SEQ ID NO: 39, 74 or 83, a CDR2 comprising a sequence set forth in SEQ ID NO: 40, 75 or 84 and a CDR3 comprising a sequence set forth in SEQ ID NO: 41, 76 or 85;
- (viii) a VL comprising a sequence set forth in SEQ ID NO: 63 or 73;
- (ix) a VH comprising a CDR1 comprising a sequence set forth in SEQ ID NO: 33, a CDR2 comprising a sequence set forth in SEQ ID NO: 34 and a CDR3 comprising a sequence set forth in SEQ ID NO: 35; and a VL comprising a CDR1 comprising a sequence set forth in any one of SEQ ID NOs: 39, 74 or 83, a CDR2 comprising a sequence set forth in any one of SEQ ID NOs: 40, 74 or 84 and a CDR3 comprising a sequence set forth in any one of SEQ ID NOs: 41, 75 or 85; or
- (x) a VH comprising a sequence set forth in SEQ ID NO: 61 and a VL comprising a sequence set forth in SEQ ID NOs: 63 or 73.

In any aspect of the invention, the antigen binding domain further comprises at least one of:

- (i) a VH comprising a framework region (FR) 1 comprising a sequence at least about 80%, at least 85%, at least 90%, at least 92%, at least 95%, at least 97%, at least 99% identical to a sequence set forth in SEQ ID NO: 45, a FR2 comprising a sequence at least about 80%, at least 85%, at least 90%, at least 92%, at least 95%, at least 97%, at least 99% identical to a sequence set forth in SEQ ID NO: 46, a FR3 comprising a sequence at least about 80%, at least 85%, at least 90%, at least 92%, at least 95%, at least 97%, at least 99% identical to a sequence set forth in SEQ ID NO: 47, and a FR4 comprising a sequence at least about 80%, at least 85%, at least 90%, at least 92%, at least 95%, at least 97%, at least 99% identical to a sequence set forth in SEQ ID NO: 48;
- (ii) a VL comprising a FR1 comprising a sequence at least about 80%, at least 85%, at least 90%, at least 92%, at least 95%, at least 97%, at least 99% identical to a sequence set forth in SEQ ID NO: 53 or 77, a FR2 comprising a sequence at least about 80%, at least 85%, at least 90%, at least 92%, at least 95%, at least 97%, at least 99% identical to a sequence set forth in SEQ ID NO: 54 or 78, a FR3 comprising a sequence at least about 80%, at least 85%, at least 90%, at least 92%, at least 95%, at least 97%, at least 99% identical to a sequence set forth in SEQ ID NO: 55 or 79, and a FR4 comprising a sequence at least about 80%, at least 85%, at least 90%, at least 92%, at least 95%, at least 97%, at least 99% identical to a sequence set forth in SEQ ID NO: 56 or 80;
- (iii) a VH comprising a FR1 comprising a sequence set forth in SEQ ID NO: 45, a FR2 comprising a sequence set forth in SEQ ID NO: 46, a FR3 comprising a sequence set forth in SEQ ID NO: 47, and a FR4 comprising a sequence set forth in SEQ ID NO: 48;
- (iv) a VL comprising a FR1 comprising a sequence set forth in SEQ ID NO: 53 or 77, a FR2 comprising a sequence set forth in SEQ ID NO: 54 or 78, a FR3 comprising a sequence set forth in SEQ ID NO: 55 or 79, and a FR4 comprising a sequence set forth in SEQ ID NO: 56 or 80; or
- (v) a VH comprising a FR1 comprising a sequence set forth in SEQ ID NO: 45, a FR2 comprising a sequence set forth in SEQ ID NO: 46, a FR3 comprising a sequence set forth in SEQ ID NO: 47, and a FR4 comprising a sequence set forth in SEQ ID NO: 48; and a VL comprising a FR1 comprising a sequence set forth in SEQ ID NO: 53 or 77, a FR2 comprising a sequence set forth in SEQ ID NO: 54 or 78, a FR3 comprising a sequence set forth in SEQ ID NO: 55 or 79, and a FR4 comprising a sequence set forth in SEQ ID NO: 56 or 80.

In another aspect, the antigen binding site comprises a heavy chain complementarity determining region 1 (CDRH1) according to the sequence set forth in any one of SEQ ID NOs: 87, 101 or 115, a CDRH2 according to the sequence set forth in any one of SEQ ID NOs: 88, 102, 116 or 129 and a CDRH3 according to the sequence set forth in any one of SEQ ID NOs: 89, 103, 117, or 130. In another aspect, the antigen binding site comprises a CDRH1 comprising a sequence at least about 80%, at least 85%, at least 90%, at least 92%, at least 95%, at least 97%, at least 99% identical to the sequence set forth in any one of SEQ ID NOs: 87, 101 or 115, a CDRH2 comprising a sequence at least about 80%, at least 85%, at least 90%, at least 92%, at least 95%, at least 97%, at least 99% identical to a sequence set forth in any one of SEQ ID NOs: 88, 102, 116 or 129; and a CDRH3 comprising a sequence at least about 80%, at least 85%, at least 90%, at least 92%, at least 95%, at least 97%, at least 99% identical to a sequence set forth in any one of SEQ ID NO: 89, 103, 117, or 130.

In any aspect, the antigen binding site comprises a light chain complementarity determining region 1 (CDRL1) according to the sequence set forth in SEQ ID NOs: 131 or 74, a CDRL2 according to the sequence set forth in SEQ ID NOs: 132 or 75 and a CDRL3 according to the sequence set forth in SEQ ID NOs: 133 or 76. In another aspect, the antigen binding site comprises a CDRL1 comprising a sequence at least about 80%, at least 85%, at least 90%, at least 92%, at least 95%, at least 97%, at least 99% identical to the sequence set forth in SEQ ID NOs: 131 or 74, a CDRL2 comprising a sequence at least about 80%, at least 85%, at least 90%, at least 92%, at least 95%, at least 97%, at least 99% identical to a sequence set forth in SEQ ID NOs: 132 or 75 and a CDRL3 comprising a sequence at least about 80%, at least 85%, at least 90%, at least 92%, at least 95%, at least 97%, at least 99% identical to a sequence set forth in SEQ ID NOs: 133 or 76.

The present invention also provides an antigen binding site comprising an antigen binding domain of an antibody, wherein the antigen binding domain binds to or specifically binds to HIV-1, wherein the antigen binding domain comprises at least one of:

(i) a VH comprising a complementarity determining region (CDR) 1 comprising a sequence at least about 80%, at least 85%, at least 90%, at least 92%, at least 95%, at least 97%, at least 99% identical to a sequence set forth in SEQ ID NO: 87, a CDR2 comprising a sequence at least about 80%, at least 85%, at least 90%, at least 92%, at least 95%, at least 97%, at least 99% identical to a sequence set forth in SEQ ID NO: 88 and a CDR3 comprising a sequence at least about 80%, at least 85%, at least 90%, at least 92%, at least 95%, at least 97%, at least 99% identical to a sequence set forth in SEQ ID NO: 89;

(ii) a VH comprising a sequence at least about 95% or 96% or 97% or 98% or 99% identical to a sequence set forth in SEQ ID NO: 15;

(iii) a VL comprising a CDR1 comprising a sequence at least about 80%, at least 85%, at least 90%, at least 92%, at least 95%, at least 97%, at least 99% identical to a sequence set forth in any one of SEQ ID NOs: 131, 74 or 83, a CDR2 comprising a sequence at least about 80%, at least 85%, at least 90%, at least 92%, at least 95%, at least 97%, at least 99% identical to a sequence set forth in any one of SEQ ID NOs: 132, 75 or 84 and a CDR3 comprising a sequence at least about 80%, at least 85%, at least 90%, at least 92%, at least 95%, at least 97%, at least 99% identical to a sequence set forth in any one of SEQ ID NOs: 133, 76 or 85;

(iv) a VL comprising a sequence at least about 95% identical to a sequence set forth in SEQ ID NO: 63 or 73;

(v) a VH comprising a CDR1 comprising a sequence set forth in SEQ ID NO: 87, a CDR2 comprising a sequence set forth in SEQ ID NO: 88 and a CDR3 comprising a sequence set forth in SEQ ID NO: 89;

(vi) a VH comprising a sequence set forth in SEQ ID NO: 15;

(vii) a VL comprising a CDR1 comprising a sequence set forth in any one of of SEQ ID NOs: 131, 74 or 83, a CDR2 comprising a sequence set forth in any one of SEQ ID NOs: 132, 75 or 84 and a CDR3 comprising a sequence set forth in any one of SEQ ID NOs: 133, 76 or 85;

(viii) a VL comprising a sequence set forth in SEQ ID NOs: 63 or 73;

(ix) a VH comprising a CDR1 comprising a sequence set forth in SEQ ID NO: 87, a CDR2 comprising a sequence set forth in SEQ ID NO: 88 and a CDR3 comprising a sequence set forth in SEQ ID NO: 89; and a VL comprising a CDR1 comprising a sequence set forth in any one of SEQ ID NOs: 131, 74 or 83, a CDR2 comprising a sequence set forth in any one of SEQ ID NOs: 132, 75 or 84 and a CDR3 comprising a sequence set forth in any one of SEQ ID NOs: 133, 76 or 85; or (x) a VH comprising a sequence set forth in SEQ ID NO: 15 and a VL comprising a sequence set forth in SEQ ID NO: 63 or 73.

In any aspect of the invention, the antigen binding domain further comprises at least one of:

(i) a VH comprising a framework region (FR) 1 comprising a sequence at least about 80%, at least 85%, at least 90%, at least 92%, at least 95%, at least 97%, at least 99% identical to a sequence set forth in SEQ ID NO: 93, a FR2 comprising a sequence at least about 80%, at least 85%, at least 90%, at least 92%, at least 95%, at least 97%, at least 99% identical to a sequence set forth in SEQ ID NO: 94, a FR3 comprising a sequence at least about 80%, at least 85%, at least 90%, at least 92%, at least 95%, at least 97%, at least 99% identical to a sequence set forth in SEQ ID NO: 95, and a FR4 comprising a sequence at least about 80%, at least 85%, at least 90%, at least 92%, at least 95%, at least 97%, at least 99% identical to a sequence set forth in SEQ ID NO: 96;

(ii) a VL comprising a FR1 comprising a sequence at least about 80%, at least 85%, at least 90%, at least 92%, at least 95%, at least 97%, at least 99% identical to a sequence set forth in SEQ ID NO: 137 or 77, a FR2 comprising a sequence at least about 80%, at least 85%, at least 90%, at least 92%, at least 95%, at least 97%, at least 99% identical to a sequence set forth in SEQ ID NO: 138 or 78, a FR3 comprising a sequence at least about 80%, at least 85%, at least 90%, at least 92%, at least 95%, at least 97%, at least 99% identical to a sequence set forth in SEQ ID NO: 139 or 79, and a FR4 comprising a sequence at least about 80%, at least 85%, at least 90%, at least 92%, at least 95%, at least 97%, at least 99% identical to a sequence set forth in SEQ ID NO: 140 or 80;

(iii) a VH comprising a FR1 comprising a sequence set forth in SEQ ID NO: 93, a FR2 comprising a sequence set forth in SEQ ID NO: 94, a FR3 comprising a sequence set forth in SEQ ID NO: 95, and a FR4 comprising a sequence set forth in SEQ ID NO: 96;

(iv) a VL comprising a FR1 comprising a sequence set forth in SEQ ID NO: 137 or 77, a FR2 comprising a sequence set forth in SEQ ID NO: 138 or 78, a FR3 comprising a sequence set forth in SEQ ID NO: 139 or 79, and a FR4 comprising a sequence set forth in SEQ ID NO: 140 or 80; or (v) a VH comprising a FR1 comprising a sequence set forth in SEQ ID NO: 93, a FR2 comprising a sequence set forth in SEQ ID NO: 94, a FR3 comprising a sequence set forth in SEQ ID NO: 95, and a FR4 comprising a sequence set forth in SEQ ID NO: 96; and a VL comprising a FR1 comprising a sequence set forth in SEQ ID NO: 137 or 77, a FR2 comprising a sequence set forth in SEQ ID NO: 138 or 78, a FR3 comprising a sequence set forth in SEQ ID NO: 139 or 79, and a FR4 comprising a sequence set forth in SEQ ID NO: 140 or 80.

The present invention also provides an antigen binding site comprising an antigen binding domain of an antibody, wherein the antigen binding domain binds to or specifically binds to human immunodeficiency virus type 1 (HIV-1), wherein the antigen binding domain comprises at least one of:

(i) a VH comprising a complementarity determining region 1 (CDRH1) comprising a sequence at least about 80%, at least 85%, at least 90%, at least 92%, at least 95%, at least 97%, at least 99% identical to a sequence set forth in SEQ ID NO: 101, a CDRH2 comprising a sequence at least about 80%, at least 85%, at least 90%, at least 92%, at least 95%, at least 97%, at least 99% identical to a sequence set forth in SEQ ID NO: 102 and a CDRH3 comprising a sequence at least about 80%, at least 85%, at least 90%, at least 92%, at least 95%, at least 97%, at least 99% identical to a sequence set forth in SEQ ID NO: 103;

(ii) a VH comprising a sequence at least about 95% or 96% or 97% or 98% or 99% identical to a sequence set forth in SEQ ID NO: 31;

(iii) a VL comprising a CDR1 comprising a sequence at least about 80%, at least 85%, at least 90%, at least 92%, at least 95%, at least 97%, at least 99% identical to a sequence set forth in SEQ ID NO: 131, 74 or 83, a CDR2 comprising a sequence at least about 80%, at least 85%, at least 90%, at least 92%, at least 95%, at least 97%, at least 99% identical to a sequence set forth in SEQ ID NO: 132, 75 or 84 and a CDR3 comprising a sequence at least about 80%, at least 85%, at least 90%, at least 92%, at least 95%, at least 97%, at least 99% identical to a sequence set forth in SEQ ID NO: 133, 76 or 85;

(iv) a VL comprising a sequence at least about 95% identical to a sequence set forth in SEQ ID NO: 63 or 73;

(v) a VH comprising a CDR1 comprising a sequence set forth in SEQ ID NO: 101, a CDR2 comprising a sequence set forth in SEQ ID NO: 102 and a CDR3 comprising a sequence set forth in SEQ ID NO: 103;

(vi) a VH comprising a sequence set forth in SEQ ID NO: 31;

(vii) a VL comprising a CDR1 comprising a sequence set forth in any one of SEQ ID NOs: 131, 74 or 83, a CDR2 comprising a sequence set forth in any one of SEQ ID NOs: 132, 75 or 84 and a CDR3 comprising a sequence set forth in any one of SEQ ID NOs: 133, 76 or 85;

(viii) a VL comprising a sequence set forth in SEQ ID NOs: 63 or 73;

(ix) a VH comprising a CDR1 comprising a sequence set forth in SEQ ID NO: 101, a CDR2 comprising a sequence set forth in SEQ ID NO: 102 and a CDR3 comprising a sequence set forth in SEQ ID NO: 103; and a VL comprising a CDR1 comprising a sequence set forth in any one of SEQ ID NOs: 131, 74 or 83, a CDR2 comprising a sequence set forth in any one of SEQ ID NOs: 132, 75 or 84 and a CDR3 comprising a sequence set forth in any one of SEQ ID NOs: 133, 75 or 85; or (x) a VH comprising a sequence set forth in SEQ ID NO: 31 and a VL comprising a sequence set forth in SEQ ID NO: 63 or 73.

In any aspect of the invention, the antigen binding domain further comprises at least one of:

(i) a VH comprising a framework region (FR) 1 comprising a sequence at least about 80%, at least 85%, at least 90%, at least 92%, at least 95%, at least 97%, at least 99% identical to a sequence set forth in SEQ ID NO: 107, a FR2 comprising a sequence at least about 80%, at least 85%, at least 90%, at least 92%, at least 95%, at least 97%, at least 99% identical to a sequence set forth in SEQ ID NO: 108, a FR3 comprising a sequence at least about 80%, at least 85%, at least 90%, at least 92%, at least 95%, at least 97%, at least 99% identical to a sequence set forth in SEQ ID NO: 109, and a FR4 comprising a sequence at least about 80%, at least 85%, at least 90%, at least 92%, at least 95%, at least 97%, at least 99% identical to a sequence set forth in SEQ ID NO: 110;

(ii) a VL comprising a FR1 comprising a sequence at least about 80%, at least 85%, at least 90%, at least 92%, at least 95%, at least 97%, at least 99% identical to a sequence set forth in SEQ ID NO: 137 or 77, a FR2 comprising a sequence at least about 80%, at least 85%, at least 90%, at least 92%, at least 95%, at least 97%, at least 99% identical to a sequence set forth in SEQ ID NO: 138 or 78, a FR3 comprising a sequence at least about 80%, at least 85%, at least 90%, at least 92%, at least 95%, at least 97%, at least 99% identical to a sequence set forth in SEQ ID NO: 139 or 79, and a FR4 comprising a sequence at least about 80%, at least 85%, at least 90%, at least 92%, at least 95%, at least 97%, at least 99% identical to a sequence set forth in SEQ ID NO: 140 or 80;

(iii) a VH comprising a FR1 comprising a sequence set forth in SEQ ID NO: 107, a FR2 comprising a sequence set forth in SEQ ID NO: 108, a FR3 comprising a sequence set forth in SEQ ID NO: 109, and a FR4 comprising a sequence set forth in SEQ ID NO: 110;

(iv) a VL comprising a FR1 comprising a sequence set forth in SEQ ID NO: 137 or 77, a FR2 comprising a sequence set forth in SEQ ID NO: 138 or 78, a FR3 comprising a sequence set forth in SEQ ID NO: 139 or 79, and a FR4 comprising a sequence set forth in SEQ ID NO: 140 or 80; or (v) a VH comprising a FR1 comprising a sequence set forth in SEQ ID NO: 107, a FR2 comprising a sequence set forth in SEQ ID NO: 108, a FR3 comprising a sequence set forth in SEQ ID NO: 109, and a FR4 comprising a sequence set forth in SEQ ID NO: 110; and a VL comprising a FR1 comprising a sequence set forth in SEQ ID NO: 137 or 77, a FR2 comprising a sequence set forth in SEQ ID NO: 138 or 78, a FR3 comprising a sequence set forth in SEQ ID NO: 139 or 79, and a FR4 comprising a sequence set forth in SEQ ID NO: 140 or 80.

The present invention also provides an antigen binding site comprising an antigen binding domain of an antibody, wherein the antigen binding domain binds to or specifically binds to human immunodeficiency virus type 1 (HIV-1), wherein the antigen binding domain comprises at least one of:

(i) a VH comprising a complementarity determining region (CDR) 1 comprising a sequence at least about 80%, at least 85%, at least 90%, at least 92%, at least 95%, at least 97%, at least 99% identical to a sequence set forth in SEQ ID NO: 115, a CDR2 comprising a sequence at least about 80%, at least 85%, at least 90%, at least 92%, at least 95%, at least 97%, at least 99% identical to a sequence set forth in SEQ ID NO: 116 and a CDR3 comprising a sequence at least about 80%, at least 85%, at least 90%, at least 92%, at least 95%, at least 97%, at least 99% identical to a sequence set forth in SEQ ID NO: 117;

(ii) a VH comprising a sequence at least about 95% or 96% or 97% or 98% or 99% identical to a sequence set forth in SEQ ID NO: 61;

(iii) a VL comprising a CDR1 comprising a sequence at least about 80%, at least 85%, at least 90%, at least 92%, at least 95%, at least 97%, at least 99% identical to a sequence set forth in any one of SEQ ID NOs: 131, 74 or 83, a CDR2 comprising a sequence at least about 80%, at least 85%, at least 90%, at least 92%, at least 95%, at least 97%, at least 99% identical to a sequence set forth in any one of SEQ ID NOs: 132, 75 or 84 and a CDR3 comprising a sequence at least about 80%, at least 85%, at least 90%, at least 92%, at least 95%, at least 97%, at least 99% identical to a sequence set forth in any one of SEQ ID NOs: 133, 76 or 85;

(iv) a VL comprising a sequence at least about 95% identical to a sequence set forth in SEQ ID NO: 63 or 73;

(v) a VH comprising a CDR1 comprising a sequence set forth in SEQ ID NO: 115, a CDR2 comprising a sequence set forth in SEQ ID NO: 116 and a CDR3 comprising a sequence set forth in SEQ ID NO: 117;

(vi) a VH comprising a sequence set forth in SEQ ID NO: 61;

(vii) a VL comprising a CDR1 comprising a sequence set forth in any one of SEQ ID NOs: 131, 74 or 83, a CDR2 comprising a sequence set forth in any one of SEQ ID NOs: 132, 75 or 84 and a CDR3 comprising a sequence set forth in any one of SEQ ID NOs: 133, 76 or 85;

(viii) a VL comprising a sequence set forth in SEQ ID NO: 63 or 73;

(ix) a VH comprising a CDR1 comprising a sequence set forth in SEQ ID NO: 115, a CDR2 comprising a sequence set forth in SEQ ID NO: 116 and a CDR3 comprising a sequence set forth in SEQ ID NO: 117; and a VL comprising a CDR1 comprising a sequence set forth in any one of SEQ ID NOs: 131, 74 or 83, a CDR2 comprising a sequence set forth in any one of SEQ ID NOs: 132, 74 or 84 and a CDR3 comprising a sequence set forth in any one of SEQ ID NOs: 133, 75 or 85; or (x) a VH comprising a sequence set forth in SEQ ID NO: 61 and a VL comprising a sequence set forth in SEQ ID NO: 63 or 73.

In any aspect of the invention, the antigen binding domain further comprises at least one of:

(i) a VH comprising a framework region (FR) 1 comprising a sequence at least about 80%, at least 85%, at least 90%, at least 92%, at least 95%, at least 97%, at least 99% identical to a sequence set forth in SEQ ID NO: 121, a FR2 comprising a sequence at least about 80%, at least 85%, at least 90%, at least 92%, at least 95%, at least 97%, at least 99% identical to a sequence set forth in in SEQ ID NO: 122, a FR3 comprising a sequence at least about 80%, at least 85%, at least 90%, at least 92%, at least 95%, at least 97%, at least 99% identical to a sequence set forth in SEQ ID NO: 123, and a FR4 comprising a sequence at least about 80%, at least 85%, at least 90%, at least 92%, at least 95%, at least 97%, at least 99% identical to a sequence set forth in SEQ ID NO: 124;

(ii) a VL comprising a FR1 comprising a sequence at least about 80%, at least 85%, at least 90%, at least 92%, at least 95%, at least 97%, at least 99% identical to a sequence set forth in SEQ ID NO: 137 or 77, a FR2 comprising a sequence at least about 80%, at least 85%, at least 90%, at least 92%, at least 95%, at least 97%, at least 99% identical to a sequence set forth in SEQ ID NO: 138 or 78, a FR3 comprising a sequence at least about 80%, at least 85%, at least 90%, at least 92%, at least 95%, at least 97%, at least 99% identical to a sequence set forth in SEQ ID NO: 139 or 79, and a FR4 comprising a sequence at least about 80%, at least 85%, at least 90%, at least 92%, at least 95%, at least 97%, at least 99% identical to a sequence set forth in SEQ ID NO: 140 or 80;

(iii) a VH comprising a FR1 comprising a sequence set forth in SEQ ID NO: 121, a FR2 comprising a sequence set forth in SEQ ID NO: 122, a FR3 comprising a sequence set forth in SEQ ID NO: 123, and a FR4 comprising a sequence set forth in SEQ ID NO: 124;

(iv) a VL comprising a FR1 comprising a sequence set forth in SEQ ID NO: 137 or 77, a FR2 comprising a sequence set forth in SEQ ID NO: 138 or 78, a FR3 comprising a sequence set forth in SEQ ID NO: 139 or 79, and a FR4 comprising a sequence set forth in SEQ ID NO: 140 or 80; or (v) a VH comprising a FR1 comprising a sequence set forth in SEQ ID NO: 121, a FR2 comprising a sequence set forth in SEQ ID NO: 122, a FR3 comprising a sequence set forth in SEQ ID NO: 123, and a FR4 comprising a sequence set forth in SEQ ID NO: 124; and a VL comprising a FR1 comprising a sequence set forth in SEQ ID NO: 137 or 77, a FR2 comprising a sequence set forth in SEQ ID NO: 138 or 78, a FR3 comprising a sequence set forth in SEQ ID NO: 139 or 79, and a FR4 comprising a sequence set forth in SEQ ID NO: 140 or 80.

As described herein, the antigen binding site may be in the form of:

(i) a single domain antibody (sdAb);

(ii) a single chain Fv fragment (scFv);

(iii) a dimeric scFv (di-scFv);

(iv) one of (ii) or (iii) linked to a constant region of an antibody, Fc or a heavy chain constant domain (CH) 2 and/or CH3;

(v) one of (i) to (iv) linked to a protein that binds to an immune effector cell;

(vi) one of (i) to (iv) linked to a modified immune cell receptor, such as a modified T cell receptor; or (vii) one of (i) to (iv) in the context of a chimeric antigen receptor (CAR) or variant T cell receptor.

Further, as described herein, the antigen binding site may be in the form of:

(i) a diabody;

(ii) a triabody;

(iii) a tetrabody;

(iv) a Fab;

(v) a F(ab')2;

(vi) a Fv;

(vii) a bispecific antibody or other form of multispecific antibody;

(viii) one of (i) to (vii) linked to a constant region of an antibody, Fc or a heavy chain constant domain (CH) 2 and/or CH3; or (ix) one of (i) to (vii) linked to a protein that binds to an immune effector cell.

(x) one of (i) to (vii) linked to a protein that binds to an immune effector cell;

(xi) one of (i) to (vii) linked to a modified immune cell receptor, such as a modified T cell receptor; or (xiii) one of (i) to (vii) in the context of a chimeric antigen receptor (CAR) or variant T cell receptor.

The foregoing antigen binding sites can also be referred to as antigen binding domains of antibodies. Further still, in any embodiment or aspect described herein, the term "antigen binding site" may be used interchangeably with the term "antigen binding protein". Accordingly, it will be understood that the present invention relates to antigen binding proteins, or antigen binding fragments thereof, having the defined features and sequences described herein.

In any aspect of the invention, an antigen binding site as described herein is an antibody or antigen binding fragment thereof. Preferably, the antigen binding site is an antibody, preferably a monoclonal antibody.

As used herein the antigen binding site may be a variable domain.

The present invention also provides a human immunodeficiency virus type 1 (HIV-1) antibody comprising a light chain variable region and a heavy chain variable region, wherein said light chain variable region comprises:

a CDR L1 as set forth in any one of SEQ ID NOs: 39, 74 or 83, a CDR L2 as set forth in any one of SEQ ID NOs: 40, 75 or 84 and a CDR L3 as set forth in any one of SEQ ID NOs: 41, 76 or 85; and wherein said heavy chain variable region comprises:

a CDR H1 as set forth in SEQ ID NO:1, a CDR H2 as set forth in SEQ ID NO: 2, and a CDR H3 as set forth in SEQ ID NO: 3.

In any aspect of the invention, the HIV-1 antibody comprises a light chain variable region that comprises the sequence of SEQ ID NO: 63 or 73.

In any aspect of the invention, a HIV-1 antibody comprises a heavy chain variable region that comprises the sequence of SEQ ID NO: 15.

In any aspect of the invention, a HIV-1 antibody comprises a light chain variable region that comprises a FR L1 as set forth in SEQ ID NO: 53 or 77, FR L2 as set forth in SEQ ID NO: 54 or 78, a FR L3 as set forth in SEQ ID NO: 55 or 79 and a FR L4 as set forth in SEQ ID NO: 56 or 80.

In any aspect of the invention, a HIV-1 antibody comprises a heavy chain variable region that comprises a FR H1 as set forth in SEQ ID NO: 7, FR H2 as set forth in SEQ ID NO: 8, a FR H3 as set forth in SEQ ID NO:9 and a FR H4 as set forth in SEQ ID NO: 10.

The present invention also provides a human immunodeficiency virus type 1 (HIV-1) antibody comprising a light chain variable region and a heavy chain variable region, wherein said light chain variable region comprises:

a CDR L1 as set forth in any one of SEQ ID NOs: 39, 74 or 83, a CDR L2 as set forth in any one of SEQ ID NOs: 40, 75 or 84 and a CDR L3 as set forth in any one of SEQ ID NOs: 41, 76 or 85; and wherein said heavy chain variable region comprises:

a CDR H1 as set forth in SEQ ID NO: 17, a CDR H2 as set forth in SEQ ID NO: 18, and a CDR H3 as set forth in SEQ ID NO: 19.

In any aspect of the invention, a HIV-1 antibody comprises a light chain variable region that comprises the sequence of SEQ ID NO: 63 or 73.

In any aspect of the invention, a HIV-1 antibody comprises a heavy chain variable region that comprises the sequence of SEQ ID NO: 31.

In any aspect of the invention, a HIV-1 antibody comprises a light chain variable region that comprises a FR L1 as set forth in SEQ ID NO: 53 or 77, FR L2 as set forth in SEQ ID NO: 54 or 78, a FR L3 as set forth in SEQ ID NO: 55 or 79 and a FR L4 as set forth in SEQ ID NO: 56 or 80.

In any aspect of the invention, a HIV-1 antibody comprises a heavy chain variable region that comprises a FR H1 as set forth in SEQ ID NO: 23, FR H2 as set forth in SEQ ID NO: 24, a FR H3 as set forth in SEQ ID NO: 25 and a FR H4 as set forth in SEQ ID NO: 26.

The present invention also provides a human immunodeficiency virus type 1 (HIV-1) antibody comprising a light chain variable region and a heavy chain variable region, wherein said light chain variable region comprises:

a CDR L1 as set forth in any one of SEQ ID NOs: 39, 74 or 83, a CDR L2 as set forth in any one of SEQ ID NOs: 40, 75 or 84 and a CDR L3 as set forth in any one of SEQ ID NOs: 41, 76 or 85; and wherein said heavy chain variable region comprises:

a CDR H1 as set forth in SEQ ID NO: 33, a CDR H2 as set forth in SEQ ID NO: 34, and a CDR H3 as set forth in SEQ ID NO: 35.

In any aspect of the invention, a HIV-1 antibody comprises a light chain variable region that comprises the sequence of SEQ ID NO: 63 or 73.

In any aspect of the invention, a HIV-1 antibody comprises a heavy chain variable region that comprises the sequence of SEQ ID NO: 61.

In any aspect of the invention, a HIV-1 antibody comprises a light chain variable region that comprises a FR L1 as set forth in SEQ ID NO: 53 or 77, FR L2 as set forth in SEQ ID NO: 54 or 78, a FR L3 as set forth in SEQ ID NO: 55 or 79 and a FR L4 as set forth in SEQ ID NO: 56 or 80.

In any aspect of the invention, a HIV-1 antibody comprises a heavy chain variable region that comprises a FR H1 as set forth in SEQ ID NO: 45, FR H2 as set forth in SEQ ID NO: 46, a FR H3 as set forth in SEQ ID NO: 47 and a FR H4 as set forth in SEQ ID NO: 48.

The present invention also provides a human immunodeficiency virus type 1 (HIV-1) antibody comprising a light chain variable region and a heavy chain variable region, wherein said light chain variable region comprises:

a CDR L1 as set forth in any one of SEQ ID NOs: 131, 74 or 83, a CDR L2 as set forth in any one of SEQ ID NOs: 132, 75 or 84 and a CDR L3 as set forth in any one of SEQ ID NOs: 133, 76 or 85; and wherein said heavy chain variable region comprises:

a CDR H1 as set forth in SEQ ID NO: 87, a CDR H2 as set forth in SEQ ID NO: 88, and a CDR H3 as set forth in SEQ ID NO: 89.

In any aspect of the invention, a HIV-1 antibody comprises a light chain variable region that comprises a FR L1 as set forth in SEQ ID NO: 137 or 77, FR L2 as set forth in SEQ ID NO: 138 or 78, a FR L3 as set forth in SEQ ID NO: 139 or 79 and a FR L4 as set forth in SEQ ID NO: 14 or 80.

In any aspect of the invention, a HIV-1 antibody comprises a heavy chain variable region that comprises a FR H1 as set forth in SEQ ID NO: 93, FR H2 as set forth in SEQ ID NO: 94, a FR H3 as set forth in SEQ ID NO: 95 and a FR H4 as set forth in SEQ ID NO: 96.

The present invention also provides a human immunodeficiency virus type 1 (HIV-1) antibody comprising a light chain variable region and a heavy chain variable region, wherein said light chain variable region comprises:

a CDR L1 as set forth in any one of SEQ ID NOs: 131, 74 or 83, a CDR L2 as set forth in any one of SEQ ID NOs: 132, 75 or 84 and a CDR L3 as set forth in any one of SEQ ID NOs: 133, 76 or 85; and wherein said heavy chain variable region comprises:

a CDR H1 as set forth in SEQ ID NO: 101, a CDR H2 as set forth in SEQ ID NO: 102, and a CDR H3 as set forth in SEQ ID NO: 103.

In any aspect of the invention, a HIV-1 antibody comprises a light chain variable region that comprises a FR L1 as set forth in SEQ ID NO: 137 or 77, FR L2 as set forth in SEQ ID NO: 138 or 78, a FR L3 as set forth in SEQ ID NO: 139 or 79 and a FR L4 as set forth in SEQ ID NO: 140 or 80.

In any aspect of the invention, a HIV-1 antibody comprises a heavy chain variable region that comprises a FR H1 as set forth in SEQ ID NO: 107, FR H2 as set forth in SEQ ID NO: 108, a FR H3 as set forth in SEQ ID NO: 109 and a FR H4 as set forth in SEQ ID NO: 110.

The present invention also provides a human immunodeficiency virus type 1 (HIV-1) antibody comprising a light chain variable region and a heavy chain variable region, wherein said light chain variable region comprises:

a CDR L1 as set forth in any one of SEQ ID NOs: 131, 74 or 83, a CDR L2 as set forth in any one of SEQ ID NOs: 132, 75 or 84 and a CDR L3 as set forth in any one of SEQ ID NOs: 133, 76 or 85; and wherein said heavy chain variable region comprises:

a CDR H1 as set forth in SEQ ID NO: 115, a CDR H2 as set forth in SEQ ID NO: 116, and a CDR H3 as set forth in SEQ ID NO: 117.

In any aspect of the invention, a HIV-1 antibody comprises a light chain variable region that comprises a FR L1 as set forth in SEQ ID NO: 137 or 77, FR L2 as set forth in SEQ ID NO: 138 or 78, a FR L3 as set forth in SEQ ID NO: 139 or 79 and a FR L4 as set forth in SEQ ID NO: 140 or 80.

In any aspect of the invention, a HIV-1 antibody comprises a heavy chain variable region that comprises a FR H1 as set forth in SEQ ID NO: 121, FR H2 as set forth in SEQ ID NO: 122, a FR H3 as set forth in SEQ ID NO: 123 and a FR H4 as set forth in SEQ ID NO: 124.

In any aspect or embodiment, the antibody is a naked antibody. Specifically, the antibody is in a non-conjugated form and is not adapted to form a conjugate.

Reference herein to a protein or antibody that "binds to" human immunodeficiency virus type 1 (HIV-1) provides literal support for a protein or antibody that "binds specifically to" or "specifically binds to" HIV-1.

The present invention also provides antigen binding domains or antigen binding fragments of the foregoing antibodies.

The invention also provides a fusion protein comprising an antigen binding site, immunoglobulin variable domain, antibody, dab (single domain antibody), di-scFv, scFv, Fab, Fab', F(ab')2, Fv fragment, diabody, triabody, tetrabody, linear antibody, single-chain antibody molecule, or multi-specific antibody as described herein.

The invention also provides a conjugate in the form of an antigen binding site, immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody or fusion protein as described herein conjugated to a label or a cytotoxic agent.

The invention also provides an antibody for binding to an antigen binding site, immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody, fusion protein, or conjugate as described herein.

The invention also provides a nucleic acid encoding an antigen binding site, immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody, fusion protein or conjugate as described herein. In any embodiment, the nucleic acid comprises the nucleotide sequences of any of the complementarity determining regions as described in Table 1 below (e.g. CDRH1, CDRH2, CDRH3, CDRL1, CDRL2, and/or CDRL3). Preferably, the nucleic acid further comprises the nucleotide sequences of any of the framework regions as described in Table 1 below (e.g. FRH1, FRH2, FRH3, FRH4, FRL1, FRL2, FRL3 and/or FRL4), including amino acid variation at particular residues which can be determined by aligning the various framework regions derived from each antibody.

In one example, such a nucleic acid is included in an expression construct in which the nucleic acid is operably linked to a promoter. Such an expression construct can be in a vector, e.g., a plasmid.

In examples of the invention directed to single polypeptide chain antigen binding sites, the expression construct may comprise a promoter linked to a nucleic acid encoding that polypeptide chain.

In examples directed to multiple polypeptide chains that form an antigen binding site, an expression construct comprises a nucleic acid encoding a polypeptide comprising, e.g., a VH operably linked to a promoter and a nucleic acid encoding a polypeptide comprising, e.g., a VL operably linked to a promoter.

In another example, the expression construct is a bicistronic expression construct, e.g., comprising the following operably linked components in 5' to 3' order:

(i) a promoter;

(ii) a nucleic acid encoding a first polypeptide;

(iii) an internal ribosome entry site; and (iv) a nucleic acid encoding a second polypeptide, wherein the first polypeptide comprises a VH and the second polypeptide comprises a VL, or vice versa.

The present invention also contemplates separate expression constructs one of which encodes a first polypeptide comprising a VH and another of which encodes a second polypeptide comprising a VL. For example, the present invention also provides a composition comprising:

(i) a first expression construct comprising a nucleic acid encoding a polypeptide comprising a VH operably linked to a promoter; and (ii) a second expression construct comprising a nucleic acid encoding a polypeptide comprising a VL operably linked to a promoter.

The invention provides a cell comprising a vector or nucleic acid described herein. Preferably, the cell is isolated, substantially purified or recombinant. In one example, the cell comprises the expression construct of the invention or:

(i) a first expression construct comprising a nucleic acid encoding a polypeptide comprising a VH operably linked to a promoter; and (ii) a second expression construct comprising a nucleic acid encoding a polypeptide comprising a VL operably linked to a promoter, wherein the first and second polypeptides associate to form an antigen binding site of the present invention.

Examples of cells of the present invention include bacterial cells, yeast cells, insect cells or mammalian cells including human cells.

The invention also provides a pharmaceutical composition comprising an antigen binding site, or comprising a CDR and/or FR sequence as described herein, or an immunoglobulin variable domain, antibody, dab (single domain antibody), di-scFv, scFv, Fab, Fab', F(ab')2, Fv fragment, diabody, triabody, tetrabody, linear antibody, single-chain antibody molecule, or multispecific antibody, fusion protein, or conjugate as described herein and a pharmaceutically acceptable carrier, diluent or excipient.

The invention also provides a diagnostic composition comprising an antigen binding site, or comprising a CDR and/or FR sequence as described herein, or antigen binding site, immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody, fusion protein or conjugate as described herein, a diluent and optionally a label.

The invention also provides a kit or article of manufacture comprising an antigen binding site, or comprising a CDR and/or FR sequence as described herein or an immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody, fusion protein or conjugate as described herein.

An antigen binding site, a protein or antibody as described herein preferably comprises a human constant region, e.g., an IgG constant region, such as an IgG1, IgG2, IgG3 or IgG4 constant region or mixtures thereof, preferably an IgG1 constant region. In the case of an antibody or protein comprising a VH and a VL, the VH can be linked to a human heavy chain constant region and the VL can be linked to a human light chain constant region.

In order to determine the CDR and FR boundaries of an antibody described herein, the methodology described in Stanfield, Wilson and Smider was followed (Stanfield, Wilson and Smider *Sci Immunol.* (2016) July; 1(1): aaf7962). A skilled person would understand how to identify the CDR and FR boundaries of an antibody described herein using alternative methods.

The functional characteristics of an antigen binding site of the invention will be taken to apply mutatis mutandis to an antigen binding domain or antibody of the invention.

An antigen binding site as described herein may be purified, substantially purified, isolated and/or recombinant.

An antigen binding site of the invention may be part of a supernatant taken from media in which a hybridoma expressing an antigen binding site of the invention has been grown.

In another aspect, there is provided an epitope which binds to any antigen binding site as described herein. In an aspect, the epitope is located within the CD4 binding site (CD4bs) of the C3 domain of gp120, the β23 domain of the C4 gp120 protein and/or β24-α5 connection of the C5 domain of gp120. In another aspect, the epitope comprises residues 366, 371, 457 and 471 of gp120. In yet another aspect, the epitope comprises residues 366 and 471, preferably residue 471 of gp120.

In any aspect of the invention, any antigen binding sites as described herein have substantially no polyreactivity or autoreactivity to self-antigens. In a further aspect, any of the antigen binding sites described herein show substantially no polyreactivity or autoreactivity to human self-antigens including one or more of U1-RNP, snRNP/Sm, Sm, SS_A, SS-B, Scl-70, CenpB and Jo-1.

In an aspect of the invention, any antigen binding site described herein is capable of neutralising HIV-1 with a potency of at least 30 fold, 40 fold, 50 fold or higher than an antibody comprising VH and VL according to SEQ ID NO:70 and 71. In another aspect, any antigen binding site described herein is capable of neutralising HIV-1 with a potency of at least 10 fold or higher than an antibody comprising VH and VL according to SEQ ID NO:72 and 73.

In another aspect, any antigen binding site described herein is capable of neutralising HIV-1 species of at least one clade, two, three, four, five, six, seven or more clades. In another aspect, any antigen binding site described herein is capable of neutralising HIV-1 species belonging to one or more of the clades A, B, C, AC, G, CRF07_BC or CFR01_AE.

In another aspect, any antigen binding site described herein is capable of neutralising one or more HIV-1 species belonging to clade B selected from the list consisting of MN, 6535, HXB-2, QH0692, pREJO4541, pRHPA4259, AD8, JRCSF, YU-2, ZM53M.PB12, X2278 and TRO11.

In another aspect, any antigen binding site described herein is capable of neutralising one or more HIV-1 species belonging to clade A including BG505 and 398F1.

In another aspect, any antigen binding site described herein is capable of neutralising one or more HIV-1 species belonging to clade C including Du156, ZM135M.PL10a, CAP210.200.E8, CAP45.2.00.G3, 25710, CE1176 and CEO217, preferably 25710, CE1176 and CEO217.

In another aspect, any antigen binding site described herein is capable of neutralising one or more HIV-1 species belonging to clade G including X1632.

In another aspect, any antigen binding site described herein is capable of neutralising one or more HIV-1 species belonging to clade CRF01_AE including CNE8 and CNE55, preferably CNE55.

In another aspect, the antigen binding site binds to or specifically binds to an invariant antigen of any of the HIV-1 strains described herein or known in the art.

In a preferred aspect, any antigen binding site described herein is capable of neutralising at least 60%, at least 65% or at least 70% of the above-mentioned HIV-1 species.

In another aspect of the invention, there is provided a method of producing any antigen binding site described herein comprising one or more steps as outlined in the Examples herein. In one aspect, the method comprises a step of expressing a nucleic acid encoding an antigen binding site or antibody described herein under conditions suitable for expression of the antigen binding site or antibody.

In any aspect of the invention, there is provided a method for treating, preventing or inhibiting a human immunodeficiency virus type-1 (HIV-1) infection in a subject in need thereof, comprising administering an effective amount of any antigen binding site described herein to a subject, thereby treating, preventing or inhibiting a HIV-1 infection in the subject in need thereof.

In another aspect, the invention provides a method for neutralising a human immunodeficiency virus type-1 (HIV-1) infection in a subject in need thereof, comprising administering an effective amount of any antigen binding site described herein to a subject, thereby neutralising a HIV-1 infection in the subject in need thereof.

In any aspect, the method may further comprise the identification of a subject having a HIV-1 infection. The presence of a HIV-1 infection may be determined by any known means in the art including detectable HIV-1 viral load in blood, sputum and/or urine or detectable antibodies produced by the subject in response to HIV-1 infection. In an aspect, a subject having a HIV-1 infection may also present with one or more symptoms including headache, fever, tiredness, swollen lymph nodes, sore throat, thrush, rash, muscle and joint pain, ulcers in mouth, night sweats and/or diarrhoea, breathing difficulty, coughing, weight loss, nausea, white spots in the mouth, genital sores, fatigue, pneumonia and cognitive decline.

In any aspect, an antigen binding site described herein is capable of reducing one or more symptoms associated with HIV-1 infection known in the art or described herein.

In an aspect, the subject may be receiving treatment for a HIV-1 infection including nucleoside reverse transcriptase inhibitors (NRTIs) such as abacavir, emtricitabine, lamivudine, tenofovir disoproxil fumarate, zidovudine; non-nucleoside reverse transcriptase inhibitors (NNRTIs) such as doravirine, efavirenz, etravirine, nevirapine or rilpivirine; protease inhibitors including atazanavir, darunavir, fosamprenavir, ritonavir, saquinavir or tipranavir; fusion inhibitors such as enfuvirtide; CCR5 antagonists including maraviroc, integrase inhibitors such as dolutegravir and raltegravir; post-attachment inhibitors including ibalixumab-uiyk, pharmacokinetic enhancers such as cobicistat and combination therapies thereof or combination HIV medicines known in the art. In this aspect, the antigen binding site and the treatment may be delivered sequentially or concurrently.

In any aspect of the invention, an antigen binding site described herein may be delivered topically, orally, intravenously, intramuscularly or cutaneously. In another aspect, the antigen binding site may be administered once, twice, three times, four times, five times, six times or more.

In any aspect, the invention provides a method for increasing survival of a subject comprising administering an effective amount of any antigen binding site described herein to a subject, thereby for increasing survival in the subject in need thereof.

In an aspect of the invention, there is provided use of an effective amount of any antigen binding site described herein in the preparation of a medicament for treating, preventing or inhibiting a human immunodeficiency virus type-1 (HIV-1) infection in a subject.

In a further aspect, there is provided use of an effective amount any antigen binding site described herein in the preparation of a medicament for:

- neutralising a human immunodeficiency virus type-1 (HIV-1) infection in a subject; and/or
- increasing survival of a subject having a HIV-1 infection.

In an aspect of the invention, there is provided use of an effective amount of any antigen binding site described herein for treating, preventing or inhibiting a human immunodeficiency virus type-1 (HIV-1) infection in a subject.

In another aspect, there is provided an effective amount of any antigen binding site described herein for use in treating, preventing or inhibiting a human immunodeficiency virus type-1 (HIV-1) infection in a subject.

In any aspect of the invention, there is provided a composition comprising any antigen binding site described herein, and a pharmaceutically acceptable carrier, diluent or excipient.

In any aspect of the invention, the amount of any antigen binding site described herein may be administered at a dose in the range of about 0.1 to about 100 μg, about 0.1 to about 250 μg, about 0.1 to about 500 μg, about 0.1 to about 750 μg, about 0.1 to about 1000 μg, about 0.1 to about 0.25 mg, about 0.1 to about 0.5 mg, about 0.1 to about 0.75 mg, about 0.1 to about 1.0 mg, about 0.1 to about 1.25 mg or about 0.1 to about 1.5 mg, about 0.1 to about 10 mg, about 0.1 to about 50 mg, about 0.1 to about 100 mg, about 0.1 to about 150 mg, about 0.1 to about 200 mg, about 0.1 to about 250 mg, about 0.1 to about 300 mg, about 0.1 to about 350 mg, about 0.1 to about 400 mg, about 0.1 to about 450 mg, about 0.1 to about 500 mg, about 0.1 to about 550 mg, about 0.1 to about 600 mg, about 0.1 to about 650 mg, about 0.1 to about 700 mg, about 0.1 to about 750 mg, about 0.1 to about 800 mg, about 0.1 to about 850 mg, about 0.1 to about 900 mg, about 0.1 to about 950 mg, about 0.1 to about 1000 mg.

The invention also provides a cell comprising a vector or nucleic acid molecule described herein.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE DRAWINGS

FIG. 7. Bovine BrNAbs bind to different forms of HIV Env. Bovine BrNAbs were tested in direct ELISA assays to evaluate their binding to different forms of Env (monomeric gp120, uncleaved gp140 and SOSIP gp140) as well as ConM SOSIP which is an Env trimer based on a consensus sequence of all HIV-1 group M isolates. Tabulated $EC_{50}$ values are provided for each tested antibody in μg/ml. Data representative of two repeat assays.

FIG. 13. Neutralization activity of bovine BrNAbs against CD4bs mutations in cross-clade HIV viruses.

DETAILED DESCRIPTION OF THE EMBODIMENTS

Figure 1A:
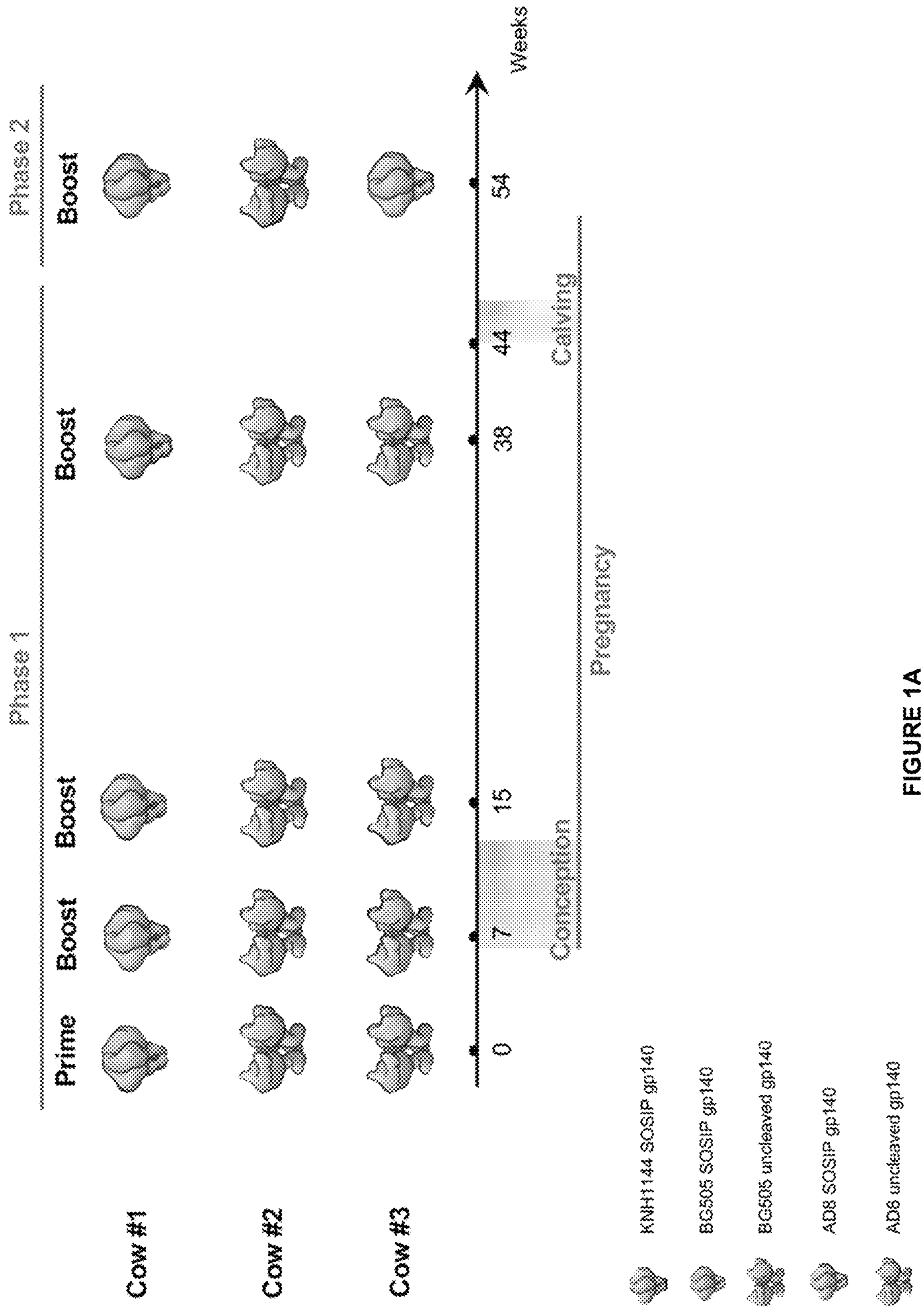
FIG. 1. Vaccination regimen of cows during pregnancy and Isolation of cross-clade neutralizing antibodies from clade A vaccinated cow. (A) Cows were immunized at week 0, 7, 15, 38 and 54 with HIV Env antigens formulated in Seppic Montanide (ISA206) adjuvant subcutaneously. Blood sampling was performed at weeks indicated in the scheme. Cow #1 (also referred herein to cow #617) was vaccinated with KNH1144 SOSIP gp140 and BG505 gp140 while cow #2 (also referred to herein as cow #8434) and #3 (also referred to herein as cow #35) were vaccinated with AD8 uncleaved gp140 followed by BG505 uncleaved gp140 and AD8 SOSIP gp140, respectively. (B) vaccination of cows with clade A and B cell sorting with clade B HIV virus resulted in isolation of potent BrNAb. (C) Cow PBMCs were sorted for IgG+ cells that bound to biotinylated AD8 SOSIP-AviTag conjugated to PE and APC fluorophores. (D) Bovine BrNAbs showed potent cross-clade neutralization against tier 1 and tier 2 viruses. (E) Autologous Env binding of bovine IgGs in sera of vaccinated cows. Binding was measured against Env vaccine through direct ELISA. (F) Neutralisation assays were performed against seven pseudoviruses from clades A, B and C, and tiers 1A, 1B and 2; as negative control, MuLV pseudovirus was used. The values show ID50s. Heatmap scale shows no neutralisation from a value of ID50=10 (white values), to the highest neutralisation achieved at ID50=1000 (red values).

It will be understood that the invention disclosed and defined in this specification extends to all alternative combinations of two or more of the individual features mentioned or evident from the text or drawings. All of these different combinations constitute various alternative aspects of the invention.

Further aspects of the present invention and further embodiments of the aspects described in the preceding paragraphs will become apparent from the following description, given by way of example and with reference to the accompanying drawings.

Reference will now be made in detail to certain embodiments of the invention. While the invention will be described in conjunction with the embodiments, it will be understood that the intention is not to limit the invention to those embodiments. On the contrary, the invention is intended to coverall alternatives, modifications, and equivalents, which may be included within the scope of the present invention as defined by the claims.

The inventors have herein generated a new therapeutic approach to the treatment of HIV-1 infection based on the generation of broadly neutralising antibodies (BrNAbs) against the HIV-1 Env protein. In particular, the inventors have generated antigen binding sites based on bovine BrNAbs which have higher potency than human BrNAbs due to their long finger-like CDRH3 regions that make intimate contact with conserved deeply recessed target sites on the Env protein.

The antigen binding sites and antibodies developed herein are associated with one or more, or all, of the following technical advantages:

- They are broadly neutralising HIV-1 antibodies which are capable of neutralizing multiple HIV-1 viral strains by targeting conserved epitopes of the HIV-1 Env protein.
- They may comprise a human constant region and a bovine variable region, which provides utility for use in humans.
- They have high affinity binding to a number of variants of the Env gp120 monomer and trimer on infectious virion and infected cells.
- They have been shown to have up to 50 fold better potency than the commercially available therapeutic antibodies that are used for the treatment of HIV-1 infection, including antibody VRC01.
- They are capable of binding to multiple forms of HIV-1 Env including monomeric gp120, uncleaved gp140 and SOSIP gp140.
- They are capable of binding to the Env trimer ConM SOSIP, which has a consensus sequence common to all HIV-1 group M isolates.
- They can neutralise the HIV-1 virus at lower concentrations than other HIV-1 antibodies, as shown by $IC_{50}$ values.
- They are not polyreactive or autoreactive, unlike antibody VRC01, highlighting their safety as anti-HIV therapeutics.
- Their activity is not dependent on the light chain variable region, as the use of different light chain variable regions as in conjunction with heavy chain variable regions of the invention shown herein retains antibody function.

The above advantages are significant in so far as they demonstrate that the antigen binding sites and antibodies described herein hold utility in the prevention, attenuation, treatment, neutralisation and/or inhibition of HIV-1 infection.

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects, and vice versa, unless the context clearly dictates otherwise. For example, reference to "a" includes a single as well as two or more; reference to "an" includes a single as well as two or more; reference to "the" includes a single as well as two or more and so forth.

Those skilled in the art will appreciate that the present invention is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

One skilled in the art will recognize many methods and materials similar or equivalent to those described herein, which could be used in the practice of the present invention. The present invention is in no way limited to the methods and materials described.

All of the patents and publications referred to herein are incorporated by reference in their entirety.

The present invention is not to be limited in scope by the specific examples described herein, which are intended for the purpose of exemplification only. Functionally-equivalent products, compositions and methods are clearly within the scope of the present invention.

Any example or embodiment of the present invention herein shall be taken to apply mutatis mutandis to any other example or embodiment of the invention unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat Sequences of Proteins of Immunological Interest, National Institutes of Health, Bethesda, Md., 1987 and 1991, Bork et al., J Mol. Biol. 242, 309-320, 1994, Chothia and Lesk J. Mol Biol. 196:901-917, 1987, Chothia et al. Nature 342, 877-883, 1989 and/or or Al-Lazikani et al., J Mol Biol 273, 927-948, 1997.

The term "and/or", e.g., "X and/or Y" shall be understood to mean either "X and Y" or "X or Y" and shall be taken to provide explicit support for both meanings or for either meaning.

As used herein the term "derived from" shall be taken to indicate that a specified integer may be obtained from a particular source albeit not necessarily directly from that source.

Reference herein to a range of, e.g., residues, will be understood to be inclusive. For example, reference to "a region comprising amino acids 56 to 65" will be understood in an inclusive manner, i.e., the region comprises a sequence of amino acids as numbered 56, 57, 58, 59, 60, 61, 62, 63, 64 and 65 in a specified sequence.

Selected Definitions

The term "human immunodeficiency virus type 1" or "HIV-1" as provided herein includes any of the HIV-1 naturally occurring forms, homologs or variants that maintain the activity of HIV-1 (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form.

The term "isolated protein" or "isolated polypeptide" is a protein or polypeptide that by virtue of its origin or source of derivation is not associated with naturally-associated components that accompany it in its native state; is substantially free of other proteins from the same source. A protein may be rendered substantially free of naturally associated components or substantially purified by isolation, using protein purification techniques known in the art. By "substantially purified" is meant the protein is substantially free of contaminating agents, e.g., at least about 70% or 75% or 80% or 85% or 90% or 95% or 96% or 97% or 98% or 99% free of contaminating agents.

The term "recombinant" shall be understood to mean the product of artificial genetic recombination. Accordingly, in the context of a recombinant protein comprising an antibody antigen binding domain, this term does not encompass an antibody naturally-occurring within a subject's body that is the product of natural recombination that occurs during B cell maturation. However, if such an antibody is isolated, it is to be considered an isolated protein comprising an antibody antigen binding domain. Similarly, if nucleic acid encoding the protein is isolated and expressed using recombinant means, the resulting protein is a recombinant protein comprising an antibody antigen binding domain. A recombinant protein also encompasses a protein expressed by artificial recombinant means when it is within a cell, tissue or subject, e.g., in which it is expressed.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulphide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

As used herein, the term "antigen binding site" is used interchangeably with "antigen binding domain" and shall be taken to mean a region of an antibody that is capable of specifically binding to an antigen, i.e., a VH or a VL or an Fv comprising both a VH and a VL. The antigen binding domain need not be in the context of an entire antibody, e.g., it can be in isolation (e.g., a domain antibody) or in another form, e.g., as described herein, such as a scFv.

For the purposes for the present disclosure, the term "antibody" includes a protein capable of specifically binding to one or a few closely related antigens (e.g., those present in HIV-1) by virtue of an antigen binding domain contained within a Fv. This term includes four chain antibodies (e.g., two light chains and two heavy chains), recombinant or modified antibodies (e.g., chimeric antibodies, humanized antibodies, human antibodies, CDR-grafted antibodies, primatized antibodies, de-immunized antibodies, synhumanized antibodies, half-antibodies, bispecific antibodies). An antibody generally comprises constant domains, which can be arranged into a constant region or constant fragment or fragment crystallizable (Fc). Exemplary forms of antibodies comprise a four-chain structure as their basic unit. Full-length antibodies comprise two heavy chains (~50 to 70 kD) covalently linked and two light chains (~23 kDa each). A light chain generally comprises a variable region (if present) and a constant domain and in mammals is either a κ light chain or a λ light chain. A heavy chain generally comprises a variable region and one or two constant domain(s) linked by a hinge region to additional constant domain(s).

Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable region (VH or VL wherein each are ~110 amino acids in length) and one or more constant domains at the C-terminus. The constant domain of the light chain (CL which is ~110 amino acids in length) is aligned with and disulfide bonded to the first constant domain of the heavy chain (CH1 which is 330 to 440 amino acids in length). The light chain variable region is aligned with the variable region of the heavy chain. The antibody heavy chain can comprise 2 or more additional CH domains (such as, CH2, CH3 and the like) and can comprise a hinge region between the CH1 and CH2 constant domains. Antibodies can be of any type (e.g., IgG, IgE, IgM, IgD, IgA, and IgY), class (e.g., IgG1, IgG2, IgG3, IgG4, IgA1 and IgA2) or subclass. In one example, the antibody is a murine (mouse or rat) antibody or a primate (such as, human) antibody. In one example, the antibody is humanized, synhumanized, chimeric, CDR-grafted or deimmunized.

The terms "full-length antibody", "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

As used herein, "variable region" refers to the portions of the light and/or heavy chains of an antibody as defined herein that is capable of specifically binding to an antigen and, includes amino acid sequences of complementarity determining regions (CDRs); i.e., CDR1, CDR2, and CDR3, and framework regions (FRs). For example, the variable region comprises three or four FRs (e.g., FR1, FR2, FR3 and optionally FR4) together with three CDRs. VH refers to the variable region of the heavy chain. VL refers to the variable region of the light chain.

As used herein, the term "complementarity determining regions" (syn. CDRs; i.e., CDR1, CDR2, and CDR3) refers to the amino acid residues of an antibody variable region the presence of which are major contributors to specific antigen binding. Each variable region domain (VH or VL) typically has three CDRs identified as CDR1, CDR2 and CDR3. The CDRs of VH are also referred to herein as CDR H1, CDR H2 and CDR H3, respectively, wherein CDR H1 corresponds to CDR 1 of VH, CDR H2 corresponds to CDR 2 of VH and CDR H3 corresponds to CDR 3 of VH. Likewise, the CDRs of VL are referred to herein as CDR L1, CDR L2 and CDR L3, respectively, wherein CDR L1 corresponds to CDR 1 of VL, CDR L2 corresponds to CDR 2 of VL and CDR L3 corresponds to CDR 3 of VL.

"Framework regions" (FRs) are those variable region residues other than the CDR residues. The FRs of VH are also referred to herein as FR H1, FR H2, FR H3 and FR H4, respectively, wherein FR H1 corresponds to FR1 of VH, FR H2 corresponds to FR2 of VH, FR H3 corresponds to FR3 of VH and FR H4 corresponds to FR4 of VH. Likewise, the FRs of VL are referred to herein as FR L1, FR L2, FR L3 and FR L4, respectively, wherein FR L1 corresponds to FR1 of VL, FR L2 corresponds to FR2 of VL, FR L3 corresponds to FR3 of VL and FR L4 corresponds to FR4 of VL.

As used herein, the term "Fv" shall be taken to mean any protein, whether comprised of multiple polypeptides or a single polypeptide, in which a VL and a VH associate and form a complex having an antigen binding domain, i.e., capable of specifically binding to an antigen. The VH and the VL which form the antigen binding domain can be in a single polypeptide chain or in different polypeptide chains. Furthermore, an Fv of the invention (as well as any protein of the invention) may have multiple antigen binding domains which may or may not bind the same antigen. This term shall be understood to encompass fragments directly derived from an antibody as well as proteins corresponding to such a fragment produced using recombinant means. In some examples, the VH is not linked to a heavy chain constant domain (CH) 1 and/or the VL is not linked to a light chain constant domain (CL).

Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., CH2 or CH3 domain, e.g., a minibody. A "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a VH and a single constant domain. Two Fab' fragments are obtained per antibody treated in this manner. A Fab' fragment can also be produced by recombinant means.

A "F(ab')2 fragment" of an antibody consists of a dimer of two Fab' fragments held together by two disulfide bonds, and is obtained by treating a whole antibody molecule with the enzyme pepsin, without subsequent reduction. A "Fab2" fragment is a recombinant fragment comprising two Fab fragments linked using, for example a leucine zipper or a CH3 domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker. The linker may be a one or more amino acids or a disulphide bond.

As used herein, the term "binds" in reference to the interaction of an antigen binding site or an antigen binding domain thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabelled "A"), in a reaction containing labelled "A" and the protein, will reduce the amount of labelled "A" bound to the antibody.

As used herein, the term "specifically binds" or "binds specifically" shall be taken to mean that an antigen binding site of the invention reacts or associates more frequently, more rapidly, with greater duration and/or with greater affinity with a particular antigen or cell expressing same than it does with alternative antigens or cells. For example, an antigen binding site binds to the Env protein of HIV-1 with materially greater affinity (e.g., 1.5 fold or 2 fold or 5 fold or 10 fold or 20 fold or 40 fold or 60 fold or 80 fold to 100 fold or 150 fold or 200 fold) than other known antigen binding sites. In an example of the present invention, an antigen binding site that "specifically binds" to HIV-1 with an affinity at least 1.5 fold or 2 fold or greater (e.g., 5 fold or 10 fold or 20 fold r 50 fold or 100 fold or 200 fold) than it does to another type of HIV, such as HIV-2. Generally, but not necessarily, reference to binding means specific binding, and each term shall be understood to provide explicit support for the other term.

As used herein, the term "does not detectably bind" shall be understood to mean that an antigen binding site, e.g., an antibody, binds to a candidate antigen at a level less than 10%, or 8% or 6% or 5% above background. The background can be the level of binding signal detected in the absence of the protein and/or in the presence of a negative control protein (e.g., an isotype control antibody) and/or the level of binding detected in the presence of a negative control antigen. The level of binding is detected using biosensor analysis (e.g. Biacore) in which the antigen binding site is immobilized and contacted with an antigen.

As used herein, the term "epitope" (syn. "antigenic determinant") shall be understood to mean a region of HIV-1 (eg the HIV-1 Env protein) to which an antigen binding site comprising an antigen binding domain of an antibody binds. Unless otherwise defined, this term is not necessarily limited to the specific residues or structure to which the antigen binding site makes contact. For example, this term includes the region spanning amino acids contacted by the antigen binding site and 5-10 (or more) or 2-5 or 1-3 amino acids outside of this region. In some examples, the epitope comprises a series of discontinuous amino acids that are positioned close to one another when antigen binding site is folded, i.e., a "conformational epitope". The skilled artisan will also be aware that the term "epitope" is not limited to peptides or polypeptides. For example, the term "epitope" includes chemically active surface groupings of molecules such as sugar side chains, phosphoryl side chains, or sulfonyl side chains, and, in certain examples, may have specific three dimensional structural characteristics, and/or specific charge characteristics.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared according to the methods described herein or by methods known in the art including by the hybridoma methodology described by Kohler et al., Nature, 256:495 (1975). Alternatively, they may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)).

The present invention provides variable region antigen-binding sequences derived from bovine antibodies. Accordingly, chimeric antibodies of primary interest herein include antibodies having one or more bovine antigen binding sequences (e.g., CDRs) and containing one or more sequences derived from a human antibody, e.g., an FR or C region sequence. In addition, chimeric antibodies of primary interest herein include those comprising a bovine variable region antigen binding sequence of one antibody class or subclass and another sequence, e.g., FR or C region sequence, derived from another antibody class or subclass, preferably human.

A "humanized antibody" is generally considered to be a human antibody that has one or more amino acid residues introduced into it from a source that is non-human. These nonhuman amino acid residues are often referred to as "import" residues, which are typically taken from an "import" variable region. Humanization is traditionally performed following the method of Winter and co-workers (Jones et al., Nature, 321:522-525 (1986); Reichmann et al., Nature, 332:323-327 (1988); Verhoeyen et al., Science, 239:1534-1536 (1988)), by substituting import hypervariable region sequences for the corresponding sequences of a human antibody.

Accordingly, such "humanized" antibodies are chimeric antibodies (U.S. Pat. No. 4,816,567) wherein substantially less than an intact human variable region has been substituted by the corresponding sequence from a non-human species.

An "antibody fragment" comprises a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

The phrase "functional fragment or analog" of an antibody is a fragment or analog that retains binding ability when compared with the full-length antibody.

A neutralizing antibody as described herein is one that can neutralize the ability of the HIV-1 virus to initiate and/or perpetuate an infection in a host (ie a human) and/or in target cells in vitro. It will be understood that the antigen binding sites described herein can neutralize viral infectivity in a number of ways. They may interfere with virion binding to receptors, block virus uptake into cells, prevent uncoating of the viral genomes in endosomes, or cause aggregation of virus particles.

It will be understood that the term "broadly neutralizing antibodies (BrNAbs)" refers to neutralizing antibodies that neutralize more than one HIV-1 virus species (from diverse clades and different strains within a clade), which may be demonstrated in any neutralization assay known in the art or described herein. It is generally understood that BrNAbs are unique in that they target conserved epitopes of the virus, and whilst the virus may mutate, the targeted epitopes will still exist. A broadly neutralizing antibody may neutralize at least 2, 3, 4, 5, 6, 7, 8, 9, 10, 11, 12, 13, 14, 15, 16, 17, 18, 19, 20 or more different strains of HIV-1, the strains belonging to the same or different clades. A broad neutralizing antibody may neutralize multiple HIV-1 species belonging to at least 2, 3, 4, 5, or 6 different clades including clades A, B, C, AC, G, CRF07_BC and CRF01_AE.

As used herein, the terms "preventing", "prevent" or "prevention" include administering an antigen binding site of the invention to thereby stop or hinder the development of at least one symptom of HIV-1. This term also encompasses treatment of a subject in remission to prevent or hinder relapse.

As used herein, the terms "treating", "treat" or "treatment" include administering an antigen binding site described herein to thereby reduce or eliminate at least one symptom of HIV-1.

As used herein, the term "subject" shall be taken to mean any animal, preferably humans.

BG505.SOSIP is a structural and antigenic mimic of the closed state of mature prefusion Env, It is a soluble gp140 molecule that is a derivative of the clade A HIV-1 strain BG505, with a number of stabilizing mutations that allow for proper structural and antigenic mimicry of the closed state of mature prefusion Env. Specifically, BG505.SOSIP is truncated at residue 664 in gp41 and includes the trimer-stabilizing gp120-gp41 disulfide bridge between residues 501 and 605 (termed SOS) and an Ile-to-Pro mutation at gp41 residue 559 (termed IP), as well as a Thr-to-Asn mutation at residue 332 to introduce a glycosylation site and a modification of the native $_{508}$REKR$_{511}$ furin cleavage site to six Arg residues for improved cleavage.

The AD8.SOSIP.6R.644 protein incorporates a similar set of mutations utilized in BG505.SOSIP. AD8.SOSIP.6R.644 was derived from the Env sequence of NL(AD8) (Freed E O, et al (1995). *J Virol* 69:3949-54) and a soluble gp140 protein was generated by truncating the MPER, TM and CT from residue 664 (HXB-2 numbering used here and subsequently). Introduction of A501C, I559P, and T605C substitutions were used to stabilize the gp140 in the closed state, and the wild-type cleavage site (R508EKR) was replaced with six arginine residues to facilitate more efficient cleavage. A C-terminal linker and 6×His tag (ASGSGHHHHHH) were introduced to facilitate purification of the protein.

Antibodies

In one example, an antigen binding site as described herein according to any example is an antibody.

Methods for generating antibodies are known in the art and/or described in Harlow and Lane (editors) Antibodies: A Laboratory Manual, Cold Spring Harbor Laboratory, (1988). Generally, in such methods HIV-1 or a region thereof (e.g., an extracellular region) or immunogenic fragment or epitope thereof or a cell expressing and displaying same (i.e., an immunogen), optionally formulated with any suitable or desired carrier, adjuvant, or pharmaceutically acceptable excipient, is administered to a non-human animal, preferably a cow. The immunogen may be administered intranasally, intramuscularly, subcutaneously, intravenously, intradermally, intraperitoneally, or by other known route.

The production of polyclonal antibodies may be monitored by sampling blood of the immunized animal at various points following immunization. One or more further immunizations may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (mAbs).

Monoclonal antibodies are one exemplary form of antibody contemplated by the present invention. The term "monoclonal antibody" or "mAb" refers to a homogeneous antibody population capable of binding to the same antigen(s), for example, to the same epitope within the antigen. This term is not intended to be limited with regard to the source of the antibody or the manner in which it is made.

For the production of mAbs any one of a number of known techniques may be used, such as, for example, the procedure exemplified in U.S. Pat. No. 4,196,265 or Harlow and Lane (1988), supra.

In one example, mAbs may be generated as described previously in Haydarchi et al (2016) *mAbs,* 9:3, pp Pages 550-566 or Tiller et al (2008) *J Immunol Methods, January* 1; 329(1-2): 112-124 whereby single HIV-specific B cells were sorted, followed by single cell RT-PCR and cloning.

In another example, a suitable animal such as a cow is immunized with an immunogen under conditions sufficient to stimulate antibody producing cells. Following immunization, somatic cells with the potential for producing antibodies, specifically B lymphocytes (B cells), are selected for use in the mAb generating protocol. These cells may be obtained from biopsies of spleens, tonsils or lymph nodes, or from a peripheral blood sample.

Hybrids are amplified by culture in a selective medium comprising an agent that blocks the de novo synthesis of nucleotides in the tissue culture media. Exemplary agents are aminopterin, methotrexate and azaserine.

The amplified hybridomas are subjected to a functional selection for antibody specificity and/or titer, such as, for example, by flow cytometry and/or immunohistochemistry and/or immunoassay (e.g. radioimmunoassay, enzyme immunoassay, cytotoxicity assay, plaque assay, dot immunoassay, and the like).

Alternatively, ABL-MYC technology (NeoClone, Madison WI 53713, USA) is used to produce cell lines secreting MAbs (e.g., as described in Largaespada et al, *J. Immunol. Methods.* 197: 85-95, 1996). Antibodies can also be produced or isolated by screening a display library, e.g., a phage display library, e.g., as described in U.S. Pat. No. 6,300,064 and/or U.S. Pat. No. 5,885,793.

The antibody of the present invention may be a synthetic antibody. For example, the antibody is a chimeric antibody, a humanized antibody, a human antibody synhumanized antibody, primatized antibody or a de-immunized antibody.

Antibody Binding Domain Containing Proteins

Single-Domain Antibodies

In some examples, a protein of the invention is or comprises a single-domain antibody (which is used interchangeably with the term "domain antibody" or "dAb"). A single-domain antibody is a single polypeptide chain comprising all or a portion of the heavy chain variable region of an antibody. In certain examples, a single-domain antibody is a human single-domain antibody (Domantis, Inc., Waltham, MA; see, e.g., U.S. Pat. No. 6,248,516).

Diabodies, Triabodies, Tetrabodies

In some examples, a protein of the invention is or comprises a diabody, triabody, tetrabody or higher order protein complex such as those described in WO98/044001 and/or WO94/007921.

For example, a diabody is a protein comprising two associated polypeptide chains, each polypeptide chain comprising the structure $V_L$-X-$V_H$ or $V_H$-X-$V_L$, wherein $V_L$ is an antibody light chain variable region, $V_H$ is an antibody heavy chain variable region, X is a linker comprising insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding domain, i.e., to form a Fv molecule capable of specifically binding to one or more antigens. The $V_L$ and $V_H$ can be the same in each polypeptide chain or the $V_L$ and $V_H$ can be different in each polypeptide chain so as to form a bispecific diabody (i.e., comprising two Fvs having different specificity).

Single Chain Fv (scFv)

A skilled person will be aware that scFvs comprise $V_H$ and $V_L$ regions in a single polypeptide chain and a polypeptide linker between the $V_H$ and $V_L$ which enables the scFv to form the desired structure for antigen binding (i.e., for the $V_H$ and $V_L$ of the single polypeptide chain to associate with one another to form a Fv). For example, the linker comprises in excess of 12 amino acid residues with $(Gly_4Ser)_3$ being one of the more favored linkers for a scFv.

The present invention also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv.

Alternatively, or in addition, the present invention encompasses a dimeric scFv, i.e., a protein comprising two scFv molecules linked by a non-covalent or covalent linkage, e.g., by a leucine zipper domain (e.g., derived from Fos or Jun). Alternatively, two scFvs are linked by a peptide linker of sufficient length to permit both scFvs to form and to bind to an antigen, e.g., as described in US20060263367.

Heavy Chain Antibodies

Heavy chain antibodies differ structurally from many other forms of antibodies, in so far as they comprise a heavy chain, but do not comprise a light chain. Accordingly, these antibodies are also referred to as "heavy chain only antibodies". Heavy chain antibodies are found in, for example, camelids and cartilaginous fish (also called IgNAR).

Other Antibodies and Proteins Comprising Antigen Binding Domains Thereof

The present invention also contemplates other antibodies and proteins comprising antigen-binding domains thereof, such as:

(i) "key and hole" bispecific proteins as described in U.S. Pat. No. 5,731,168;

(ii) heteroconjugate proteins, e.g., as described in U.S. Pat. No. 4,676,980;

(iii) heteroconjugate proteins produced using a chemical cross-linker, e.g., as described in U.S. Pat. No. 4,676,980; and (iv) $Fab_3$ (e.g., as described in EP19930302894).

Light Chains

It will be understood that the antigen binding sites or antibodies described herein may utilise any light chain including, but not limited to, those exemplified herein in the examples.

The heavy chain CDRs (CDRH1-CDRH3) of the antigen binding sites or antibodies described herein have been tested with a number of different light chain variable regions including those defined by SEQ ID NOs:63 and 73 which contain different complementarity determining regions. The data herein, including FIG. 10, demonstrate that the antigen binding sites or antibodies described herein may therefore be used with any light chain, including that defined by the complementarity determining regions set out in SEQ ID NOs: 83-85.

A skilled person will understand the minimal features required in a suitable light chain for use in accordance with the invention. For instance, ultra-long CDR3s are shown to have restricted light chain pairings (Saini et al., 2003) that may specifically provide a structural framework for supporting ultra-long CDRH3 (Wang et al., Cell 153, 1379-1393 (2013). There appears to be a selective pressure for the use of three Vλ1 genes (Vλ1x and two new Vλ1d and Vλ1e genes) in IgM with unusually long CDR3H (Saini et al., Int. Immunol., 15 (2003), pp. 845-853).

Mutations to Proteins

The present invention also provides an antigen binding site or a nucleic acid encoding same having at least 80% identity to a sequence disclosed herein. In one example, an antigen binding site or nucleic acid of the invention comprises sequence at least about 85% or 90% or 95% or 97% or 98% or 99% identical to a sequence disclosed herein.

Alternatively, or additionally, the antigen binding site comprises a CDR (e.g., three CDRs) at least about 80% or 85% or 90% or 95% or 97% or 98% or 99% identical to CDR(s) of a $V_H$ or $V_L$ as described herein according to any example.

In another example, a nucleic acid of the invention comprises a sequence at least about 80% or 85% or 90% or 95% or 97% or 98% or 99% identical to a sequence encoding an antigen binding site having a function as described herein according to any example. The present invention also encompasses nucleic acids encoding an antigen binding site of the invention, which differs from a sequence exemplified herein as a result of degeneracy of the genetic code.

The percentage of identity of a nucleic acid or polypeptide is determined by GAP (Needleman and Wunsch. *Mol. Biol.* 48, 443-453, 1970) analysis (GCG program) with a gap creation penalty=5, and a gap extension penalty=0.3. The query sequence is at least 50 residues in length, and the GAP analysis aligns the two sequences over a region of at least 50 residues. For example, the query sequence is at least 100 residues in length and the GAP analysis aligns the two sequences over a region of at least 100 residues. For example, the two sequences are aligned over their entire length.

The present invention also contemplates a nucleic acid that hybridizes under stringent hybridization conditions to a nucleic acid encoding an antigen binding site described herein. A "moderate stringency" is defined herein as being a hybridization and/or washing carried out in 2×SSC buffer, 0.1% (w/v) SDS at a temperature in the range 45° C. to 65° C., or equivalent conditions. A "high stringency" is defined herein as being a hybridization and/or wash carried out in 0.1×SSC buffer, 0.1% (w/v) SDS, or lower salt concentration, and at a temperature of at least 65° C., or equivalent conditions. Reference herein to a particular level of stringency encompasses equivalent conditions using wash/hybridization solutions other than SSC known to those skilled in the art. For example, methods for calculating the temperature at which the strands of a double stranded nucleic acid will dissociate (also known as melting temperature, or Tm) are known in the art. A temperature that is similar to (e.g., within 5° C. or within 10° C.) or equal to the Tm of a nucleic acid is considered to be high stringency. Medium stringency is to be considered to be within 10° C. to 20° C. or 10° C. to 15° C. of the calculated Tm of the nucleic acid.

The present invention also contemplates mutant forms of an antigen binding site of the invention comprising one or more conservative amino acid substitutions compared to a sequence set forth herein. In some examples, the antigen binding site comprises 10 or fewer, e.g., 9 or 8 or 7 or 6 or 5 or 4 or 3 or 2 or 1 conservative amino acid substitutions. A "conservative amino acid substitution" is one in which the amino acid residue is replaced with an amino acid residue having a similar side chain and/or hydropathicity and/or hydrophilicity.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Hydropathic indices are described, for example in Kyte and Doolittle *J. Mol. Biol.,* 157:105-132, 1982 and hydrophylic indices are described in, e.g., U.S. Pat. No. 4,554,101.

The present invention also contemplates non-conservative amino acid changes. For example, of particular interest are substitutions of charged amino acids with another charged amino acid and with neutral or positively charged amino acids. In some examples, the antigen binding site comprises 10 or fewer, e.g., 9 or 8 or 7 or 6 or 5 or 4 or 3 or 2 or 1 non-conservative amino acid substitutions.

In one example, the mutation(s) occur within a FR of an antigen binding domain of an antigen binding site of the invention. In another example, the mutation(s) occur within a CDR of an antigen binding site of the invention.

Exemplary methods for producing mutant forms of an antigen binding site include:

mutagenesis of DNA (Thie et al., *Methods Mol. Biol.* 525: 309-322, 2009) or RNA (Kopsidas et al., *Immunol. Lett.* 107:163-168, 2006; Kopsidas et al. *BMC Biotechnology,* 7:1 8, 2007; and WO1999/058661);

introducing a nucleic acid encoding the polypeptide into a mutator cell, e.g., XL-1Red, XL-mutS and XL-mutS-Kanr bacterial cells (Stratagene);

DNA shuffling, e.g., as disclosed in Stemmer, *Nature* 370: 389-91, 1994; and site directed mutagenesis, e.g., as described in Dieffenbach (ed) and Dveksler (ed) (In: PCR Primer: A Laboratory Manual, Cold Spring Harbor Laboratories, NY, 1995).

Exemplary methods for determining biological activity of the mutant antigen binding sites of the invention will be apparent to the skilled artisan and/or described herein, e.g., antigen binding. For example, methods for determining antigen binding, competitive inhibition of binding, affinity, association, dissociation and therapeutic efficacy are described herein.

Constant Regions

The present invention encompasses antigen binding sites and/or antibodies described herein comprising a constant region of an antibody. This includes antigen binding fragments of an antibody fused to an Fc.

Sequences of constant regions useful for producing the proteins of the present invention may be obtained from a number of different sources. In some examples, the constant region or portion thereof of the protein is derived from a human antibody. The constant region or portion thereof may be derived from any antibody class, including IgM, IgG, IgD, IgA and IgE, and any antibody isotype, including IgG1, IgG2, IgG3 and IgG4. In one example, the constant region is human isotype IgG4 or a stabilized IgG4 constant region.

In one example, the Fc region of the constant region has a reduced ability to induce effector function, e.g., compared to a native or wild-type human IgG1 or IgG3 Fc region. In one example, the effector function is antibody-dependent cell-mediated cytotoxicity (ADCC) and/or antibody-dependent cell-mediated phagocytosis (ADCP) and/or complement-dependent cytotoxicity (CDC). Methods for assessing the level of effector function of an Fc region containing protein are known in the art and/or described herein.

In one example, the Fc region is an IgG4 Fc region (i.e., from an IgG4 constant region), e.g., a human IgG4 Fc region. Sequences of suitable IgG4 Fc regions will be apparent to the skilled person and/or available in publically available databases (e.g., available from National Center for Biotechnology Information).

In one example, the constant region is a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington DC United States Department of Health and Human Services, 1987 and/or 1991). This position corresponds to position 228 of the hinge region according to the EU numbering system (Kabat et al., Sequences of Proteins of Immunological Interest Washington DC United States Department of Health and Human Services, 2001 and Edelman et al., *Proc. Natl. Acad. USA*, 63, 78-85, 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulphide (S—S) bonds in the same positions (see for example WO2010/080538).

Additional examples of stabilized IgG4 antibodies are antibodies in which arginine at position 409 in a heavy chain constant region of human IgG4 (according to the EU numbering system) is substituted with lysine, threonine, methionine, or leucine (e.g., as described in WO2006/033386). The Fc region of the constant region may additionally or alternatively comprise a residue selected from the group consisting of: alanine, valine, glycine, isoleucine and leucine at the position corresponding to 405 (according to the EU numbering system). Optionally, the hinge region comprises a proline at position 241 (i.e., a CPPC sequence) (as described above).

In another example, the Fc region is a region modified to have reduced effector function, i.e., a "non-immunostimulatory Fc region". For example, the Fc region is an IgG1 Fc region comprising a substitution at one or more positions selected from the group consisting of 268, 309, 330 and 331. In another example, the Fc region is an IgG1 Fc region comprising one or more of the following changes E233P, L234V, L235A and deletion of G236 and/or one or more of the following changes A327G, A330S and P331S (Armour et al., *Eur J Immunol.* 29:2613-2624, 1999; Shields et al., *J Biol Chem.* 276(9):6591-604, 2001). Additional examples of non-immunostimulatory Fc regions are described, for example, in Dall'Acqua et al., *J Immunol.* 177: 1129-1138 2006; and/or Hezareh *J Virol;* 75: 12161-12168, 2001).

In another example, the Fc region is a chimeric Fc region, e.g., comprising at least one $C_H2$ domain from an IgG4 antibody and at least one $C_H3$ domain from an IgG1 antibody, wherein the Fc region comprises a substitution at one or more amino acid positions selected from the group consisting of 240, 262, 264, 266, 297, 299, 307, 309, 323, 399, 409 and 427 (EU numbering) (e.g., as described in WO2010/085682). Exemplary substitutions include 240F, 262L, 264T, 266F, 297Q, 299A, 299K, 307P, 309K, 309M, 309P, 323F, 399S, and 427F.

Additional Modifications

The present invention also contemplates additional modifications to an antibody or antigen binding site comprising an Fc region or constant region.

For example, the antibody comprises one or more amino acid substitutions that increase the half-life of the protein. For example, the antibody comprises a Fc region comprising one or more amino acid substitutions that increase the affinity of the Fc region for the neonatal Fc region (FcRn). For example, the Fc region has increased affinity for FcRn at lower pH, e.g., about pH 6.0, to facilitate Fc/FcRn binding in an endosome. In one example, the Fc region has increased affinity for FcRn at about pH 6 compared to its affinity at about pH 7.4, which facilitates the re-release of Fc into blood following cellular recycling. These amino acid substitutions are useful for extending the half-life of a protein, by reducing clearance from the blood.

Exemplary amino acid substitutions include T250Q and/or M428L or T252A, T254S and T266F or M252Y, S254T and T256E or H433K and N434F according to the EU numbering system. Additional or alternative amino acid substitutions are described, for example, in US20070135620 or U.S. Pat. No. 7,083,784.

Protein Production

In one example, an antigen binding site described herein according to any example is produced by culturing a hybridoma under conditions sufficient to produce the protein, e.g., as described herein and/or as is known in the art.

Recombinant Expression

In another example, an antigen binding site described herein according to any example is recombinant.

In the case of a recombinant protein, nucleic acid encoding same can be cloned into expression constructs or vectors, which are then transfected into host cells, such as *E. coli* cells, yeast cells, insect cells, or mammalian cells, such as simian COS cells, Chinese Hamster Ovary (CHO) cells, human embryonic kidney (HEK) cells, or myeloma cells that do not otherwise produce the protein. Exemplary cells used for expressing a protein are CHO cells, myeloma cells or HEK cells. Molecular cloning techniques to achieve these ends are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art, see, e.g., U.S. Pat. No. 4,816,567 or 5,530,101.

Following isolation, the nucleic acid is inserted operably linked to a promoter in an expression construct or expression vector for further cloning (amplification of the DNA) or for expression in a cell-free system or in cells.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding a protein (e.g., derived from the information provided herein), an enhancer element, a promoter, and a transcription termination sequence. The skilled artisan will be aware of suitable sequences for expression of a protein. Exemplary signal sequences include prokaryotic secretion signals (e.g., pelB, alkaline phosphatase, penicillinase, Ipp, or heat-stable enterotoxin II), yeast secretion signals (e.g., invertase leader, α factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The host cells used to produce the protein may be cultured in a variety of media, depending on the cell type used. Commercially available media such as Ham's FI0 (Sigma), Minimal Essential Medium ((MEM), (Sigma), RPMI-1640 (Sigma), and Dulbecco's Modified Eagle's Medium ((DMEM), Sigma) are suitable for culturing mammalian cells. Media for culturing other cell types discussed herein are known in the art.

Isolation of Proteins

Methods for isolating a protein are known in the art and/or described herein.

Where an antigen binding site is secreted into culture medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. Alternatively, or additionally, supernatants can be filtered and/or separated from cells expressing the protein, e.g., using continuous centrifugation.

The antigen binding site prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Ed Harlow and David Lane (editors) Antibodies: A Laboratory Manual, Cold Spring Harbor Laboratory, (1988).

The skilled artisan will also be aware that a protein can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. The resulting protein is then purified using methods known in the art, such as, affinity purification. For example, a protein comprising a hexa-his tag is purified by contacting a sample comprising the protein with nickel-nitrilotriacetic acid (Ni-NTA) that specifically binds a hexa-his tag immobilized on a solid or semi-solid support, washing the sample to remove unbound protein, and subsequently eluting the bound protein. Alternatively, or in addition a ligand or antibody that binds to a tag is used in an affinity purification method.

Assaying Activity of an Antigen Binding Site Binding to HIV-1 Env and Mutants Thereof It will be apparent to the skilled artisan from the disclosure herein that antigen binding sites of the present invention bind to a HIV-1 Env antigen. Methods for assessing binding to a protein are known in the art, e.g., as described in Scopes (In: Protein purification: principles and practice, Third Edition, Springer Verlag, 1994). Such a method generally involves immobilizing the antigen, binding site and contacting it with labelled antigen (HIV-1 Env). Following washing to remove non-specific bound protein, the amount of label and, as a consequence, bound antigen is detected. Of course, the antigen binding site can be labelled and the antigen immobilized. Panning-type assays can also be used. Alternatively, or additionally, surface plasmon resonance assays can be used.

Optionally, the dissociation constant (Kd), association constant (Ka) and/or affinity constant ($K_D$) of an immobilized antigen binding site for HIV-1 Env or an epitope thereof is determined. The "Kd" or "Ka" or "$K_D$" for HIV-1 Env is in one example measured by a radiolabelled or fluorescently-labelled HIV-1 Env ligand binding assay. In the case of a "Kd", this assay equilibrates the antigen binding site with a minimal concentration of labelled HIV-1 Env or epitope thereof in the presence of a titration series of unlabelled HIV-1 Env. Following washing to remove unbound HIV-1 Env or epitope thereof, the amount of label is determined, which is indicative of the Kd of the protein.

According to another example the Kd, Ka or $K_D$ is measured by using surface plasmon resonance assays, e.g., using BIAcore surface plasmon resonance (BIAcore, Inc., Piscataway, NJ) with immobilized HIV-1 Env or an antigen thereof or immobilized antigen binding site.

Human Immunodeficiency Virus Type 1 (HIV-1)

The antigen binding sites or antibodies described herein are useful for treating, attenuating or preventing HIV-1 in a subject in need thereof. In particular, the antigen binding sites or antibodies described herein are particularly useful for targeting the HIV-1 Env protein. The HIV-1 Env protein, which forms the viral envelope, is one of the only proteins that is accessible to antibody-directed immunity. The env gene encodes the glycosylated Env polypeptide of about 160 kDa (gp160) that is subsequently cleaved by a host cell protease to generate the viral envelope proteins gp120 and gp41. These two chains associate non-covalently in trimers to form the viral envelope spikes extending from the virion envelope.

There are many different types of strains or species of HIV-1 that belong to particular clades including A, B, C, AC, G, CRF07_BC or CFR01_AE. HIV-1 species belonging to clade B include MN, 6535, HXB-2, QH0692, pREJO4541, pRHPA4259, AD8, JRCSF, YU-2, ZM53M.PB12, X2278 and TRO11. HIV-1 species belonging to clade A include BG505 and 398F1. HIV-1 species belonging to clade C include Du156, ZM135M.PL10a, CAP210.200.E8, CAP45.2.00.G3, 25710, CE1176 and CEO217, preferably 25710, CE1176 and CEO217. HIV-1 species belonging to clade G include X1632. HIV-1 species belonging to clade CRF01_AE include CNE8 and CNE55, preferably CNE55.

The extensive variation among different strains of HIV-1, especially in gp120, and the ability of the virus to evolve during the course of a single infection and to adapt to drugs and immunologic attack rapidly present problems in therapy and vaccine development. Most of the variability among strains of HIV occurs in the envelope sequence in five variable domains of gp120, designated V1 through V5 (comprising amino acids 128 to 152, 182 to 195, 300 to 330, 395 to 415, and 460 to 467, respectively). The third variable region, called the V3 loop (formed by joining two cysteine residues), is a dominant antibody-neutralizing domain of gp120 and plays an important role in determining viral tropism. Four regions that are relatively invariant have been designated C1 through C4 (amino acids 33 to 60, 87 to 126, 231 to 276, and 460 to 467). These regions presumably maintain essential viral structures. The viral envelope ultimately must be understood as a fusion machine that allows viral entry into target cells. Fusion depends on sequential binding of gp120 to CD4 and the chemokine receptors, but the fusogenic domain is located in gp41. The fusion peptide that is inserted into the target cell membrane is formed at the new amino terminus created by proteolytic cleavage of the gp160 precursor protein.

The antigen binding sites or antibodies described herein are capable of targeting multiple forms of the HIV-1 Env protein including gp120, uncleaved gp140 and SOSIP gp140. As used herein, unless the context specifies or requires otherwise, reference to an antigen binding site of the invention binding to or specifically binding to HIV-1 also is a reference to that antigen binding site of the invention binding to or specifically binding to gp120 or any variant thereof including those described herein, gp140 or any variant thereof including those described herein, gp160 or any variant thereof including those described herein, or any other env gene product or variant thereof.

A subject that has been infected with HIV-1 may be asymptomatic or symptomatic. In the first few months of infection, a subject may demonstrate flu like symptoms including headache, fever, tiredness, swollen lymph nodes, sore throat, thrush, rash, muscle and joint pain, ulcers in mouth or on genitals, night sweats and/or diarrhoea. Clinically, this will typically correlate with detectable HIV-1 viral load in blood, sputum and/or urine as well as detectable antibodies produced by the subject in response to HIV-1 infection. Symptoms in the later phases of HIV-1 infection include high fevers, chills and night sweats, rashes, breathing difficulty and persistent coughing, severe weight loss, nausea, white spots in the mouth, genital sores, fatigue, pneumonia and cognitive decline.

Thus, it is envisaged that the antigen binding sites and antibodies described herein are capable of treating one or more of the above-described symptoms associated with HIV-1 infection.

The existence of, improvement in, or treatment of HIV-1 infection may be determined by any clinically or biochemically relevant method as described herein or known in the art, including assessment of blood, sputum and/or urine for HIV-1 viral load and HIV-1 antibodies. A positive response to treatment with any antigen binding site or antibody may be determined by any method known in the art and may include a:

- reduced viral load;
- reduced HIV-1 antibody titre;
- reduced headache, fever, tiredness;
- reduced swollen lymph nodes;
- reduced sore throat;
- reduced thrush, rash, muscle and/or joint pain;
- reduced ulcers in mouth or on genitals;
- reduced night sweats, chills and/or diarrhoea;
- reduced high fevers;
- reduced breathing difficulty and/or persistent coughing;
- reduced severe weight loss, nausea and/or white spots in the mouth;
- reduced genital sores;
- reduced fatigue;
- recovery from pneumonia; and/or
- improved cognitive capacity.

The determination of any of the above may be considered to be a positive response (i.e. treatment) to the antigen binding sites, antibodies and/or compositions described herein. Alternatively, a reduction in the requirement for standard HIV-1 medication that offers symptomatic relief may be considered to be a positive response to the compounds and/or compositions described herein.

Similarly, it is envisaged that antigen binding sites and antibodies described herein are capable of preventing HIV-1 infection is a subject, including those at high risk, by preventing increases to one or more of the above described clinical correlates or symptoms.

In an aspect of the invention, the subject, having received a treatment for a given HIV-1 infection, as described above, may have a 10%, 20%, 30%, 40%, 50%, 60%, 70%, 80%, 90% or greater reduction in the measurable parameters of any of those symptoms described above, as may be determined upon physical examination or by any of the clinical tests described above. Alternatively, where the infection is eradicated, there may be a complete, lasting disappearance of all detectable manifestations of the HIV-1 infection, such that the subject does not have any detectable signs of infection according to those parameters described above or others known in the art. The subject may have substantially undetectable signs of HIV-1 infection. A HIV-1 infection that is "substantially undetectable" generally refers to a circumstance where therapy has depleted the extent, severity or other physical measure of an HIV-1 infection so that through using relevant standard assessment techniques known in the art to determine the presence of one or more symptoms described above, as a consequence of the treatment, is not clearly detectable.

In one embodiment, the method is particularly useful for extending survival of the subject, including overall survival as well as progression free survival. It will be understood that overall survival is the length of time from either the date of diagnosis or the start of treatment of a HIV-1 infection, that patients diagnosed with the HIV-1 are still alive. It will be understood that progression free survival is the length of time during and after the treatment of HIV-1 infection that a patient lives with the HIV-1 infection but it does not get worse.

Survival analysis can be performed using well-known techniques in the art including the Kaplan-Meier method. The Kaplan-Meier method estimates the survival function from life-time data. In medical research, it can be used to measure the fraction of patients living for a certain amount of time after treatment. A plot of the Kaplan-Meier method of the survival function is a series of horizontal steps of declining magnitude which, when a large enough sample is taken, approaches the true survival function for that population. The value of the survival function between successive distinct sampled observations ("clicks") is assumed to be constant.

An important advantage of the Kaplan-Meier curve is that the method can take into account "censored" data-losses from the sample before the final outcome is observed (for instance, if a patient withdraws from a study). On the plot, small vertical tick-marks indicate losses, where patient data has been censored. When no truncation or censoring occurs, the Kaplan-Meier curve is equivalent to the empirical distribution.

Diagnosis

In an aspect of the invention, HIV-1 expressing cells or virus may be used to screen a biological sample obtained from a patient infected with HIV-1 for the presence of antibodies that preferentially bind to the cell expressing HIV-1 polypeptides using standard biological techniques. For example, in certain embodiments, the antibodies may be labelled, and the presence of label associated with the cell detected, e.g., using FMAT or FACs analysis. In particular embodiments, the biological sample is blood, serum, plasma, bronchial lavage, or saliva. Methods of the present invention may be practiced using high throughput techniques.

Compositions

In some examples, an antigen binding site or antibody described herein can be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term "parenteral" as used herein includes subcutaneous, intravenous, intramuscular, intraperitoneal, intrathecal, intraventricular, intrasternal, and intracranial injection or infusion techniques.

Methods for preparing an antigen binding site into a suitable form for administration to a subject (e.g. a pharmaceutical composition) are known in the art and include, for example, methods as described in Remington's Pharmaceutical Sciences (18th ed., Mack Publishing Co., Easton, Pa., 1990) and U.S. Pharmacopeia: National Formulary (Mack Publishing Company, Easton, Pa., 1984).

The pharmaceutical compositions of this invention are particularly useful for parenteral administration, such as intravenous administration or administration into a body cavity or lumen of an organ or joint. The compositions for administration will commonly comprise a solution of an antigen binding site dissolved in a pharmaceutically acceptable carrier, for example an aqueous carrier. A variety of aqueous carriers can be used, e.g., buffered saline and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of an antigen binding site of the present invention in these formulations can vary widely, and will be selected primarily based on fluid volumes, viscosities, body weight and the like in accordance with the particular mode of administration selected and the patient's needs. Exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives.

Upon formulation, an antigen binding site of the present invention will be administered in a manner compatible with the dosage formulation and in such amount as is therapeutically/prophylactically effective. Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, liposomal forms and the like. Pharmaceutical "slow release" capsules or compositions may also be used. Slow release formulations are generally designed to give a constant drug level over an extended period and may be used to deliver an antigen binding site of the present invention.

WO2002/080967 describes compositions and methods for administering aerosolized compositions comprising antibodies for the treatment of, e.g., asthma, which are also suitable for administration of an antigen binding site of the present invention.

Dosages and Administration

Suitable dosages of an antigen binding site of the present invention will vary depending on the specific an antigen binding site and/or the subject being treated. It is within the ability of a skilled physician to determine a suitable dosage, e.g., by commencing with a sub-optimal dosage and incrementally modifying the dosage to determine an optimal or useful dosage. Alternatively, to determine an appropriate dosage for treatment/prophylaxis, data from the cell culture assays or animal studies are used, wherein a suitable dose is within a range of circulating concentrations that include the $ED_{50}$ of the active compound with little or no toxicity. The dosage may vary within this range depending upon the dosage form employed and the route of administration utilized. A therapeutically/prophylactically effective dose can be estimated initially from cell culture assays. A dose may be formulated in animal models to achieve a circulating plasma concentration range that includes the $IC_{50}$ (i.e., the concentration or amount of the compound which achieves a half-maximal inhibition of symptoms) as determined in cell culture. Such information can be used to more accurately determine useful doses in humans. Levels in plasma maybe measured, for example, by high performance liquid chromatography.

In some examples, a method of the present invention comprises administering a prophylactically or therapeutically effective amount of a protein described herein.

The term "therapeutically effective amount" is the quantity which, when administered to a subject in need of treatment, improves the prognosis and/or state of the subject and/or that reduces or inhibits one or more symptoms of a clinical condition described herein to a level that is below that observed and accepted as clinically diagnostic or clinically characteristic of that condition. The amount to be administered to a subject will depend on the particular characteristics of the condition to be treated, the type and stage of condition being treated, the mode of administration, and the characteristics of the subject, such as general health, other diseases, age, sex, genotype, and body weight. A person skilled in the art will be able to determine appropriate dosages depending on these and other factors. Accordingly, this term is not to be construed to limit the present invention to a specific quantity, e.g., weight or amount of protein(s), rather the present invention encompasses any amount of the antigen binding site(s) sufficient to achieve the stated result in a subject.

As used herein, the term "prophylactically effective amount" shall be taken to mean a sufficient quantity of a protein to prevent or inhibit or delay the onset of one or more detectable symptoms of a clinical condition. The skilled artisan will be aware that such an amount will vary depending on, for example, the specific antigen binding site(s) administered and/or the particular subject and/or the type or severity or level of condition and/or predisposition (genetic or otherwise) to the condition. Accordingly, this term is not to be construed to limit the present invention to a specific quantity, e.g., weight or amount of antigen binding site(s), rather the present invention encompasses any amount of the antigen binding site(s) sufficient to achieve the stated result in a subject.

Kits

The present invention additionally comprises a kit comprising one or more of the following:

(i) an antigen binding site of the invention or expression construct(s) encoding same;
(ii) a cell of the invention;
(iii) a complex of the invention; or
(iii) a pharmaceutical composition of the invention.

In the case of a kit for detecting HIV-1 Env, the kit can additionally comprise a detection means, e.g., linked to an antigen binding site of the invention.

In the case of a kit for therapeutic/prophylactic use, the kit can additionally comprise a pharmaceutically acceptable carrier.

Optionally a kit of the invention is packaged with instructions for use in a method described herein according to any example.

TABLE 1

Summary of amino acid and nucleotide sequences

| Antibody or protein ID | Region | SEQ ID NO: | Amino acid or nucleotide sequence |
|---|---|---|---|
| H 1842 | CDRH1 (protein) | 1 | DKAVG |
| | CDRH2 (protein) | 2 | SIDTGGNADYNPGLKS |

TABLE 1-continued

Summary of amino acid and nucleotide sequences

| Antibody or protein ID | Region | SEQ ID NO: | Amino acid or nucleotide sequence |
|---|---|---|---|
| | CDRH3 (protein) | 3 | VHQKTLRSCPSDYPYICDCEDTGSHCCRATNCP YYCNHGRDRMCTGRTYTYEWHVEA |
| | CDRH1 (DNA) | 4 | GACAAGGCTGTAGGC |
| | CDRH2 (DNA) | 5 | AGTATAGACACTGGCGGAAACGCAGATTATAA CCCAGGCCTGAAATCC |
| | CDRH3 (DNA) | 6 | GTGCACCAGAAGACACTCCGTAGTTGTCCTTC TGATTATCCTTATATTTGTGATTGTGAAGATACT GGTAGTCATTGCTGTCGGGCTACTAATTGTCC TTATTACTGCAATCATGGCCGTGATCGTATGTG TACCGGTCGTACTTACACGTACGAGTGGCACG TCGAAGCC |
| | FRH1 (protein) | 7 | KVQLQESGPSLVKPSQTLSLTCTASGFSLS |
| | FRH2 (protein) | 8 | WVRQAPGQALEWLG |
| | FRH 3 (protein) | 9 | RLSITKDNAKSQVSLSVSSVTTEGSATYYCST |
| | FRH 4 (protein) | 10 | WGQGLLVTVSS |
| | FRH 1 (DNA) | 11 | AAGGTGCAGCTGCAGGAGTCGGGCCCCAGCC TGGTGAAGCCGTCACAGACCCTCTCGCTCACC TGCACGGCCTCTGGATTCTCATTGAGC |
| | FRH 2 (DNA) | 12 | TGGGTCCGCCAGGCTCCAGGGCAGGCGCTGG AGTGGCTCGGT |
| | FRH 3 (DNA) | 13 | CGGCTCAGCATCACCAAGGATAACGCCAAGAG CCAAGTCTCTCTGTCAGTAAGCAGCGTGACAA CTGAGGGCTCGGCCACGTATTACTGTTCTACT |
| | FRH 4 (DNA) | 14 | TGGGGCCAGGGACTCCTGGTCACCGTCTCCT CA |
| | VH (protein) | 15 | KVQLQESGPSLVKPSQTLSLTCTASGFSLSDKAV GWVRQAPGQALEWLGSIDTGGNADYNPGLKSR LSITKDNAKSQVSLSVSSVTTEGSATYYCSTVHQ KTLRSCPSDYPYICDCEDTGSHCCRATNCPYYC NHGRDRMCTGRTYTYEWHVEAWGQGLLVTVSS |
| | VH (DNA) | 16 | AAGGTGCAGCTGCAGGAGTCGGGCCCCAGCC TGGTGAAGCCGTCACAGACCCTCTCGCTCACC TGCACGGCCTCTGGATTCTCATTGAGCGACAA GGCTGTAGGCTGGGTCCGCCAGGCTCCAGGG CAGGCGCTGGAGTGGCTCGGTAGTATAGACA CTGGCGGAAACGCAGATTATAACCCAGGCCTG AAATCCCGGCTCAGCATCACCAAGGATAACGC CAAGAGCCAAGTCTCTCTGTCAGTAAGCAGCG TGACAACTGAGGGCTCGGCCACGTATTACTGT TCTACTGTGCACCAGAAGACACTCCGTAGTTG TCCTTCTGATTATCCTTATATTTGTGATTGTGAA GATACTGGTAGTCATTGCTGTCGGGCTACTAA TTGTCCTTATTACTGCAATCATGGCCGTGATCG TATGTGTACCGGTCGTACTTACACGTACGAGT GGCACGTCGAAGCCTGGGGCCAGGGACTCCT GGTCACCGTCTCCTCA |
| H 1872 | CDRH1 (protein) | 17 | DKAVG |
| | CDRH2 (protein) | 18 | TIDTTGNAVYNPGLKS |
| | CDRH3 (protein) | 19 | VHQKTRRSCPSDYSFICDCEGTGSHCCRASNCP YYCNYGRDRMCTGRSNIHEWHVDA |
| | CDRH1 (DNA) | 20 | GACAAGGCTGTAGGC |
| | CDRH2 (DNA) | 21 | ACTATAGACACTACTGGAAACGCAGTCTATAAC CCAGGCCTGAAATCC |

TABLE 1-continued

Summary of amino acid and nucleotide sequences

| Antibody or protein ID | Region | SEQ ID NO: | Amino acid or nucleotide sequence |
|---|---|---|---|
| | CDRH3 (DNA) | 22 | GTGCACCAGAAGACACGTCGCAGTTGTCCTTC TGATTATAGTTTCATTTGTGATTGTGAAGGTAC TGGCAGTCATTGCTGTCGGGCTTCTAATTGTC CTTATTACTGCAATTACGGCCGTGATCGTATGT GTACGGGCAGGAGTAACATTCACGAATGGCAC GTCGATGCC |
| | FRH1 (protein) | 23 | KVQLRESGPSLVKPSQTLSLTCTASGFSLS |
| | FRH2 (protein) | 24 | WVRQAPGQPLEWLG |
| | FRH3 (protein) | 25 | RLSITKDNSKSQVSLSLSSVTTEDSATYHCST |
| | FRH4 (protein) | 26 | WGQGLLVTVSS |
| | FRH1 (DNA) | 27 | AAGGTGCAGCTGCGGGAGTCGGGCCCCAGCC TGGTGAAGCCGTCACAGACCCTCTCGCTCACC TGCACAGCCTCTGGATTCTCATTGAGC |
| | FRH2 (DNA) | 28 | TGGGTTCGCCAGGCTCCAGGGCAGCCGCTGG AGTGGCTCGGT |
| | FRH3 (DNA) | 29 | CGGCTCAGCATCACCAAGGATAACTCCAAGAG CCAGGTCTCTCTGTCACTAAGCAGCGTGACAA CTGAGGACTCGGCCACATATCACTGTTCTACT |
| | FRH4 (DNA) | 30 | TGGGGCCAAGGTCTCCTGGTCACCGTCTCCTCA |
| | VH (protein) | 31 | KVQLRESGPSLVKPSQTLSLTCTASGFSLSDKAV GWVRQAPGQPLEWLGTIDTTGNAVYNPGLKSRL SITKDNSKSQVSLSLSSVTTEDSATYHCSTVHQK TRRSCPSDYSFICDCEGTGSHCCRASNCPYYCN YGRDRMCTGRSNIHEWHVDAWGQGLLVTVSS |
| | VH (DNA) | 32 | AAGGTGCAGCTGCGGGAGTCGGGCCCCAGCC TGGTGAAGCCGTCACAGACCCTCTCGCTCACC TGCACAGCCTCTGGATTCTCATTGAGCGACAA GGCTGTAGGCTGGGTTCGCCAGGCTCCAGGG CAGCCGCTGGAGTGGCTCGGTACTATAGACAC TACTGGAAACGCAGTCTATAACCCAGGCCTGA AATCCCGGCTCAGCATCACCAAGGATAACTCC AAGAGCCAGGTCTCTCTGTCACTAAGCAGCGT GACAACTGAGGACTCGGCCACATATCACTGTT CTACTGTGCACCAGAAGACACGTCGCAGTTGT CCTTCTGATTATAGTTTCATTTGTGATTGTGAA GGTACTGGCAGTCATTGCTGTCGGGCTTCTAA TTGTCCTTATTACTGCAATTACGGCCGTGATCG TATGTGTACGGGCAGGAGTAACATTCACGAAT GGCACGTCGATGCCTGGGGCCAAGGTCTCCT GGTCACCGTCTCCTCA |
| 2129 | CDRH1 (protein) | 33 | DKAVG |
| | CDRH2 (protein) | 34 | SIDTGGNAGYNPGLKS |
| | CDRH3 (protein) | 35 | VHQKTRRSCPVDYYYSCDCEGSGSHCCSASNC PYYCKYGRDRVCTDKHTYSYEWYVDA |
| | CDRH1 (DNA) | 36 | GACAAGGCTGTAGGC |
| | CDRH2 (DNA) | 37 | AGTATAGACACTGGTGGAAACGCAGGCTATAA CCCAGGCCTGAAATCC |
| | CDRH3 (DNA) | 38 | GTGCACCAGAAGACACGACGTAGTTGTCCTGT TGATTATTATTATAGTTGCGACTGTGAAGGTAG TGGTAGTCATTGTTGCTCGGCTTCTAATTGTCC TTATTACTGCAAGTATGGCCGTGATAGAGTTTG TACTGACAAACATACTTACAGTTACGAATGGTA CGTCGATGCC |
| | CDRL1 (protein) | 39 | SGSSSNVGNGYVS |
| | CDRL2 (protein) | 40 | GDTSRAS |

TABLE 1-continued

Summary of amino acid and nucleotide sequences

| Antibody or protein ID | Region | SEQ ID NO: | Amino acid or nucleotide sequence |
|---|---|---|---|
| | CDRL3 (protein) | 41 | ASAEDGSSNAV |
| | CDRL1 (DNA) | 42 | TCTGGAAGCAGCAGCAATGTTGGAAATGGATA TGTGAGC |
| | CDRL2 (DNA) | 43 | GGTGACACCAGTCGAGCCTCG |
| | CDRL3 (DNA) | 44 | GCATCTGCTGAGGATGGTAGCAGTAATGCTGTT |
| | FRH1 (protein) | 45 | KVQLRESGPSLVKPSQTLSLTCTASGFSLS |
| | FRH2 (protein) | 46 | WVRQAPGKALEWLG |
| | FRH3 (protein) | 47 | RLSITKGNSKSQVSLSVSSVTTEDSATYYCST |
| | FRH4 (protein) | 48 | WGQGLLVTVSS |
| | FRH1 (DNA) | 49 | AAGGTGCAGCTGCGGGAGTCGGGCCCCAGCC TGGTGAAGCCGTCACAGACCCTCTCGCTCACC TGCACGGCCTCTGGATTCTCATTAAGC |
| | FRH2 (DNA) | 50 | TGGGTCCGCCAGGCTCCAGGGAAGGCGCTGG AGTGGCTCGGT |
| | FRH3 (DNA) | 51 | CGGCTCAGCATCACCAAGGGTAACTCCAAGAG CCAAGTCTCTCTGTCAGTGAGTAGCGTGACGA CTGAGGACTCGGCCACATATTACTGTTCTACT |
| | FRH4 (DNA) | 52 | TGGGGCCAGGGACTCCTGGTCACCGTCTCCTCA |
| | FRL1 (protein) | 53 | QAVLTQPSSVSGSLGQRVSTTC |
| | FRL2 (protein) | 54 | WYQLIPGSAPRTLIY |
| | FRL3 (protein) | 55 | GVPDRFSGSRSGNTVTLTISSLQAEDEADYFC |
| | FRL4 (protein) | 56 | FGRGTTLTVV |
| | FRL1 (DNA) | 57 | CAGGCTGTGCTGACTCAGCCATCATCCGTGTC CGGGTCCCTGGGCCAGAGGGTCTCCACCACC TGC |
| | FRL2 (DNA) | 58 | TGGTACCAACTGATTCCAGGATCGGCCCCCAG AACCCTCATCTAT |
| | FRL3 (DNA) | 59 | GGGGTCCCCGACCGATTCTCCGGCTCCAGGT CTGGGAACACAGTCACCCTGACCATCAGCTCG CTCCAGGCTGAGGACGAGGCAGATTATTTCTGC |
| | FRL4 (DNA) | 60 | TTCGGCAGAGGGACCACACTGACAGTCGTC |
| | VH (protein) | 61 | KVQLRESGPSLVKPSQTLSLTCTASGFSLSDKAV GWVRQAPGKALEWLGSIDTGGNAGYNPGLKSR LSITKGNSKSQVSLSVSSVTTEDSATYYCSTVHQ KTRRSCPVDYYYSCDCEGSGSHCCSASNCPYY CKYGRDRVCTDKHTYSYEWYVDAWGQGLLVTVSS |
| | VH (DNA) | 62 | AAGGTGCAGCTGCGGGAGTCGGGCCCCAGCC TGGTGAAGCCGTCACAGACCCTCTCGCTCACC TGCACGGCCTCTGGATTCTCATTAAGCGACAA GGCTGTAGGCTGGGTCCGCCAGGCTCCAGGG AAGGCGCTGGAGTGGCTCGGTAGTATAGACAC TGGTGGAAACGCAGGCTATAACCCAGGCCTGA AATCCCGGCTCAGCATCACCAAGGGTAACTCC AAGAGCCAAGTCTCTCTGTCAGTGAGTAGCGT GACGACTGAGGACTCGGCCACATATTACTGTT CTACTGTGCACCAGAAGACACGACGTAGTTGT CCTGTTGATTATTATTATAGTTGCGACTGTGAA GGTAGTGGTAGTCATTGTTGCTCGGCTTCTAAT TGTCCTTATTACTGCAAGTATGGCCGTGATAGA GTTTGTACTGACAAACATACTTACAGTTACGAA TGGTACGTCGATGCCTGGGGCCAGGGACTCC TGGTCACCGTCTCCTCA |

TABLE 1-continued

Summary of amino acid and nucleotide sequences

| Antibody or protein ID | Region | SEQ ID NO: | Amino acid or nucleotide sequence |
|---|---|---|---|
| | VL (protein) | 63 | QAVLTQPSSVSGSLGQRVSTTCSGSSSNVGNG YVSWYQLIPGSAPRTLIYGDTSRASGVPDRFSGS RSGNTVTLTISSLQAEDEADYFCASAEDGSSNAV FGRGTTLTV |
| | VL (DNA) | 64 | AATTCGCAGGCTGTGCTGACTCAGCCATCATC CGTGTCCGGGTCCCTGGGCCAGAGGGTCTCC ACCACCTGCTCTGGAAGCAGCAGCAATGTTGG AAATGGATATGTGAGCTGGTACCAACTGATTC CAGGATCGGCCCCCAGAACCCTCATCTATGGT GACACCAGTCGAGCCTCGGGGGTCCCCGACC GATTCTCCGGCTCCAGGTCTGGGAACACAGTC ACCCTGACCATCAGCTCGCTCCAGGCTGAGGA CGAGGCAGATTATTTCTGCGCATCTGCTGAGG ATGGTAGCAGTAATGCTGTTTTCGGCAGAGGG ACCACACTGACAGTC |
| Gp120 (protein) | | 65 | MRVKEKYQHLWRWGWKWGTMLLGILMICSATE KLWVTVYYGVPVWKEATTTLFCASDAKAYDTEV HNVWATHACVPTDPNPQEVVLENVTENFNMWK NNMVEQMHEDIISLWDQSLKPCVKLTPLCVTLNC TDLRNVTNINNSSEGMRGEIKNCSFNITTSIRDKV KKDYALFYRLDVVPIDNDNTSYRLINCNTSTITQA CPKVSFEPIPIHYCTPAGFAILKCKDKKFNGTGPC KNVSTVQCTHGIRPVVSTQLLLNGSLAEEEVVIR SSNFTDNAKNIIVQLKESVEINCTRPNNNTRKSIHI GPGRAFYTTGDIIGDIRQAHCNISRTKWNNTLNQI ATKLKEQFGNNKTIVFNQSSGGDPEIVMHSFNC GGEFFYCNSTQLFNSTWNFNGTWNLTQSNGTE GNDTITLPCRIKQIINMWQEVGKAMYAPPIRGQIR CSSNITGLILTRDGGNNHNNDTETFRPGGGDMR DNWRSELYKYKVVKIEPLGVAPTKAKRRVVQRET |
| Gp140 (protein) | | 66 | MRVKEKYQHLWRWGWKWGTMLLGILMICSATE KLWVTVYYGVPVWKEATTTLFCASDAKAYDTEV HNVWATHACVPTDPNPQEVVLENVTENFNMWK NNMVEQMHEDIISLWDQSLKPCVKLTPLCVTLNC TDLRNVTNINNSSEGMRGEIKNCSFNITTSIRDKV KKDYALFYRLDVVPIDNDNTSYRLINCNTSTITQA CPKVSFEPIPIHYCTPAGFAILKCKDKKFNGTGPC KNVSTVQCTHGIRPVVSTQLLLNGSLAEEEVVIR SSNFTDNAKNIIVQLKESVEINCTRPNNNTRKSIHI GPGRAFYTTGDIIGDIRQAHCNISRTKWNNTLNQI ATKLKEQFGNNKTIVFNQSSGGDPEIVMHSFNC GGEFFYCNSTQLFNSTWNFNGTWNLTQSNGTE GNDTITLPCRIKQIINMWQEVGKAMYAPPIRGQIR CSSNITGLILTRDGGNNHNNDTETFRPGGGDMR DNWRSELYKYKVVKIEPLGVAPTKAKRRVVQRE TGAVGTIGAMFLGFLGAAGSTMGAASITLTVQAR LLLSGIVQQQNNLLRAIEAQQHLLQLTVWGIKQL QARVLAVERYLRDQQLLGIWGCSGKLICTTAVP WNASWSNKSLEQIWNNMTWMEWDREINNYTSL IHSLIEESQNQQEKNEQELLELDKWASLWNWFNI TNWLWYIK |
| Gp160 (protein) | | 67 | MKVKGIRKNYQHLWKWGIMLLGMLMICSAVENL WVTVYYGVPVWKEATTTLFCASDAKAYDTEVHN VWATHACVPTDPNPQEVVLENVTENFNMWKNN MVEQMHEDIISLWDQSLKPCVKLTPLCVTLNCTD LRNVTNINNSSEGMRGEIKNCSFNITTSIRDKVKK DYALFYRLDVVPIDNDNTSYRLINCNTSTITQACP KVSFEPIPIHYCTPAGFAILKCKDKKFNGTGPCKN VSTVQCTHGIRPVVSTQLLLNGSLAEEEVVIRSS NFTDNAKNIIVQLKESVEINCTRPNNNTRKSIHIGP GRAFYTTGDIIGDIRQAHCNISRTKWNNTLNQIAT KLKEQFGNNKTIVFNQSSGGDPEIVMHSFNCGG EFFYCNSTQLFNSTWNFNGTWNLTQSNGTEGN DTITLPCRIKQIINMWQEVGKAMYAPPIRGQIRCS SNITGLILTRDGGNNHNNDTETFRPGGGDMRDN WRSELYKYKVVKIEPLGVAPTKAKRRVVQREKR AVGTIGAMFLGFLGAAGSTMGAASITLTVQARLL LSGIVQQQNNLLRAIEAQQHLLQLTVWGIKQLQA RVLAVERYLRDQQLLGIWGCSGKLICTTAVPWN ASWSNKTLDMIWNNMTWMEWEREIDNYTGLIYT |

TABLE 1-continued

| Antibody or protein ID | Region | SEQ ID NO: | Amino acid or nucleotide sequence |
|---|---|---|---|

Summary of amino acid and nucleotide sequences

| Antibody or protein ID | Region | SEQ ID NO: | Amino acid or nucleotide sequence |
|---|---|---|---|
| | | | LIEESQNQQEKNEQELLELDKWASLWNWFDITN WLWYIKIFIMIVGGLIGLRIVFTVLSIVNRVRQGYS PSLFQTHLPAPRGPDRPEGIEEEGGDRDRDRSV RLVDGFLALFWDDLRSLCLFSYHRLRDLLLIVARI VELLGRRGWEALKYWWNLLQYWSQELRNSAVS LLNATAIAVAEGTDRVIEIVQRIYRAILHIPTRIRQG LERLLL |
| SOSIP gp140 (protein) | | 68 | MRVKEKYQHLWRWGWKWGTMLLGILMICSATE KLWVTVYYGVPVWKEATTTLFCASDAKAYDTKV HNVWATHACVPTDPNPQEVVLENVTENFNMWK NNMVEQMHEDIISLWDQSLKPCVKLTPLCVTLNC TDLRNVTNINNSSEGMRGEIKNCSFNITTSIRDKV KKDYALFYRLDVVPIDNDNTSYRLINCNTSTITQA CPKVSFEPIPIHYCTPAGFAILKCKDKKFNGTGPC KNVSTVQCTHGIRPVVSTQLLLNGSLAEEEVVIR SSNFTDNAKNIIVQLKESVEINCTRPNNNTRKSIHI GPGRWFYTTGDIIGDIRQAHCNISRTKWNNTLNQ IATKLKEQFGNNKTIVFNQSSGGDPEIVMHSFNC GGEFFYCNSTQLFNSTWNFNGTWNLTQSNGTE GNDTITLPCRIKQIINMWQEVGKAMYAPPIRGQIR CSSNITGLILTRDGGNNHNNDTETFRPGGGDMR DNWRSELYKYKVVKIEPLGVAPTKCKRRVVQRE KRAVGTIGAMFLGFLGAAGSTMGAASMTLTVQA RNLLSGIVQQQNNLLRAPEAQQHLLQLTVWGIKQ LQARVLAVERYLRDQQLLGIWGCSGKLICCTAVP WNASWSNKSLEQIWNNMTWMEWDREINNYTSL IHSLIEESQNQQEKNEQELLELASGLNDIFEAQKI EWHE |
| Trimer gp140 (ConM SOSIP) (protein) | | 69 | MRVMGIQRNCQHLWRWGILIFGMLMICSAAENL WVTVYYGVPVWKEANTTLFCASDAKAYDTEVHN VWATHACVPTDPNPQEIVLENVTENFNMWKNN MVEQMHEDIISLWDQSLKPCVKLTPLCVTLNCTD VNATNNSTNMGEIKNCSFNITTEIRDKKQKVYALF YRLDVVPINDNSYRLINCNTSAITQACPKVSFEPI PIHYCAPAGFAILKCNDKKFNGTGPCKNVSTVQC THGIKPVVSTQLLLNGSLAEEEIIIRSENITDNAKTII VQLNESVEINCTRPNNNTRKSIRIGPGQAFYATG DIIGDIRQAHCNISGAEWNKTLQQVAAKLREHFN NKTIIFKPSSGGDLEITTHSFNCGGEFFYCNTSGL FNSTWNGTNETITLPCRIKQIVNMWQRVGQAMY APPIAGNITCKSNITGLLLTRDGGTNNTETFRPGG GDMRDNWRSELYKYKVVKIEPLGVAPTKAKRRV VEREKRAVGIGAVFLGFLGAAGSTMGAASITLTV QARQLLSGIVQQQSNLLRAIEAQQHLLQLTVWGI KQLQARVLAVERYLKDQQLLGIWGCSGKLICTTN VPWNSSWSNKSQDEIWDNMTWMQWEREISNY TDIIYSLIEESQNQQEKNEQDLLALDKWASLWNW FDITNWLWYIKIFIMIVGGLIGLRIVFAVLSIVNRVR QGYSPLSFQTLIPNPRGPDRPGGIEEEGGEQDR DRSIRLVSGFLALAWDDLRSLCLFSYHRLRDFILI AARTVELLGRRGWEALKYLWNLLQYWGQELKN SAISLLDTTAIAVAEGTDRVIEVVQRACRAILHIPR RIRQGFERALL |
| VRCO1 VH (protein) | | 70 | QVQLVQSGGQMKKPGESMRISCRASGYEFIDCT LNWIRLAPGKRPEWMGWLKPRGGAVNYARPLQ GRVTMTRDVYSDTAFLELRSLTVDDTAVYFCTR GKNCDYNWDFEHWGRGTPVIVSS |
| VRCO1 VL (protein) | | 71 | EIVLTQSPGTLSLSPGETAIISCRTSQYGSLAWYQ QRPGQAPRLVIYSGSTRAAGIPDRFSGSRWGPD YNLTISNLESGDFGVYYCQQYEFFGQGTKVQVDIK |
| NC-COW1 VH (protein) | | 72 | QVQLRESGPSLMKPSQTLSLTCTVSGSSLNDKS VGWVRQAPGKALQWLGSVDTSGNTDYNPGLKS RLSITKDNSKSRISLTVTGMTTEDSATYYCITAHQ KTNKKECPEDYTYNPRCPQQYGWSDCDCMGD RFGGYCRQDGCSNYIHRSTYEWYVSAWGQGLL VTVSS |

TABLE 1-continued

Summary of amino acid and nucleotide sequences

| Antibody or protein ID | Region | SEQ ID NO: | Amino acid or nucleotide sequence |
|---|---|---|---|
| NC-COW1<br>VL (protein) | | 73 | HSYELTQPSSVSGSLGQRVSVTCSGSSSNVGN<br>GYVSWYQLIPGSAPRTIIYGDTSRASGVPERFSG<br>SRSGNTATLTISSLQAEDEADFFCASPDDSSSNA<br>VFGSGTTLTVL |
| NC-COW1<br>CDRL1<br>(protein) | | 74 | SGSSSNVGNGYVS |
| NC-COW1<br>CDRL2<br>(protein) | | 75 | GDTSRAS |
| NC-COW1<br>CDRL3<br>(protein) | | 76 | ASPDDSSSNAV |
| NC-COW1<br>FRL1<br>(protein) | | 77 | SYELTQPSSVSGSLGQRVSVTC |
| NC-COW1<br>FRL2<br>(protein) | | 78 | WYQLIPGSAPRTIIY |
| NC-COW1<br>FRL3<br>(protein) | | 79 | GVPERFSGSRSGNTATLTISSLQAEDEADFFC |
| NC-COW1<br>FRL4<br>(protein) | | 80 | FGSGTTLTVL |
| CDRH2<br>(protein) | | 81 | $\mathbf{X}_1$IDT$\mathbf{X}_2$GNA$\mathbf{X}_3$YNPGLKS<br>Wherein X1 = S or T; X2 = G or T; X3 = G, D or V |
| CDRH3<br>(protein | | 82 | VHQKT$\mathbf{X}_1$RSCP$\mathbf{X}_2$DY$\mathbf{X}_3\mathbf{X}_4\mathbf{X}_5$CDCE$\mathbf{X}_6\mathbf{X}_7$GSHCC$\mathbf{X}_8$<br>A$\mathbf{X}_9$NCPYYC$\mathbf{X}_{10}\mathbf{X}_{11}$GRDR$\mathbf{X}_{12}$CT$\mathbf{X}_{13}\mathbf{X}_{14}$X$\mathbf{X}_{15}\mathbf{X}_{16}\mathbf{X}_{17}\mathbf{X}_{18}$<br>$\mathbf{X}_{19}$EW$\mathbf{X}_{20}$V$\mathbf{X}_{21}$A<br>wherein X1 = R or L; X2 = S or V; X3 = P, S or Y;<br>X4 = Y or F; X5 = I or S; X6 = G or D; X7 = T or S;<br>X8 = R or S; X9 = S or T; X10 = N or K;<br>X11 = Y or H; X12 = M or V; X13 = G or D; X14 = R<br>or K; X15= H or no amino acid at this position;<br>X16 = T or S; X17 = Y or N; X18 = T, I or S;<br>X19 = Y or H; X20 = H or Y; X21 = D or E. |
| CDRL1<br>(protein) | | 83 | SGSSSNVGNGYVS |
| CDRL2<br>(protein) | | 84 | GDTSRAS |
| CDRL3<br>(protein) | | 85 | AS$\mathbf{X}_1\mathbf{X}_2$D$\mathbf{X}_3$SSNAV<br>wherein X1 = A or P; X2 = E or D; X3 = G or S. |
| KNH664<br>(protein) | | 86 | TVYYGVPVWKDAETTLFCASDAKAYETEKHNVW<br>ATHACVPTDPNPQEIPLENVTEEFNMWKNKMVE<br>QMHTDIISLWDQSLQPCVKLTPLCVTLNCTDATN<br>GTIGNITDEMKGEIKNCSFNITTEIRDKKQKVYSLF<br>YRLDVVPIEPDSSNSSRNSSEYRLINCNTSAITQA<br>CPKVSFEPIPIHYCAPAGFAILKCRDKEFNGTGKC<br>KNVSTVQCTHGIKPVVSTQLLLNGSLAEGEVRIR<br>SENITNNAKTIIVQLVEPVRINCTRPNNNTRESVRI<br>GPGQAFFATGDIIGDIRQAHCNVSRSQWNKTLQ<br>QVAAQLGEHFKNKAITFNSSSGGDLEITTHSFNC<br>GGEFFYCNTSGLFNSTWKANNGTWKANISESNN<br>TEITLQCRIKQIINMWQRTGQAIYAPPIQGVIRCES<br>NITGLLLTRDGGEGNNESEIFRPGGGDMRDNWR<br>SELYKYKVVKIEPLGVAPTRARRRVVGREKRAVG<br>IGAVFLGFLGAAGSTMGAASITLTVQARQLLSGIV<br>QQQSNLLRAIEAQQHMLKLTVWGIKQLQARVLA |

TABLE 1-continued

Summary of amino acid and nucleotide sequences

| Antibody or protein ID | Region | SEQ ID NO: | Amino acid or nucleotide sequence |
|---|---|---|---|
| | | | VERYLRDQQLLGIWGCSGKLICTTNVPWNSSWS NKSHDEIWNNMTWLQWDKEISNYTNLIYSLIEES QNQQEKNEQDLLALGSGSGSGSGHHHHHH |
| 1842 (IMGT) | CDRH1 (protein) | 87 | GFSLSDKA |
| | CDRH2 (protein) | 88 | IDTGGNA |
| | CDRH3 (protein) | 89 | STVHQKTLRSCPSDYPYICDCEDTGSHCCRATN CPYYCNHGRDRMCTGRTYTYEWHVEA |
| | CDRH1 (DNA) | 90 | GGATTCTCATTGAGCGACAAGGCT |
| | CDRH2 (DNA) | 91 | ATAGACACTGGCGGAAACGCA |
| | CDRH3 (DNA) | 92 | TCTACTGTGCACCAGAAGACACTCCGTAGTTG TCCTTCTGATTATCCTTATATTTGTGATTGTGAA GATACTGGTAGTCATTGCTGTCGGGCTACTAA TTGTCCTTATTACTGCAATCATGGCCGTGATCG TATGTGTACCGGTCGTACTTACACGTACGAGT GGCACGTCGAAGCC |
| | FRH1 (protein) | 93 | KVQLQESGPSLVKPSQTLSLTCTAS |
| | FRH2 (protein) | 94 | VGWVRQAPGQALEWLGS |
| | FRH 3 (protein) | 95 | DYNPGLKSRLSITKDNAKSQVSLSVSSVTTEGSATYYC |
| | FRH 4 (protein) | 96 | WGQGLLVTVSS |
| | FRH 1 (DNA) | 97 | AAGGTGCAGCTGCAGGAGTCGGGCCCCAGCC TGGTGAAGCCGTCACAGACCCTCTCGCTCACC TGCACGGCCTCT |
| | FRH 2 (DNA) | 98 | GTAGGCTGGGTCCGCCAGGCTCCAGGGCAGG CGCTGGAGTGGCTCGGTAGT |
| | FRH 3 (DNA) | 99 | GATTATAACCCAGGCCTGAAATCCCGGCTCAG CATCACCAAGGATAACGCCAAGAGCCAAGTCT CTCTGTCAGTAAGCAGCGTGACAACTGAGGGC TCGGCCACGTATTACTGT |
| | FRH 4 (DNA) | 100 | TGGGGCCAGGGACTCCTGGTCACCGTCTCCTCA |
| H 1872 (IMGT) | CDRH1 (protein) | 101 | GFSLSDKA |
| | CDRH2 (protein) | 102 | IDTTGNA |
| | CDRH3 (protein) | 103 | STVHQKTRRSCPSDYSFICDCEGTGSHCCRASN CPYYCNYGRDRMCTGRSNIHEWHVDA |
| | CDRH1 (DNA) | 104 | GGATTCTCATTGAGCGACAAGGCT |
| | CDRH2 (DNA) | 105 | ATAGACACTACTGGAAACGCA |
| | CDRH3 (DNA) | 106 | TCTACTGTGCACCAGAAGACACGTCGCAGTTG TCCTTCTGATTATAGTTTCATTTGTGATTGTGAA GGTACTGGCAGTCATTGCTGTCGGGCTTCTAA TTGTCCTTATTACTGCAATTACGGCCGTGATCG TATGTGTACGGGCAGGAGTAACATTCACGAAT GGCACGTCGATGCC |
| | FRH1 (protein) | 107 | KVQLRESGPSLVKPSQTLSLTCTAS |
| | FRH2 (protein) | 108 | VGWRQAPGQPLEWLGT |
| | FRH3 (protein) | 109 | VYNPGLKSRLSITKDNSKSQVSLSLSSVTTEDSA TYHC |
| | FRH4 (protein) | 110 | WGQGLLVTVSS |
| | FRH1 (DNA) | 111 | AAGGTGCAGCTGCGGGAGTCGGGCCCCAGCC TGGTGAAGCCGTCACAGACCCTCTCGCTCACC TGCACAGCCTCT |

TABLE 1-continued

Summary of amino acid and nucleotide sequences

| Antibody or protein ID | Region | SEQ ID NO: | Amino acid or nucleotide sequence |
|---|---|---|---|
| | FRH2 (DNA) | 112 | GTAGGCTGGGTTCGCCAGGCTCCAGGGCAGC<br>CGCTGGAGTGGCTCGGTACT |
| | FRH3 (DNA) | 113 | GTCTATAACCCAGGCCTGAAATCCCGGCTCAG<br><br>CATCACCAAGGATAACTCCAAGAGCCAGGTCT<br>CTCTGTCACTAAGCAGCGTGACAACTGAGGAC<br>TCGGCCACATATCACTGT |
| | FRH4 (DNA) | 114 | TGGGGCCAAGGTCTCCTGGTCACCGTCTCCTCA |
| 2129 (IMGT) | CDRH1 (protein) | 115 | GFSLSDKA |
| | CDRH2 (protein) | 116 | IDTGGNA |
| | CDRH3 (protein) | 117 | STVHQKTRRSCPVDYYYSCDCEGSGSHCCSAS<br>NCPYYCKYGRDRVCTDKHTYSYEWYVDA |
| | CDRH1 (DNA) | 118 | GGATTCTCATTAAGCGACAAGGCT |
| | CDRH2 (DNA) | 119 | ATAGACACTGGTGGAAACGCA |
| | CDRH3 (DNA) | 120 | TCTACTGTGCACCAGAAGACACGACGTAGTTG<br>TCCTGTTGATTATTATTATAGTTGCGACTGTGA<br>AGGTAGTGGTAGTCATTGTTGCTCGGCTTCTA<br>ATTGTCCTTATTACTGCAAGTATGGCCGTGATA<br>GAGTTTGTACTGACAAACATACTTACAGTTACG<br>AATGGTACGTCGATGCC |
| | FRH1 (protein) | 121 | KVQLRESGPSLVKPSQTLSLTCTAS |
| | FRH2 (protein) | 122 | VGWVRQAPGKALEWLGS |
| | FRH3 (protein) | 123 | GYNPGLKSRLSITKGNSKSQVSLSVSSVTTEDSA<br>TYYC |
| | FRH4 (protein) | 124 | WGQGLLVTVSS |
| | FRH1 (DNA) | 125 | AAGGTGCAGCTGCGGGAGTCGGGCCCCAGCC<br>TGGTGAAGCCGTCACAGACCCTCTCGCTCACC<br>TGCACGGCCTCT |
| | FRH2 (DNA) | 126 | GTAGGCTGGGTCCGCCAGGCTCCAGGGAAGG<br>CGCTGGAGTGGCTCGGTAGT |
| | FRH3 (DNA) | 127 | GGCTATAACCCAGGCCTGAAATCCCGGCTCAG<br>CATCACCAAGGGTAACTCCAAGAGCCAAGTCT<br>CTCTGTCAGTGAGTAGCGTGACGACTGAGGAC<br>TCGGCCACATATTACTGT |
| | FRH4 (DNA) | 128 | TGGGGCCAGGGACTCCTGGTCACCGTCTCCTCA |
| CDRH2 (protein; IMGT) | | 129 | IDT$\mathbf{X}_1$GNA<br>Wherein X1 = G or T |
| CDRH3 (protein; IMGT) | | 130 | STVHQKT$\mathbf{X}_1$RSCP$\mathbf{X}_2$DY$\mathbf{X}_3\mathbf{X}_4\mathbf{X}_5$CDCE$\mathbf{X}_6\mathbf{X}_7$GSHCC<br>$\mathbf{X}_8$A$\mathbf{X}_9$NCPYYC$\mathbf{X}_{10}\mathbf{X}_{11}$GRDR$\mathbf{X}_{12}$CT$\mathbf{X}_{13}\mathbf{X}_{14}\mathbf{X}_{15}\mathbf{X}_{16}\mathbf{X}_{17}$<br>$\mathbf{X}_{18}\mathbf{X}_{19}$EW$\mathbf{X}_{20}$V$\mathbf{X}_{21}$A<br>wherein X1 = R or L; X2 = S or V; X3 = P, S or Y; X4 = Y or F; X5 = I or S; X6 = G or D; X7 = T or S; X8 = R or S; X9 = S or T; X10 = N or K; X11 = Y or H; X12 = M or V; X13 = G or D; X14 = R or K; X15 = H or no amino acid at this position; X16 = T or S; X17 = Y or N; X18 = T, I or S; X19 = Y or H; X20 = H or Y; X21 = D or E. |
| | CDRL1 (protein) | 131 | SSNVGNGY |
| | CDRL2 (protein) | 132 | GDT |
| | CDRL3 (protein) | 133 | ASAEDGSSNAV |
| | CDRL1 (DNA) | 134 | AGCAGCAATGTTGGAAATGGATAT |
| | CDRL2 (DNA) | 135 | GGTGACACC |

TABLE 1-continued

| Summary of amino acid and nucleotide sequences | | | |
|---|---|---|---|
| Antibody or protein ID | Region | SEQ ID NO: | Amino acid or nucleotide sequence |
| | CDRL3 (DNA) | 136 | GCATCTGCTGAGGATGGTAGCAGTAATGCTGTT |
| | FRL1 (protein) | 137 | QAVLTQPSSVSGSLGQRVSTTCSGS |
| | FRL2 (protein) | 138 | VSWYQLIPGSAPRTLIY |
| | FRL3 (protein) | 139 | SRASGVPDRFSGSRSGNTVTLTISSLQAEDEADYFC |
| | FRL4 (protein) | 140 | FGRGTTLTVV |
| | FRL1 (DNA) | 141 | CAGGCTGTGCTGACTCAGCCATCATCCGTGTC CGGGTCCCTGGGCCAGAGGGTCTCCACCACC TGCTCTGGAAGC |
| | FRL2 (DNA) | 142 | GTGAGCTGGTACCAACTGATTCCAGGATCGGC CCCCAGAACCCTCATCTAT |
| | FRL3 (DNA) | 143 | AGTCGAGCCTCGGGGGTCCCCGACCGATTCT CCGGCTCCAGGTCTGGGAACACAGTCACCCT GACCATCAGCTCGCTCCAGGCTGAGGACGAG GCAGATTATTTCTGC |
| | FRL4 (DNA) | 144 | TTCGGCAGAGGGACCACACTGACAGTCGTC |

EXAMPLES

Example 1—Generation and Validation of Bovine BrNAbs

The inventors herein set out to generate and validate anti-HIV bovine BrNAbs as novel HIV therapeutic/prophylactic agents with utility as HIV vaccines.

Methods

Cow immunisation: Holstein Friesian cattle (*Bos taurus*) were vaccinated subcutaneously into the flank, using Seppic Montanide (ISA206) adjuvant. Female cows were immunised prior to and during pregnancy period and revaccinated after calving (FIG. 1A). Cow #617 received 100 μg KNH1 SOSIP.v1 or BG505 SOSIP 6R 664 trimer followed by 50 ug BG505 6R SOSIP 664 after calving. Cow #35 and #8434 received 500 ug AD8 uncleaved gp140 trimer during pregnancy while revaccinated with 50 μg BG505 SOSIP 6R 664 and 100 μg AD8 SOSIP 6R 664, respectively. Sera samples were collected after calving at week 54 (phase 1) and week 59 (phase 2). Peripheral blood mononuclear cells (PBMC) from each cow were also isolated from bloods collected after phase 1 and phase 2 as described previously (Heydarchi, B., et al. MAbs, 2017. 9(3): p. 550-566).

Serum ELISA and neutralization of sera samples: IgG titres in sera against autologous Env vaccine antigens were measured by direct ELISA, with incubations performed at room temperature (RT) except when stated. Casein buffer 1× (Sigma) was used as sample diluent for each step. Briefly, 96-well plates were coated with 1 μg/ml recombinant Env gp140 proteins (BG505 SOSIP gp140, AD8 Unc gp140) in coating buffer (200 mM Tris-HCl, 100 mM NaCl, pH 8.8) overnight at 4° C. The plate was washed four times with PBS+ 0.1% Tween and four times with PBS then blocked with casein buffer 1× (Sigma). Sera samples were added in half-$log_{10}$ dilutions and incubated for 3 hrs at RT. Afterward, 1/1000 dilution of HRP-conjugated sheep-anti-bovine IgG (BioRad, #AAI23P) was loaded and incubated for 1 hr at RT. Finally, color development was performed using TMB (Sigma, cat no: T5525) according to manufacturer instructions and the reaction was stopped using 1M $H_2SO_4$. Absorbance was measured at 450 nm against a reference of 690 nm.

For neutralization assay of sera samples, HIV-1 pseudoviruses were produced as described previously (Kramski, M., et al. Antimicrob Agents Chemother, 2012. 56(8): p. 4310-9; Montefiori, D. C. Curr Protoc Immunol, 2005. Chapter 12: p. Unit 12 11). Pseudoviruses were produced in HEK 293T cells by co-transfecting a backbone plasmid with one of Env expressing plasmids. TZM-bl neutralization assay was performed for sera samples collected pre-immunisation, at phase 1 (week 54) and phase 2 (week 59). The assay was performed as described previously (Montefiori, D. C., Curr Protoc Immunol, 2005. Chapter 12: p. Unit 12 11). Briefly, 50 μl of pseudovirus in complete DMEM (DMEM+10% FBS) (200 TCID50) was mixed with serial dilutions of serum samples in a final volume of 100 μl in 96-well plates (Corning, flat bottom, non-pyrogenic), and incubated for 1 hr at 37° C. Thereafter, $10^4$ TZM-bl cells (containing 125 mM of DEAE-Dextran (Sigma) was added to each well and plates were incubated for 72 hours at 37° C. Inhibition of infection was calculated by measuring relative luminescence units (RLUs) using Britelite plus (PerkinElmer) in a FLUOstar Omega (BMG Labtech) plate reader. ID50 neutralizing antibody titers are expressed as the reciprocal of the sample dilution required to reduce RLU by 50%.

HIV-1 Env Production, Expression and Purification:

Vaccine proteins including HIV-1 NL AD8 (AD8) Unc gp140 Env (clade B) was expressed using stably-transfected Hela cells line and AD8 6R SOSIP.664 were produced by transient transfection of HeLa and HEK 293T cells Center, R. J., et al., Vaccine, 2009. 27(47): p. 6605-6612) or Expi293 cells. KNH1144 SOSIP gp140 (clade A) produced as in (Kang, Y., et al., Vaccine, 2009. 27(37): p. 5120-5132), and BG505 SOSIP gp140 (clade A). Proteins were purified with lentil-lectin column and size exclusion chromatography as previously described (Sanders, R. W., et al., PLoS Pathog, 2013. 9(9): p. e1003618; and Center, R. J., et al., Vaccine, 2009. 27(47): p. 6605-12).

AD8 SOSIP gp140 v4.1 was produced using an Env-expression plasmid encoding the Env from NL(AD8) (Freed, E. O., G. Englund, and M. A. Martin, J Virol, 1995. 69(6): p. 3949-54) modified according to the "v4.1" mutations described previously (de Taeye, S. W., et al., Cell, 2015. 163(7): p. 1702-15) with either a C-terminal D7324 epitope tag or AviTag. Proteins were expressed in Expi293F cells by co-transfecting the Env-expression plasmid with a human furin protease expression plasmid. Env was purified from culture supernatant using a 2G12-sepharose affinity resin (prepared by coupling anti-HIV-1 mAb 2G12 to CNBr-sepharose resin) and eluted using 3M $MgCl_2$. The Env was immediately buffer exchanged into PBS and trimeric Env was further purified by size exclusion chromatography using a HiLoad 16/600 Superdex prep grade column (GE Healthcare Life Sciences). For biotinylation of AviTag trimers, BirA enzyme was used according to manufacturer's instructions (Avidity, LLC).

Monomeric AD8 gp120 was also produced as described previously (Center, R. J., et al., Vaccine, 2009. 27(47): p. 6605-12; Center, R. J., et al. J Virol, 2000. 74(10): p. 4448-55; Gonelli, C. A., et al. Viruses, 2019. 11(6)). BG505 WT. SEKS (uncleaved gp140) was produced as described above for AD8 SOSIP gp140 protein, except that the Env expression plasmid (Ringe, R. P., et al. Proc Natl Acad Sci USA, 2013. 110(45): p. 18256-61) was not co-transfected with a furin expression plasmid.

Small-angle X-ray scattering: Small-angle X-ray scattering (SAXS) measurements were conducted at the Australian Synchrotron SAXS/WAXS Beamline equipped with a co-flow system to avoid radiation damage and enable higher X-ray flux (11,500 eV) and with an in-line size exclusion chromatography (SEC) to limit protein sample dilution (Kirby, N., et al., Acta Crystallogr D Struct Biol, 2016. 72(Pt 12): p. 1254-1266; Kirby, N. M., et al., J. Appl. Crystallogr, 2013. 46: p. 1670-1680; Ryan, T. M., et al., J. Appl. Crystallogr, 2018. 51: p. 97-111). Fifty microliters of the purified AD8 SOSIP (2 mg/ml) was injected over a precision Superose 6 5/150 increase column (GE Healthcare) equilibrated and eluted with PBS (pH 7.4) with a solution containing 1 mM EDTA and 0.2% sodium azide. The sample to detector length used was 3256 mm, providing a q range of 0.007-0.515 $Å^{-1}$. Collected SAXS data was reduced using the Sactterbrain software, analysed by CHROMIXS (Panjkovich, A. and D. I. Svergun, Bioinformatics, 2018. 34(11): p. 1944-1946), and the ATSAS 3.0.2 software package (Franke, D., et al. J Appl Crystallogr, 2017. 50(Pt 4): p. 1212-1225). SAXS patterns, the radius of gyration (Rg), the maximal particle dimension (Dmax), and the pairwise distance distribution histogram [P(r) plot] were analyzed by using the ATSAS software suite (PV, K., et al. Journal of Applied Crystallography, 2003. 36: p. 1277-1282). Ab initio modelling was performed using DAMMIF (Franke, D. and D. I. Svergun, J Appl Crystallogr, 2009. 42(Pt 2): p. 342-346) and the models were averaged by DAMAVER. A summary of the SAXS data acquisition parameters is provided in Table 2. The first 100 data points (before the void volume) were averaged as buffer scattering data and subtracted from the corresponding protein scattering data.

TABLE 2

| SAXS data collection parameters | |
|---|---|
| Instrument/source | Australian Synchrotron SAXS/WAXS beamline equipped with Pilatus 1M detector and sheath-flow cell for SEC-SAXS. |
| Wavelength (Å) | 1.0332 |
| Beam energy (kEv) | 12 |
| Beam size (μm) | 250 × 130 |
| Sample-to-detector distance (mm) | 1426 |
| q measurement range ($Å^{-1}$) | 0.005-0.300 |
| Absolute scaling method | Comparison with scattering from 1 mm pure water |
| Normalization | To transmitted intensity from beamstop counter |
| Exposure time | 1 s measurements from SEC-SAXS elution |
| Sample temperature (K) | 295 |
| SEC-SAXS parameters | |
| Column | Superdex 200 5 × 150 |
| Flow rate (mL/min) | 0.4 |
| Loading concentration (mg/mL) | 2 |
| Injection volume (μL) | 50 |
| Solvent | 20 mM Phosphate buffer, pH 7.4, 150 mM NaCl, 0.5 mM TCEP, 0.1% sodium azide |
| Software employed | |
| SAXS data reduction | I(q) vs q using Scatterbrain 2.8.2, SEC-SAXS solvent subtraction using CHROMIXS from ATSAS 2.8.3 |
| Basic analysis (Guinier, P(r), molecular mass) | PRIMUSqt from ATSAS 2.8.3 |
| Ab initio modelling | GASBOR, fitting to reciprocal space, models aligned and compared using DAMAVER and DAMCLUST from ATSAS 2.8.3 |
| Calculation of theoretical intensities | CRYSOL from ATSAS 2.8.3 |
| Atomic structure (hybrid) modelling | CORAL from ATSAS 2.8.3 |
| Structural parameters | |
| Mass from $V_c$ (kDa) (expected mass, ratio to expected in brackets) | 263.0 (232.2, 1.13) |

TABLE 2-continued

| SAXS data collection parameters | |
|---|---|
| Guinier analysis | |
| $R_g$ (Å) | 53.25 ± 0.16 |
| I(0) ($cm^{-1}$) | 0.13 ± 0.00025 |
| $qR_g$ min, max | 0.35, 1.29 |
| P(r) analysis | |
| $R_g$ (Å) | 53.31 ± 0.13 |
| I(0) ($cm^{-1}$) | 0.12 ± 0.00021 |
| $D_{max}$ (Å) | 174.59 |
| Porod volume ($Å^3$) | 905887.00 |
| Ab initio modelling DAMMIF (10 calculations, default parameters | |
| q range for fitting (Å) | 0.00955-0.1507 |
| Constant subtracted | $5.643 \times 10^{-5}$ |
| Symmetry, anisotropy assumptions | P3, none |
| Number of Shannon channels | 7.050 |
| $\chi^2$ range | 0.77-1.05 |
| NSD (standard deviations) | 0.797 |
| DAMMIN (default parameters) | |
| q range for fitting (Å) | 0.00955-0.1507 |
| Symmetry, anisotropy assumptions | P3, none |
| $\chi^2$ | 0.77 |
| Constant adjustment | $5.643 \times 10^{-5}$ |

Single Particle Negative Stain Electron Microscopy: Purified AD8 SOSIP v4.1 (100 ng/μl) was placed on glow-discharged carbon coated copper mesh grids and stained with 1% uranyl formate. Grids were screened for appropriate stain thickness and particle distribution and images were collected using an FEI Talos L120C electron microscope. Images were collected at 73,000× magnification with a −1.8 μm defocus for a final magnified pixel size of 1.9 Å/pix. Negatively stained AD8 particles were then automatically picked based on an empirical evaluation of maximum particle radius of 110 Å, characteristic particle radius of 80 Å, and with threshold peak high of 5 standard deviation above the noise using cisTEM software version 1.0.0-beta (Grant, T., A. Rohou, and N. Grigorieff, Elife, 2018. 7). Further, a 2D classification was performed on 38,000 particles in cisTEM that resulted in 50 classes. The initial model was generated ab initio using the data set and processed under the filter for particles from 20 Å to 8 Å in the first step of classification within cisTEM. Best 18 classes representing different orientations of AD8 were selected for further iterative 3D classification under C3 symmetry. This was followed by a local refinement and a final 3D refinement in cisTEM. UCSF Chimera was used to generate figures (Pettersen, E. F., et al. J Comput Chem, 2004. 25(13): p. 1605-12).

Figure 2A:
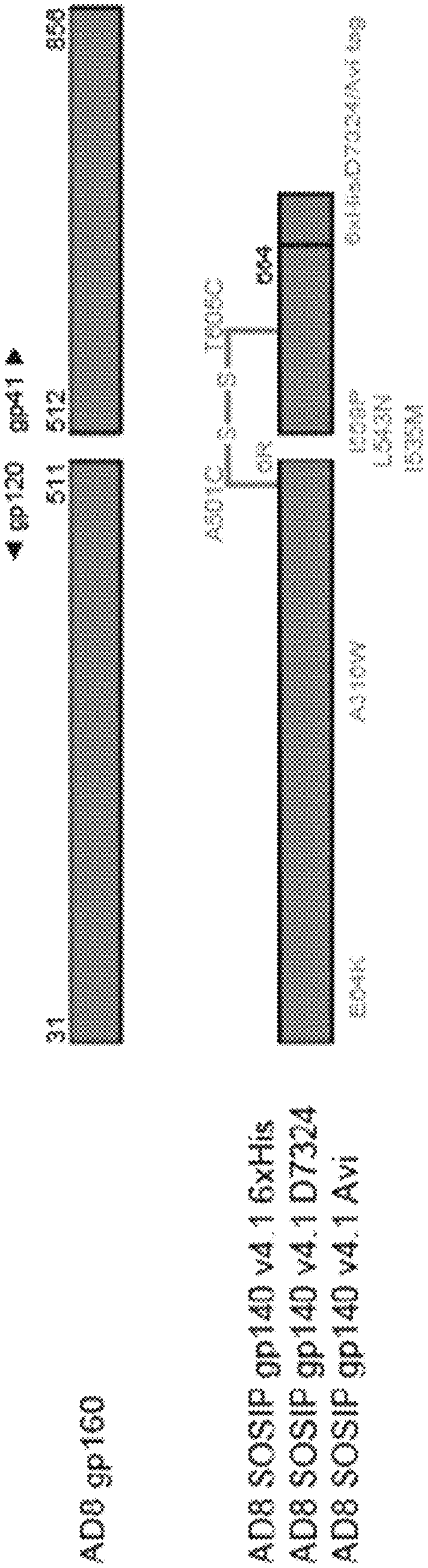
FIG. 2. Design and characterization of AD8 SOSIP trimers. (A) Linear representation of mature AD8 gp160, SOSIP gp140 v4.1 (with either a 6×His, D7324, or Avi tag at the C-terminus at position 664), and gp120. All Envs were expressed with their wild-type signal peptide. SOSIP v4.1 mutations were introduced as previously described (de Taeye, S. W., et al., Cell, 2015. 163(7): p. 1702-15). (B) SEC profile of 2G12-purified AD8 SOSIP gp140 v4.1 6×His run on a Superdex S200 16/600 column. (C) SDS-PAGE analysis using an 8-16% Tris-glycine gel of 3 separate lots (numbered 1-3) of 2G12/SEC purified 6×His-tagged AD8 SOSIP gp140 v4.1. Proteins were running with or without reducing agent. Lane M was loaded with Spectra Multicolor Broad Range Protein Ladder. (D) BN-PAGE analysis using a 4-16% Bis-Tris NativePAGE gel. Trimeric AD8 SOSIP gp140 v4.1 with Avi, 6×His (3 separate lots), or a D7324 tag were analysed as well as monomeric AD8 gp120. Lane M was loaded with NativeMark Unstained Protein Standard. For both (C) and (D), gels were stained with Coomassie Blue. Capture ELISA on AD8 SOSIP v4.1 His tag (E) and D7324 tag (F) using human BrNAbs. (G) Small angle x-ray scattering data; (H) Negative staining using 1% Uranyl Acetate on freshly glow discharged carbon coated copper grids. Images were taken on FEI Talos L120C microscope. Pixel size: 1.9 Å 73000× magnification. (I) 2D classes showing different views and (J) 3D volume map for AD8-SOSIP.
Figure 2B:
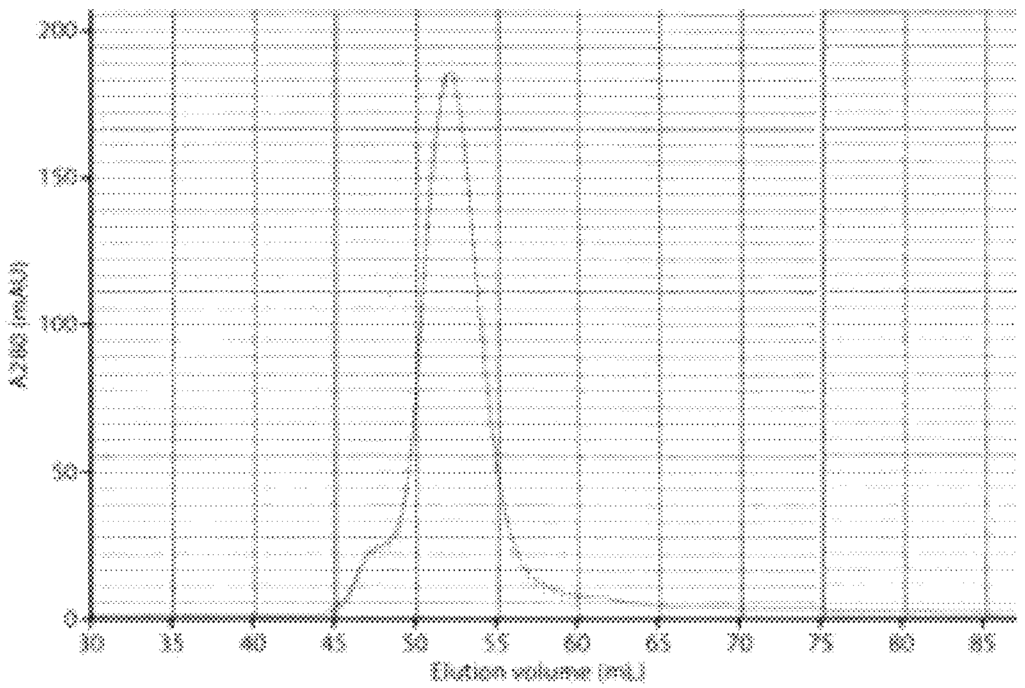
Figure 2C:
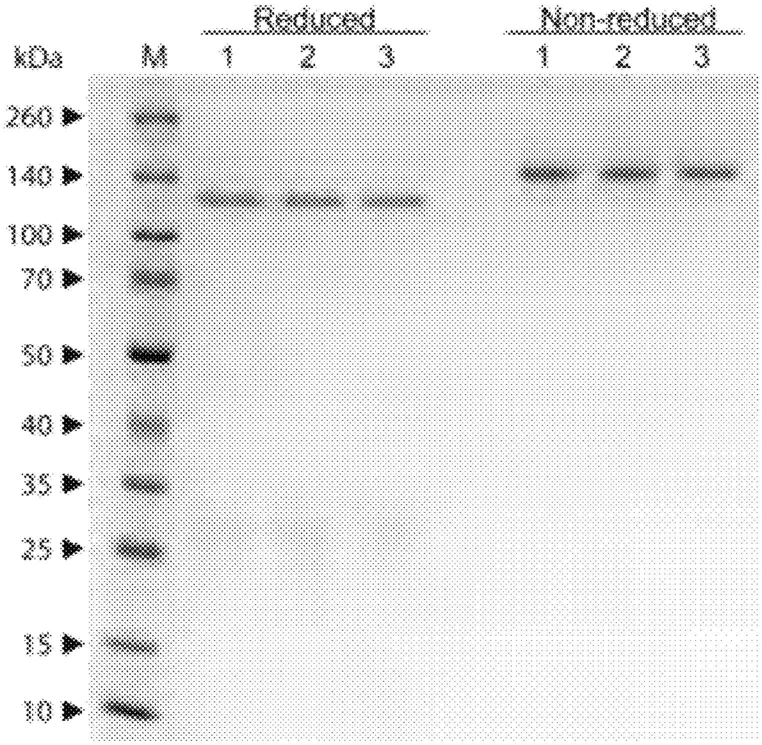
Figure 2D:
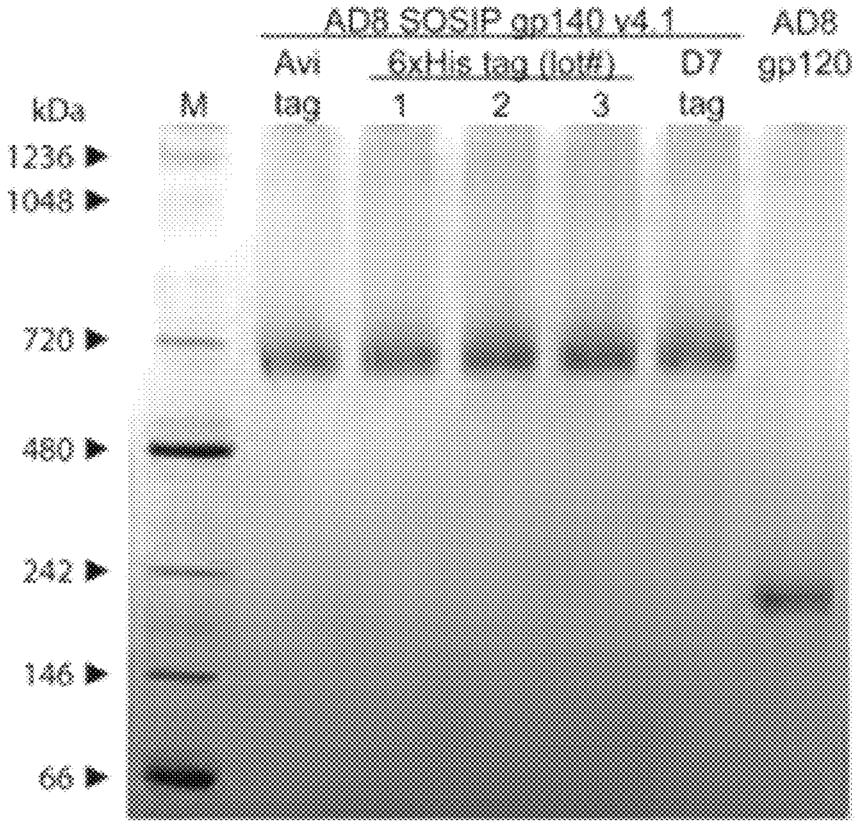
Figure 2E:
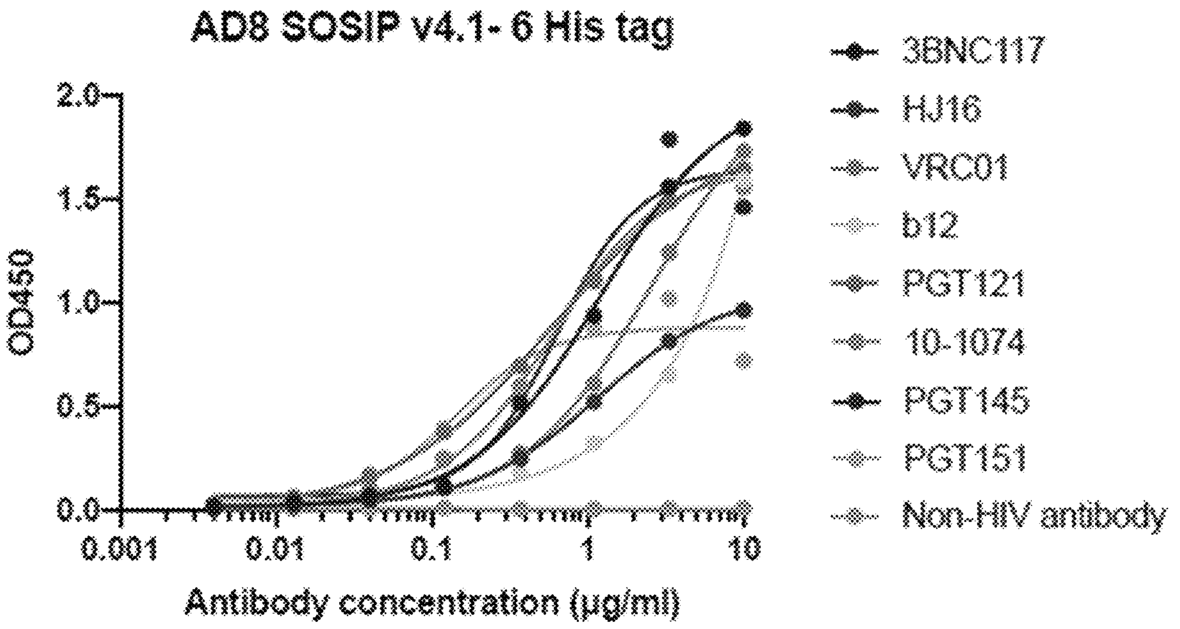
Figure 2F:
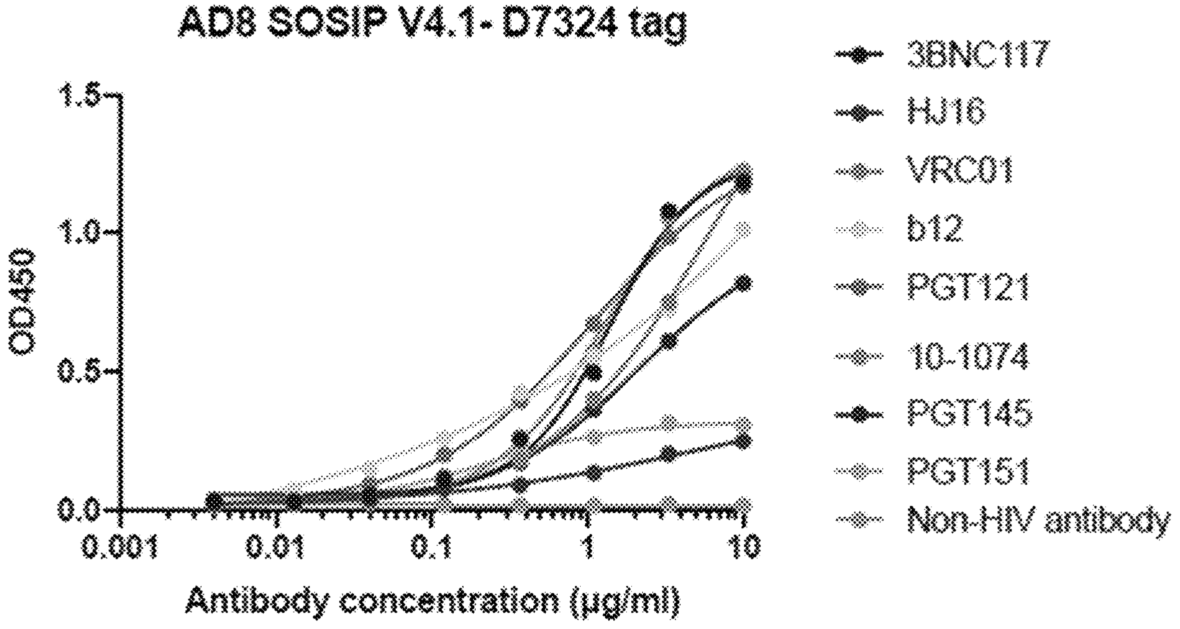
Figure 2G:
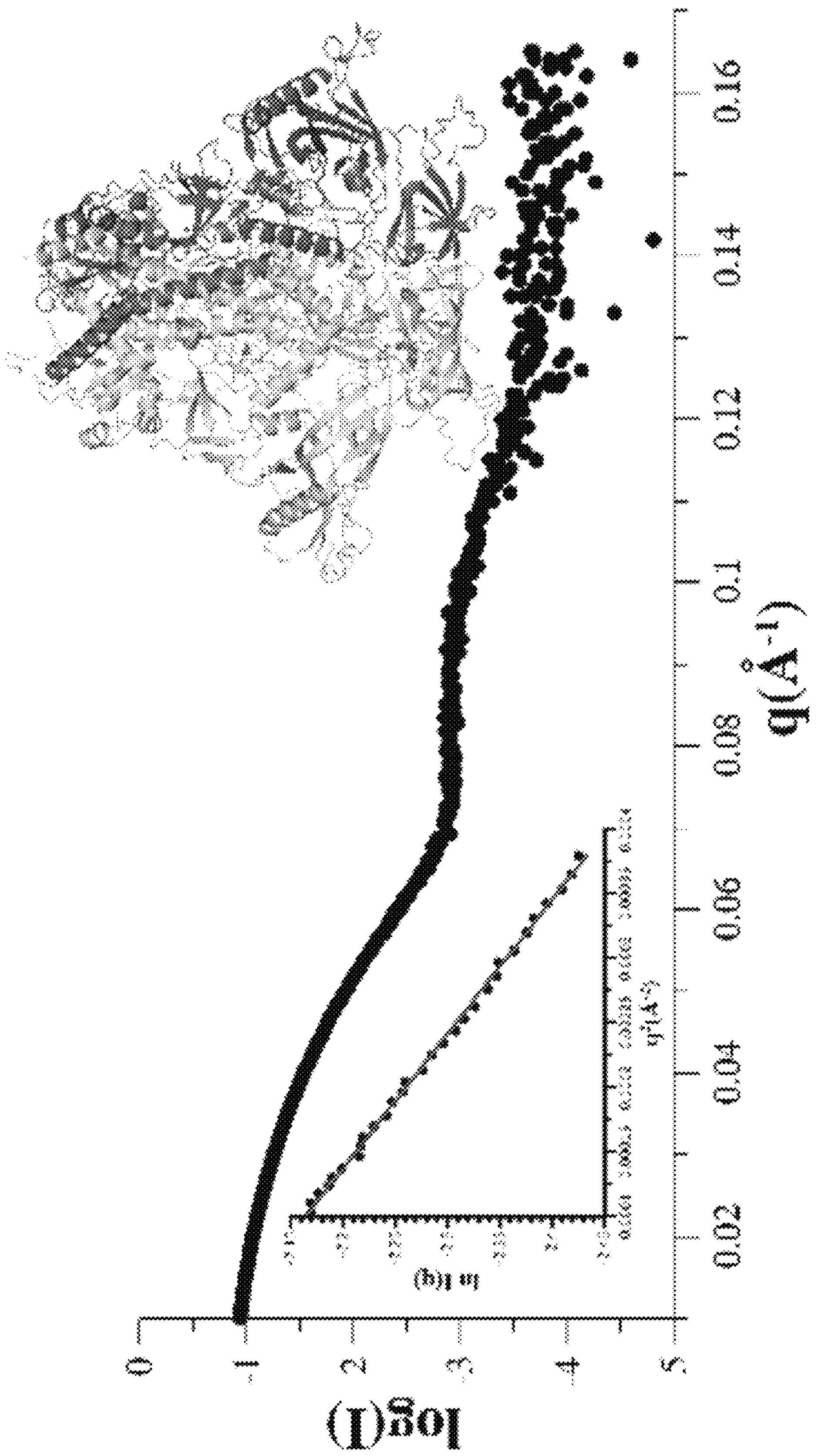
Figure 2H:
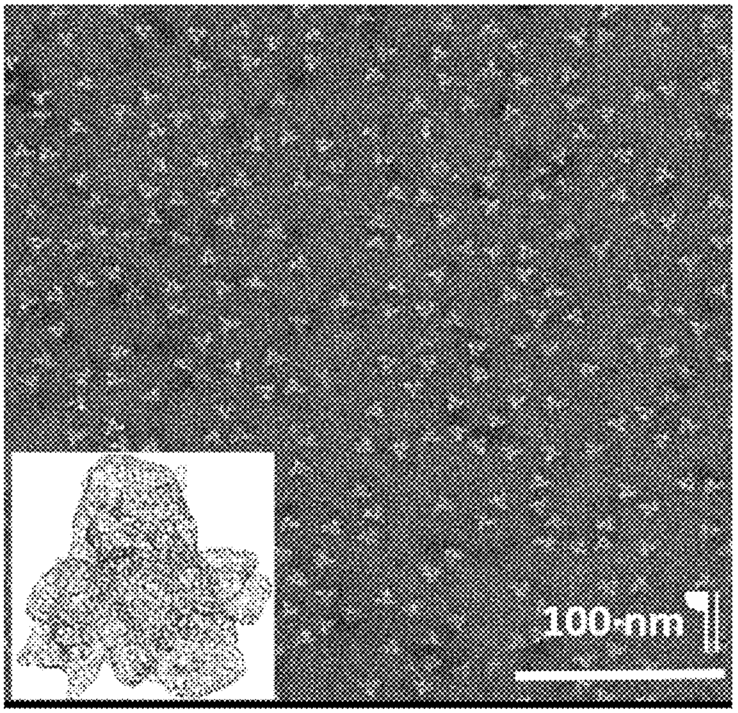
Figure 2I:
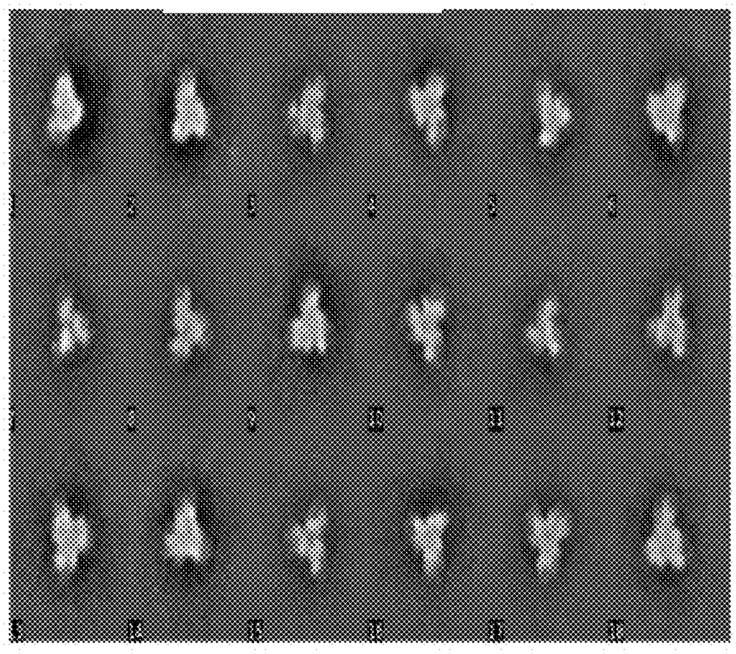
Figure 2J:
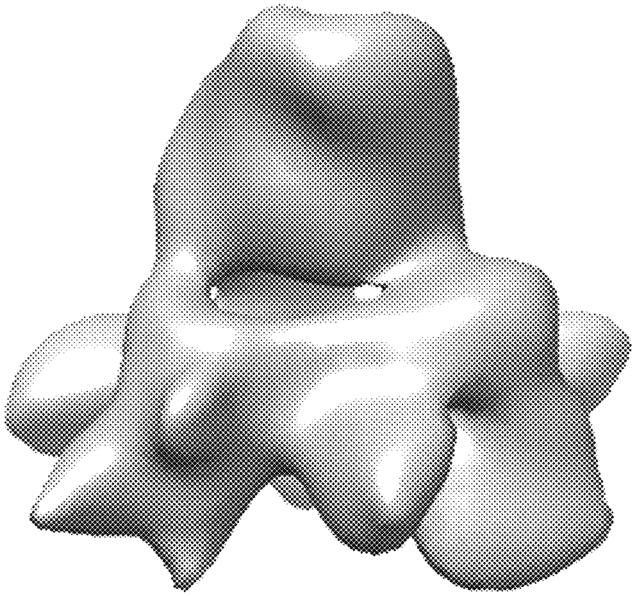

Single cell sorting by Fluorescence-Activated Cell Sorting (FACS): Sorting of bovine PBMC was performed as described previously (Heydarchi, B., et al., MAbs, 2017. 9(3): p. 550-566) with minor modifications (FIG. 2B). In brief, 2.5 million cryopreserved PBMC was thawed and resuspended in 10 ml pre-warmed 37° C. RPMI 1640 medium (Life technologies) (containing 10% FBS, 20 μg/ml or 10 U/ml DNaseI) for 5 minutes at room temperature followed by centrifugation at 500×g for 10 mins at 4° C. The cell were resuspend in chilled PBS and LIVE/DEAD™ Fixable Aqua Dead Cell Stain (Thermo Fisher Scientific) was added and incubated for 10 minutes on ice. PBMCs were then stained with Alexa-flour 488 conjugated anti-bovine IgG (Sigma, B6901) and 50 nM of biotinylated A8 SOSIP.v4.1-avi gp140 coupled to streptavidin-APC and PE (Life Technologies) in equimolar ratios. The cells were incubated for 1 hr at 4° C. in PBS containing 1 mM EDTA and 1% horse serum (Sigma). Then, IgG+ AD8 SOSIP gp140 v4.1-PE+/AD8 SOSIP gp140 v4.1-APC+cells were single-sorted into 96-well plates containing lysis buffer (3.7 μl/well PBS, 10 mM DTT and 8 U RNasin (Promega)) on an ARIA III sorter and were immediately frozen at −80° C.

Single cell cDNA synthesis, RT-PCR and cloning: cDNA was synthesized from mRNA of each single cell (Tiller, T., et al., Journal of Immunological Methods, 2008. 329(1-2): p. 112-124) and antibody variable genes were amplified as described previously (Heydarchi, B., et al., MAbs, 2017. 9(3): p. 550-566) with minor modifications. Briefly, antibody heavy gamma (γ) and light lambda (λ) variable genes were amplified independently in nested PCR using MyTaq HS Red Mix (Bioline) according to the manufacturer's instruction. The PCR reaction primers and conditions are listed in Table 3. PCR1 reactions were set up in 25 μl with 2.5 μl cDNA while volume of PCR2 reactions were 50 μl using 5 μl PCR1 product. The PCR reaction was performed as 94° C. 5 minutes, 50 cycles of 94° C. for 45 seconds, 60° C. for 45 seconds and 72° C. for 45 seconds and final extension at 72° C. for 10 minutes. The annealing temperature of PCR1 for lambda gene was 58° C. The amplified bovine VH/VL genes were cloned into the human constant heavy (CH) and constant light (CL) region expression vectors in pFUSEssCHIg-hG1 and pFUSE2ss-CLIg-hL2 (Invivogen), using EcoRI/NheI and EcoRI/AvrII restriction enzymes, respectively.

TABLE 3

| Primer code | SEQ ID NO: | Sequence 5'-3' | | PCR Reaction |
|---|---|---|---|---|
| Primers used for producing chimeric bovine-human full antibodies | | | | |
| odp 2569 | 145 | ATGAACCCACTGTGGACCCTC | Forward | H1 |
| odp 2570 | 146 | AGAACTCAGAGGGTAGACTTTCGG | Reverse | H1 |
| odp 3667 | 147 | CTTTCGGGGCTGTGGTGGAGGC | Reverse | H1 |
| odp 3668 | 148 | **GAATTC**GMAGGTGCAGCTGCRGGAGTC | Forward (EcoRI) | H2 |
| odp 2568 | 149 | **GCTAGC**TGAGGAGACGGTGACCAGGAG | Reverse (NheI) | H2 |
| odp 3670 | 150 | CACCATGGCCTGGTCCCCTCTG | Forward | L1 |
| odp 3671 | 151 | GACCCCAGACTCACCATCTC | Forward | L1 |
| odp 3672 | 152 | AGGGCTGCGGGCTCAGAAGGCAGC | Forward | L1 |
| odp 3673 | 153 | CTGCCCCTCCTCACTCTCTGC | Forward | L1 |
| odp 3674 | 154 | GGAACCTTTCCTGCAGCTC | Forward | L1 |
| odp 3675 | 155 | GCTTGCTTATGGCTCAGGTC | Forward | L1 |
| odp 2573 | 156 | ATGTCCACCATGGCCTGGTCC | Forward | L1 |
| odp 2574 | 157 | CTTGTTGCCGTTGAGCTCCTC | Reverse | L1 |
| odp 2571 | 158 | **GAATTC**GCAGGCTGTGCTGACTCAG | Forward (EcoRI) | L2 |
| odp 3677 | 159 | **CCTAGG**ACGACKGTCAGTGTGGTSCC | Reverse (AvrII) | L2 |
| odp 2781 | 160 | CTCAACTCTACGTCTTTGTTTC | Forward | Sequencing |

Restriction enzyme sites are in bold and the nucleotides inserted to keep the frame reading in the expression vector are in Italic and underlined. H: heavy chain, L: light chain. Reaction number shows whether the primer was used in nester RT-PCR reaction 1 or reaction 2.

Antibody production and purification: Antibody plasmids containing heavy chain and light chain genes were co-transfected (2:3 ratio) in Expi293F cells using Expifectamine (Thermo Fisher Scientific) according to manufacturer instructions. Supernatants containing antibodies were harvested 4 days after transfection and sterilised using 0.22 μm filters. Antibody supernatants were purified over Protein G Agarose Fast Flow (Merck Millipore). NC-Cow1 antibody was produced as an anti-HIV-1 bovine antibody control by codon optimisation of genes available from the GenBank (MF167446.1 and MF167436.1). Antibody supernatants were purified using Protein G Agarose Fast Flow (Merck Millipore). Antibodies were eluted from chromatography columns using 50 mM glycine (pH=2.7) and immediately neutralised by addition of 1/10 volume of 1 M Tris (pH=8.0) before being buffer exchanged into PBS, concentration using Amicon 50 kDa spin membranes (Millipore) and sterilization using 0.22 μm filters.

Generation of HIV-1 AD8 pseudovirus mutant: Specific amino acid changes to HIV-1 AD8 gp160 Env were introduced using the following PCR reaction set up: 100 ng Full-length AD8 gp160 Env plasmid, 5% Dimethyl sulfoxide (DMSO), 10 μl 5× Phusion Reaction buffer (New England BioLabs), 1 μl dNTP mix (10 mM, Promega), 3 U Phusion HF DNA Polymerase (New England BioLabs, (MEL-2000 units/ml)), 0.5 μl from each forward and Reverse primer (20 μM) (Table 4) and nuclease-free H2O up to the total volume of 50 μl. The PCR reaction was performed as following: 95° C. 5 min, 30 cycles of 95° C. 30 sec, 48° C. 30 sec, 72° C. 8 min and final extension of 72° C. 15 min. Mutations were confirmed by sequence analysis.

TABLE 4

Primers used for site directed mutagenesis of full length AD8 gp160 Env

| Primer code | SEQ ID NO: | Sequence 5'-3' | | Mutation |
|---|---|---|---|---|
| odp 3770 | 161 | cacaagaagtagtattgg**C**aaatgtgacaga | Forward | E87A |
| odp 3771 | 162 | attttctgtcacattt**G**ccaatactacttc | Reverse | E87A |
| odp 3772 | 163 | taaagccatgtgta**GC**attaaccccactctgtg | Forward | K121A |
| odp 3773 | 164 | acacagagtggggttaa**TGC**tacacatggc | Reverse | K121A |
| odp 3774 | 165 | aagactatgcactttttttataga**GC**tgatgtagtaccaatag | Forward | L179A |
| odp 3775 | 166 | tcattatctattggtactacatct**GC**tctataaaaaagtgcatag | Reverse | L179A |
| odp 3776 | 167 | ttgatgtagtaccaatag**C**taatgataatactagctatagg | Forward | D185A |
| odp 3777 | 168 | acctatagctagtattatcatta**G**ctattggtactaca | Reverse | D185A |
| odp 3778 | 169 | tataggttgataaattgt**GC**tacctcaaccattacacagg | Forward | N197A |
| odp 3779 | 170 | tgtgtaatggttgaggta**GC**acaatttatcaacctatagc | Reverse | N197A |
| odp 3782 | 171 | tcaactcaactgctgtta**GC**tggcagtctagc | Forward | N262A |
| odp 3783 | 172 | ttcttctgctagactgcca**GC**taacagcagttgag | Reverse | N262A |
| odp 3784 | 173 | agaggtagtaattagatctagt**GC**tttcacagacaatgc | Forward | N276A |
| odp 3785 | 174 | ttgcattgtctgtgaaa**GC**actagatctaattactacctc | Reverse | N276A |
| odp 3786 | 175 | tctagtaatttcacag**C**caatgcaaaaaacataatagtac | Forward | D279A |
| odp 3787 | 176 | atgtttttgcattg**G**ctgtgaaattactagatctaattactac | Reverse | D279A |
| odp 3788 | 177 | atttcacagacaatgca**GC**aaacataatagtacagttg | Forward | K282A |
| odp 3789 | 178 | aactgtactattatgtt**TGC**tgcattgtctgtgaaattac | Reverse | K282A |
| odp 3790 | 179 | ttcacagacaatgcaaaa**GC**cataatagtacagttg | Forward | N283A |
| odp 3791 | 180 | ttcaactgtactattat**GGC**ttttgcattgtctgtg | Reverse | N283A |
| odp 3792 | 181 | agtatacatatagga**G**caggaagagcattttatac | Forward | P313A |
| odp 3793 | 182 | tgttgtataaaatgctcttcctg**C**tcctatatgtatac | Reverse | P313A |
| odp 3794 | 183 | aggagatataagacaa**AA**acattgcaacattagtagaac | Forward | A329K |
| odp 3795 | 184 | ttgttctactaatgtt**TT**aatgtgcttgtcttatatctcc | Reverse | A329K |
| odp 3796 | 185 | aagacaagcacattgca**C**cattagtagaacaaaatgg | Forward | N332? |

TABLE 4-continued

Primers used for site directed mutagenesis of full length AD8 gp160 Env

| Primer code | SEQ ID NO: | Sequence 5'-3' | | Mutation |
|---|---|---|---|---|
| odp 3797 | 186 | tgttattccattttgttctactaatg**G**tgcaatgtgcttgtcttatatc | Reverse | N332T |
| odp 3800 | 187 | aataaaacaatagtctttaat**GC**atcctcaggaggggaccc | Forward | Q363A |
| odp 3801 | 188 | acaatttctgggtcccctcctgaggat**GC**attaaagactattgttttatt attccc | Reverse | Q363A |
| odp 3802 | 189 | aacaatagtctttaatcaa**G**cctcaggaggggacccagaaattg | Forward | S364A |
| odp 3803 | 190 | ttctgggtcccctcctgagg**C**ttgattaaagactattgttttattattcc | Reverse | S364A |
| odp 3804 | 191 | aatagtctttaatcaatcc**G**caggaggggacccagaaattgtaatgc | Forward | S365A |
| odp 3805 | 192 | aatttctgggtcccctcctg**C**ggattgattaaagactattgttttattatt cc | Reverse | S365A |
| odp 3806 | 193 | tagtctttaatcaatcctcag**C**aggggacccagaaattgtaatgc | Forward | G366A |
| odp 3807 | 194 | attacaatttctgggtcccct**G**ctgaggattgattaaagac | Reverse | G366A |
| odp 3808 | 195 | tagtctttaatcaatcctcaggag**C**ggacccagaaattgtaatgc | Forward | G367A |
| odp 3809 | 196 | tgcattacaatttctgggtcc**G**ctcctgaggattgattaaagac | Reverse | G367A |
| odp 3810 | 197 | ttaatcaatcctcaggagggg**C**cccagaaattgtaatgcac | Forward | D368A |
| odp 3811 | 198 | aactgtgcattacaatttctggg**G**cccctcctgaggattg | Reverse | D368A |
| odp 3812 | 199 | aatcaatcctcaggaggggac**G**cagaaattgtaatgcacag | Forward | P369A |
| odp 3813 | 200 | aactgtgcattacaatttctg**C**gtcccctcctgagg | Reverse | P369A |
| odp 3814 | 201 | aatcaatcctcaggaggggacccag**C**aattgtaatgcacag | Forward | E370A |
| odp 3815 | 202 | taaaactgtgcattacaatt**G**ctgggtcccctcctgagg | Reverse | E370A |
| odp 3816 | 203 | aatcctcaggaggggacccagaa**GC**tgtaatgcacagttttaattgtgg | Forward | 1371A |
| odp 3817 | 204 | aattaaaactgtgcattaca**GC**ttctgggtcccctcc | Reverse | 1371A |
| odp 3818 | 205 | atcaatcctcaggaggggacccagaaattg**C**aatgcacagttttaattgt gg | Forward | V372A |
| odp 3819 | 206 | ttcccctccacaattaaaactgtgcatt**G**caatttctgggtcccctcc | Reverse | V372A |
| odp 3820 | 207 | acccagaaattgta**GC**gcacagttttaattgtggaggg | Forward | M373A |
| odp 3821 | 208 | ttcccctccacaattaaaactgtgc**GC**tacaatttctggg | Reverse | M373A |
| odp 3822 | 209 | atgacactatcacactcccatgt**GC**aataaaacaaattataaacatgtg | Forward | R419A |
| odp 3823 | 210 | atgtttataatttgttttatt**GC**acatgggagtgtgatagtgtc | Reverse | R419A |

TABLE 4-continued

Primers used for site directed mutagenesis of full length AD8 gp160 Env

| Primer code | SEQ ID NO: | Sequence 5'-3' | | Mutation |
|---|---|---|---|---|
| odp 3824 | 211 | atattacagggctgatatta**G**caagagatggtggaaataacc | Forward | T455A |
| odp 3825 | 212 | ttgtggttatttccaccatctcttg**C**taatatcagccctg | Reverse | T455A |
| odp 3826 | 213 | tacagggctgatattaacaagag**C**tggtggaaataaccacaataatgatac | Forward | D457A |
| odp 3827 | 214 | ttgtggttatttccacca**G**ctcttgttaatatcagccctg | Reverse | D457A |
| odp 3828 | 215 | taccgagacctttagacctg**C**aggaggagatatgagggac | Forward | G471A |
| odp 3829 | 216 | ttgtccctcatatctcctcct**G**caggtctaaaggtctcgg | Reverse | G471A |
| odp 3830 | 217 | agacctttagacctggag**C**aggagatatgagggacaattgg | Forward | G472A |
| odp 3831 | 218 | attgtccctcatatctcct**G**ctccaggtctaaaggtctcgg | Reverse | G472A |
| odp 3832 | 219 | acctttagacctggaggag**C**agatatgagggacaattggag | Forward | G473A |
| odp 3833 | 220 | ttctccaattgtccctcatatct**G**ctcctccaggtctaaaggtctcgg | Reverse | G473A |
| odp 3834 | 221 | tagacctggaggaggag**C**tatgagggacaattggagaagtg | Forward | D474A |
| odp 3835 | 222 | ttctccaattgtccctcata**G**ctcctcctccaggtctaaagg | Reverse | D474A |
| odp 3836 | 223 | ttagacctggaggaggagat**GC**gagggacaattggagaagtg | Forward | M475A |
| odp 3837 | 224 | ttctccaattgtccctc**GC**atctcctcctccaggtctaaagg | Reverse | M475A |
| odp 3838 | 225 | tggaggaggagatatg**GC**ggacaattggagaagtg | Forward | R476A |
| odp 3839 | 226 | acttctccaattgtcc**GC**catatctcctcctccaggtctaaagg | Reverse | R476A |
| odp 1377 | 227 | ggtacataatgtttgggccac | Forward | Sequencing |
| odp 1379 | 228 | gctgttaaatggcagtctagc | Forward | Sequencing |
| odp 1441 | 229 | ctactgtaattcaacacaactg | Forward | Sequencing |

Nucleotides to be mutated are shown in capital letters and bold font.

ELISA assays of HIV-1 monoclonal antibodies: To screen HIV Env binding mAbs, ELISA plates were coated with 2 μg/ml D7324 Sheep Anti-gp120 (Aalto Bio Reagents) at 4° C. in 1×PBS overnight. Plates were washed 4× with PBS+0.1% tween and 2× with PBS, then blocked with 5% Skim milk in 1×PBS at room temperature for 1 hr. The plates were washed and 600 ng/ml D7324 tagged AD8 SOSIP gp140 v4.1 trimer was added and incubated for 1 hour at room temperature. Plates were washed and 1/1000 dilutions of goat anti-human IgG gamma HRP (KPL Cat No. 474-1002) (pre-incubated with 2% normal sheep serum) was added to the wells. The plate was incubated at room temperature for 1 h, washed then developed by adding SureBlue TMB (Australian Biosearch) according to the manufacturer's instructions. The absorbance was measured at 450 nm against a reference of 690 nm.

To assess the binding of mAbs to mutated HIV Env gp160, harvested pseudoviruses were lysed with 1× Triton X-100 detergent (Astral Scientific). The plates were coated with D7324 Sheep Anti-gp120, blocked with skim milk and lysed pseudoviruses were captured on ELISA for 2 hours at 37° C. Then serial dilutions of mAbs were added before addition of goat anti-human gamma HRP.

For experiments involving antibody binding to untagged HIV Env (monomeric AD8 gp120, AD8 uncleaved gp140, AD8 SOSIP gp140 v4.1 and ConM SOSIP gp140), plates were coated directly with 1 μg/ml Env proteins at 4° C. in 1×PBS overnight then washed and blocked before addition of mAbs and goat anti-human gamma HRP.

Competition ELISA: To investigate the epitopes of AD8 Env-binding mAbs, a competition ELISA was performed using competing antibodies that were biotinylated with EZ-Link Sulfo-NHS-LC-Biotin kit (Thermo Fisher Scientific). The plates were coated with 1/1000 dilution of anti-6×His antibody (Abcam #9108) and incubated overnight at 4° C. Then, the plates were washed and blocked with 5% skim milk in PBS+0.1% tween T (0.1%) for 1 hour at room temperature. Following washing, 500 ng/ml His-tagged AD8 SOSIP gp140 v4.1 trimer was added and the plates were incubated for 2 hours at room temperature. Then, bovine mAbs in the following amounts were added: 1 μg/ml (MEL-1842, MEL-1872, MEL-2129, MEL-2000, MEL-2028 and MEL-782), 2 μg/ml (MEL-2010, MEL-33, MEL-130, MEL-563 and MEL-663), and 5 μg/ml (MEL-1905, MEL-1967, MEL-2114, MEL-F2, MEL-198 and MEL-D1). After washing, the biotinylated human mAbs were added in the following amounts to give sufficient signal: 1 μg/ml (PGT121, PGT145, 10-1074, PGT151), 2 μg/ml (VRC01 and 3BNC117), 5 μg/ml (b12, HJ16). Then, 1/1000 dilutions of Streptavidin horse-radish peroxidase was added and incubated for 1 hour at room temperature followed by addition of SureBlue according to the manufacturer's instructions.

For self-competition of bovine BrNAbs, the assay was performed as above except using biotinylated bovine mAbs as the following amounts: 1 μg/ml for MEL-2028, MEL-2000, MEL-782, MEL-2129, MEL-1842, MEL-1872, 2 μg/ml for MEL-2010, MEL-33, MEL-130, MEL-563, 5 μg/ml for MEL-1905, MEL-1967, MEL-2114, MEL-F2, MEL-198 and MEL-D1.

Neutralization assays of anti-HIV-1 monoclonal antibodies: The neutralization assay of TZM-bl was performed as described previously (Heydarchi, B., et al., MAbs, 2017. 9(3): p. 550-566). Wild-type and single mutated HIV pseudoviruses were produced by co-transfection of full length Env expression plasmids and a proviral reporter plasmid (pNL-4.3DenvNefEGFP). Supernatant was harvested after 72 hours and sterile filtered through a 0.22 μm filter. Neutralization activity was measured by incubation of mAbs with pseudovirus for 1 hour at 37° C. before transferring onto TZM-bl cells.

Polyreactivity assays: HEp-2 cell staining assay. The HEp-2 cell-staining kit (Aesku Diagnostics) was used according to manufacturer's instructions. In brief, 2.5 μg of mAbs and controls were added to HEp-2 cell containing wells and incubated in a moist chamber at room temperature for 30 min. Slides were washed with PBS then 25 μl FITC-conjugated goat anti-human IgG was applied with incubation of 30 minutes at room temperature. The slide was washed and mounted on coverslips using the provided mounting medium. Slides were viewed at 20× magnification and imaged on the Zeiss LSM780 confocal microscope. All images were captured with the following conditions: digital gain 800, laser power 2.0%. Samples showing fluorescence greater than the negative control (provided by the vendor) were considered positive for HEp-2 staining.

Polyreactivity assay: Single autoantigen reactivity. Single antigen ELISA assays was performed using AESKULISA ANA-8Pro (Aesku) for U1-ribonucleoprotein (RNP), SnRNP/Sm, Sm, SS-A, SS-B, Jo-1, Scl-70, and CenpB. The 96 wells were coated with these cellular and nuclear antigens for the qualitative detection of mAbs reactivity. The cut-off calibrator, negative control and positive control were provided by the manufacturer.

Results

Figure 1B:
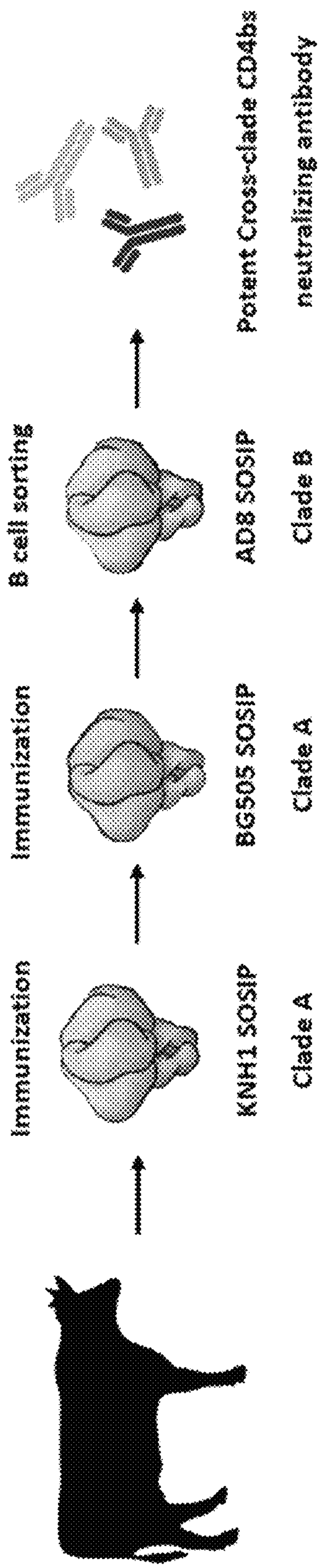
Figure 1C:
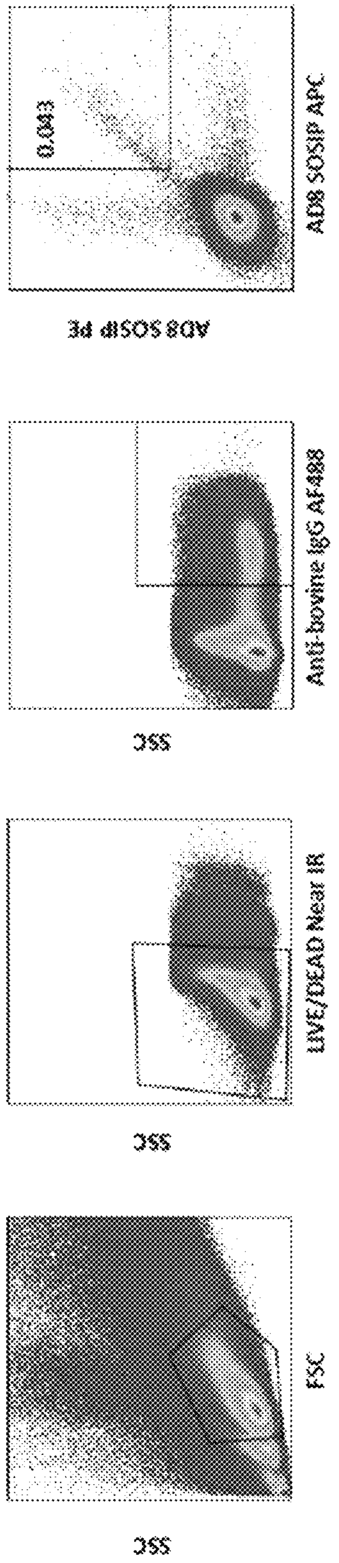
Figure 1D:
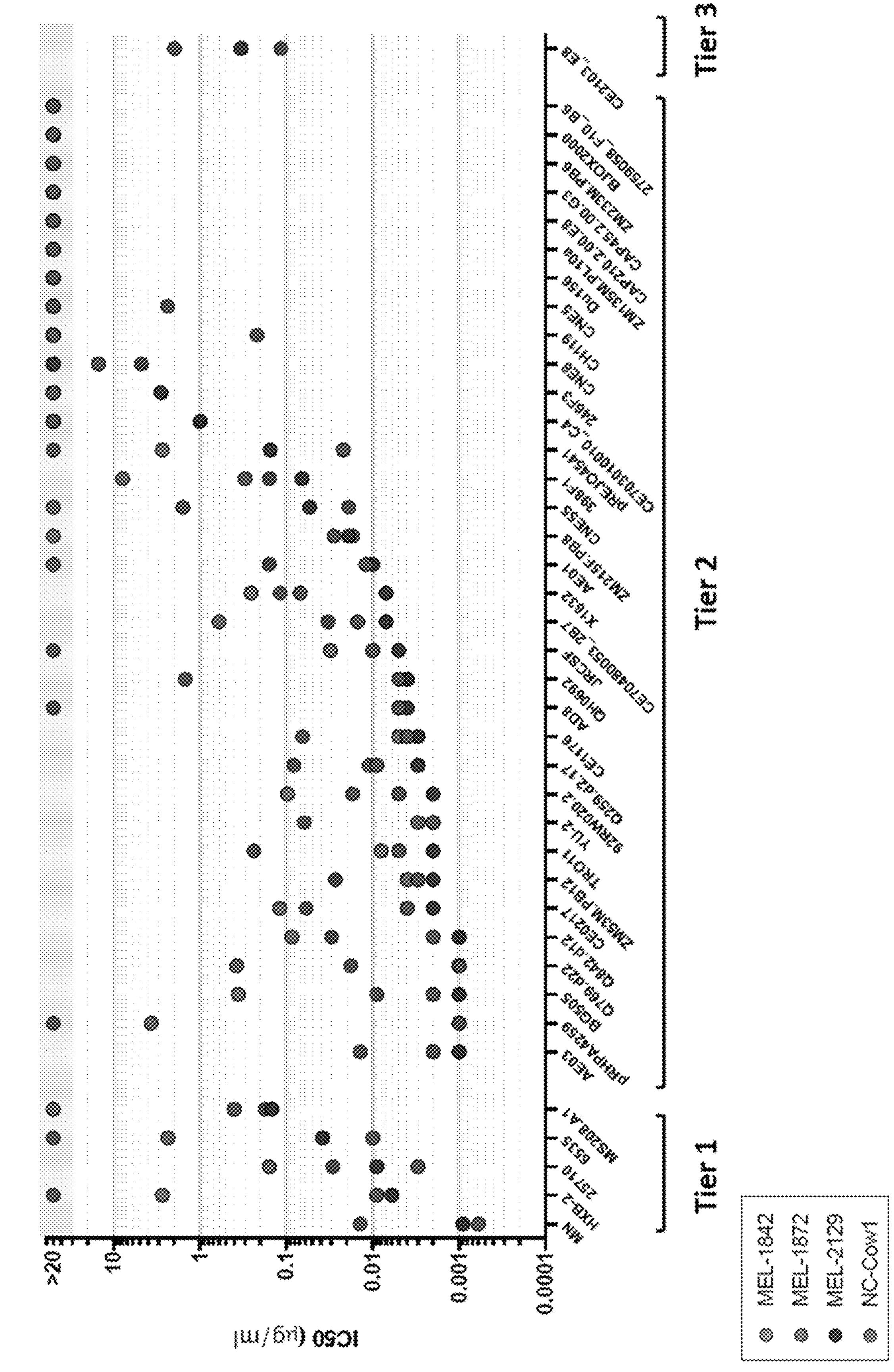
Figure 1E:
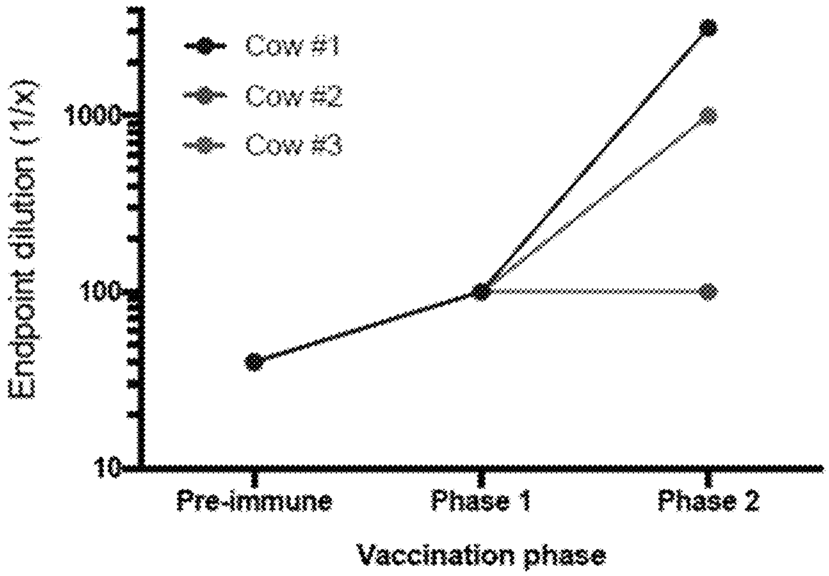
Figure 1F:
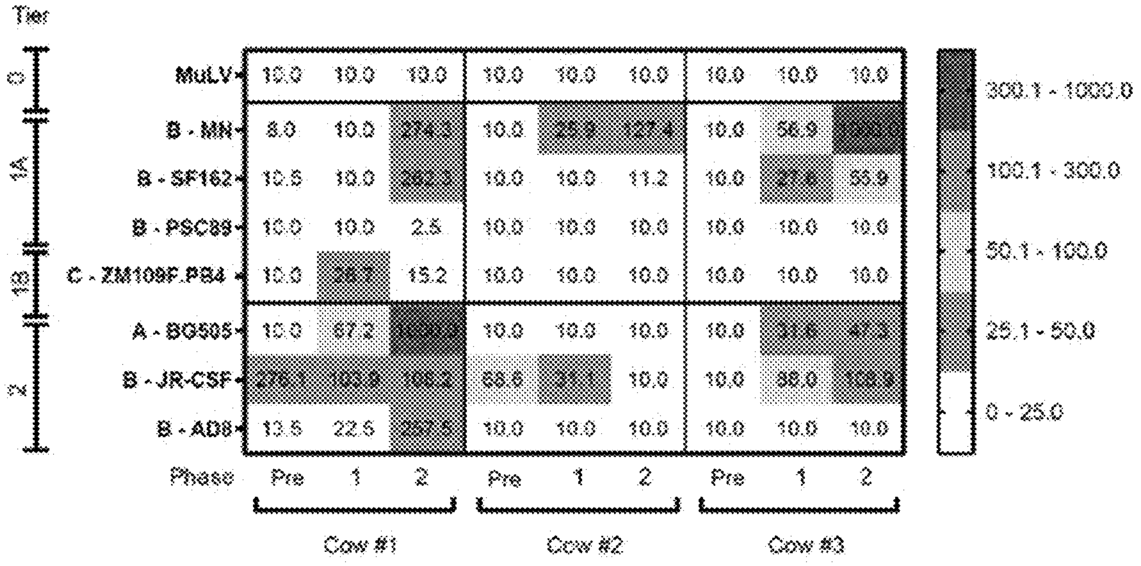

Serum binding and neutralization. Holstein Friesian cattle were vaccinated prior to, during and after pregnancy with different HIV Env proteins. In order to evaluate the antibody responses against HIV-1 vaccines, sera from different time-points were collected and binding of bovine IgGs to autologous Env immunogen was measured by direct ELISA (FIG. 1E). Pre-immune sera presented low binding while all samples at phase 1 presented binding titres of 100. At phase 2, re-vaccination with BG505 SOSIP gp140 in cow #1 (also referred to herein as cow #617) increased binding to above 3000, while changing the immunogen in cow #3 (from AD8 Unc gp140 on phase 1 to AD8 SOSIP gp140 on phase 2) showed a moderate increase in antibody titre (1000). Cow #2 on the other hand, did not show an improved antibody titer despite changing the immunogen from AD8 Unc gp140 at phase 1 to BG505 SOSIP gp140 at phase 2. Neutralizing activity of sera from vaccinated animals was also investigated in a neutralization assay against a panel of 7 pseudoviruses, including autologous Envs (FIG. 1F). Cow #1 and #2 showed neutralization against JR-CSF in pre-immunization phase while neutralization decreased post-immunization. Neutralization against other tested viruses was induced only after immunization. Cow #1 showed the highest neutralizing activity against 2 pseudoviruses at phase 1 (ZM109F.PB4 and BG505 with ID50 values of 26.7 and 67.2 respectively) and both potency and breadth increased at phase 2 with neutralizing activity against pseudoviruses MN, SF162, BG505, and AD8 (ID50 values of 274.3, 262.3, 1000, and 257.5, respectively).

Although both cows vaccinated with AD8 Unc gp140 were unable to induce autologous neutralization, both cows #2 and #3 induced neutralizing antibodies against multiple pseudoviruses. On phase 1, cow #2 induced neutralization against MN (ID50 of 25.9), and this increased in phase 2 for MN (ID50 of 127.4). Cow #3 showed neutralization against MN, SF162, BG505 and JR-CSF at phase 1 (ID50s of 56.9, 27.6, 31.6 and 88, respectively), and the neutralizing activity enhanced against all mentioned viruses at phase #2 (ID50 values of 1000, 55.9, 47.3 and 108.9, respectively).

HIV-1-specific bovine monoclonal antibodies. The secreted AD8 SOSIP gp140 v4.1 Env proteins were affinity-purified using the 2G12 antibody followed by SEC on a Superdex S200 16/600 column and characterised in reducing/non reducing SDS gel, BN-PAGE analysis and capture ELISA (FIG. 2). Characterization of AD8 SOSIP V4.1 confirmed that the proteins were predominantly trimeric and exposed epitopes of human BrNAbs. Through performing negative stain electron microscopy and Small-angle X-ray scattering on AD8 SOSIP v 4.1 (FIG. 2), the trimeric structure of Env was confirmed which was similar to BG505 SOSIP.664 and closely resembled native Env spikes. AD8 SOSIP gp140 v4.1 binding to human bNAbs was confirmed in capture ELISA.

Figure 3A:
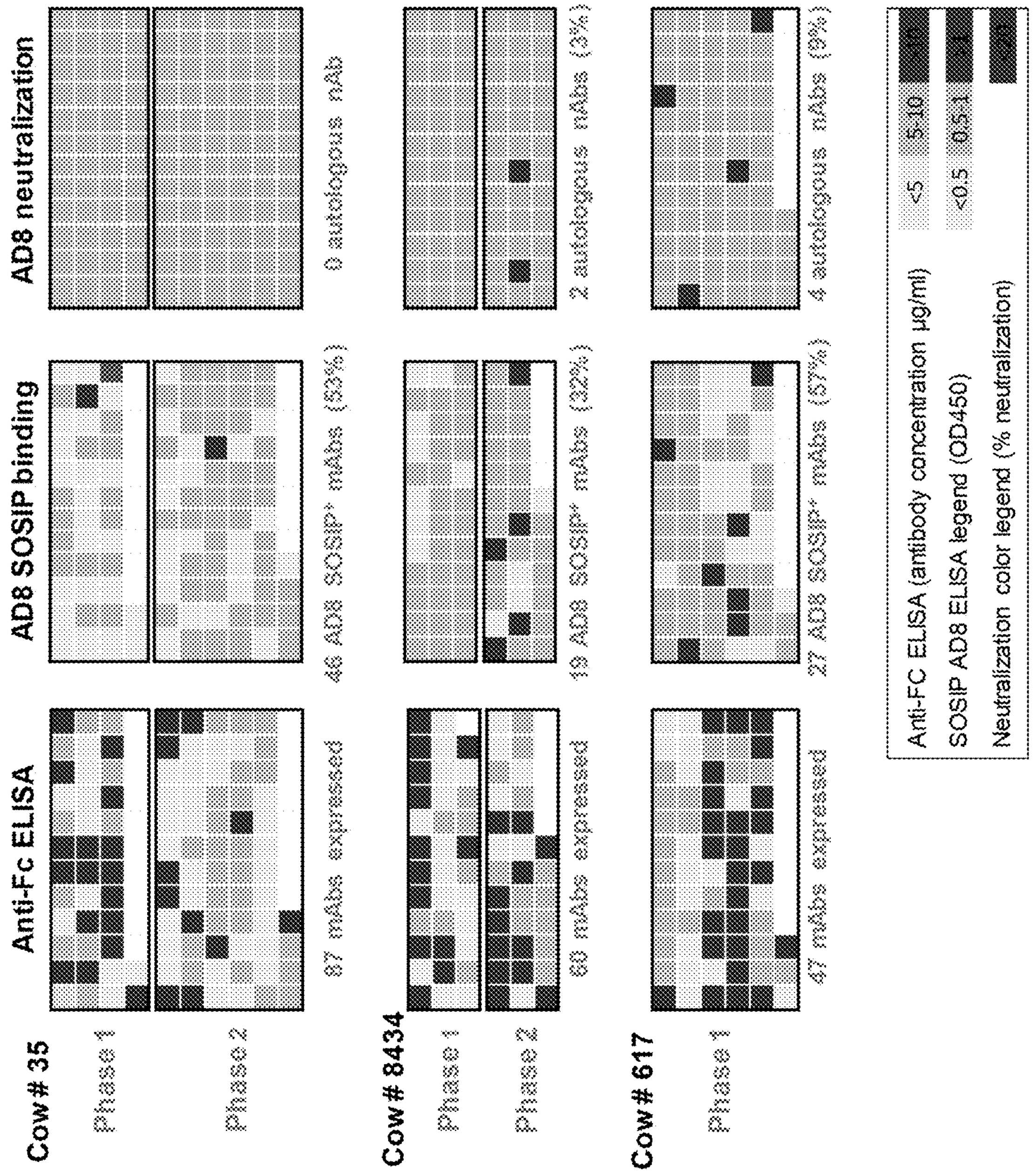
FIG. 3. Workflow of isolating anti-HIV bovine antibodies. (A) Functional screening of isolated monoclonal antibodies. Amplified bovine variable genes were cloned into the expression vectors and plasmids expressing paired heavy/light chains were co-transfected into 293 cells. The expression of monoclonal antibodies was confirmed in anti-Fc ELISA and binding to AD8 SOSIP was investigated in capture ELISA using D7324 tagged AD8 SOSIP gp140 v4.1. Purified antibodies then were assessed in TZM-bl neutralization assay. Heavy chains of 1842 and 1872 monoclonal antibodies were paired with the light chain of 2129 antibody. nAbs: Neutralising antibodies. (B) Binding of purified bovine mAbs to AD8 SOSIP gp140 v4.1 in capture ELISA.

HIV-1 Env-specific single B cells were sorted by FACS from PBMCs of animals #35, #8434 and #617 using AD8 SOSIP gp140 v4.1. AD8 strain (clade B) which is among difficult to neutralize HIV-1 viruses and we used this Env bait to isolate B cells from AD8 vaccinated animals (cow #2 and #3) and isolate B cells producing cross-clade anti-HIV-1 antibodies from the animal vaccinated with clade A Env (cow #1) (FIG. 1B). HIV Env-specific single B cells (IgG+ and AD8 SOISP gp140 trimer+) were sorted from PBMC of HIV vaccinated cows (FIG. 1C) and after antibody variable gene amplification and further cloning of such genes into human antibody constant region expression vector, forty seven chimeric mAbs were successfully produced from cow #1, from which twenty seven showed binding to AD8 SOSIP four of which isolated from this cow showed autologous neutralization against AD8 pseudovirus. Out of eighty seven chimeric mAbs constructed from cow #35, forty six mAbs could bind to AD8 SOSIP gp140 v4.1 trimer in capture ELISA (FIG. 3A).

Figure 4A:
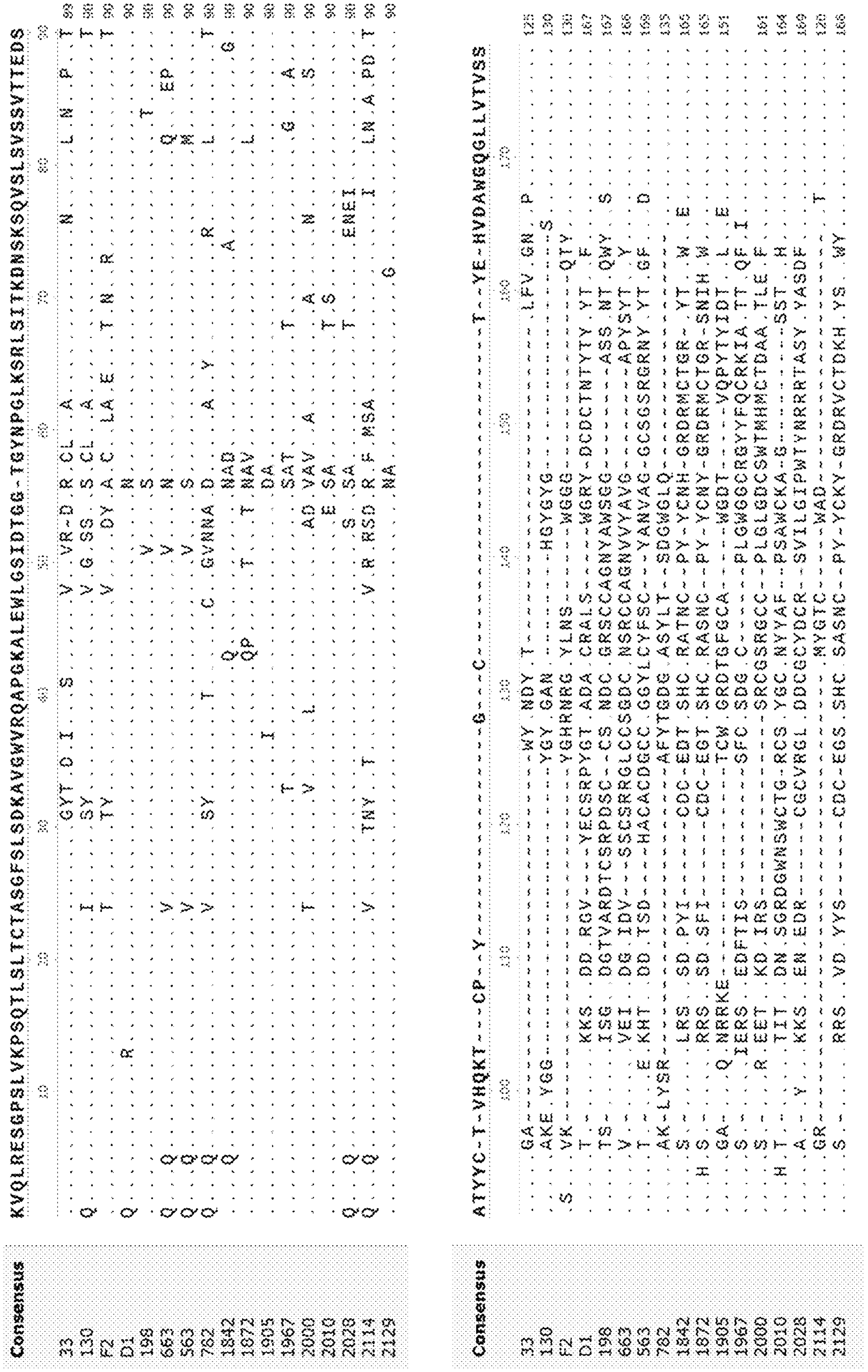
FIG. 4. (A) Alignment of heavy chains of isolated bovine mAbs. (B) CDRH3 sequence and alignment of 2129, 1842 and 1872 CDRH3s.

However, none of these mAbs could neutralize autologous HIV AD8 pseudovirus. From cow #8434, sixty chimeric mAbs were produced and although only nineteen mAb showed binding to SOSIP AD8 gp140, two of these antibodies showed autologous neutralization against AD8 pseudovirus in TZM-bl neutralization assay. MEL-1842 and MEL-1872 mAbs shower higher Env binding against AD8 SOSIP gp140 than VRC01 antibody (FIG. 3B). Out of forty seven produced mAbs from cow #617, twenty seven chimeric mAb showed binding to AD8 SOSIP gp140 v4.1. Nevertheless, four mAb isolated from this cow showed autologous neutralization against AD8 pseudovirus. Sequences and alignments of the heavy and light chain sequences for isolated mAbs are listed in FIG. 4.

Figure 5D:
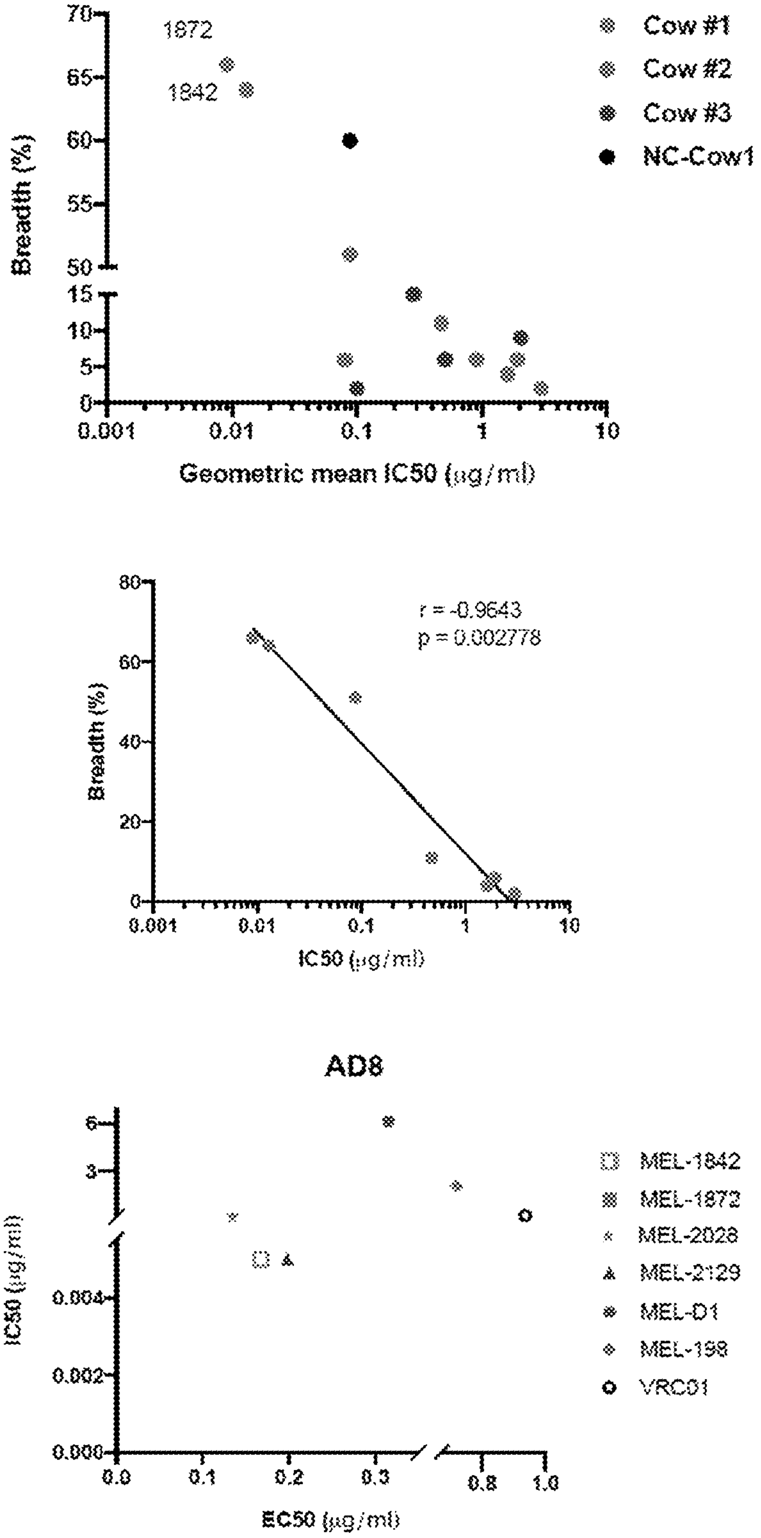
FIG. 5. Neutralisation profile of bovine antibodies. Evaluation of purified chimeric bovine-human mAbs for neutralization breadth and potency, (A) $IC_{50}$. (B) $IC_{80}$. (C) Categorization of neutralization activity of bovine BrNAbs against clade A, B, C, AE, BC, AC and G HIV viruses. (D) Correlation of neutralization and Env binding in isolated monoclonal antibodies. Correlations between the neutralizing breadth and neutralization activity ($IC_{50}$) of AD8 SOSIP binding antibodies. Correlations between the neutralizing breadth and neutralization activity ($IC_{50}$) of antibodies from cow #1. Correlation between $IC_{50}$ and $EC_{50}$ of monoclonal antibodies against AD8 strain. (E) Neutralization profile of BrNAb MEL-1842, MEL-1872 and MEL-2129. Comparison of $IC_{50}$ and $IC_{80}$ values of isolated monoclonal mAbs with BrNAb NC-COW1. Categorization and comparison of neutralization activity against different HIV clades using $IC_{50}$ and $IC_{80}$ values. The black lines represent the geometric mean $IC_{50}$s and $IC_{80}$s.

Bovine anti-HIV BrNAbs with ultra-long CDRH3: To understand the neutralisation properties of AD8 SOSIP gp140 v4.1 binding antibodies, TZM-bl neutralization was performed using a virus panel including HIV 12-virus global panel as well as several clade A, B and C viruses. Anti-HIV mAbs isolated from cow #35 showed a narrow breadth while mAbs of cow #8434 showed a moderate breadth against clade B viruses (FIG. 5A, FIG. 5B and FIG. 5C). Most of the isolated bNAbs from all three cows neutralized <50% of HIV-1 viruses with geometric mean $IC_{50}$ of above 0.09 μg/mL (FIG. 5D), while three mAbs of MEL-2129, MEL-1872 and MEL-1842 from cow #617 showed the highest breadth (64%, 66% and 51%, respectively) (FIG. 5A). Among them, MEL-1842 and MEL-1872 mAbs demonstrated the greatest potency (with geometric mean $IC_{50}$ of 0.013 μg/ml and 0.009 μg/ml and $IC_{80}$ of 0.045 μg/ml and 0.033 μg/ml, respectively; FIG. 5A and FIG. 5B). Among mAbs isolated from cow #617, there was a correlation between low geometric mean $IC_{50}$ and high breadth (FIG. 5D). However, for AD8 neutralizing mAbs there was a lack of correlation between $IC_{50}$ and $EC_{50}$ for this strain. Antibody MEL-1842, MEL-1872 and MEL-2129 all showed cross-clade neutralization against tier 1 and tier 2 viruses with MEL-1872 neutralizing most of tier 2 viruses with $IC_{50}$ value of 0.1 μg/ml (FIG. 1D).

Figure 5E:
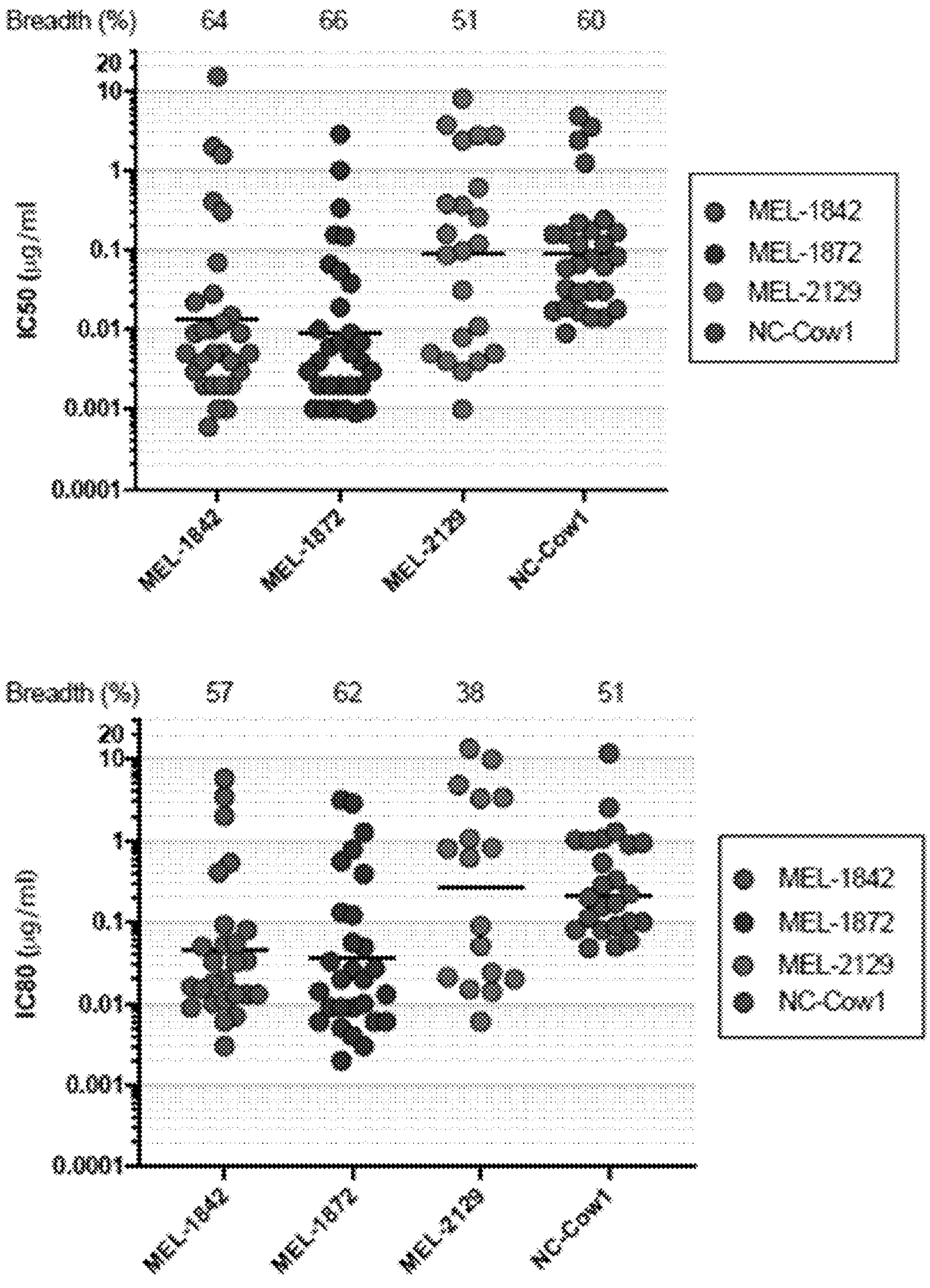
Figure 5F:
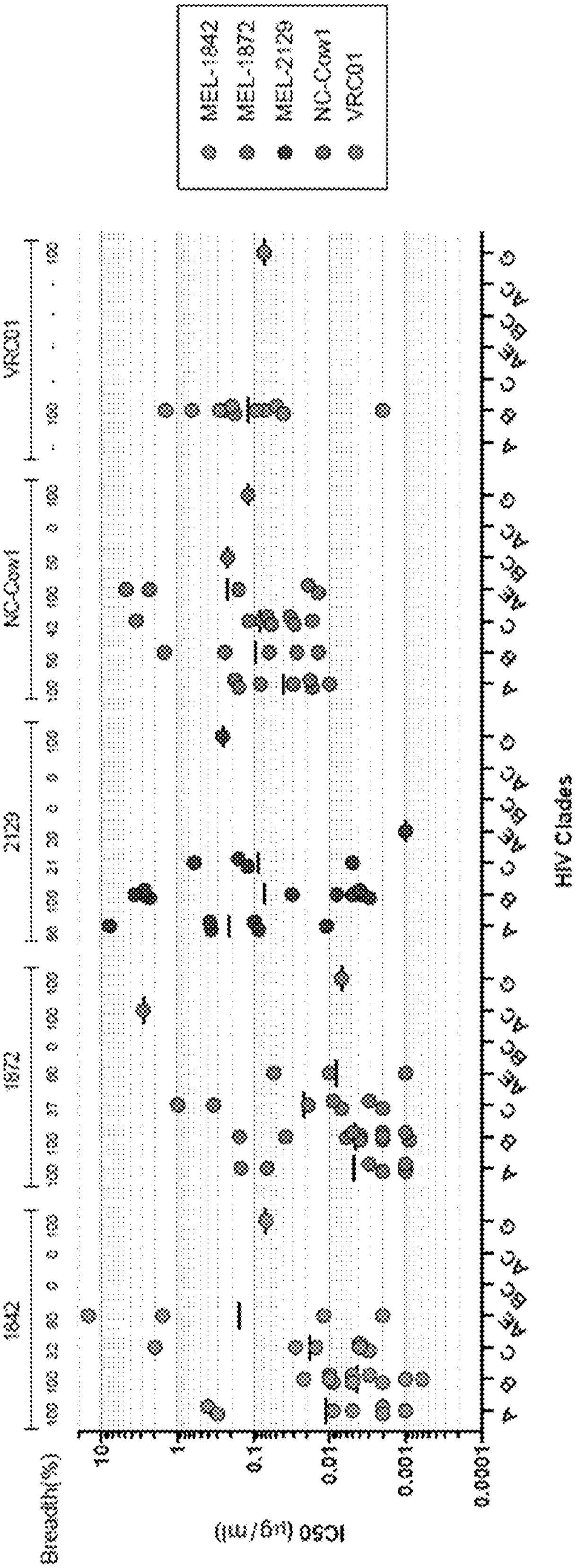
Figure 5G:
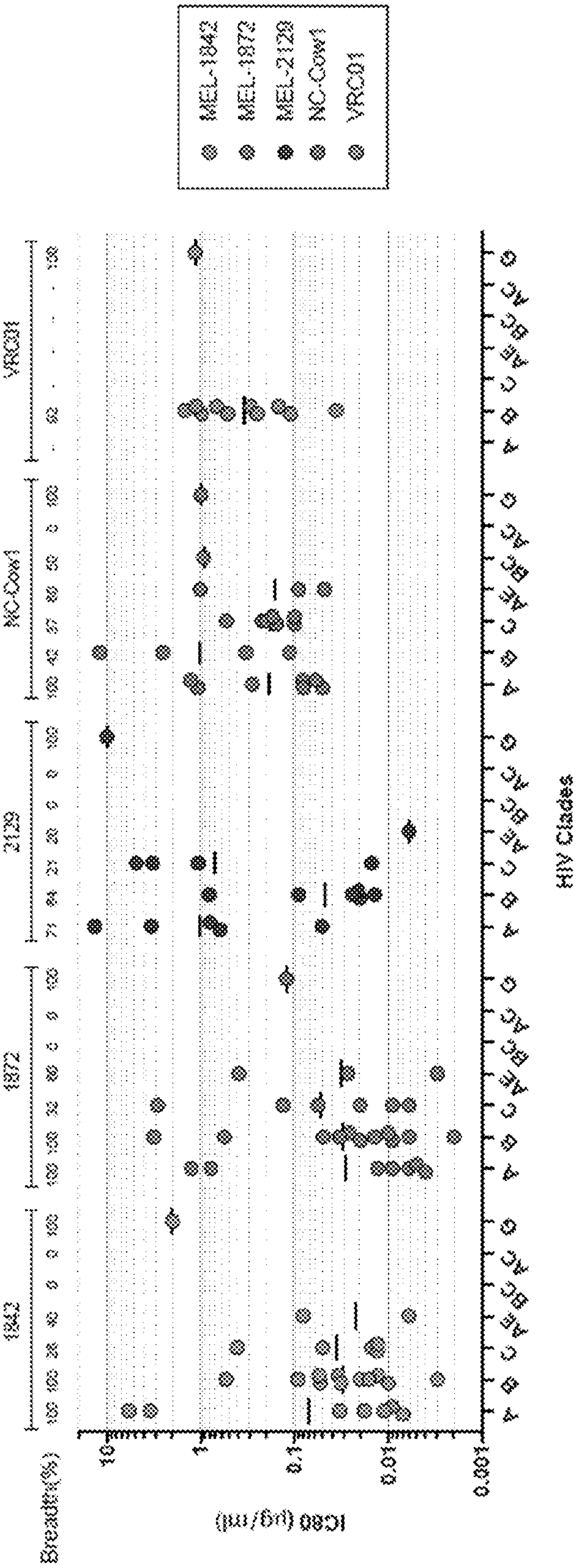

Antibodies MEL-1842 and MEL-1872 demonstrated broader and more potent HIV-1 neutralizing activity compared with NC-Cow1 (60% breadth with $IC_{50}$ of 0.09 μg/ml) against tested viruses (FIG. 5E). MEL-1842 and MEL-1872 showed the greatest potency against clade B viruses with geometric mean $IC_{50}$ of 0.004 μg/ml followed by clade A viruses with geometric mean $IC_{50}$ of 0.011 μg/ml and 0.005 μg/ml, respectively (FIG. 5E). Antibody MEL-1872 was 29-fold more potent than VRC01 (Geometric mean $IC_{50}$ of 0.117 μg/ml) against tested clade B viruses (FIG. 5C) and 21-fold more potent than CHO1-31 against tested clade A viruses (Geometric mean $IC_{50}$ of 0.042 μg/ml).

Figure 11:
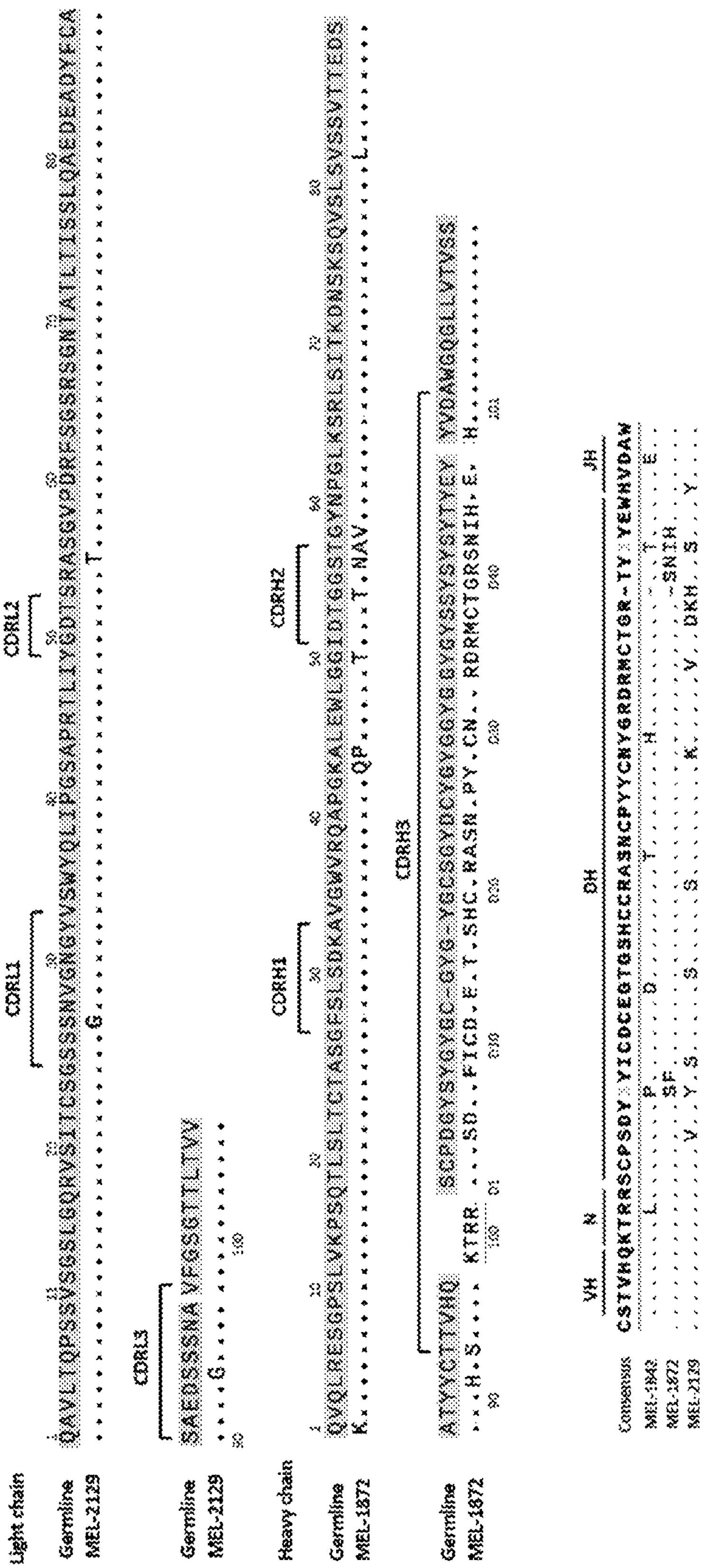
FIG. 11. Alignment of heavy and light chain sequences of MEL-1872 mAb with the germline genes. Alignment of IGLV30 germline gene, IGLJ4*01 germline gene, IGHV1-7*02 germline gene, IGHD8-2*01 germline gene, IGHJ2-4*01 germline gene.
Figure 12A:
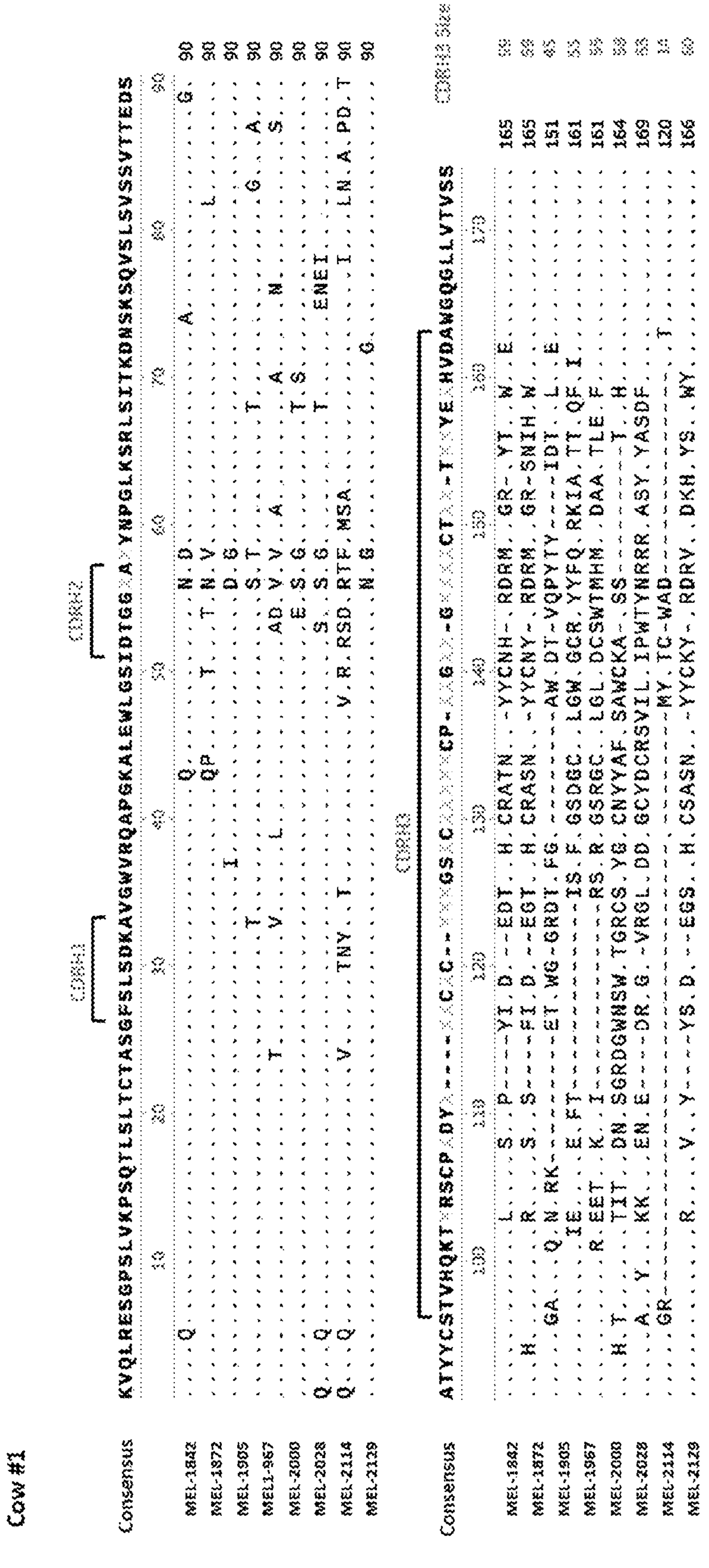
FIG. 12. Alignment of heavy chain sequences of isolated monoclonal antibodies.
Figure 12B:
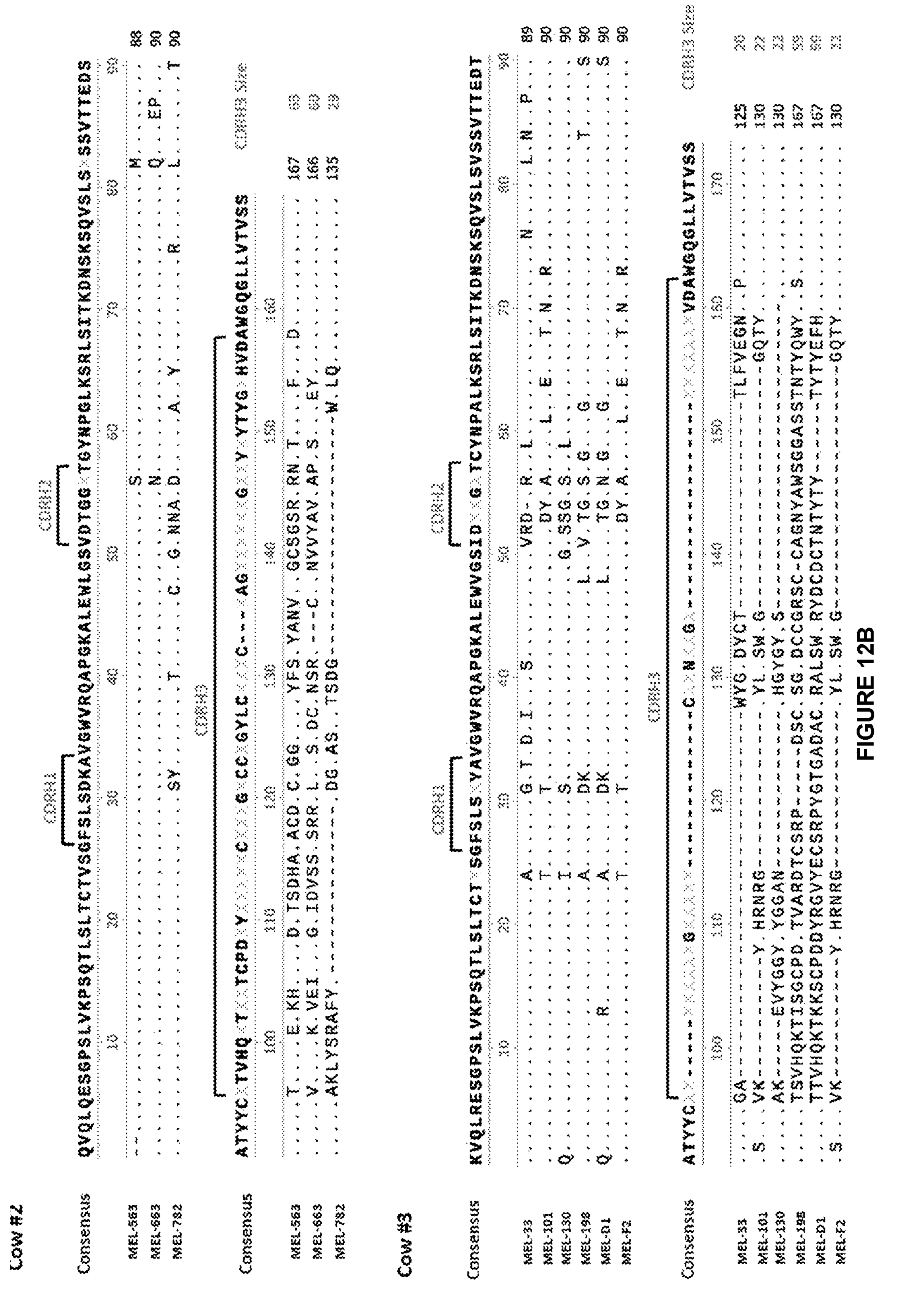
Figure 14:
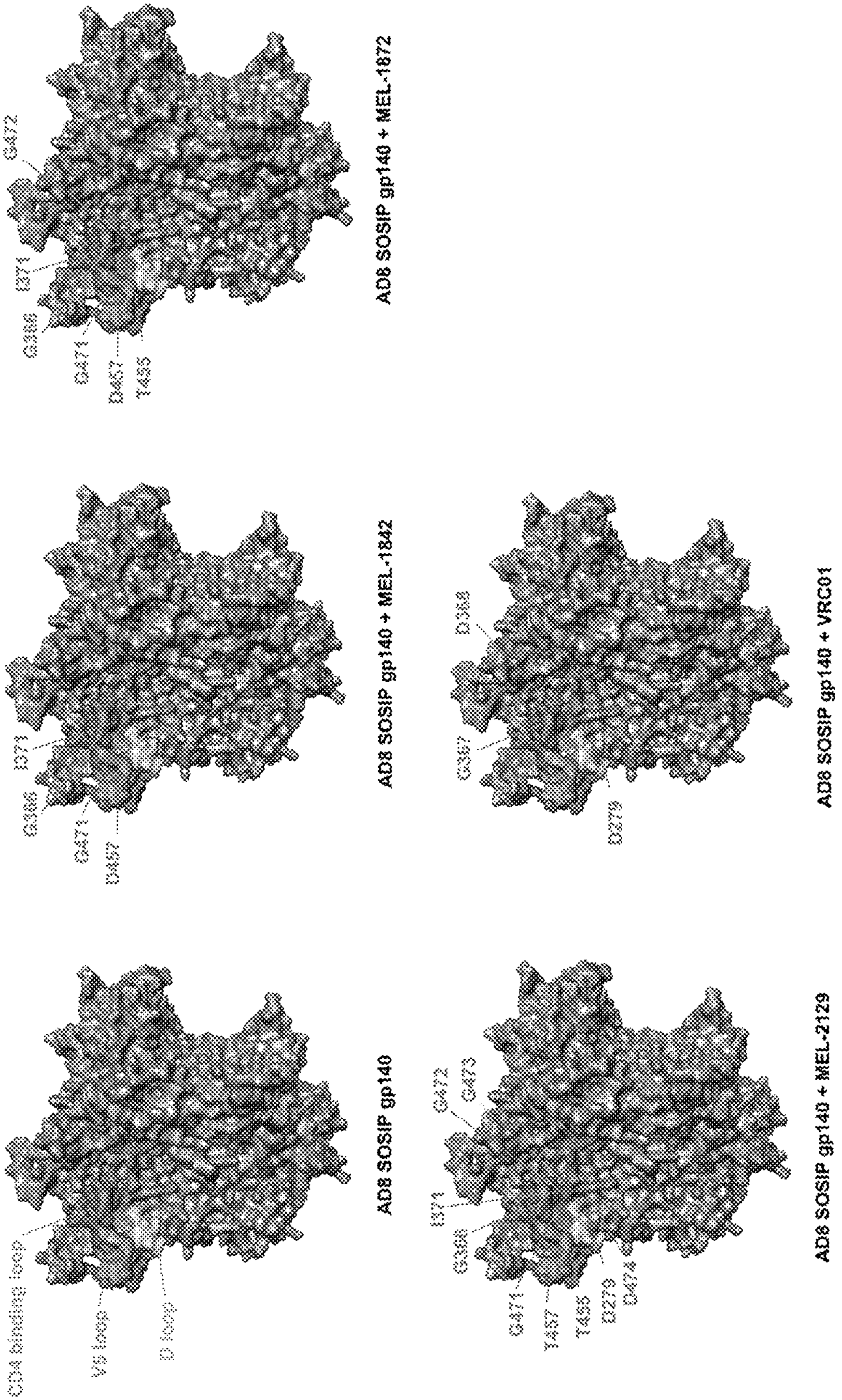
FIG. 14. Binding of bovine bNAbs to CD4bs. Indicated on the BG505 SOSIP.664 trimer (top left) are residues from the D loop (275-283: SNFTDNAKN), CD4 binding loop (362-375: NQSSGGDPEIVMHS), and V5 loop (458-469: GGNNHNNDTETFR). Binding site residues of antibodies MEL-1842, MEL-1872, MEL-2129 and VRC01 to AD8 SOSIP V4.1 are also indicated.

Sequences of the isolated antibody variable genes are listed in FIG. 12 and Table 1. Three mAbs (MEL-1842, MEL-1872 and MEL-2129) belonged to the same antibody clonal family with ultralong CDRH3 length of 58 amino acids for MEL-2129 mAb and 57 amino acids for MEL-1842 and MEL-1872 mAbs. The alignment of germline genes with the heavy-chain and light chain gene used to produce MEL-1872 mAbs are shown in FIG. 11. Sequences were then annotated with IMGT High V-Quest (http://www.imgt.org/HighV-QUEST/) (Table 5). As shown, there are limited hyperosmotic mutations in the light gene and VH and JH of the heavy gene while compared to germline DH (IGHD8-2*01), there are significant mutations in CDRH3 region of MEL-1872 mAb.

TABLE 5

IMGT V-quest analysis of heavy chain for anti-HIV-1 bovine mAbs

| Cow | ID | V-gene allele | V-gene ID (%) | J-gene allele | J-gene ID (%) | D-gene allele | CDR1-IMGT (aa) | CDR2-IMGT (aa) | CDR3-IMGT (aa) |
|---|---|---|---|---|---|---|---|---|---|
| 1 | MEL-1842 | Bostau IGHV1-7*02 | 94.39 | Bostau IGHJ2-4*01 | 89.58 | Bostau IGHD8-2*01 | 8 | 7 | 59 |
| | MEL-1872 | Bostau IGHV1-7*02 | 93.33 | Bostau IGHJ2-4*01 | 91.67 | Bostau IGHD8-2*01 | 8 | 7 | 59 |
| | MEL-1905 | Bostau IGHV1-7*02 | 95.14 | Bostau IGHJ2-4*01 | 91.67 | Bostau IGHD6-2*01 | 8 | 7 | 45 |
| | MEL-1967 | Bostau IGHV1-7*02 | 96.14 | Bostau IGHJ2-4*01 | 93.75 | Bostau IGHD8-2*01 | 8 | 7 | 55 |
| | MEL-2000 | Bostau IGHV1-7*02 | 92.63 | Bostau IGHJ2-4*01 | 93.75 | Bostau IGHD8-2*01 | 8 | 7 | 55 |
| | MEL-2010 | Bostau IGHV1-7*02 | 95.79 | Bostau IGHJ2-4*01 | 95.83 | Bostau IGHD8-2*01 | 8 | 7 | 58 |
| | MEL-2028 | Bostau IGHV1-7*02 | 93.68 | Bostau IGHJ2-4*01 | 93.75 | Bostau IGHD8-2*01 | 8 | 7 | 63 |
| | MEL-2114 | Bostau IGHV1-10*02 | 89.47 | Bostau IGHJ2-4*01 | 89.58 | Bostau IGHD3-1*01 | 8 | 7 | 14 |
| | MEL-2129 | Bostau IGHV1-7*02 | 96.14 | Bostau IGHJ2-4*01 | 93.75 | Bostau IGHD8-2*01 | 8 | 7 | 60 |
| 2 | Mel-563 | Bostau IGHV1-7*02 | 97.54 | Bostau IGHJ2-4*01 | 93.75 | Bostau IGHD8-2*01 | 8 | 7 | 63 |
| | Mel-663 | Bostau IGHV1-7*02 | 92.98 | Bostau IGHJ2-4*01 | 97.92 | Bostau IGHD8-2*01 | 8 | 7 | 60 |
| | MEL-782 | Bostau IGHV1-10*01 | 93.68 | Bostau IGHJ2-4*01 | 91.67 | Bostau IGHD6-2*01 | 8 | 7 | 29 |
| 3 | MEL-33 | Bostau IGHV1-21*03 | 61.05 | Bostau IGHJ2-4*01 | 89.58 | Bostau IGHD6-2*01 | 8 | 7 | 19 |
| | MEL-130 | Bostau IGHV1-21*03 | 99.65 | Bostau IGHJ2-4*01 | 85.42 | Bostau IGHD7-3*01 | 8 | 7 | 24 |
| | | Bostau IGHV1-33*01 | | | | | | | |
| | MEL-101 | Bostau IGHV1-27*03 | 91.58 | Bostau IGHJ2-4*01 | 95.83 | Bostau IGHD7-3*01 | 8 | 7 | 24 |
| | MEL-F2 | Bostau IGHV1-27*03 | 91.58 | Bostau IGHJ2-4*01 | 95.83 | Bostau IGHD7-3*01 | 8 | 7 | 24 |
| | MEL-D1 | Bostau IGHV1-7*02 | 98.60 | Bostau IGHJ2-4*01 | 91.67 | Bostau IGHD8-2*01 | 8 | 7 | 61 |
| | MEL-198 | Bostau IGHV1-7*02 | 96.14 | Bostau IGHJ2-4*01 | 87.50 | Bostau IGHD8-2*01 | 8 | 7 | 61 |

NA: The germline sequence could not be assigned with IMGT.

Figure 6B:
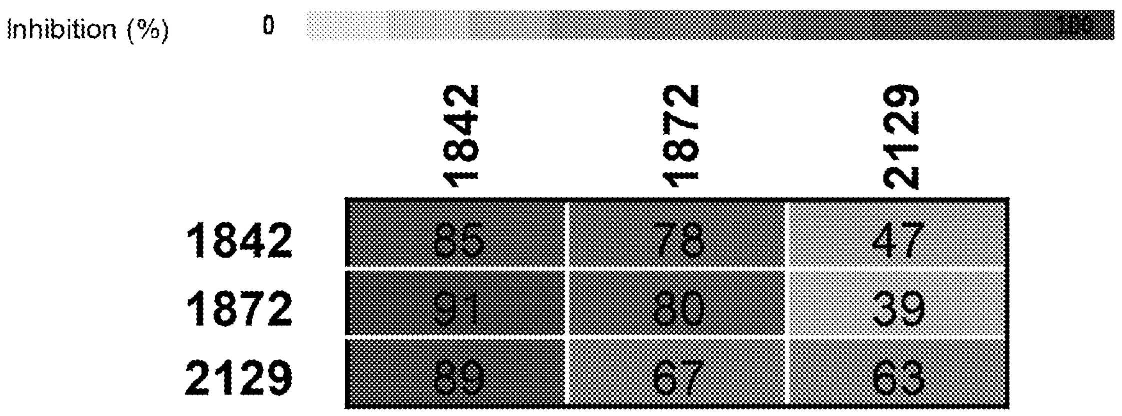
FIG. 6. Epitope mapping of bovine monoclonal antibodies. (A) Bovine compete with Human BrNAb for Env binding. The table shows the competition ELISA assay with values demonstrating Env binding inhibition (percentage) of human BrNAbs by bovine antibodies. (B) Competition ELISA between antibodies MEL-1842, MEL-1872 and MEL-2129 showed these antibodies bind to the same or proximate epitopes. Higher inhibition values are shown in red, and lower inhibitions values are in increasingly pale shades of orange. Data representative of two repeat assays. (C) Bovine BrNAbs bind to different form of HIV Env. Bovine BrNAbs were tested in direct ELISA assays to evaluate their binding to different forms of Env (monomeric gp120, uncleaved gp140 and SOSIP gp140) as well as ConM SOSIP which is an Env trimers based on a consensus sequence of all HIV-1 group M isolates. (D) The effect of alanine mutagenesis on binding of bovine antibodies to AD8 gp120 captured from lysed virions. ELISA assay was performed using a constant half maximal effective concentration (EC50) of each antibody to AD8 WT Env. Stars also show significant neutralization IC50 increase of each antibody against mutated virus compared to WT virus (5-fold for all mAbs, except 198). PGT121 (V3-glycan epitope) and b12 and VRC01 (CD4bs epitope) were included for comparison.

Bovine BrNAbs bind to CD4 binding site (CD4bs) on HIV Env: Competition ELISA with reference human BrNAbs targeting four known epitopes was performed to evaluate interference with bovine mAbs binding to the AD8 SOSIP gp140 v4.1. As shown in FIG. 6A, bovine BrNAbs (2129, 1842 and 1872 mAbs) inhibited Env binding of human CD4bs BrNAbs (b12, VRC01, HJ16 and 3BNC117), with the exception of 2129 that showed incomplete inhibition of HJ16 binding. Some of bovine non-BrNAbs (only Env binding mAbs) demonstrated partial competition (25-50%) with V2-apex human BrNAbs (PGT145) and gp120- gp41 interface human BrNAbs (PGT151). As shown in FIG. 6B, competition ELISA between bovine BrNAbs showed strong competition between MEL-1842 and MEL-1872 mAbs demonstrating that these mAbs may share a common or proximate binding site(s). On the other hand, MEL-2129 mAb showed lower inhibitory effect on Env binding of MEL-1842 and MEL-1872 mAbs.

Figure 6C:
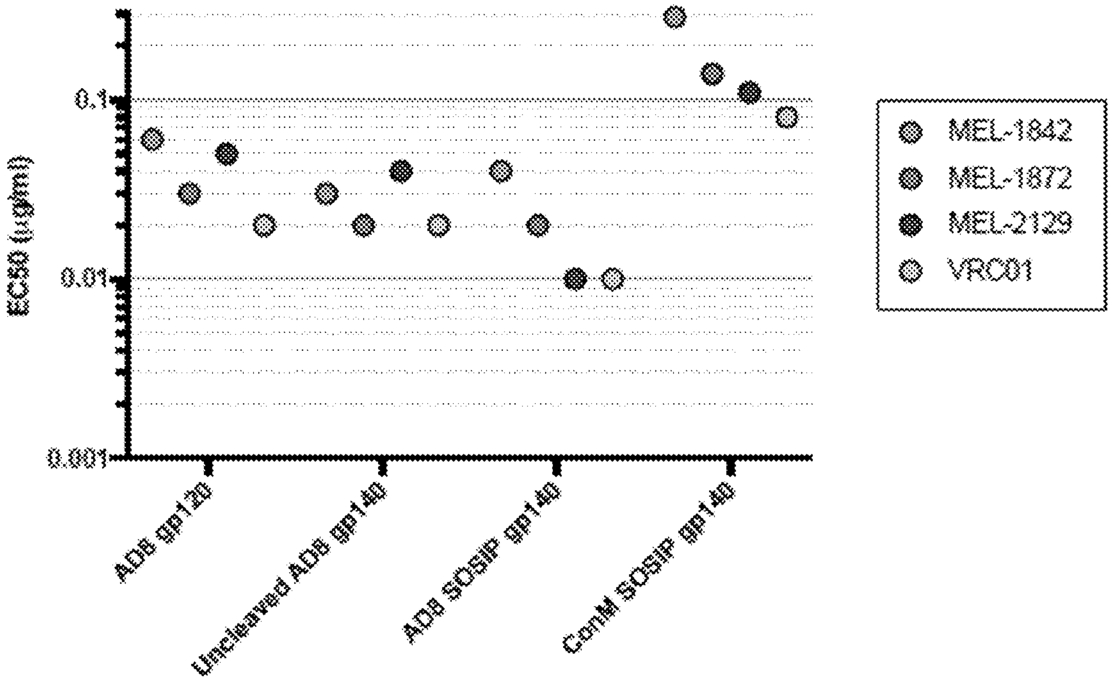

Bovine BrNAbs bind to different form of HIV Env. As shown in FIG. 6C, bovine BrNAbs displayed binding to monomeric AD8 gp120, uncleaved HIV gp140 and AD8 SOSIP gp140 v4.1 confirming that their epitopes are present on gp120 monomers and both cleaved and uncleaved Env trimers. These mAbs could also bind to ConM SOSIP which is an Env trimer based on a consensus sequence of all HIV-1 group M isolates. This trimer displays most of BrNAbs' epitopes and is made to minimise clade-specific and strain-specific antigenic determinants.

Epitope mapping of bovine BrNAbs with HIV Env mutants: Affinity binding of bovine BrNAbs to a panel of thirty-three AD8 Env mutants (HIV AD8 lysed virions) showed that mutations located primarily in the CD4 binding site (CD4bs), C4 and C5 regions of Env impeded the binding of these mAbs (FIG. 6D, FIG. 14, FIG. 8A and FIG. 8B). For MEL-1842, MEL-1872 and MEL-2129 mAbs (which are from the same clonal lineage antibody family) the most significant loss of binding was observed for mutations G366A, I371A, D457A and G471A which resulted in 530% binding compared with WT Env. The mutations N262A, T455A and G472A also inhibited the binding of MEL-1872 and MEL-2129 mAbs. Additionally, the mutations D279A, G473A and D474A also resulted in a substantial loss of binding for MEL-2129 (all 530% binding compared with WT AD8 Env). VRC01 and b12 were used as controls and exhibited the lowest binding percentage to mutations introduced in the CD4 binding site (CD4bs), as expected. VRC01 showed a significant decrease in Env binding in response to mutations to the N-linked glycan at position 279, and the residues G367A, and G368A (≤30% binding). b12 also demonstrated a similarly low decrease in binding to G368A (≤30% binding). For PGT121, the mutation of the glycan at position 332 resulted in the most substantial decrease in binding.

Figure 6D:
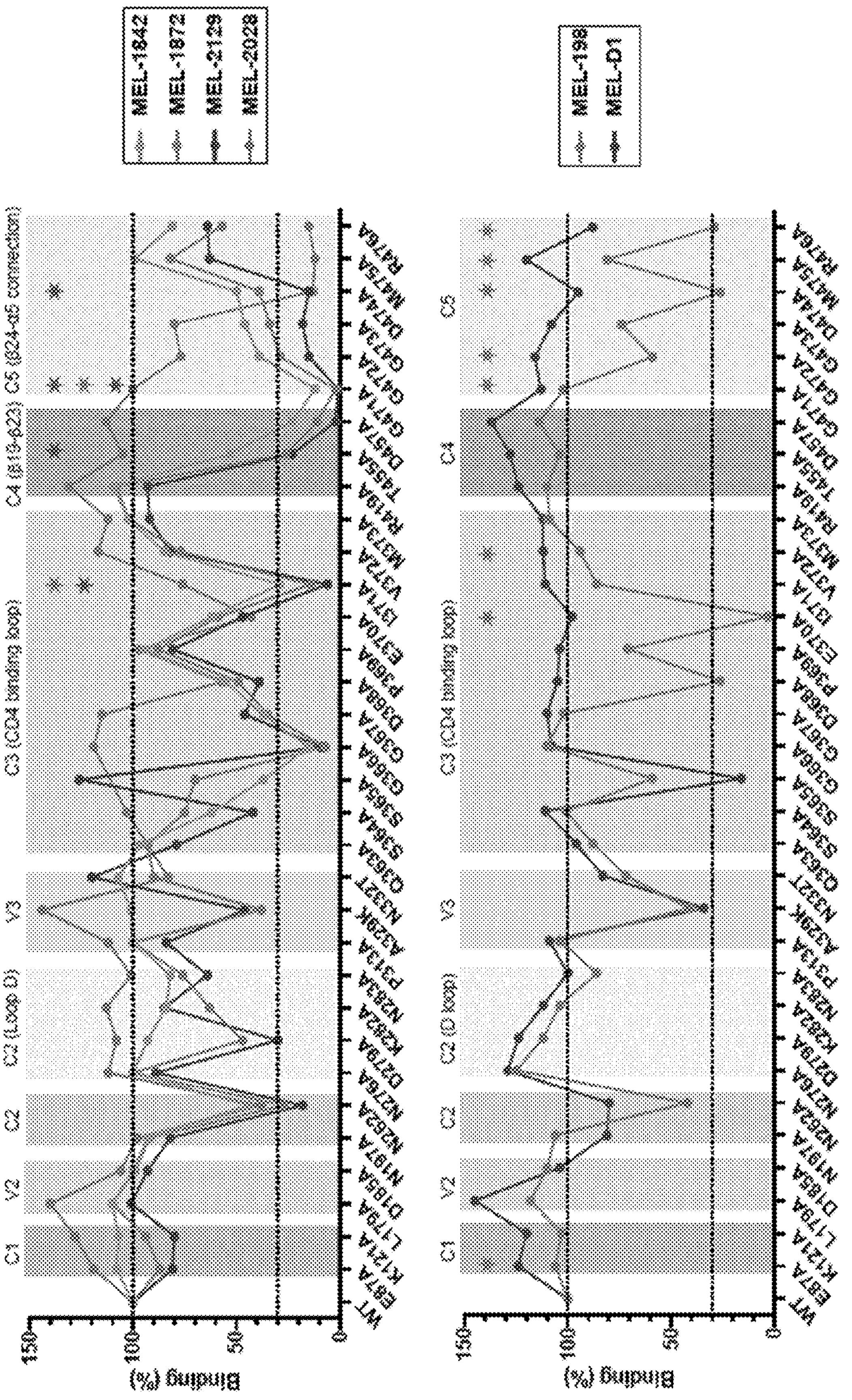
Figure 6E:
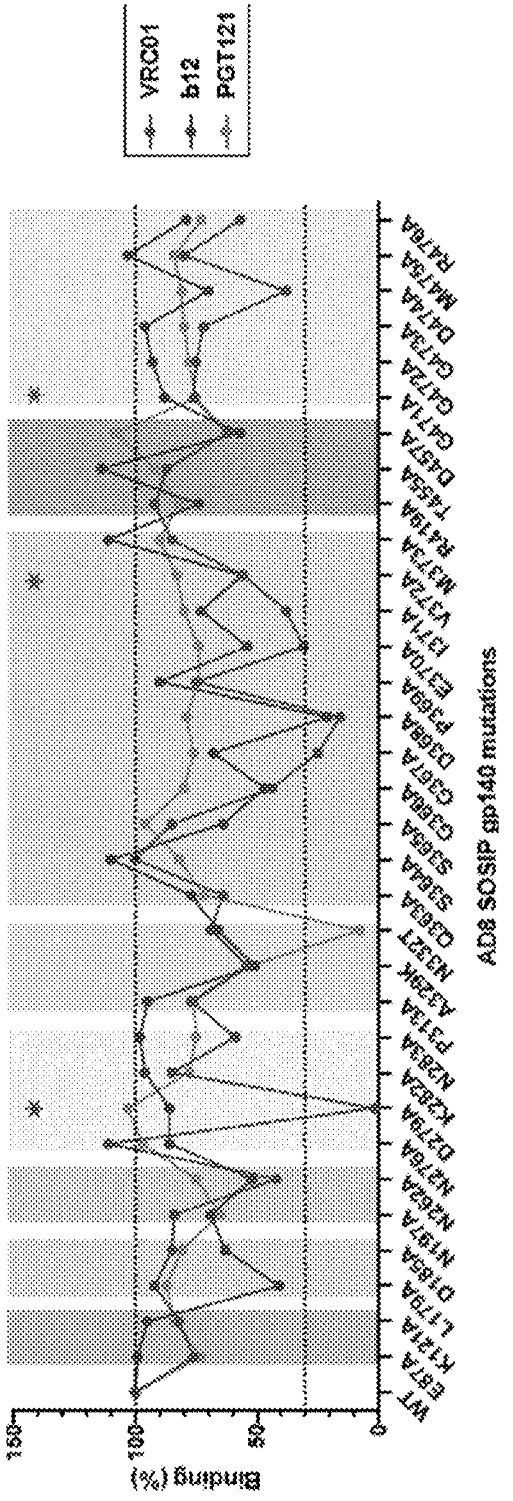
Figure 8A:
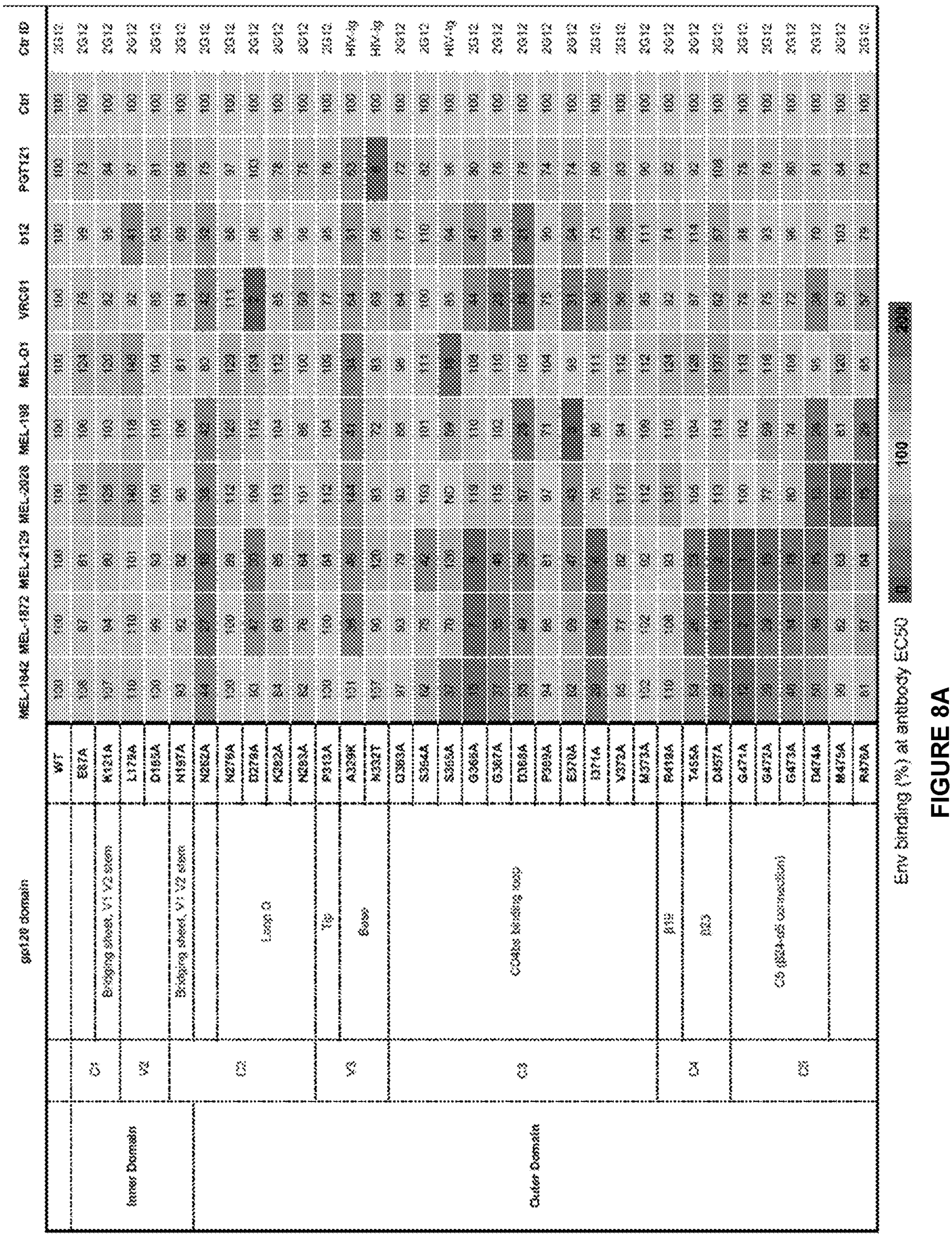
FIG. 8. Heatmap of relative binding affinities and neutralization activity of monoclonal antibodies to AD8 Env mutants. (A) Heatmap of relative binding affinities of monoclonal antibodies to AD8 Env mutants. ELISA assay was performed using a constant half maximal effective concentration ($EC_{50}$) of each antibody to AD8 WT Env. PGT121 (V3-glycan epitope) and b12 and VRC01 (CD4bs epitope) were included for comparison. The amount of lysed virus/amount of Env added was equilibrated according to 2G12 capture ELISA binding. IgG Polyclonal serum (NIH, #3957) was used for mutants that did not bind well to 2G12. (B) Heatmap of relative neutralization activity of monoclonal antibodies against AD8 Env mutants. The shading refer to the changes in $IC_{50}$ and $IC_{80}$ ranging from 0.001 μg/ml (light shading) to 10 μg/ml (dark shading). Values in lighter shading show low $IC_{50}$ and better neutralization while, those in darker shading show high $IC_{50}$ values and less neutralization activity. Unshaded values indicates values of >4 or >10, meaning that the $IC_{50}$ could not be achieved for the viruses with that particular mutation to Env. PGT121 (V3-glycan epitope) and b12 and VRC01 (CD4bs epitope) were included for comparison. Data representative of 2 repeat assays.

Neutralization activity of bovine BrNAbs was also assessed in TZM-bl neutralization assay using a panel of twenty-seven mutated AD8 pseudoviruses. As shown in FIG. 6D, G471A mutation resulted in the most significant effect on neutralization of MEL-1842, MEL-1872 and MEL-2129 mAbs with increasing the IC50 and IC80 values to ≥4 μg/ml. I371A mutation also impeded the neutralization activity of MEL-2129 and MEL-1872 mAbs effectively while MEL-1842 mAb was insensitive to this mutation. In agreement with ELISA assay, in addition to the mentioned mutations, a few more mutations in CD4 binding site (CD4bs), C4 (T455A) and C5 (D474A) showed incomplete neutralization impediment for these bovine BrNAbs. As expected, D279A mutation rendered VRC01 unable to neutralize AD8 mutated pseudovirus. In addition to G471A mutation, G366A and V372A mutations also inhibited neutralization activity of b12. PGT121 was affected by E370A and N332T mutations.

A neutralization assay with multi-clade panel of viruses and their corresponding CD4bs mapping mutations (N279A, N280D, G458Y) showed evidence of CD4bs specificity for MEL-1842, MEL-1872 and MEL-2129 with at least three of the viruses (FIG. 13).

Figure 9A:
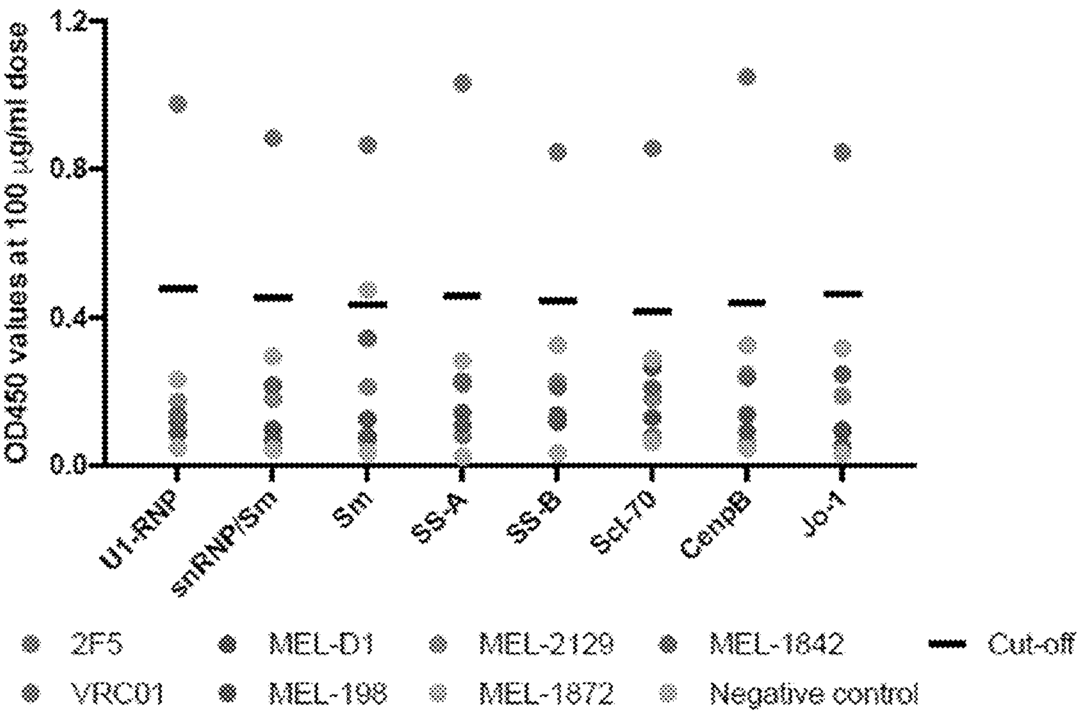
FIG. 9. Assessment of bovine BrNAb polyreactivity. (A) Assessment of antibody polyreactivity against human antigens. ELISA assay was performed against human antigens using constant amount of 100 μg/ml from tested mAbs. (B) Polyreactivity test in Hep-2 cells. Bovine BrNAbs MEL-1842, MEL-1872, MEL-2129 and MEL-198 did not show any polyreactivity against human Hep-2 cells. 2F5 is human anti-HIV BrNAb with polyreactivity while anti-HIV BrNAb PGT121 is not polyreactive.
Figure 9B:
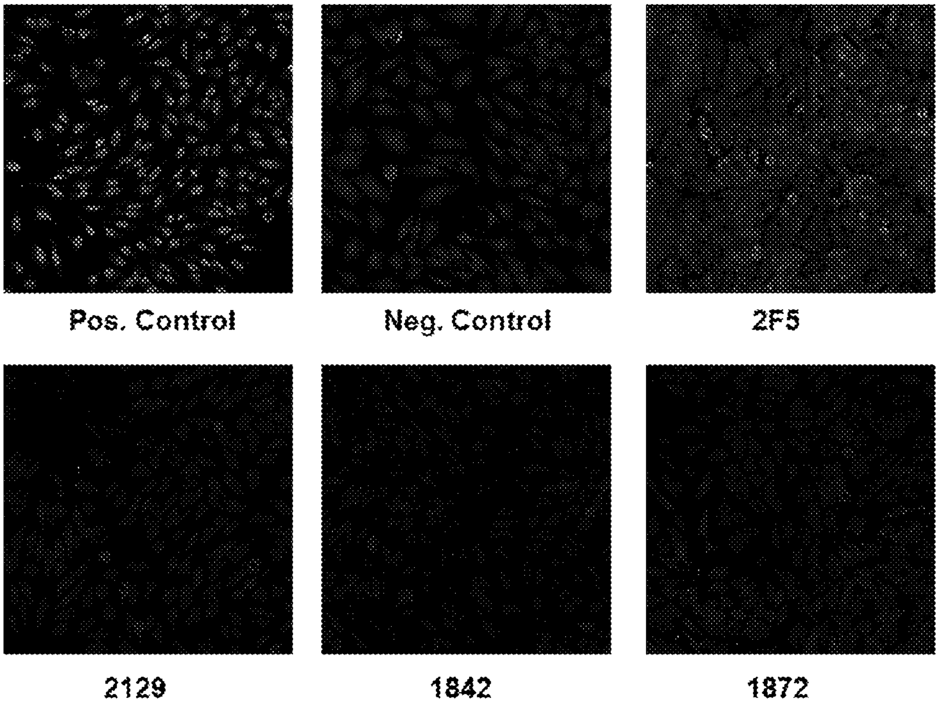

Bovine BrNAbs are not polyreactive: Autoreactivity and polyreactivity of 2129, 1842 and 1879 mAbs were evaluated in HEp-2 staining and ELISA assay against some human autoantigens. These bovine BrNAbs showed no autoreactivity or polyreactivity against tested antigens (FIGS. 9A and B).

Figure 10C:
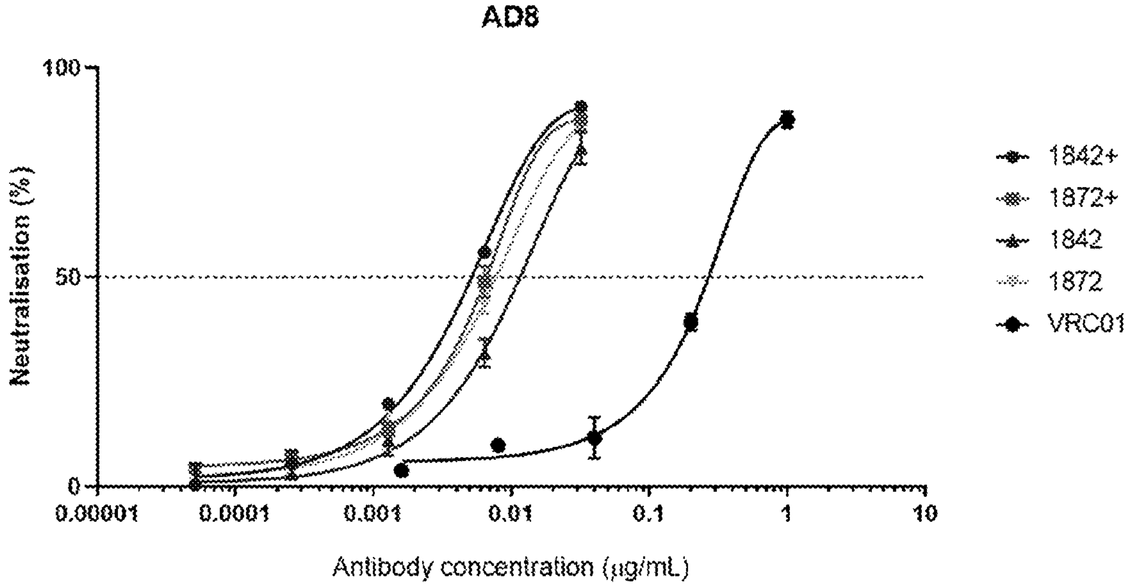
FIG. 10. Bovine BrNAbs maintain their function using different antibody light chains. A. The heavy and light chain sequences of antibody NC-COW1. B. Amino acid sequence alignment of the variable light chain of antibody 2129 and NC-COW1; and amino acid sequence alignment of the variable heavy chain of antibodies NC-COW1; 2129, 1872 and 1842. C. Bovine BrNAbs were tested in direct ELISA assays to evaluate their binding to the monomeric gp120 form of Env using different variable light chains.

Bovine BrNAbs retain their function when utilising different light chains. As shown in FIG. 10A-B, sequence alignment of the VL of 2129 and NC-Cow1 shows that these sequences are different, and the amino acid sequence alignment of the variable heavy chain of antibodies NC-COW1; 2129, 1872 and 1842 confirms some differences in these sequences also. Bovine BrNAbs were tested in direct ELISA assays to evaluate their binding to the monomeric gp120 form of Env using different variable light chains. mAbs with "+" symbol are produced using NC-Cow light chain while the ones without any symbol are produced with 2129 light chain. VRC01 is produced with VRC01 heavy chain and VRC01 light chain. This data shows that the mAbs maintain their function using different antibody light chains, highlighting that their function is dependent on the antibody's heavy chain (FIG. 10C).

Among reported anti-HIV-1 neutralizing antibodies, CAP256-VRC26.25 (targeting V1V2 apex) has been the most potent antibody with geometric mean $IC_{50}$ of 0.012 μg/mL (median $IC_{50}$=0.006 μg/ml, breadth 59%) thus far. The CDRH3 of CAP256-VRC26.25 comprises 36 amino acids and is one of the longest human CDRH3s identified. There is a correlation between neutralization potency and CDRH3 length. CAP256-VRC26.25 has a protruding CDRH3 comprising a two-stranded antiparallel β sheet that is stabilized with a disulfide bond. Although CAP256-VRC26.25 has approximately 70% breadth on clade C viruses, it shows limited breadth (<30%) on clade B viruses due to the relative rarity of acidic and basic residues recognized by the antibody at positions 164 and 169, respectively. NC-Cow1 is also the only potent anti-HIV-1 bovine CD4bs BrNAb with a protruding CDRH3 of 60 amino acids and broad neutralization against clade A viruses but moderate neutralization against clade B and C viruses. A bovine antibody isolated in this study (MEL-1872) showed higher potency with geometric mean $IC_{50}$ of 0.009 μg/ml (median $IC_{50}$=0.006 μg/ml) and breadth (66%) than CAP256-VRC26.25. Additionally, it showed more breadth and potency compared with NC-Cow1 against tested viruses (66% versus 60% breadth; Geometric mean $IC_{50}$ of 0.009 μg/ml versus 0.090 μg/0 ml). Although MEL-1872 and NC-Cow1 mAbs showed similar breadth against clade A and C viruses, the former antibody showed more potency (8-fold and 4-fold, respectively). MEL-1872 mAb also neutralized clade B viruses with more potency (above 23-fold) and breadth (100% versus 50%) than NC-Cow1. Although like NC-Cow1, MEL-1872 mAb was isolated from a BG505 SOSIP (clade A) vaccinated cow, the usage of a tier-2 HIV-1 Env with different clade (AD8 SOSIP; clade B) for HIV-1-specific B cell sorting is likely the explanation of why MEL-1872 neutralization was broader and more potent than NC-Cow1 and other CD4bs antibodies that were isolated using Env binding-based HIV-1-specific B cell selection.

Although there are numerous approved drugs against HIV-1 infection, they are limited to wealthy nations and lifelong treatment can be associated with significant toxicity and economic cost. Passive antibody prophylaxis and immunotherapy could hold a valuable place in both the prevention and treatment of HIV-1 infection. Disulphide bonds in bovine CDRH3 results in a rigid structure that might survive the acidic environment of mucosal environment better than human BrNAbs [9]. This rigid structure in bovine CDRH3 provides an excellent opportunity to design novel small molecule drug inhibitors accessing deep recessed epitopes on HIV-1 Env more efficiently than human BrNAbs.

In conclusion, these data highlight those technical advantages identified by the inventors including that the defined broadly neutralising HIV-1 antibodies are capable of neutralizing multiple HIV-1 viral strains by targeting conserved epitopes of the HIV-1 Env protein, that they have higher potency than commercially available therapeutic antibodies, that they are capable of binding to multiple forms of HIV-1 Env and that they are not polyreactive or autoreactive, unlike antibody VRC01, highlighting their safety as anti-HIV therapeutics. These findings are significant in so far as they demonstrate that the antigen binding sites and antibodies described herein hold utility in the prevention, attenuation, treatment and neutralisation of HIV-1 infection.

What is claimed is:

1. An antibody or antigen binding fragment thereof for binding human immunodeficiency virus type 1 (HIV-1), wherein the antibody or antigen binding fragment thereof comprises:

a) a heavy chain complementarity determining region 1 (CDRH1) set forth in SEQ ID NO: 1, a CDRH2 set forth in SEQ ID NO: 2, a CDRH3 set forth in SEQ ID NO: 3, a light chain complementarity determining region 1 (CDRL1) set forth in SEQ ID NO: 39, a CDRL2 set forth in SEQ ID NO: 40, and a CDRL3 set forth in SEQ ID NO: 41;

b) a CDRH1 set forth in SEQ ID NO: 1, a CDRH2 set forth in SEQ ID NO: 2, a CDRH3 set forth in SEQ ID NO: 3, a CDRL1 set forth in SEQ ID NO: 74, a CDRL2 set forth in SEQ ID NO: 75, and a CDRL3 set forth in SEQ ID NO: 76;

c) a CDRH1 set forth in SEQ ID NO: 1, a CDRH2 set forth in SEQ ID NO: 2, a CDRH3 set forth in SEQ ID NO: 3, a CDRL1 set forth in SEQ ID NO: 83, a CDRL2 set forth in SEQ ID NO: 84, and a CDRL3 set forth in SEQ ID NO: 85;

d) a CDRH1 set forth in SEQ ID NO: 87, a CDRH2 set forth in SEQ ID NO: 88, a CDRH3 set forth in SEQ ID NO: 89, a CDRL1 set forth in SEQ ID NO: 131, a CDRL2 set forth in SEQ ID NO: 132, and a CDRL3 set forth in SEQ ID NO: 133;

e) a CDRH1 set forth in SEQ ID NO: 87, a CDRH2 set forth in SEQ ID NO: 88, a CDRH3 set forth in SEQ ID NO: 89, a CDRL1 set forth in SEQ ID NO: 131, a CDRL2 set forth in SEQ ID NO: 132, and a CDRL3 set forth in SEQ ID NO: 76;

f) a CDRH1 set forth in SEQ ID NO: 87, a CDRH2 set forth in SEQ ID NO: 88, a CDRH3 set forth in SEQ ID NO: 89, a CDRL1 set forth in SEQ ID NO: 131, a CDRL2 set forth in SEQ ID NO: 132, and a CDRL3 set forth in SEQ ID NO: 85;

g) a CDRH1 set forth in SEQ ID NO: 17, a CDRH2 set forth in SEQ ID NO: 18, a CDRH3 set forth in SEQ ID NO: 19, a CDRL1 set forth in SEQ ID NO: 39, a CDRL2 set forth in SEQ ID NO: 40, and a CDRL3 set forth in SEQ ID NO: 41;

h) a CDRH1 set forth in SEQ ID NO: 17, a CDRH2 set forth in SEQ ID NO: 18, a CDRH3 set forth in SEQ ID NO: 19, a CDRL1 set forth in SEQ ID NO: 74, a CDRL2 set forth in SEQ ID NO: 75, and a CDRL3 set forth in SEQ ID NO: 76;

i) a CDRH1 set forth in SEQ ID NO: 17, a CDRH2 set forth in SEQ ID NO: 18, a CDRH3 set forth in SEQ ID NO: 19, a CDRL1 set forth in SEQ ID NO: 83, a CDRL2 set forth in SEQ ID NO: 84, and a CDRL3 set forth in SEQ ID NO: 85;

j) a CDRH1 set forth in SEQ ID NO: 101, a CDRH2 set forth in SEQ ID NO: 102, a CDRH3 set forth in SEQ ID NO: 103, a CDRL1 set forth in SEQ ID NO: 131, a CDRL2 set forth in SEQ ID NO: 132, and a CDRL3 set forth in SEQ ID NO: 133;

k) a CDRH1 set forth in SEQ ID NO: 101, a CDRH2 set forth in SEQ ID NO: 102, a CDRH3 set forth in SEQ ID NO: 103, a CDRL1 set forth in SEQ ID NO: 131, a CDRL2 set forth in SEQ ID NO: 132, and a CDRL3 set forth in SEQ ID NO: 76;

l) a CDRH1 set forth in SEQ ID NO: 101, a CDRH2 set forth in SEQ ID NO: 102, a CDRH3 set forth in SEQ ID NO: 103, a CDRL1 set forth in SEQ ID NO: 131, a CDRL2 set forth in SEQ ID NO: 132, and a CDRL3 set forth in SEQ ID NO: 85;

m) a CDRH1 set forth in SEQ ID NO: 33, a CDRH2 set forth in SEQ ID NO: 34, a CDRH3 set forth in SEQ ID NO: 35, a CDRL1 set forth in SEQ ID NO: 39, a CDRL2 set forth in SEQ ID NO: 40, and a CDRL3 set forth in SEQ ID NO: 41;

n) a CDRH1 set forth in SEQ ID NO: 33, a CDRH2 set forth in SEQ ID NO: 34, a CDRH3 set forth in SEQ ID NO: 35, a CDRL1 set forth in SEQ ID NO: 74, a CDRL2 set forth in SEQ ID NO: 75, and a CDRL3 set forth in SEQ ID NO: 76;

o) a CDRH1 set forth in SEQ ID NO: 33, a CDRH2 set forth in SEQ ID NO: 34, a CDRH3 set forth in SEQ ID NO: 35, a CDRL1 set forth in SEQ ID NO: 83, a CDRL2 set forth in SEQ ID NO: 84, and a CDRL3 set forth in SEQ ID NO: 85;

p) a CDRH1 set forth in SEQ ID NO: 115, a CDRH2 set forth in SEQ ID NO: 116, a CDRH3 set forth in SEQ ID NO: 117, a CDRL1 set forth in SEQ ID NO: 131, a CDRL2 set forth in SEQ ID NO: 132, and a CDRL3 set forth in SEQ ID NO: 133;

q) a CDRH1 set forth in SEQ ID NO: 115, a CDRH2 set forth in SEQ ID NO: 116, a CDRH3 set forth in SEQ ID NO: 117, a CDRL1 set forth in SEQ ID NO: 131, a CDRL2 set forth in SEQ ID NO: 132, and a CDRL3 set forth in SEQ ID NO: 76; or r) a CDRH1 set forth in SEQ ID NO: 115, a CDRH2 set forth in SEQ ID NO: 116, a CDRH3 set forth in SEQ ID NO: 117, a CDRL1 set forth in SEQ ID NO: 131, a CDRL2 set forth in SEQ ID NO: 132, and a CDRL3 set forth in SEQ ID NO: 85.

2. The antibody or antigen binding fragment thereof of claim 1, wherein the antibody or antigen binding fragment thereof comprises a heavy chain variable region set forth in SEQ ID NO: 15, and a light chain variable region set forth in SEQ ID NO: 63 or 73.

3. The antibody or antigen binding fragment thereof of claim 1, wherein the antibody or antigen binding fragment thereof comprises a heavy chain variable region set forth in SEQ ID NO: 31, and a light chain variable region set forth in SEQ ID NO: 63 or 73.

4. The antibody or antigen binding fragment thereof of claim 1, wherein the antibody or antigen binding fragment thereof comprises a heavy chain variable region set forth in SEQ ID NO: 61, and a light chain variable region set forth in SEQ ID NO: 63 or 73.

5. A fusion protein comprising an antibody or antigen binding fragment thereof according to claim 1.

6. A conjugate in the form of an antibody or antigen binding fragment thereof according to claim 1, conjugated to a label or a cytotoxic agent.

7. A nucleic acid encoding an antibody or antigen binding fragment thereof according to claim 1.

8. A cell comprising a nucleic acid according to claim 7.

9. A pharmaceutical composition comprising an antibody or antigen binding fragment thereof according to claim 1 and a pharmaceutically acceptable carrier, diluent, or excipient.

10. A method for treating, inhibiting, or neutralising a human immunodeficiency virus type-1 (HIV-1) infection in a subject in need thereof, or increasing survival of a subject, comprising administering an effective amount of the antibody or antigen binding fragment thereof of claim 1 to a subject, thereby treating, inhibiting, or neutralising a HIV-1 infection, or increasing survival in the subject in need thereof.

* * * * *

SEQUENCE LISTING

```
<160> NUMBER OF SEQ ID NOS: 229

<210> SEQ ID NO 1
<211> LENGTH: 5
<212> TYPE: PRT
<213> ORGANISM: Bos taurus

<400> SEQUENCE: 1

Asp Lys Ala Val Gly
1               5


<210> SEQ ID NO 2
<211> LENGTH: 16
<212> TYPE: PRT
<213> ORGANISM: Bos taurus

<400> SEQUENCE: 2

Ser Ile Asp Thr Gly Gly Asn Ala Asp Tyr Asn Pro Gly Leu Lys Ser
1               5                   10                  15


<210> SEQ ID NO 3
<211> LENGTH: 57
<212> TYPE: PRT
<213> ORGANISM: Bos taurus

<400> SEQUENCE: 3

Val His Gln Lys Thr Leu Arg Ser Cys Pro Ser Asp Tyr Pro Tyr Ile
1               5                   10                  15

Cys Asp Cys Glu Asp Thr Gly Ser His Cys Cys Arg Ala Thr Asn Cys
            20                  25                  30

Pro Tyr Tyr Cys Asn His Gly Arg Asp Arg Met Cys Thr Gly Arg Thr
        35                  40                  45

Tyr Thr Tyr Glu Trp His Val Glu Ala
    50                  55


<210> SEQ ID NO 4
<211> LENGTH: 15
<212> TYPE: DNA
<213> ORGANISM: Bos taurus

<400> SEQUENCE: 4

gacaaggctg taggc                                                      15


<210> SEQ ID NO 5
<211> LENGTH: 48
<212> TYPE: DNA
<213> ORGANISM: Bos taurus

<400> SEQUENCE: 5

agtatagaca ctggcggaaa cgcagattat aacccaggcc tgaaatcc                  48


<210> SEQ ID NO 6
<211> LENGTH: 171
<212> TYPE: DNA
```

<213> ORGANISM: Bos taurus

<400> SEQUENCE: 6
gtgcaccaga agacactccg tagttgtcct tctgattatc cttatatttg tgattgtgaa 60
gatactggta gtcattgctg tcgggctact aattgtcctt attactgcaa tcatggccgt 120
gatcgtatgt gtaccggtcg tacttacacg tacgagtggc acgtcgaagc c 171

<210> SEQ ID NO 7
<211> LENGTH: 30
<212> TYPE: PRT
<213> ORGANISM: Bos taurus

<400> SEQUENCE: 7

Lys Val Gln Leu Gln Glu Ser Gly Pro Ser Leu Val Lys Pro Ser Gln
1 5 10 15

Thr Leu Ser Leu Thr Cys Thr Ala Ser Gly Phe Ser Leu Ser
20 25 30

<210> SEQ ID NO 8
<211> LENGTH: 14
<212> TYPE: PRT
<213> ORGANISM: Bos taurus

<400> SEQUENCE: 8

Trp Val Arg Gln Ala Pro Gly Gln Ala Leu Glu Trp Leu Gly
1 5 10

<210> SEQ ID NO 9
<211> LENGTH: 32
<212> TYPE: PRT
<213> ORGANISM: Bos taurus

<400> SEQUENCE: 9

Arg Leu Ser Ile Thr Lys Asp Asn Ala Lys Ser Gln Val Ser Leu Ser
1 5 10 15

Val Ser Ser Val Thr Thr Glu Gly Ser Ala Thr Tyr Tyr Cys Ser Thr
20 25 30

<210> SEQ ID NO 10
<211> LENGTH: 11
<212> TYPE: PRT
<213> ORGANISM: Bos taurus

<400> SEQUENCE: 10

Trp Gly Gln Gly Leu Leu Val Thr Val Ser Ser
1 5 10

<210> SEQ ID NO 11
<211> LENGTH: 90
<212> TYPE: DNA
<213> ORGANISM: Bos taurus

<400> SEQUENCE: 11
aaggtgcagc tgcaggagtc gggccccagc ctggtgaagc cgtcacagac cctctcgctc 60
acctgcacgg cctctggatt ctcattgagc 90

<210> SEQ ID NO 12
<211> LENGTH: 42
<212> TYPE: DNA
<213> ORGANISM: Bos taurus

<400> SEQUENCE: 12

```
tgggtccgcc aggctccagg gcaggcgctg gagtggctcg gt                      42


<210> SEQ ID NO 13
<211> LENGTH: 96
<212> TYPE: DNA
<213> ORGANISM: Bos taurus

<400> SEQUENCE: 13

cggctcagca tcaccaagga taacgccaag agccaagtct ctctgtcagt aagcagcgtg     60

acaactgagg gctcggccac gtattactgt tctact                              96


<210> SEQ ID NO 14
<211> LENGTH: 33
<212> TYPE: DNA
<213> ORGANISM: Bos taurus

<400> SEQUENCE: 14

tggggccagg gactcctggt caccgtctcc tca                                 33


<210> SEQ ID NO 15
<211> LENGTH: 165
<212> TYPE: PRT
<213> ORGANISM: Bos taurus

<400> SEQUENCE: 15

Lys Val Gln Leu Gln Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Gln Ala Leu Glu Trp Leu
        35                  40                  45

Gly Ser Ile Asp Thr Gly Gly Asn Ala Asp Tyr Asn Pro Gly Leu Lys
    50                  55                  60

Ser Arg Leu Ser Ile Thr Lys Asp Asn Ala Lys Ser Gln Val Ser Leu
65                  70                  75                  80

Ser Val Ser Ser Val Thr Thr Glu Gly Ser Ala Thr Tyr Tyr Cys Ser
                85                  90                  95

Thr Val His Gln Lys Thr Leu Arg Ser Cys Pro Ser Asp Tyr Pro Tyr
            100                 105                 110

Ile Cys Asp Cys Glu Asp Thr Gly Ser His Cys Cys Arg Ala Thr Asn
        115                 120                 125

Cys Pro Tyr Tyr Cys Asn His Gly Arg Asp Arg Met Cys Thr Gly Arg
    130                 135                 140

Thr Tyr Thr Tyr Glu Trp His Val Glu Ala Trp Gly Gln Gly Leu Leu
145                 150                 155                 160

Val Thr Val Ser Ser
                165


<210> SEQ ID NO 16
<211> LENGTH: 495
<212> TYPE: DNA
<213> ORGANISM: Bos taurus

<400> SEQUENCE: 16

aaggtgcagc tgcaggagtc gggccccagc ctggtgaagc cgtcacagac cctctcgctc     60

acctgcacgg cctctggatt ctcattgagc gacaaggctg taggctgggt ccgccaggct    120

ccagggcagg cgctggagtg gctcggtagt atagacactg gcggaaacgc agattataac    180
```

```
ccaggcctga aatcccggct cagcatcacc aaggataacg ccaagagcca agtctctctg    240

tcagtaagca gcgtgacaac tgagggctcg gccacgtatt actgttctac tgtgcaccag    300

aagacactcc gtagttgtcc ttctgattat ccttatattt gtgattgtga agatactggt    360

agtcattgct gtcgggctac taattgtcct tattactgca atcatggccg tgatcgtatg    420

tgtaccggtc gtacttacac gtacgagtgg cacgtcgaag cctggggcca gggactcctg    480

gtcaccgtct cctca                                                      495


<210> SEQ ID NO 17
<211> LENGTH: 5
<212> TYPE: PRT
<213> ORGANISM: Bos taurus

<400> SEQUENCE: 17

Asp Lys Ala Val Gly
1               5


<210> SEQ ID NO 18
<211> LENGTH: 16
<212> TYPE: PRT
<213> ORGANISM: Bos taurus

<400> SEQUENCE: 18

Thr Ile Asp Thr Thr Gly Asn Ala Val Tyr Asn Pro Gly Leu Lys Ser
1               5                   10                  15


<210> SEQ ID NO 19
<211> LENGTH: 57
<212> TYPE: PRT
<213> ORGANISM: Bos taurus

<400> SEQUENCE: 19

Val His Gln Lys Thr Arg Arg Ser Cys Pro Ser Asp Tyr Ser Phe Ile
1               5                   10                  15

Cys Asp Cys Glu Gly Thr Gly Ser His Cys Cys Arg Ala Ser Asn Cys
            20                  25                  30

Pro Tyr Tyr Cys Asn Tyr Gly Arg Asp Arg Met Cys Thr Gly Arg Ser
        35                  40                  45

Asn Ile His Glu Trp His Val Asp Ala
    50                  55


<210> SEQ ID NO 20
<211> LENGTH: 15
<212> TYPE: DNA
<213> ORGANISM: Bos taurus

<400> SEQUENCE: 20

gacaaggctg taggc                                                       15


<210> SEQ ID NO 21
<211> LENGTH: 48
<212> TYPE: DNA
<213> ORGANISM: Bos taurus

<400> SEQUENCE: 21

actatagaca ctactggaaa cgcagtctat aacccaggcc tgaaatcc                   48


<210> SEQ ID NO 22
<211> LENGTH: 171
<212> TYPE: DNA
```

<213> ORGANISM: Bos taurus

<400> SEQUENCE: 22
gtgcaccaga agacacgtcg cagttgtcct tctgattata gtttcatttg tgattgtgaa 60
ggtactggca gtcattgctg tcgggcttct aattgtcctt attactgcaa ttacggccgt 120
gatcgtatgt gtacgggcag gagtaacatt cacgaatggc acgtcgatgc c 171

<210> SEQ ID NO 23
<211> LENGTH: 30
<212> TYPE: PRT
<213> ORGANISM: Bos taurus

<400> SEQUENCE: 23

Lys Val Gln Leu Arg Glu Ser Gly Pro Ser Leu Val Lys Pro Ser Gln
1 5 10 15

Thr Leu Ser Leu Thr Cys Thr Ala Ser Gly Phe Ser Leu Ser
20 25 30

<210> SEQ ID NO 24
<211> LENGTH: 14
<212> TYPE: PRT
<213> ORGANISM: Bos taurus

<400> SEQUENCE: 24

Trp Val Arg Gln Ala Pro Gly Gln Pro Leu Glu Trp Leu Gly
1 5 10

<210> SEQ ID NO 25
<211> LENGTH: 32
<212> TYPE: PRT
<213> ORGANISM: Bos taurus

<400> SEQUENCE: 25

Arg Leu Ser Ile Thr Lys Asp Asn Ser Lys Ser Gln Val Ser Leu Ser
1 5 10 15

Leu Ser Ser Val Thr Thr Glu Asp Ser Ala Thr Tyr His Cys Ser Thr
20 25 30

<210> SEQ ID NO 26
<211> LENGTH: 11
<212> TYPE: PRT
<213> ORGANISM: Bos taurus

<400> SEQUENCE: 26

Trp Gly Gln Gly Leu Leu Val Thr Val Ser Ser
1 5 10

<210> SEQ ID NO 27
<211> LENGTH: 90
<212> TYPE: DNA
<213> ORGANISM: Bos taurus

<400> SEQUENCE: 27
aaggtgcagc tgcgggagtc gggccccagc ctggtgaagc cgtcacagac cctctcgctc 60
acctgcacag cctctggatt ctcattgagc 90

<210> SEQ ID NO 28
<211> LENGTH: 42
<212> TYPE: DNA
<213> ORGANISM: Bos taurus

<400> SEQUENCE: 28
tgggttcgcc aggctccagg gcagccgctg gagtggctcg gt 42

<210> SEQ ID NO 29
<211> LENGTH: 96
<212> TYPE: DNA
<213> ORGANISM: Bos taurus

<400> SEQUENCE: 29
cggctcagca tcaccaagga taactccaag agccaggtct ctctgtcact aagcagcgtg 60
acaactgagg actcggccac atatcactgt tctact 96

<210> SEQ ID NO 30
<211> LENGTH: 33
<212> TYPE: DNA
<213> ORGANISM: Bos taurus

<400> SEQUENCE: 30
tggggccaag gtctcctggt caccgtctcc tca 33

<210> SEQ ID NO 31
<211> LENGTH: 165
<212> TYPE: PRT
<213> ORGANISM: Bos taurus

<400> SEQUENCE: 31

Lys Val Gln Leu Arg Glu Ser Gly Pro Ser Leu Val Lys Pro Ser Gln
1 5 10 15

Thr Leu Ser Leu Thr Cys Thr Ala Ser Gly Phe Ser Leu Ser Asp Lys
20 25 30

Ala Val Gly Trp Val Arg Gln Ala Pro Gly Gln Pro Leu Glu Trp Leu
35 40 45

Gly Thr Ile Asp Thr Thr Gly Asn Ala Val Tyr Asn Pro Gly Leu Lys
50 55 60

Ser Arg Leu Ser Ile Thr Lys Asp Asn Ser Lys Ser Gln Val Ser Leu
65 70 75 80

Ser Leu Ser Ser Val Thr Thr Glu Asp Ser Ala Thr Tyr His Cys Ser
85 90 95

Thr Val His Gln Lys Thr Arg Arg Ser Cys Pro Ser Asp Tyr Ser Phe
100 105 110

Ile Cys Asp Cys Glu Gly Thr Gly Ser His Cys Cys Arg Ala Ser Asn
115 120 125

Cys Pro Tyr Tyr Cys Asn Tyr Gly Arg Asp Arg Met Cys Thr Gly Arg
130 135 140

Ser Asn Ile His Glu Trp His Val Asp Ala Trp Gly Gln Gly Leu Leu
145 150 155 160

Val Thr Val Ser Ser
165

<210> SEQ ID NO 32
<211> LENGTH: 495
<212> TYPE: DNA
<213> ORGANISM: Bos taurus

<400> SEQUENCE: 32
aaggtgcagc tgcgggagtc gggccccagc ctggtgaagc cgtcacagac cctctcgctc 60
acctgcacag cctctggatt ctcattgagc gacaaggctg taggctgggt tcgccaggct 120
ccagggcagc cgctggagtg gctcggtact atagacacta ctggaaacgc agtctataac 180

```
ccaggcctga aatcccggct cagcatcacc aaggataact ccaagagcca ggtctctctg    240

tcactaagca gcgtgacaac tgaggactcg gccacatatc actgttctac tgtgcaccag    300

aagacacgtc gcagttgtcc ttctgattat agtttcattt gtgattgtga aggtactggc    360

agtcattgct gtcgggcttc taattgtcct tattactgca attacggccg tgatcgtatg    420

tgtacgggca ggagtaacat tcacgaatgg cacgtcgatg cctggggcca aggtctcctg    480

gtcaccgtct cctca                                                     495


<210> SEQ ID NO 33
<211> LENGTH: 5
<212> TYPE: PRT
<213> ORGANISM: Bos taurus

<400> SEQUENCE: 33

Asp Lys Ala Val Gly
1               5


<210> SEQ ID NO 34
<211> LENGTH: 16
<212> TYPE: PRT
<213> ORGANISM: Bos taurus

<400> SEQUENCE: 34

Ser Ile Asp Thr Gly Gly Asn Ala Gly Tyr Asn Pro Gly Leu Lys Ser
1               5                   10                  15


<210> SEQ ID NO 35
<211> LENGTH: 58
<212> TYPE: PRT
<213> ORGANISM: Bos taurus

<400> SEQUENCE: 35

Val His Gln Lys Thr Arg Arg Ser Cys Pro Val Asp Tyr Tyr Tyr Ser
1               5                   10                  15

Cys Asp Cys Glu Gly Ser Gly Ser His Cys Cys Ser Ala Ser Asn Cys
            20                  25                  30

Pro Tyr Tyr Cys Lys Tyr Gly Arg Asp Arg Val Cys Thr Asp Lys His
        35                  40                  45

Thr Tyr Ser Tyr Glu Trp Tyr Val Asp Ala
    50                  55


<210> SEQ ID NO 36
<211> LENGTH: 15
<212> TYPE: DNA
<213> ORGANISM: Bos taurus

<400> SEQUENCE: 36

gacaaggctg taggc                                                      15


<210> SEQ ID NO 37
<211> LENGTH: 48
<212> TYPE: DNA
<213> ORGANISM: Bos taurus

<400> SEQUENCE: 37

agtatagaca ctggtggaaa cgcaggctat aacccaggcc tgaaatcc                  48


<210> SEQ ID NO 38
<211> LENGTH: 174
<212> TYPE: DNA
```

<213> ORGANISM: Bos taurus

<400> SEQUENCE: 38
gtgcaccaga agacacgacg tagttgtcct gttgattatt attatagttg cgactgtgaa 60
ggtagtggta gtcattgttg ctcggcttct aattgtcctt attactgcaa gtatggccgt 120
gatagagttt gtactgacaa acatacttac agttacgaat ggtacgtcga tgcc 174

<210> SEQ ID NO 39
<211> LENGTH: 13
<212> TYPE: PRT
<213> ORGANISM: Bos taurus

<400> SEQUENCE: 39

Ser Gly Ser Ser Ser Asn Val Gly Asn Gly Tyr Val Ser
1 5 10

<210> SEQ ID NO 40
<211> LENGTH: 7
<212> TYPE: PRT
<213> ORGANISM: Bos taurus

<400> SEQUENCE: 40

Gly Asp Thr Ser Arg Ala Ser
1 5

<210> SEQ ID NO 41
<211> LENGTH: 11
<212> TYPE: PRT
<213> ORGANISM: Bos taurus

<400> SEQUENCE: 41

Ala Ser Ala Glu Asp Gly Ser Ser Asn Ala Val
1 5 10

<210> SEQ ID NO 42
<211> LENGTH: 39
<212> TYPE: DNA
<213> ORGANISM: Bos taurus

<400> SEQUENCE: 42
tctggaagca gcagcaatgt tggaaatgga tatgtgagc 39

<210> SEQ ID NO 43
<211> LENGTH: 21
<212> TYPE: DNA
<213> ORGANISM: Bos taurus

<400> SEQUENCE: 43
ggtgacacca gtcgagcctc g 21

<210> SEQ ID NO 44
<211> LENGTH: 33
<212> TYPE: DNA
<213> ORGANISM: Bos taurus

<400> SEQUENCE: 44
gcatctgctg aggatggtag cagtaatgct gtt 33

<210> SEQ ID NO 45
<211> LENGTH: 30
<212> TYPE: PRT
<213> ORGANISM: Bos taurus

<400> SEQUENCE: 45

Lys Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser
            20                  25                  30

<210> SEQ ID NO 46
<211> LENGTH: 14
<212> TYPE: PRT
<213> ORGANISM: Bos taurus

<400> SEQUENCE: 46

Trp Val Arg Gln Ala Pro Gly Lys Ala Leu Glu Trp Leu Gly
1               5                   10

<210> SEQ ID NO 47
<211> LENGTH: 32
<212> TYPE: PRT
<213> ORGANISM: Bos taurus

<400> SEQUENCE: 47

Arg Leu Ser Ile Thr Lys Gly Asn Ser Lys Ser Gln Val Ser Leu Ser
1               5                   10                  15

Val Ser Ser Val Thr Thr Glu Asp Ser Ala Thr Tyr Tyr Cys Ser Thr
            20                  25                  30

<210> SEQ ID NO 48
<211> LENGTH: 11
<212> TYPE: PRT
<213> ORGANISM: Bos taurus

<400> SEQUENCE: 48

Trp Gly Gln Gly Leu Leu Val Thr Val Ser Ser
1               5                   10

<210> SEQ ID NO 49
<211> LENGTH: 90
<212> TYPE: DNA
<213> ORGANISM: Bos taurus

<400> SEQUENCE: 49
aaggtgcagc tgcgggagtc gggccccagc ctggtgaagc cgtcacagac cctctcgctc     60
acctgcacgg cctctggatt ctcattaagc                                      90

<210> SEQ ID NO 50
<211> LENGTH: 42
<212> TYPE: DNA
<213> ORGANISM: Bos taurus

<400> SEQUENCE: 50
tgggtccgcc aggctccagg gaaggcgctg gagtggctcg gt                        42

<210> SEQ ID NO 51
<211> LENGTH: 96
<212> TYPE: DNA
<213> ORGANISM: Bos taurus

<400> SEQUENCE: 51
cggctcagca tcaccaaggg taactccaag agccaagtct ctctgtcagt gagtagcgtg     60
acgactgagg actcggccac atattactgt tctact                               96

<210> SEQ ID NO 52
<211> LENGTH: 33
<212> TYPE: DNA
<213> ORGANISM: Bos taurus

<400> SEQUENCE: 52
tggggccagg gactcctggt caccgtctcc tca 33

<210> SEQ ID NO 53
<211> LENGTH: 22
<212> TYPE: PRT
<213> ORGANISM: Bos taurus

<400> SEQUENCE: 53

Gln Ala Val Leu Thr Gln Pro Ser Ser Val Ser Gly Ser Leu Gly Gln
1 5 10 15

Arg Val Ser Thr Thr Cys
20

<210> SEQ ID NO 54
<211> LENGTH: 15
<212> TYPE: PRT
<213> ORGANISM: Bos taurus

<400> SEQUENCE: 54

Trp Tyr Gln Leu Ile Pro Gly Ser Ala Pro Arg Thr Leu Ile Tyr
1 5 10 15

<210> SEQ ID NO 55
<211> LENGTH: 32
<212> TYPE: PRT
<213> ORGANISM: Bos taurus

<400> SEQUENCE: 55

Gly Val Pro Asp Arg Phe Ser Gly Ser Arg Ser Gly Asn Thr Val Thr
1 5 10 15

Leu Thr Ile Ser Ser Leu Gln Ala Glu Asp Glu Ala Asp Tyr Phe Cys
20 25 30

<210> SEQ ID NO 56
<211> LENGTH: 10
<212> TYPE: PRT
<213> ORGANISM: Bos taurus

<400> SEQUENCE: 56

Phe Gly Arg Gly Thr Thr Leu Thr Val Val
1 5 10

<210> SEQ ID NO 57
<211> LENGTH: 66
<212> TYPE: DNA
<213> ORGANISM: Bos taurus

<400> SEQUENCE: 57
caggctgtgc tgactcagcc atcatccgtg tccgggtccc tgggccagag ggtctccacc 60
acctgc 66

<210> SEQ ID NO 58
<211> LENGTH: 45
<212> TYPE: DNA
<213> ORGANISM: Bos taurus

<400> SEQUENCE: 58
tggtaccaac tgattccagg atcggccccc agaaccctca tctat 45

<210> SEQ ID NO 59
<211> LENGTH: 96
<212> TYPE: DNA
<213> ORGANISM: Bos taurus

<400> SEQUENCE: 59
ggggtccccg accgattctc cggctccagg tctgggaaca cagtcaccct gaccatcagc 60
tcgctccagg ctgaggacga ggcagattat ttctgc 96

<210> SEQ ID NO 60
<211> LENGTH: 30
<212> TYPE: DNA
<213> ORGANISM: Bos taurus

<400> SEQUENCE: 60
ttcggcagag ggaccacact gacagtcgtc 30

<210> SEQ ID NO 61
<211> LENGTH: 166
<212> TYPE: PRT
<213> ORGANISM: Bos taurus

<400> SEQUENCE: 61

```
Lys Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Ala Gly Tyr Asn Pro Gly Leu Lys
    50                  55                  60

Ser Arg Leu Ser Ile Thr Lys Gly Asn Ser Lys Ser Gln Val Ser Leu
65                  70                  75                  80

Ser Val Ser Ser Val Thr Thr Glu Asp Ser Ala Thr Tyr Tyr Cys Ser
                85                  90                  95

Thr Val His Gln Lys Thr Arg Arg Ser Cys Pro Val Asp Tyr Tyr Tyr
            100                 105                 110

Ser Cys Asp Cys Glu Gly Ser Gly Ser His Cys Cys Ser Ala Ser Asn
        115                 120                 125

Cys Pro Tyr Tyr Cys Lys Tyr Gly Arg Asp Arg Val Cys Thr Asp Lys
    130                 135                 140

His Thr Tyr Ser Tyr Glu Trp Tyr Val Asp Ala Trp Gly Gln Gly Leu
145                 150                 155                 160

Leu Val Thr Val Ser Ser
                165
```

<210> SEQ ID NO 62
<211> LENGTH: 498
<212> TYPE: DNA
<213> ORGANISM: Bos taurus

<400> SEQUENCE: 62
aaggtgcagc tgcgggagtc gggccccagc ctggtgaagc cgtcacagac cctctcgctc 60
acctgcacgg cctctggatt ctcattaagc gacaaggctg taggctgggt ccgccaggct 120
ccagggaagg cgctggagtg gctcggtagt atagacactg gtggaaacgc aggctataac 180

-continued

```
ccaggcctga aatcccggct cagcatcacc aagggtaact ccaagagcca agtctctctg    240

tcagtgagta gcgtgacgac tgaggactcg gccacatatt actgttctac tgtgcaccag    300

aagacacgac gtagttgtcc tgttgattat tattatagtt gcgactgtga aggtagtggt    360

agtcattgtt gctcggcttc taattgtcct tattactgca agtatggccg tgatagagtt    420

tgtactgaca aacatactta cagttacgaa tggtacgtcg atgcctgggg ccagggactc    480

ctggtcaccg tctcctca                                                  498
```

<210> SEQ ID NO 63
<211> LENGTH: 109
<212> TYPE: PRT
<213> ORGANISM: Bos taurus

<400> SEQUENCE: 63

```
Gln Ala Val Leu Thr Gln Pro Ser Ser Val Ser Gly Ser Leu Gly Gln
1               5                   10                  15

Arg Val Ser Thr Thr Cys Ser Gly Ser Ser Ser Asn Val Gly Asn Gly
            20                  25                  30

Tyr Val Ser Trp Tyr Gln Leu Ile Pro Gly Ser Ala Pro Arg Thr Leu
        35                  40                  45

Ile Tyr Gly Asp Thr Ser Arg Ala Ser Gly Val Pro Asp Arg Phe Ser
    50                  55                  60

Gly Ser Arg Ser Gly Asn Thr Val Thr Leu Thr Ile Ser Ser Leu Gln
65                  70                  75                  80

Ala Glu Asp Glu Ala Asp Tyr Phe Cys Ala Ser Ala Glu Asp Gly Ser
                85                  90                  95

Ser Asn Ala Val Phe Gly Arg Gly Thr Thr Leu Thr Val
            100                 105
```

<210> SEQ ID NO 64
<211> LENGTH: 333
<212> TYPE: DNA
<213> ORGANISM: Bos taurus

<400> SEQUENCE: 64

```
aattcgcagg ctgtgctgac tcagccatca tccgtgtccg ggtccctggg ccagagggtc     60

tccaccacct gctctggaag cagcagcaat gttggaaatg gatatgtgag ctggtaccaa    120

ctgattccag gatcggcccc cagaaccctc atctatggtg acaccagtcg agcctcgggg    180

gtccccgacc gattctccgg ctccaggtct gggaacacag tcaccctgac catcagctcg    240

ctccaggctg aggacgaggc agattatttc tgcgcatctg ctgaggatgg tagcagtaat    300

gctgttttcg gcagagggac cacactgaca gtc                                 333
```

<210> SEQ ID NO 65
<211> LENGTH: 508
<212> TYPE: PRT
<213> ORGANISM: Bos taurus

<400> SEQUENCE: 65

```
Met Arg Val Lys Glu Lys Tyr Gln His Leu Trp Arg Trp Gly Trp Lys
1               5                   10                  15

Trp Gly Thr Met Leu Leu Gly Ile Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
```

-continued

```
    50                  55                  60

Val His Asn Val Trp Ala Thr His Ala Cys Val Pro Thr Asp Pro Asn
65                  70                  75                  80

Pro Gln Glu Val Val Leu Glu Asn Val Thr Glu Asn Phe Asn Met Trp
                85                  90                  95

Lys Asn Asn Met Val Glu Gln Met His Glu Asp Ile Ile Ser Leu Trp
            100                 105                 110

Asp Gln Ser Leu Lys Pro Cys Val Lys Leu Thr Pro Leu Cys Val Thr
        115                 120                 125

Leu Asn Cys Thr Asp Leu Arg Asn Val Thr Asn Ile Asn Asn Ser Ser
    130                 135                 140

Glu Gly Met Arg Gly Glu Ile Lys Asn Cys Ser Phe Asn Ile Thr Thr
145                 150                 155                 160

Ser Ile Arg Asp Lys Val Lys Lys Asp Tyr Ala Leu Phe Tyr Arg Leu
                165                 170                 175

Asp Val Val Pro Ile Asp Asn Asp Asn Thr Ser Tyr Arg Leu Ile Asn
            180                 185                 190

Cys Asn Thr Ser Thr Ile Thr Gln Ala Cys Pro Lys Val Ser Phe Glu
        195                 200                 205

Pro Ile Pro Ile His Tyr Cys Thr Pro Ala Gly Phe Ala Ile Leu Lys
    210                 215                 220

Cys Lys Asp Lys Lys Phe Asn Gly Thr Gly Pro Cys Lys Asn Val Ser
225                 230                 235                 240

Thr Val Gln Cys Thr His Gly Ile Arg Pro Val Val Ser Thr Gln Leu
                245                 250                 255

Leu Leu Asn Gly Ser Leu Ala Glu Glu Glu Val Val Ile Arg Ser Ser
            260                 265                 270

Asn Phe Thr Asp Asn Ala Lys Asn Ile Ile Val Gln Leu Lys Glu Ser
        275                 280                 285

Val Glu Ile Asn Cys Thr Arg Pro Asn Asn Asn Thr Arg Lys Ser Ile
    290                 295                 300

His Ile Gly Pro Gly Arg Ala Phe Tyr Thr Thr Gly Asp Ile Ile Gly
305                 310                 315                 320

Asp Ile Arg Gln Ala His Cys Asn Ile Ser Arg Thr Lys Trp Asn Asn
                325                 330                 335

Thr Leu Asn Gln Ile Ala Thr Lys Leu Lys Glu Gln Phe Gly Asn Asn
            340                 345                 350

Lys Thr Ile Val Phe Asn Gln Ser Ser Gly Gly Asp Pro Glu Ile Val
        355                 360                 365

Met His Ser Phe Asn Cys Gly Gly Glu Phe Phe Tyr Cys Asn Ser Thr
    370                 375                 380

Gln Leu Phe Asn Ser Thr Trp Asn Phe Asn Gly Thr Trp Asn Leu Thr
385                 390                 395                 400

Gln Ser Asn Gly Thr Glu Gly Asn Asp Thr Ile Thr Leu Pro Cys Arg
                405                 410                 415

Ile Lys Gln Ile Ile Asn Met Trp Gln Glu Val Gly Lys Ala Met Tyr
            420                 425                 430

Ala Pro Pro Ile Arg Gly Gln Ile Arg Cys Ser Ser Asn Ile Thr Gly
        435                 440                 445

Leu Ile Leu Thr Arg Asp Gly Gly Asn Asn His Asn Asn Asp Thr Glu
    450                 455                 460

Thr Phe Arg Pro Gly Gly Gly Asp Met Arg Asp Asn Trp Arg Ser Glu
465                 470                 475                 480
```

Leu Tyr Lys Tyr Lys Val Val Lys Ile Glu Pro Leu Gly Val Ala Pro
485 490 495

Thr Lys Ala Lys Arg Arg Val Val Gln Arg Glu Thr
500 505

<210> SEQ ID NO 66
<211> LENGTH: 682
<212> TYPE: PRT
<213> ORGANISM: Bos taurus

<400> SEQUENCE: 66

Met Arg Val Lys Glu Lys Tyr Gln His Leu Trp Arg Trp Gly Trp Lys
1 5 10 15

Trp Gly Thr Met Leu Leu Gly Ile Leu Met Ile Cys Ser Ala Thr Glu
20 25 30

Lys Leu Trp Val Thr Val Tyr Tyr Gly Val Pro Val Trp Lys Glu Ala
35 40 45

Thr Thr Thr Leu Phe Cys Ala Ser Asp Ala Lys Ala Tyr Asp Thr Glu
50 55 60

Val His Asn Val Trp Ala Thr His Ala Cys Val Pro Thr Asp Pro Asn
65 70 75 80

Pro Gln Glu Val Val Leu Glu Asn Val Thr Glu Asn Phe Asn Met Trp
85 90 95

Lys Asn Asn Met Val Glu Gln Met His Glu Asp Ile Ile Ser Leu Trp
100 105 110

Asp Gln Ser Leu Lys Pro Cys Val Lys Leu Thr Pro Leu Cys Val Thr
115 120 125

Leu Asn Cys Thr Asp Leu Arg Asn Val Thr Asn Ile Asn Asn Ser Ser
130 135 140

Glu Gly Met Arg Gly Glu Ile Lys Asn Cys Ser Phe Asn Ile Thr Thr
145 150 155 160

Ser Ile Arg Asp Lys Val Lys Lys Asp Tyr Ala Leu Phe Tyr Arg Leu
165 170 175

Asp Val Val Pro Ile Asp Asn Asp Asn Thr Ser Tyr Arg Leu Ile Asn
180 185 190

Cys Asn Thr Ser Thr Ile Thr Gln Ala Cys Pro Lys Val Ser Phe Glu
195 200 205

Pro Ile Pro Ile His Tyr Cys Thr Pro Ala Gly Phe Ala Ile Leu Lys
210 215 220

Cys Lys Asp Lys Lys Phe Asn Gly Thr Gly Pro Cys Lys Asn Val Ser
225 230 235 240

Thr Val Gln Cys Thr His Gly Ile Arg Pro Val Val Ser Thr Gln Leu
245 250 255

Leu Leu Asn Gly Ser Leu Ala Glu Glu Glu Val Val Ile Arg Ser Ser
260 265 270

Asn Phe Thr Asp Asn Ala Lys Asn Ile Ile Val Gln Leu Lys Glu Ser
275 280 285

Val Glu Ile Asn Cys Thr Arg Pro Asn Asn Asn Thr Arg Lys Ser Ile
290 295 300

His Ile Gly Pro Gly Arg Ala Phe Tyr Thr Thr Gly Asp Ile Ile Gly
305 310 315 320

Asp Ile Arg Gln Ala His Cys Asn Ile Ser Arg Thr Lys Trp Asn Asn
325 330 335

Thr Leu Asn Gln Ile Ala Thr Lys Leu Lys Glu Gln Phe Gly Asn Asn

-continued

```
        340                 345                 350

Lys Thr Ile Val Phe Asn Gln Ser Ser Gly Gly Asp Pro Glu Ile Val
        355                 360                 365

Met His Ser Phe Asn Cys Gly Gly Glu Phe Phe Tyr Cys Asn Ser Thr
    370                 375                 380

Gln Leu Phe Asn Ser Thr Trp Asn Phe Asn Gly Thr Trp Asn Leu Thr
385                 390                 395                 400

Gln Ser Asn Gly Thr Glu Gly Asn Asp Thr Ile Thr Leu Pro Cys Arg
                405                 410                 415

Ile Lys Gln Ile Ile Asn Met Trp Gln Glu Val Gly Lys Ala Met Tyr
            420                 425                 430

Ala Pro Pro Ile Arg Gly Gln Ile Arg Cys Ser Ser Asn Ile Thr Gly
        435                 440                 445

Leu Ile Leu Thr Arg Asp Gly Gly Asn Asn His Asn Asn Asp Thr Glu
    450                 455                 460

Thr Phe Arg Pro Gly Gly Gly Asp Met Arg Asp Asn Trp Arg Ser Glu
465                 470                 475                 480

Leu Tyr Lys Tyr Lys Val Val Lys Ile Glu Pro Leu Gly Val Ala Pro
                485                 490                 495

Thr Lys Ala Lys Arg Arg Val Val Gln Arg Glu Thr Gly Ala Val Gly
            500                 505                 510

Thr Ile Gly Ala Met Phe Leu Gly Phe Leu Gly Ala Ala Gly Ser Thr
        515                 520                 525

Met Gly Ala Ala Ser Ile Thr Leu Thr Val Gln Ala Arg Leu Leu Leu
    530                 535                 540

Ser Gly Ile Val Gln Gln Gln Asn Asn Leu Leu Arg Ala Ile Glu Ala
545                 550                 555                 560

Gln Gln His Leu Leu Gln Leu Thr Val Trp Gly Ile Lys Gln Leu Gln
                565                 570                 575

Ala Arg Val Leu Ala Val Glu Arg Tyr Leu Arg Asp Gln Gln Leu Leu
            580                 585                 590

Gly Ile Trp Gly Cys Ser Gly Lys Leu Ile Cys Thr Thr Ala Val Pro
        595                 600                 605

Trp Asn Ala Ser Trp Ser Asn Lys Ser Leu Glu Gln Ile Trp Asn Asn
    610                 615                 620

Met Thr Trp Met Glu Trp Asp Arg Glu Ile Asn Asn Tyr Thr Ser Leu
625                 630                 635                 640

Ile His Ser Leu Ile Glu Glu Ser Gln Asn Gln Gln Glu Lys Asn Glu
                645                 650                 655

Gln Glu Leu Leu Glu Leu Asp Lys Trp Ala Ser Leu Trp Asn Trp Phe
            660                 665                 670

Asn Ile Thr Asn Trp Leu Trp Tyr Ile Lys
        675                 680


<210> SEQ ID NO 67
<211> LENGTH: 854
<212> TYPE: PRT
<213> ORGANISM: Bos taurus

<400> SEQUENCE: 67

Met Lys Val Lys Gly Ile Arg Lys Asn Tyr Gln His Leu Trp Lys Trp
1               5                   10                  15

Gly Ile Met Leu Leu Gly Met Leu Met Ile Cys Ser Ala Val Glu Asn
            20                  25                  30
```

-continued

```
Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Arg Asn Val Thr Asn Ile Asn Asn Ser Ser Glu
    130                 135                 140

Gly Met Arg Gly Glu Ile Lys Asn Cys Ser Phe Asn Ile Thr Thr Ser
145                 150                 155                 160

Ile Arg Asp Lys Val Lys Lys Asp Tyr Ala Leu Phe Tyr Arg Leu Asp
                165                 170                 175

Val Val Pro Ile Asp Asn Asp Asn Thr Ser Tyr Arg Leu Ile Asn Cys
            180                 185                 190

Asn Thr Ser Thr Ile Thr Gln Ala Cys Pro Lys Val Ser Phe Glu Pro
        195                 200                 205

Ile Pro Ile His Tyr Cys Thr Pro Ala Gly Phe Ala Ile Leu Lys Cys
    210                 215                 220

Lys Asp Lys Lys Phe Asn Gly Thr Gly Pro Cys Lys Asn Val Ser Thr
225                 230                 235                 240

Val Gln Cys Thr His Gly Ile Arg Pro Val Val Ser Thr Gln Leu Leu
                245                 250                 255

Leu Asn Gly Ser Leu Ala Glu Glu Glu Val Val Ile Arg Ser Ser Asn
            260                 265                 270

Phe Thr Asp Asn Ala Lys Asn Ile Ile Val Gln Leu Lys Glu Ser Val
        275                 280                 285

Glu Ile Asn Cys Thr Arg Pro Asn Asn Asn Thr Arg Lys Ser Ile His
    290                 295                 300

Ile Gly Pro Gly Arg Ala Phe Tyr Thr Thr Gly Asp Ile Ile Gly Asp
305                 310                 315                 320

Ile Arg Gln Ala His Cys Asn Ile Ser Arg Thr Lys Trp Asn Asn Thr
                325                 330                 335

Leu Asn Gln Ile Ala Thr Lys Leu Lys Glu Gln Phe Gly Asn Asn Lys
            340                 345                 350

Thr Ile Val Phe Asn Gln Ser Ser Gly Gly Asp Pro Glu Ile Val Met
        355                 360                 365

His Ser Phe Asn Cys Gly Gly Glu Phe Phe Tyr Cys Asn Ser Thr Gln
    370                 375                 380

Leu Phe Asn Ser Thr Trp Asn Phe Asn Gly Thr Trp Asn Leu Thr Gln
385                 390                 395                 400

Ser Asn Gly Thr Glu Gly Asn Asp Thr Ile Thr Leu Pro Cys Arg Ile
                405                 410                 415

Lys Gln Ile Ile Asn Met Trp Gln Glu Val Gly Lys Ala Met Tyr Ala
            420                 425                 430

Pro Pro Ile Arg Gly Gln Ile Arg Cys Ser Ser Asn Ile Thr Gly Leu
        435                 440                 445

Ile Leu Thr Arg Asp Gly Gly Asn Asn His Asn Asn Asp Thr Glu Thr
```

```
    450                 455                 460

Phe Arg Pro Gly Gly Gly Asp Met Arg Asp Asn Trp Arg Ser Glu Leu
465                 470                 475                 480

Tyr Lys Tyr Lys Val Val Lys Ile Glu Pro Leu Gly Val Ala Pro Thr
                485                 490                 495

Lys Ala Lys Arg Arg Val Val Gln Arg Glu Lys Arg Ala Val Gly Thr
            500                 505                 510

Ile Gly Ala Met Phe Leu Gly Phe Leu Gly Ala Ala Gly Ser Thr Met
        515                 520                 525

Gly Ala Ala Ser Ile Thr Leu Thr Val Gln Ala Arg Leu Leu Leu Ser
    530                 535                 540

Gly Ile Val Gln Gln Gln Asn Asn Leu Leu Arg Ala Ile Glu Ala Gln
545                 550                 555                 560

Gln His Leu Leu Gln Leu Thr Val Trp Gly Ile Lys Gln Leu Gln Ala
                565                 570                 575

Arg Val Leu Ala Val Glu Arg Tyr Leu Arg Asp Gln Gln Leu Leu Gly
            580                 585                 590

Ile Trp Gly Cys Ser Gly Lys Leu Ile Cys Thr Thr Ala Val Pro Trp
        595                 600                 605

Asn Ala Ser Trp Ser Asn Lys Thr Leu Asp Met Ile Trp Asn Asn Met
    610                 615                 620

Thr Trp Met Glu Trp Glu Arg Glu Ile Asp Asn Tyr Thr Gly Leu Ile
625                 630                 635                 640

Tyr Thr Leu Ile Glu Glu Ser Gln Asn Gln Gln Glu Lys Asn Glu Gln
                645                 650                 655

Glu Leu Leu Glu Leu Asp Lys Trp Ala Ser Leu Trp Asn Trp Phe Asp
            660                 665                 670

Ile Thr Asn Trp Leu Trp Tyr Ile Lys Ile Phe Ile Met Ile Val Gly
        675                 680                 685

Gly Leu Ile Gly Leu Arg Ile Val Phe Thr Val Leu Ser Ile Val Asn
    690                 695                 700

Arg Val Arg Gln Gly Tyr Ser Pro Leu Ser Phe Gln Thr His Leu Pro
705                 710                 715                 720

Ala Pro Arg Gly Pro Asp Arg Pro Glu Gly Ile Glu Glu Glu Gly Gly
                725                 730                 735

Asp Arg Asp Arg Asp Arg Ser Val Arg Leu Val Asp Gly Phe Leu Ala
            740                 745                 750

Leu Phe Trp Asp Asp Leu Arg Ser Leu Cys Leu Phe Ser Tyr His Arg
        755                 760                 765

Leu Arg Asp Leu Leu Leu Ile Val Ala Arg Ile Val Glu Leu Leu Gly
    770                 775                 780

Arg Arg Gly Trp Glu Ala Leu Lys Tyr Trp Trp Asn Leu Leu Gln Tyr
785                 790                 795                 800

Trp Ser Gln Glu Leu Arg Asn Ser Ala Val Ser Leu Leu Asn Ala Thr
                805                 810                 815

Ala Ile Ala Val Ala Glu Gly Thr Asp Arg Val Ile Glu Ile Val Gln
            820                 825                 830

Arg Ile Tyr Arg Ala Ile Leu His Ile Pro Thr Arg Ile Arg Gln Gly
        835                 840                 845

Leu Glu Arg Leu Leu Leu
    850
```

<210> SEQ ID NO 68

<211> LENGTH: 679
<212> TYPE: PRT
<213> ORGANISM: Bos taurus

<400> SEQUENCE: 68

Met Arg Val Lys Glu Lys Tyr Gln His Leu Trp Arg Trp Gly Trp Lys
1 5 10 15

Trp Gly Thr Met Leu Leu Gly Ile Leu Met Ile Cys Ser Ala Thr Glu
20 25 30

Lys Leu Trp Val Thr Val Tyr Tyr Gly Val Pro Val Trp Lys Glu Ala
35 40 45

Thr Thr Thr Leu Phe Cys Ala Ser Asp Ala Lys Ala Tyr Asp Thr Lys
50 55 60

Val His Asn Val Trp Ala Thr His Ala Cys Val Pro Thr Asp Pro Asn
65 70 75 80

Pro Gln Glu Val Val Leu Glu Asn Val Thr Glu Asn Phe Asn Met Trp
85 90 95

Lys Asn Asn Met Val Glu Gln Met His Glu Asp Ile Ile Ser Leu Trp
100 105 110

Asp Gln Ser Leu Lys Pro Cys Val Lys Leu Thr Pro Leu Cys Val Thr
115 120 125

Leu Asn Cys Thr Asp Leu Arg Asn Val Thr Asn Ile Asn Asn Ser Ser
130 135 140

Glu Gly Met Arg Gly Glu Ile Lys Asn Cys Ser Phe Asn Ile Thr Thr
145 150 155 160

Ser Ile Arg Asp Lys Val Lys Lys Asp Tyr Ala Leu Phe Tyr Arg Leu
165 170 175

Asp Val Val Pro Ile Asp Asn Asp Asn Thr Ser Tyr Arg Leu Ile Asn
180 185 190

Cys Asn Thr Ser Thr Ile Thr Gln Ala Cys Pro Lys Val Ser Phe Glu
195 200 205

Pro Ile Pro Ile His Tyr Cys Thr Pro Ala Gly Phe Ala Ile Leu Lys
210 215 220

Cys Lys Asp Lys Lys Phe Asn Gly Thr Gly Pro Cys Lys Asn Val Ser
225 230 235 240

Thr Val Gln Cys Thr His Gly Ile Arg Pro Val Val Ser Thr Gln Leu
245 250 255

Leu Leu Asn Gly Ser Leu Ala Glu Glu Glu Val Val Ile Arg Ser Ser
260 265 270

Asn Phe Thr Asp Asn Ala Lys Asn Ile Ile Val Gln Leu Lys Glu Ser
275 280 285

Val Glu Ile Asn Cys Thr Arg Pro Asn Asn Asn Thr Arg Lys Ser Ile
290 295 300

His Ile Gly Pro Gly Arg Trp Phe Tyr Thr Thr Gly Asp Ile Ile Gly
305 310 315 320

Asp Ile Arg Gln Ala His Cys Asn Ile Ser Arg Thr Lys Trp Asn Asn
325 330 335

Thr Leu Asn Gln Ile Ala Thr Lys Leu Lys Glu Gln Phe Gly Asn Asn
340 345 350

Lys Thr Ile Val Phe Asn Gln Ser Ser Gly Gly Asp Pro Glu Ile Val
355 360 365

Met His Ser Phe Asn Cys Gly Gly Glu Phe Phe Tyr Cys Asn Ser Thr
370 375 380

Gln Leu Phe Asn Ser Thr Trp Asn Phe Asn Gly Thr Trp Asn Leu Thr

```
385                 390                 395                 400

Gln Ser Asn Gly Thr Glu Gly Asn Asp Thr Ile Thr Leu Pro Cys Arg
                405                 410                 415

Ile Lys Gln Ile Ile Asn Met Trp Gln Glu Val Gly Lys Ala Met Tyr
            420                 425                 430

Ala Pro Pro Ile Arg Gly Gln Ile Arg Cys Ser Ser Asn Ile Thr Gly
        435                 440                 445

Leu Ile Leu Thr Arg Asp Gly Gly Asn Asn His Asn Asn Asp Thr Glu
    450                 455                 460

Thr Phe Arg Pro Gly Gly Gly Asp Met Arg Asp Asn Trp Arg Ser Glu
465                 470                 475                 480

Leu Tyr Lys Tyr Lys Val Val Lys Ile Glu Pro Leu Gly Val Ala Pro
                485                 490                 495

Thr Lys Cys Lys Arg Arg Val Val Gln Arg Glu Lys Arg Ala Val Gly
            500                 505                 510

Thr Ile Gly Ala Met Phe Leu Gly Phe Leu Gly Ala Ala Gly Ser Thr
        515                 520                 525

Met Gly Ala Ala Ser Met Thr Leu Thr Val Gln Ala Arg Asn Leu Leu
    530                 535                 540

Ser Gly Ile Val Gln Gln Gln Asn Asn Leu Leu Arg Ala Pro Glu Ala
545                 550                 555                 560

Gln Gln His Leu Leu Gln Leu Thr Val Trp Gly Ile Lys Gln Leu Gln
                565                 570                 575

Ala Arg Val Leu Ala Val Glu Arg Tyr Leu Arg Asp Gln Gln Leu Leu
            580                 585                 590

Gly Ile Trp Gly Cys Ser Gly Lys Leu Ile Cys Cys Thr Ala Val Pro
        595                 600                 605

Trp Asn Ala Ser Trp Ser Asn Lys Ser Leu Glu Gln Ile Trp Asn Asn
    610                 615                 620

Met Thr Trp Met Glu Trp Asp Arg Glu Ile Asn Asn Tyr Thr Ser Leu
625                 630                 635                 640

Ile His Ser Leu Ile Glu Glu Ser Gln Asn Gln Gln Glu Lys Asn Glu
                645                 650                 655

Gln Glu Leu Leu Glu Leu Ala Ser Gly Leu Asn Asp Ile Phe Glu Ala
            660                 665                 670

Gln Lys Ile Glu Trp His Glu
        675


<210> SEQ ID NO 69
<211> LENGTH: 829
<212> TYPE: PRT
<213> ORGANISM: Bos taurus

<400> SEQUENCE: 69

Met Arg Val Met Gly Ile Gln Arg Asn Cys Gln His Leu Trp Arg Trp
1               5                   10                  15

Gly Ile Leu Ile Phe Gly Met Leu Met Ile Cys Ser Ala Ala Glu Asn
            20                  25                  30

Leu Trp Val Thr Val Tyr Tyr Gly Val Pro Val Trp Lys Glu Ala Asn
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80
```

-continued

```
Gln Glu Ile Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Val Asn Ala Thr Asn Asn Ser Thr Asn Met Gly Glu
    130                 135                 140

Ile Lys Asn Cys Ser Phe Asn Ile Thr Thr Glu Ile Arg Asp Lys Lys
145                 150                 155                 160

Gln Lys Val Tyr Ala Leu Phe Tyr Arg Leu Asp Val Val Pro Ile Asn
                165                 170                 175

Asp Asn Ser Tyr Arg Leu Ile Asn Cys Asn Thr Ser Ala Ile Thr Gln
            180                 185                 190

Ala Cys Pro Lys Val Ser Phe Glu Pro Ile Pro Ile His Tyr Cys Ala
        195                 200                 205

Pro Ala Gly Phe Ala Ile Leu Lys Cys Asn Asp Lys Lys Phe Asn Gly
    210                 215                 220

Thr Gly Pro Cys Lys Asn Val Ser Thr Val Gln Cys Thr His Gly Ile
225                 230                 235                 240

Lys Pro Val Val Ser Thr Gln Leu Leu Leu Asn Gly Ser Leu Ala Glu
                245                 250                 255

Glu Glu Ile Ile Ile Arg Ser Glu Asn Ile Thr Asp Asn Ala Lys Thr
            260                 265                 270

Ile Ile Val Gln Leu Asn Glu Ser Val Glu Ile Asn Cys Thr Arg Pro
        275                 280                 285

Asn Asn Asn Thr Arg Lys Ser Ile Arg Ile Gly Pro Gly Gln Ala Phe
    290                 295                 300

Tyr Ala Thr Gly Asp Ile Ile Gly Asp Ile Arg Gln Ala His Cys Asn
305                 310                 315                 320

Ile Ser Gly Ala Glu Trp Asn Lys Thr Leu Gln Gln Val Ala Ala Lys
                325                 330                 335

Leu Arg Glu His Phe Asn Asn Lys Thr Ile Ile Phe Lys Pro Ser Ser
            340                 345                 350

Gly Gly Asp Leu Glu Ile Thr Thr His Ser Phe Asn Cys Gly Gly Glu
        355                 360                 365

Phe Phe Tyr Cys Asn Thr Ser Gly Leu Phe Asn Ser Thr Trp Asn Gly
    370                 375                 380

Thr Asn Glu Thr Ile Thr Leu Pro Cys Arg Ile Lys Gln Ile Val Asn
385                 390                 395                 400

Met Trp Gln Arg Val Gly Gln Ala Met Tyr Ala Pro Pro Ile Ala Gly
                405                 410                 415

Asn Ile Thr Cys Lys Ser Asn Ile Thr Gly Leu Leu Leu Thr Arg Asp
            420                 425                 430

Gly Gly Thr Asn Asn Thr Glu Thr Phe Arg Pro Gly Gly Gly Asp Met
        435                 440                 445

Arg Asp Asn Trp Arg Ser Glu Leu Tyr Lys Tyr Lys Val Val Lys Ile
    450                 455                 460

Glu Pro Leu Gly Val Ala Pro Thr Lys Ala Lys Arg Arg Val Val Glu
465                 470                 475                 480

Arg Glu Lys Arg Ala Val Gly Ile Gly Ala Val Phe Leu Gly Phe Leu
                485                 490                 495

Gly Ala Ala Gly Ser Thr Met Gly Ala Ala Ser Ile Thr Leu Thr Val
```

500 505 510

Gln Ala Arg Gln Leu Leu Ser Gly Ile Val Gln Gln Gln Ser Asn Leu
515 520 525

Leu Arg Ala Ile Glu Ala Gln Gln His Leu Leu Gln Leu Thr Val Trp
530 535 540

Gly Ile Lys Gln Leu Gln Ala Arg Val Leu Ala Val Glu Arg Tyr Leu
545 550 555 560

Lys Asp Gln Gln Leu Leu Gly Ile Trp Gly Cys Ser Gly Lys Leu Ile
565 570 575

Cys Thr Thr Asn Val Pro Trp Asn Ser Ser Trp Ser Asn Lys Ser Gln
580 585 590

Asp Glu Ile Trp Asp Asn Met Thr Trp Met Gln Trp Glu Arg Glu Ile
595 600 605

Ser Asn Tyr Thr Asp Ile Ile Tyr Ser Leu Ile Glu Glu Ser Gln Asn
610 615 620

Gln Gln Glu Lys Asn Glu Gln Asp Leu Leu Ala Leu Asp Lys Trp Ala
625 630 635 640

Ser Leu Trp Asn Trp Phe Asp Ile Thr Asn Trp Leu Trp Tyr Ile Lys
645 650 655

Ile Phe Ile Met Ile Val Gly Gly Leu Ile Gly Leu Arg Ile Val Phe
660 665 670

Ala Val Leu Ser Ile Val Asn Arg Val Arg Gln Gly Tyr Ser Pro Leu
675 680 685

Ser Phe Gln Thr Leu Ile Pro Asn Pro Arg Gly Pro Asp Arg Pro Gly
690 695 700

Gly Ile Glu Glu Glu Gly Gly Glu Gln Asp Arg Asp Arg Ser Ile Arg
705 710 715 720

Leu Val Ser Gly Phe Leu Ala Leu Ala Trp Asp Asp Leu Arg Ser Leu
725 730 735

Cys Leu Phe Ser Tyr His Arg Leu Arg Asp Phe Ile Leu Ile Ala Ala
740 745 750

Arg Thr Val Glu Leu Leu Gly Arg Arg Gly Trp Glu Ala Leu Lys Tyr
755 760 765

Leu Trp Asn Leu Leu Gln Tyr Trp Gly Gln Glu Leu Lys Asn Ser Ala
770 775 780

Ile Ser Leu Leu Asp Thr Thr Ala Ile Ala Val Ala Glu Gly Thr Asp
785 790 795 800

Arg Val Ile Glu Val Val Gln Arg Ala Cys Arg Ala Ile Leu His Ile
805 810 815

Pro Arg Arg Ile Arg Gln Gly Phe Glu Arg Ala Leu Leu
820 825

<210> SEQ ID NO 70
<211> LENGTH: 121
<212> TYPE: PRT
<213> ORGANISM: Bos taurus

<400> SEQUENCE: 70

Gln Val Gln Leu Val Gln Ser Gly Gly Gln Met Lys Lys Pro Gly Glu
1 5 10 15

Ser Met Arg Ile Ser Cys Arg Ala Ser Gly Tyr Glu Phe Ile Asp Cys
20 25 30

Thr Leu Asn Trp Ile Arg Leu Ala Pro Gly Lys Arg Pro Glu Trp Met
35 40 45

```
Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser
        115                 120


<210> SEQ ID NO 71
<211> LENGTH: 103
<212> TYPE: PRT
<213> ORGANISM: Bos taurus

<400> SEQUENCE: 71

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys
            100


<210> SEQ ID NO 72
<211> LENGTH: 168
<212> TYPE: PRT
<213> ORGANISM: Bos taurus

<400> SEQUENCE: 72

Gln Val Gln Leu Arg Glu Ser Gly Pro Ser Leu Met Lys Pro Ser Gln
1               5                   10                  15

Thr Leu Ser Leu Thr Cys Thr Val Ser Gly Ser Ser Leu Asn Asp Lys
            20                  25                  30

Ser Val Gly Trp Val Arg Gln Ala Pro Gly Lys Ala Leu Gln Trp Leu
        35                  40                  45

Gly Ser Val Asp Thr Ser Gly Asn Thr Asp Tyr Asn Pro Gly Leu Lys
    50                  55                  60

Ser Arg Leu Ser Ile Thr Lys Asp Asn Ser Lys Ser Arg Ile Ser Leu
65                  70                  75                  80

Thr Val Thr Gly Met Thr Thr Glu Asp Ser Ala Thr Tyr Tyr Cys Ile
                85                  90                  95

Thr Ala His Gln Lys Thr Asn Lys Lys Glu Cys Pro Glu Asp Tyr Thr
            100                 105                 110

Tyr Asn Pro Arg Cys Pro Gln Gln Tyr Gly Trp Ser Asp Cys Asp Cys
        115                 120                 125

Met Gly Asp Arg Phe Gly Gly Tyr Cys Arg Gln Asp Gly Cys Ser Asn
    130                 135                 140
```

```
Tyr Ile His Arg Ser Thr Tyr Glu Trp Tyr Val Ser Ala Trp Gly Gln
145                 150                 155                 160

Gly Leu Leu Val Thr Val Ser Ser
                165


<210> SEQ ID NO 73
<211> LENGTH: 111
<212> TYPE: PRT
<213> ORGANISM: Bos taurus

<400> SEQUENCE: 73

His Ser Tyr Glu Leu Thr Gln Pro Ser Ser Val Ser Gly Ser Leu Gly
1               5                   10                  15

Gln Arg Val Ser Val Thr Cys Ser Gly Ser Ser Ser Asn Val Gly Asn
            20                  25                  30

Gly Tyr Val Ser Trp Tyr Gln Leu Ile Pro Gly Ser Ala Pro Arg Thr
        35                  40                  45

Ile Ile Tyr Gly Asp Thr Ser Arg Ala Ser Gly Val Pro Glu Arg Phe
    50                  55                  60

Ser Gly Ser Arg Ser Gly Asn Thr Ala Thr Leu Thr Ile Ser Ser Leu
65                  70                  75                  80

Gln Ala Glu Asp Glu Ala Asp Phe Phe Cys Ala Ser Pro Asp Asp Ser
                85                  90                  95

Ser Ser Asn Ala Val Phe Gly Ser Gly Thr Thr Leu Thr Val Leu
            100                 105                 110


<210> SEQ ID NO 74
<211> LENGTH: 13
<212> TYPE: PRT
<213> ORGANISM: Bos taurus

<400> SEQUENCE: 74

Ser Gly Ser Ser Ser Asn Val Gly Asn Gly Tyr Val Ser
1               5                   10


<210> SEQ ID NO 75
<211> LENGTH: 7
<212> TYPE: PRT
<213> ORGANISM: Bos taurus

<400> SEQUENCE: 75

Gly Asp Thr Ser Arg Ala Ser
1               5


<210> SEQ ID NO 76
<211> LENGTH: 11
<212> TYPE: PRT
<213> ORGANISM: Bos taurus

<400> SEQUENCE: 76

Ala Ser Pro Asp Asp Ser Ser Ser Asn Ala Val
1               5                   10


<210> SEQ ID NO 77
<211> LENGTH: 22
<212> TYPE: PRT
<213> ORGANISM: Bos taurus

<400> SEQUENCE: 77

Ser Tyr Glu Leu Thr Gln Pro Ser Ser Val Ser Gly Ser Leu Gly Gln
1               5                   10                  15
```

```
Arg Val Ser Val Thr Cys
            20


<210> SEQ ID NO 78
<211> LENGTH: 15
<212> TYPE: PRT
<213> ORGANISM: Bos taurus

<400> SEQUENCE: 78

Trp Tyr Gln Leu Ile Pro Gly Ser Ala Pro Arg Thr Ile Ile Tyr
1               5                   10                  15


<210> SEQ ID NO 79
<211> LENGTH: 32
<212> TYPE: PRT
<213> ORGANISM: Bos taurus

<400> SEQUENCE: 79

Gly Val Pro Glu Arg Phe Ser Gly Ser Arg Ser Gly Asn Thr Ala Thr
1               5                   10                  15

Leu Thr Ile Ser Ser Leu Gln Ala Glu Asp Glu Ala Asp Phe Phe Cys
            20                  25                  30


<210> SEQ ID NO 80
<211> LENGTH: 10
<212> TYPE: PRT
<213> ORGANISM: Bos taurus

<400> SEQUENCE: 80

Phe Gly Ser Gly Thr Thr Leu Thr Val Leu
1               5                   10


<210> SEQ ID NO 81
<211> LENGTH: 16
<212> TYPE: PRT
<213> ORGANISM: Bos taurus
<220> FEATURE:
<221> NAME/KEY: MISC_FEATURE
<222> LOCATION: (1)..(1)
<223> OTHER INFORMATION: X is S or T
<220> FEATURE:
<221> NAME/KEY: MISC_FEATURE
<222> LOCATION: (5)..(5)
<223> OTHER INFORMATION: X is G or T
<220> FEATURE:
<221> NAME/KEY: MISC_FEATURE
<222> LOCATION: (9)..(9)
<223> OTHER INFORMATION: X is G, D or V

<400> SEQUENCE: 81

Xaa Ile Asp Thr Xaa Gly Asn Ala Xaa Tyr Asn Pro Gly Leu Lys Ser
1               5                   10                  15


<210> SEQ ID NO 82
<211> LENGTH: 58
<212> TYPE: PRT
<213> ORGANISM: Bos taurus
<220> FEATURE:
<221> NAME/KEY: MISC_FEATURE
<222> LOCATION: (6)..(6)
<223> OTHER INFORMATION: X is R or L
<220> FEATURE:
<221> NAME/KEY: MISC_FEATURE
<222> LOCATION: (11)..(11)
<223> OTHER INFORMATION: X is S or V
<220> FEATURE:
<221> NAME/KEY: MISC_FEATURE
<222> LOCATION: (14)..(14)
<223> OTHER INFORMATION: X is P, S or Y
```

<220> FEATURE:
<221> NAME/KEY: MISC_FEATURE
<222> LOCATION: (15)..(15)
<223> OTHER INFORMATION: X is Y or F
<220> FEATURE:
<221> NAME/KEY: MISC_FEATURE
<222> LOCATION: (16)..(16)
<223> OTHER INFORMATION: X is I or S
<220> FEATURE:
<221> NAME/KEY: MISC_FEATURE
<222> LOCATION: (21)..(21)
<223> OTHER INFORMATION: X is G or D
<220> FEATURE:
<221> NAME/KEY: MISC_FEATURE
<222> LOCATION: (22)..(22)
<223> OTHER INFORMATION: X is T or S
<220> FEATURE:
<221> NAME/KEY: MISC_FEATURE
<222> LOCATION: (28)..(28)
<223> OTHER INFORMATION: X is R or S
<220> FEATURE:
<221> NAME/KEY: MISC_FEATURE
<222> LOCATION: (30)..(30)
<223> OTHER INFORMATION: X is S or T
<220> FEATURE:
<221> NAME/KEY: MISC_FEATURE
<222> LOCATION: (37)..(37)
<223> OTHER INFORMATION: X is N or K
<220> FEATURE:
<221> NAME/KEY: MISC_FEATURE
<222> LOCATION: (38)..(38)
<223> OTHER INFORMATION: X is Y or H
<220> FEATURE:
<221> NAME/KEY: MISC_FEATURE
<222> LOCATION: (43)..(43)
<223> OTHER INFORMATION: X is M or V
<220> FEATURE:
<221> NAME/KEY: MISC_FEATURE
<222> LOCATION: (46)..(46)
<223> OTHER INFORMATION: X is G or D
<220> FEATURE:
<221> NAME/KEY: MISC_FEATURE
<222> LOCATION: (47)..(47)
<223> OTHER INFORMATION: X is R or K
<220> FEATURE:
<221> NAME/KEY: MISC_FEATURE
<222> LOCATION: (48)..(48)
<223> OTHER INFORMATION: X is SOMETHING or H
<220> FEATURE:
<221> NAME/KEY: MISC_FEATURE
<222> LOCATION: (48)..(48)
<223> OTHER INFORMATION: X is nothing or H
<220> FEATURE:
<221> NAME/KEY: MISC_FEATURE
<222> LOCATION: (49)..(49)
<223> OTHER INFORMATION: X is T or S
<220> FEATURE:
<221> NAME/KEY: MISC_FEATURE
<222> LOCATION: (50)..(50)
<223> OTHER INFORMATION: X is Y or N
<220> FEATURE:
<221> NAME/KEY: MISC_FEATURE
<222> LOCATION: (51)..(51)
<223> OTHER INFORMATION: X is T, I or S
<220> FEATURE:
<221> NAME/KEY: MISC_FEATURE
<222> LOCATION: (52)..(52)
<223> OTHER INFORMATION: X is Y or H
<220> FEATURE:
<221> NAME/KEY: MISC_FEATURE
<222> LOCATION: (55)..(55)
<223> OTHER INFORMATION: X is H or Y
<220> FEATURE:
<221> NAME/KEY: MISC_FEATURE
<222> LOCATION: (57)..(57)
<223> OTHER INFORMATION: X is D or E

<400> SEQUENCE: 82

-continued

Val His Gln Lys Thr Xaa Arg Ser Cys Pro Xaa Asp Tyr Xaa Xaa Xaa
1 5 10 15

Cys Asp Cys Glu Xaa Xaa Gly Ser His Cys Cys Xaa Ala Xaa Asn Cys
20 25 30

Pro Tyr Tyr Cys Xaa Xaa Gly Arg Asp Arg Xaa Cys Thr Xaa Xaa Xaa
35 40 45

Xaa Xaa Xaa Xaa Glu Trp Xaa Val Xaa Ala
50 55

<210> SEQ ID NO 83
<211> LENGTH: 13
<212> TYPE: PRT
<213> ORGANISM: Bos taurus

<400> SEQUENCE: 83

Ser Gly Ser Ser Ser Asn Val Gly Asn Gly Tyr Val Ser
1 5 10

<210> SEQ ID NO 84
<211> LENGTH: 7
<212> TYPE: PRT
<213> ORGANISM: Bos taurus

<400> SEQUENCE: 84

Gly Asp Thr Ser Arg Ala Ser
1 5

<210> SEQ ID NO 85
<211> LENGTH: 11
<212> TYPE: PRT
<213> ORGANISM: Bos taurus
<220> FEATURE:
<221> NAME/KEY: MISC_FEATURE
<222> LOCATION: (3)..(3)
<223> OTHER INFORMATION: X is A or P
<220> FEATURE:
<221> NAME/KEY: MISC_FEATURE
<222> LOCATION: (4)..(4)
<223> OTHER INFORMATION: X is E or D
<220> FEATURE:
<221> NAME/KEY: MISC_FEATURE
<222> LOCATION: (6)..(6)
<223> OTHER INFORMATION: X is G or S

<400> SEQUENCE: 85

Ala Ser Xaa Xaa Asp Xaa Ser Ser Asn Ala Val
1 5 10

<210> SEQ ID NO 86
<211> LENGTH: 643
<212> TYPE: PRT
<213> ORGANISM: Bos taurus

<400> SEQUENCE: 86

Thr Val Tyr Tyr Gly Val Pro Val Trp Lys Asp Ala Glu Thr Thr Leu
1 5 10 15

Phe Cys Ala Ser Asp Ala Lys Ala Tyr Glu Thr Glu Lys His Asn Val
20 25 30

Trp Ala Thr His Ala Cys Val Pro Thr Asp Pro Asn Pro Gln Glu Ile
35 40 45

Pro Leu Glu Asn Val Thr Glu Glu Phe Asn Met Trp Lys Asn Lys Met
50 55 60

Val Glu Gln Met His Thr Asp Ile Ile Ser Leu Trp Asp Gln Ser Leu
65 70 75 80

-continued

```
Gln Pro Cys Val Lys Leu Thr Pro Leu Cys Val Thr Leu Asn Cys Thr
                85                  90                  95

Asp Ala Thr Asn Gly Thr Ile Gly Asn Ile Thr Asp Glu Met Lys Gly
            100                 105                 110

Glu Ile Lys Asn Cys Ser Phe Asn Ile Thr Thr Glu Ile Arg Asp Lys
        115                 120                 125

Lys Gln Lys Val Tyr Ser Leu Phe Tyr Arg Leu Asp Val Val Pro Ile
    130                 135                 140

Glu Pro Asp Ser Ser Asn Ser Ser Arg Asn Ser Ser Glu Tyr Arg Leu
145                 150                 155                 160

Ile Asn Cys Asn Thr Ser Ala Ile Thr Gln Ala Cys Pro Lys Val Ser
                165                 170                 175

Phe Glu Pro Ile Pro Ile His Tyr Cys Ala Pro Ala Gly Phe Ala Ile
            180                 185                 190

Leu Lys Cys Arg Asp Lys Glu Phe Asn Gly Thr Gly Lys Cys Lys Asn
        195                 200                 205

Val Ser Thr Val Gln Cys Thr His Gly Ile Lys Pro Val Val Ser Thr
    210                 215                 220

Gln Leu Leu Leu Asn Gly Ser Leu Ala Glu Gly Glu Val Arg Ile Arg
225                 230                 235                 240

Ser Glu Asn Ile Thr Asn Asn Ala Lys Thr Ile Ile Val Gln Leu Val
                245                 250                 255

Glu Pro Val Arg Ile Asn Cys Thr Arg Pro Asn Asn Asn Thr Arg Glu
            260                 265                 270

Ser Val Arg Ile Gly Pro Gly Gln Ala Phe Phe Ala Thr Gly Asp Ile
        275                 280                 285

Ile Gly Asp Ile Arg Gln Ala His Cys Asn Val Ser Arg Ser Gln Trp
    290                 295                 300

Asn Lys Thr Leu Gln Gln Val Ala Ala Gln Leu Gly Glu His Phe Lys
305                 310                 315                 320

Asn Lys Ala Ile Thr Phe Asn Ser Ser Ser Gly Gly Asp Leu Glu Ile
                325                 330                 335

Thr Thr His Ser Phe Asn Cys Gly Gly Glu Phe Phe Tyr Cys Asn Thr
            340                 345                 350

Ser Gly Leu Phe Asn Ser Thr Trp Lys Ala Asn Asn Gly Thr Trp Lys
        355                 360                 365

Ala Asn Ile Ser Glu Ser Asn Asn Thr Glu Ile Thr Leu Gln Cys Arg
    370                 375                 380

Ile Lys Gln Ile Ile Asn Met Trp Gln Arg Thr Gly Gln Ala Ile Tyr
385                 390                 395                 400

Ala Pro Pro Ile Gln Gly Val Ile Arg Cys Glu Ser Asn Ile Thr Gly
                405                 410                 415

Leu Leu Leu Thr Arg Asp Gly Gly Glu Gly Asn Asn Glu Ser Glu Ile
            420                 425                 430

Phe Arg Pro Gly Gly Gly Asp Met Arg Asp Asn Trp Arg Ser Glu Leu
        435                 440                 445

Tyr Lys Tyr Lys Val Val Lys Ile Glu Pro Leu Gly Val Ala Pro Thr
    450                 455                 460

Arg Ala Arg Arg Arg Val Val Gly Arg Glu Lys Arg Ala Val Gly Ile
465                 470                 475                 480

Gly Ala Val Phe Leu Gly Phe Leu Gly Ala Ala Gly Ser Thr Met Gly
                485                 490                 495
```

-continued

```
Ala Ala Ser Ile Thr Leu Thr Val Gln Ala Arg Gln Leu Leu Ser Gly
            500                 505                 510

Ile Val Gln Gln Gln Ser Asn Leu Leu Arg Ala Ile Glu Ala Gln Gln
        515                 520                 525

His Met Leu Lys Leu Thr Val Trp Gly Ile Lys Gln Leu Gln Ala Arg
    530                 535                 540

Val Leu Ala Val Glu Arg Tyr Leu Arg Asp Gln Gln Leu Leu Gly Ile
545                 550                 555                 560

Trp Gly Cys Ser Gly Lys Leu Ile Cys Thr Thr Asn Val Pro Trp Asn
                565                 570                 575

Ser Ser Trp Ser Asn Lys Ser His Asp Glu Ile Trp Asn Asn Met Thr
            580                 585                 590

Trp Leu Gln Trp Asp Lys Glu Ile Ser Asn Tyr Thr Asn Leu Ile Tyr
        595                 600                 605

Ser Leu Ile Glu Glu Ser Gln Asn Gln Gln Glu Lys Asn Glu Gln Asp
    610                 615                 620

Leu Leu Ala Leu Gly Ser Gly Ser Gly Ser Gly Ser Gly His His His
625                 630                 635                 640

His His His


<210> SEQ ID NO 87
<211> LENGTH: 8
<212> TYPE: PRT
<213> ORGANISM: Bos taurus

<400> SEQUENCE: 87

Gly Phe Ser Leu Ser Asp Lys Ala
1               5


<210> SEQ ID NO 88
<211> LENGTH: 7
<212> TYPE: PRT
<213> ORGANISM: Bos taurus

<400> SEQUENCE: 88

Ile Asp Thr Gly Gly Asn Ala
1               5


<210> SEQ ID NO 89
<211> LENGTH: 59
<212> TYPE: PRT
<213> ORGANISM: Bos taurus

<400> SEQUENCE: 89

Ser Thr Val His Gln Lys Thr Leu Arg Ser Cys Pro Ser Asp Tyr Pro
1               5                   10                  15

Tyr Ile Cys Asp Cys Glu Asp Thr Gly Ser His Cys Cys Arg Ala Thr
            20                  25                  30

Asn Cys Pro Tyr Tyr Cys Asn His Gly Arg Asp Arg Met Cys Thr Gly
        35                  40                  45

Arg Thr Tyr Thr Tyr Glu Trp His Val Glu Ala
    50                  55


<210> SEQ ID NO 90
<211> LENGTH: 24
<212> TYPE: DNA
<213> ORGANISM: Bos taurus

<400> SEQUENCE: 90
```

ggattctcat tgagcgacaa ggct 24

<210> SEQ ID NO 91
<211> LENGTH: 21
<212> TYPE: DNA
<213> ORGANISM: Bos taurus

<400> SEQUENCE: 91
atagacactg gcggaaacgc a 21

<210> SEQ ID NO 92
<211> LENGTH: 177
<212> TYPE: DNA
<213> ORGANISM: Bos taurus

<400> SEQUENCE: 92
tctactgtgc accagaagac actccgtagt tgtccttctg attatcctta tatttgtgat 60
tgtgaagata ctggtagtca ttgctgtcgg gctactaatt gtccttatta ctgcaatcat 120
ggccgtgatc gtatgtgtac cggtcgtact tacacgtacg agtggcacgt cgaagcc 177

<210> SEQ ID NO 93
<211> LENGTH: 25
<212> TYPE: PRT
<213> ORGANISM: Bos taurus

<400> SEQUENCE: 93

Lys Val Gln Leu Gln Glu Ser Gly Pro Ser Leu Val Lys Pro Ser Gln
1 5 10 15

Thr Leu Ser Leu Thr Cys Thr Ala Ser
20 25

<210> SEQ ID NO 94
<211> LENGTH: 17
<212> TYPE: PRT
<213> ORGANISM: Bos taurus

<400> SEQUENCE: 94

Val Gly Trp Val Arg Gln Ala Pro Gly Gln Ala Leu Glu Trp Leu Gly
1 5 10 15

Ser

<210> SEQ ID NO 95
<211> LENGTH: 38
<212> TYPE: PRT
<213> ORGANISM: Bos taurus

<400> SEQUENCE: 95

Asp Tyr Asn Pro Gly Leu Lys Ser Arg Leu Ser Ile Thr Lys Asp Asn
1 5 10 15

Ala Lys Ser Gln Val Ser Leu Ser Val Ser Ser Val Thr Thr Glu Gly
20 25 30

Ser Ala Thr Tyr Tyr Cys
35

<210> SEQ ID NO 96
<211> LENGTH: 11
<212> TYPE: PRT
<213> ORGANISM: Bos taurus

<400> SEQUENCE: 96

Trp Gly Gln Gly Leu Leu Val Thr Val Ser Ser 1 5 10

<210> SEQ ID NO 97
<211> LENGTH: 75
<212> TYPE: DNA
<213> ORGANISM: Bos taurus

<400> SEQUENCE: 97
aaggtgcagc tgcaggagtc gggccccagc ctggtgaagc cgtcacagac cctctcgctc 60
acctgcacgg cctct 75

<210> SEQ ID NO 98
<211> LENGTH: 51
<212> TYPE: DNA
<213> ORGANISM: Bos taurus

<400> SEQUENCE: 98
gtaggctggg tccgccaggc tccagggcag gcgctggagt ggctcggtag t 51

<210> SEQ ID NO 99
<211> LENGTH: 114
<212> TYPE: DNA
<213> ORGANISM: Bos taurus

<400> SEQUENCE: 99
gattataacc caggcctgaa atcccggctc agcatcacca aggataacgc caagagccaa 60
gtctctctgt cagtaagcag cgtgacaact gagggctcgg ccacgtatta ctgt 114

<210> SEQ ID NO 100
<211> LENGTH: 33
<212> TYPE: DNA
<213> ORGANISM: Bos taurus

<400> SEQUENCE: 100
tggggccagg gactcctggt caccgtctcc tca 33

<210> SEQ ID NO 101
<211> LENGTH: 8
<212> TYPE: PRT
<213> ORGANISM: Bos taurus

<400> SEQUENCE: 101

Gly Phe Ser Leu Ser Asp Lys Ala
1 5

<210> SEQ ID NO 102
<211> LENGTH: 7
<212> TYPE: PRT
<213> ORGANISM: Bos taurus

<400> SEQUENCE: 102

Ile Asp Thr Thr Gly Asn Ala
1 5

<210> SEQ ID NO 103
<211> LENGTH: 59
<212> TYPE: PRT
<213> ORGANISM: Bos taurus

<400> SEQUENCE: 103

Ser Thr Val His Gln Lys Thr Arg Arg Ser Cys Pro Ser Asp Tyr Ser
1 5 10 15

Phe Ile Cys Asp Cys Glu Gly Thr Gly Ser His Cys Cys Arg Ala Ser
20 25 30

Asn Cys Pro Tyr Tyr Cys Asn Tyr Gly Arg Asp Arg Met Cys Thr Gly
35 40 45

Arg Ser Asn Ile His Glu Trp His Val Asp Ala
50 55

<210> SEQ ID NO 104
<211> LENGTH: 24
<212> TYPE: DNA
<213> ORGANISM: Bos taurus

<400> SEQUENCE: 104
ggattctcat tgagcgacaa ggct 24

<210> SEQ ID NO 105
<211> LENGTH: 21
<212> TYPE: DNA
<213> ORGANISM: Bos taurus

<400> SEQUENCE: 105
atagacacta ctggaaacgc a 21

<210> SEQ ID NO 106
<211> LENGTH: 177
<212> TYPE: DNA
<213> ORGANISM: Bos taurus

<400> SEQUENCE: 106
tctactgtgc accagaagac acgtcgcagt tgtccttctg attatagttt catttgtgat 60
tgtgaaggta ctggcagtca ttgctgtcgg gcttctaatt gtccttatta ctgcaattac 120
ggccgtgatc gtatgtgtac gggcaggagt aacattcacg aatggcacgt cgatgcc 177

<210> SEQ ID NO 107
<211> LENGTH: 25
<212> TYPE: PRT
<213> ORGANISM: Bos taurus

<400> SEQUENCE: 107

Lys Val Gln Leu Arg Glu Ser Gly Pro Ser Leu Val Lys Pro Ser Gln
1 5 10 15

Thr Leu Ser Leu Thr Cys Thr Ala Ser
20 25

<210> SEQ ID NO 108
<211> LENGTH: 17
<212> TYPE: PRT
<213> ORGANISM: Bos taurus

<400> SEQUENCE: 108

Val Gly Trp Val Arg Gln Ala Pro Gly Gln Pro Leu Glu Trp Leu Gly
1 5 10 15

Thr

<210> SEQ ID NO 109
<211> LENGTH: 38
<212> TYPE: PRT
<213> ORGANISM: Bos taurus

<400> SEQUENCE: 109

Val Tyr Asn Pro Gly Leu Lys Ser Arg Leu Ser Ile Thr Lys Asp Asn

```
1               5                   10                  15

Ser Lys Ser Gln Val Ser Leu Ser Leu Ser Ser Val Thr Thr Glu Asp
            20                  25                  30

Ser Ala Thr Tyr His Cys
        35


<210> SEQ ID NO 110
<211> LENGTH: 11
<212> TYPE: PRT
<213> ORGANISM: Bos taurus

<400> SEQUENCE: 110

Trp Gly Gln Gly Leu Leu Val Thr Val Ser Ser
1               5                   10


<210> SEQ ID NO 111
<211> LENGTH: 75
<212> TYPE: DNA
<213> ORGANISM: Bos taurus

<400> SEQUENCE: 111

aaggtgcagc tgcgggagtc gggccccagc ctggtgaagc cgtcacagac cctctcgctc      60

acctgcacag cctct                                                       75


<210> SEQ ID NO 112
<211> LENGTH: 51
<212> TYPE: DNA
<213> ORGANISM: Bos taurus

<400> SEQUENCE: 112

gtaggctggg ttcgccaggc tccagggcag ccgctggagt ggctcggtac t                51


<210> SEQ ID NO 113
<211> LENGTH: 114
<212> TYPE: DNA
<213> ORGANISM: Bos taurus

<400> SEQUENCE: 113

gtctataacc caggcctgaa atcccggctc agcatcacca aggataactc caagagccag      60

gtctctctgt cactaagcag cgtgacaact gaggactcgg ccacatatca ctgt           114


<210> SEQ ID NO 114
<211> LENGTH: 33
<212> TYPE: DNA
<213> ORGANISM: Bos taurus

<400> SEQUENCE: 114

tggggccaag gtctcctggt caccgtctcc tca                                   33


<210> SEQ ID NO 115
<211> LENGTH: 8
<212> TYPE: PRT
<213> ORGANISM: Bos taurus

<400> SEQUENCE: 115

Gly Phe Ser Leu Ser Asp Lys Ala
1               5


<210> SEQ ID NO 116
<211> LENGTH: 7
<212> TYPE: PRT
<213> ORGANISM: Bos taurus
```

<400> SEQUENCE: 116

Ile Asp Thr Gly Gly Asn Ala
1 5

<210> SEQ ID NO 117
<211> LENGTH: 60
<212> TYPE: PRT
<213> ORGANISM: Bos taurus

<400> SEQUENCE: 117

Ser Thr Val His Gln Lys Thr Arg Arg Ser Cys Pro Val Asp Tyr Tyr
1 5 10 15

Tyr Ser Cys Asp Cys Glu Gly Ser Gly Ser His Cys Cys Ser Ala Ser
20 25 30

Asn Cys Pro Tyr Tyr Cys Lys Tyr Gly Arg Asp Arg Val Cys Thr Asp
35 40 45

Lys His Thr Tyr Ser Tyr Glu Trp Tyr Val Asp Ala
50 55 60

<210> SEQ ID NO 118
<211> LENGTH: 24
<212> TYPE: DNA
<213> ORGANISM: Bos taurus

<400> SEQUENCE: 118
ggattctcat taagcgacaa ggct 24

<210> SEQ ID NO 119
<211> LENGTH: 21
<212> TYPE: DNA
<213> ORGANISM: Bos taurus

<400> SEQUENCE: 119
atagacactg gtggaaacgc a 21

<210> SEQ ID NO 120
<211> LENGTH: 180
<212> TYPE: DNA
<213> ORGANISM: Bos taurus

<400> SEQUENCE: 120
tctactgtgc accagaagac acgacgtagt tgtcctgttg attattatta tagttgcgac 60
tgtgaaggta gtggtagtca ttgttgctcg gcttctaatt gtccttatta ctgcaagtat 120
ggccgtgata gagtttgtac tgacaaacat acttacagtt acgaatggta cgtcgatgcc 180

<210> SEQ ID NO 121
<211> LENGTH: 25
<212> TYPE: PRT
<213> ORGANISM: Bos taurus

<400> SEQUENCE: 121

Lys Val Gln Leu Arg Glu Ser Gly Pro Ser Leu Val Lys Pro Ser Gln
1 5 10 15

Thr Leu Ser Leu Thr Cys Thr Ala Ser
20 25

<210> SEQ ID NO 122
<211> LENGTH: 17
<212> TYPE: PRT
<213> ORGANISM: Bos taurus

<400> SEQUENCE: 122

Val Gly Trp Val Arg Gln Ala Pro Gly Lys Ala Leu Glu Trp Leu Gly
1 5 10 15

Ser

<210> SEQ ID NO 123
<211> LENGTH: 38
<212> TYPE: PRT
<213> ORGANISM: Bos taurus

<400> SEQUENCE: 123

Gly Tyr Asn Pro Gly Leu Lys Ser Arg Leu Ser Ile Thr Lys Gly Asn
1 5 10 15

Ser Lys Ser Gln Val Ser Leu Ser Val Ser Ser Val Thr Thr Glu Asp
20 25 30

Ser Ala Thr Tyr Tyr Cys
35

<210> SEQ ID NO 124
<211> LENGTH: 11
<212> TYPE: PRT
<213> ORGANISM: Bos taurus

<400> SEQUENCE: 124

Trp Gly Gln Gly Leu Leu Val Thr Val Ser Ser
1 5 10

<210> SEQ ID NO 125
<211> LENGTH: 75
<212> TYPE: DNA
<213> ORGANISM: Bos taurus

<400> SEQUENCE: 125
aaggtgcagc tgcgggagtc gggccccagc ctggtgaagc cgtcacagac cctctcgctc 60
acctgcacgg cctct 75

<210> SEQ ID NO 126
<211> LENGTH: 51
<212> TYPE: DNA
<213> ORGANISM: Bos taurus

<400> SEQUENCE: 126
gtaggctggg tccgccaggc tccagggaag gcgctggagt ggctcggtag t 51

<210> SEQ ID NO 127
<211> LENGTH: 114
<212> TYPE: DNA
<213> ORGANISM: Bos taurus

<400> SEQUENCE: 127
ggctataacc caggcctgaa atcccggctc agcatcacca agggtaactc caagagccaa 60
gtctctctgt cagtgagtag cgtgacgact gaggactcgg ccacatatta ctgt 114

<210> SEQ ID NO 128
<211> LENGTH: 33
<212> TYPE: DNA
<213> ORGANISM: Bos taurus

<400> SEQUENCE: 128
tggggccagg gactcctggt caccgtctcc tca 33

<210> SEQ ID NO 129
<211> LENGTH: 7
<212> TYPE: PRT
<213> ORGANISM: Bos taurus
<220> FEATURE:
<221> NAME/KEY: MISC_FEATURE
<222> LOCATION: (4)..(4)
<223> OTHER INFORMATION: X is G or T

<400> SEQUENCE: 129

Ile Asp Thr Xaa Gly Asn Ala
1               5

<210> SEQ ID NO 130
<211> LENGTH: 60
<212> TYPE: PRT
<213> ORGANISM: Bos taurus
<220> FEATURE:
<221> NAME/KEY: MISC_FEATURE
<222> LOCATION: (8)..(8)
<223> OTHER INFORMATION: X is R or L
<220> FEATURE:
<221> NAME/KEY: MISC_FEATURE
<222> LOCATION: (13)..(13)
<223> OTHER INFORMATION: X is S or V
<220> FEATURE:
<221> NAME/KEY: MISC_FEATURE
<222> LOCATION: (16)..(16)
<223> OTHER INFORMATION: X is P, S or Y
<220> FEATURE:
<221> NAME/KEY: MISC_FEATURE
<222> LOCATION: (17)..(17)
<223> OTHER INFORMATION: X is Y or F
<220> FEATURE:
<221> NAME/KEY: MISC_FEATURE
<222> LOCATION: (18)..(18)
<223> OTHER INFORMATION: X is I or S
<220> FEATURE:
<221> NAME/KEY: MISC_FEATURE
<222> LOCATION: (23)..(23)
<223> OTHER INFORMATION: X is G or D
<220> FEATURE:
<221> NAME/KEY: MISC_FEATURE
<222> LOCATION: (24)..(24)
<223> OTHER INFORMATION: X is Tor S
<220> FEATURE:
<221> NAME/KEY: MISC_FEATURE
<222> LOCATION: (30)..(30)
<223> OTHER INFORMATION: X is R or S
<220> FEATURE:
<221> NAME/KEY: MISC_FEATURE
<222> LOCATION: (32)..(32)
<223> OTHER INFORMATION: X is S or T
<220> FEATURE:
<221> NAME/KEY: MISC_FEATURE
<222> LOCATION: (39)..(39)
<223> OTHER INFORMATION: X is N or K
<220> FEATURE:
<221> NAME/KEY: MISC_FEATURE
<222> LOCATION: (40)..(40)
<223> OTHER INFORMATION: X is Y or H
<220> FEATURE:
<221> NAME/KEY: MISC_FEATURE
<222> LOCATION: (45)..(45)
<223> OTHER INFORMATION: X is M or V
<220> FEATURE:
<221> NAME/KEY: MISC_FEATURE
<222> LOCATION: (48)..(48)
<223> OTHER INFORMATION: X is G or D
<220> FEATURE:
<221> NAME/KEY: MISC_FEATURE
<222> LOCATION: (49)..(49)
<223> OTHER INFORMATION: X is R or K
<220> FEATURE:
<221> NAME/KEY: MISC_FEATURE
<222> LOCATION: (50)..(50)
<223> OTHER INFORMATION: X is nothing or H
<220> FEATURE:
<221> NAME/KEY: MISC_FEATURE
<222> LOCATION: (51)..(51)
<223> OTHER INFORMATION: X is T or S
<220> FEATURE:
<221> NAME/KEY: MISC_FEATURE
<222> LOCATION: (52)..(52)
<223> OTHER INFORMATION: X is Y or N
<220> FEATURE:
<221> NAME/KEY: MISC_FEATURE
<222> LOCATION: (53)..(53)
<223> OTHER INFORMATION: X is T, I or S
<220> FEATURE:
<221> NAME/KEY: MISC_FEATURE
<222> LOCATION: (54)..(54)
<223> OTHER INFORMATION: X is Y or H
<220> FEATURE:
<221> NAME/KEY: MISC_FEATURE
<222> LOCATION: (57)..(57)
<223> OTHER INFORMATION: X is H or Y
<220> FEATURE:
<221> NAME/KEY: MISC_FEATURE
<222> LOCATION: (59)..(59)
<223> OTHER INFORMATION: X is D or E

<400> SEQUENCE: 130

```
Ser Thr Val His Gln Lys Thr Xaa Arg Ser Cys Pro Xaa Asp Tyr Xaa
1               5                   10                  15

Xaa Xaa Cys Asp Cys Glu Xaa Xaa Gly Ser His Cys Cys Xaa Ala Xaa
            20                  25                  30

Asn Cys Pro Tyr Tyr Cys Xaa Xaa Gly Arg Asp Arg Xaa Cys Thr Xaa
        35                  40                  45

Xaa Xaa Xaa Xaa Xaa Xaa Glu Trp Xaa Val Xaa Ala
    50                  55                  60
```

<210> SEQ ID NO 131
<211> LENGTH: 8
<212> TYPE: PRT
<213> ORGANISM: Bos taurus

<400> SEQUENCE: 131

```
Ser Ser Asn Val Gly Asn Gly Tyr
1               5
```

<210> SEQ ID NO 132
<211> LENGTH: 3
<212> TYPE: PRT
<213> ORGANISM: Bos taurus

<400> SEQUENCE: 132

```
Gly Asp Thr
1
```

<210> SEQ ID NO 133
<211> LENGTH: 11
<212> TYPE: PRT
<213> ORGANISM: Bos taurus

<400> SEQUENCE: 133

```
Ala Ser Ala Glu Asp Gly Ser Ser Asn Ala Val
1               5                   10
```

<210> SEQ ID NO 134
<211> LENGTH: 24
<212> TYPE: DNA
<213> ORGANISM: Bos taurus

<400> SEQUENCE: 134
agcagcaatg ttggaaatgg atat 24

<210> SEQ ID NO 135
<211> LENGTH: 9
<212> TYPE: DNA
<213> ORGANISM: Bos taurus

<400> SEQUENCE: 135 ggtgacacc 9

<210> SEQ ID NO 136
<211> LENGTH: 33
<212> TYPE: DNA
<213> ORGANISM: Bos taurus

<400> SEQUENCE: 136
gcatctgctg aggatggtag cagtaatgct gtt 33

<210> SEQ ID NO 137
<211> LENGTH: 25
<212> TYPE: PRT
<213> ORGANISM: Bos taurus

<400> SEQUENCE: 137

```
Gln Ala Val Leu Thr Gln Pro Ser Ser Val Ser Gly Ser Leu Gly Gln
1               5                   10                  15

Arg Val Ser Thr Thr Cys Ser Gly Ser
            20                  25
```

<210> SEQ ID NO 138
<211> LENGTH: 17
<212> TYPE: PRT
<213> ORGANISM: Bos taurus

<400> SEQUENCE: 138

```
Val Ser Trp Tyr Gln Leu Ile Pro Gly Ser Ala Pro Arg Thr Leu Ile
1               5                   10                  15

Tyr
```

<210> SEQ ID NO 139
<211> LENGTH: 36
<212> TYPE: PRT
<213> ORGANISM: Bos taurus

<400> SEQUENCE: 139

```
Ser Arg Ala Ser Gly Val Pro Asp Arg Phe Ser Gly Ser Arg Ser Gly
1               5                   10                  15

Asn Thr Val Thr Leu Thr Ile Ser Ser Leu Gln Ala Glu Asp Glu Ala
            20                  25                  30

Asp Tyr Phe Cys
        35
```

<210> SEQ ID NO 140
<211> LENGTH: 10
<212> TYPE: PRT
<213> ORGANISM: Bos taurus

<400> SEQUENCE: 140

```
Phe Gly Arg Gly Thr Thr Leu Thr Val Val
1               5                   10
```

<210> SEQ ID NO 141
<211> LENGTH: 75
<212> TYPE: DNA
<213> ORGANISM: Bos taurus

<400> SEQUENCE: 141
caggctgtgc tgactcagcc atcatccgtg tccgggtccc tgggccagag ggtctccacc 60
acctgctctg gaagc 75

<210> SEQ ID NO 142
<211> LENGTH: 51
<212> TYPE: DNA
<213> ORGANISM: Bos taurus

<400> SEQUENCE: 142
gtgagctggt accaactgat tccaggatcg gcccccagaa ccctcatcta t 51

<210> SEQ ID NO 143
<211> LENGTH: 108
<212> TYPE: DNA
<213> ORGANISM: Bos taurus

<400> SEQUENCE: 143
agtcgagcct cgggggtccc cgaccgattc tccggctcca ggtctgggaa cacagtcacc 60
ctgaccatca gctcgctcca ggctgaggac gaggcagatt atttctgc 108

<210> SEQ ID NO 144
<211> LENGTH: 30
<212> TYPE: DNA
<213> ORGANISM: Bos taurus

<400> SEQUENCE: 144
ttcggcagag ggaccacact gacagtcgtc 30

<210> SEQ ID NO 145
<211> LENGTH: 21
<212> TYPE: DNA
<213> ORGANISM: Bos taurus

<400> SEQUENCE: 145
atgaacccac tgtggaccct c 21

<210> SEQ ID NO 146
<211> LENGTH: 24
<212> TYPE: DNA
<213> ORGANISM: Bos taurus

<400> SEQUENCE: 146
agaactcaga gggtagactt tcgg 24

<210> SEQ ID NO 147
<211> LENGTH: 22
<212> TYPE: DNA
<213> ORGANISM: Bos taurus

<400> SEQUENCE: 147
ctttcggggc tgtggtggag gc 22

<210> SEQ ID NO 148
<211> LENGTH: 27
<212> TYPE: DNA

<213> ORGANISM: Bos taurus

<400> SEQUENCE: 148
gaattcgmag gtgcagctgc rggagtc 27

<210> SEQ ID NO 149
<211> LENGTH: 27
<212> TYPE: DNA
<213> ORGANISM: Bos taurus

<400> SEQUENCE: 149
gctagctgag gagacggtga ccaggag 27

<210> SEQ ID NO 150
<211> LENGTH: 22
<212> TYPE: DNA
<213> ORGANISM: Bos taurus

<400> SEQUENCE: 150
caccatggcc tggtcccctc tg 22

<210> SEQ ID NO 151
<211> LENGTH: 20
<212> TYPE: DNA
<213> ORGANISM: Bos taurus

<400> SEQUENCE: 151
gaccccagac tcaccatctc 20

<210> SEQ ID NO 152
<211> LENGTH: 24
<212> TYPE: DNA
<213> ORGANISM: Bos taurus

<400> SEQUENCE: 152
agggctgcgg gctcagaagg cagc 24

<210> SEQ ID NO 153
<211> LENGTH: 21
<212> TYPE: DNA
<213> ORGANISM: Bos taurus

<400> SEQUENCE: 153
ctgcccctcc tcactctctg c 21

<210> SEQ ID NO 154
<211> LENGTH: 19
<212> TYPE: DNA
<213> ORGANISM: Bos taurus

<400> SEQUENCE: 154
ggaacctttc ctgcagctc 19

<210> SEQ ID NO 155
<211> LENGTH: 20
<212> TYPE: DNA
<213> ORGANISM: Bos taurus

<400> SEQUENCE: 155
gcttgcttat ggctcaggtc 20

<210> SEQ ID NO 156
<211> LENGTH: 21

<212> TYPE: DNA
<213> ORGANISM: Bos taurus

<400> SEQUENCE: 156
atgtccacca tggcctggtc c 21

<210> SEQ ID NO 157
<211> LENGTH: 21
<212> TYPE: DNA
<213> ORGANISM: Bos taurus

<400> SEQUENCE: 157
cttgttgccg ttgagctcct c 21

<210> SEQ ID NO 158
<211> LENGTH: 25
<212> TYPE: DNA
<213> ORGANISM: Bos taurus

<400> SEQUENCE: 158
gaattcgcag gctgtgctga ctcag 25

<210> SEQ ID NO 159
<211> LENGTH: 26
<212> TYPE: DNA
<213> ORGANISM: Bos taurus

<400> SEQUENCE: 159
cctaggacga ckgtcagtgt ggtscc 26

<210> SEQ ID NO 160
<211> LENGTH: 22
<212> TYPE: DNA
<213> ORGANISM: Bos taurus

<400> SEQUENCE: 160
ctcaactcta cgtctttgtt tc 22

<210> SEQ ID NO 161
<211> LENGTH: 31
<212> TYPE: DNA
<213> ORGANISM: HIV

<400> SEQUENCE: 161
cacaagaagt agtattggca aatgtgacag a 31

<210> SEQ ID NO 162
<211> LENGTH: 30
<212> TYPE: DNA
<213> ORGANISM: HIV

<400> SEQUENCE: 162
attttctgtc acatttgcca atactacttc 30

<210> SEQ ID NO 163
<211> LENGTH: 33
<212> TYPE: DNA
<213> ORGANISM: HIV

<400> SEQUENCE: 163
taaagccatg tgtagcatta accccactct gtg 33

<210> SEQ ID NO 164

-continued

```
<211> LENGTH: 30
<212> TYPE: DNA
<213> ORGANISM: HIV

<400> SEQUENCE: 164

acacagagtg gggttaatgc tacacatggc                                        30

<210> SEQ ID NO 165
<211> LENGTH: 42
<212> TYPE: DNA
<213> ORGANISM: HIV

<400> SEQUENCE: 165

aagactatgc acttttttat agagctgatg tagtaccaat ag                          42

<210> SEQ ID NO 166
<211> LENGTH: 45
<212> TYPE: DNA
<213> ORGANISM: HIV

<400> SEQUENCE: 166

tcattatcta ttggtactac atctgctcta taaaaaagtg catag                       45

<210> SEQ ID NO 167
<211> LENGTH: 41
<212> TYPE: DNA
<213> ORGANISM: HIV

<400> SEQUENCE: 167

ttgatgtagt accaatagct aatgataata ctagctatag g                          41

<210> SEQ ID NO 168
<211> LENGTH: 38
<212> TYPE: DNA
<213> ORGANISM: HIV

<400> SEQUENCE: 168

acctatagct agtattatca ttagctattg gtactaca                              38

<210> SEQ ID NO 169
<211> LENGTH: 40
<212> TYPE: DNA
<213> ORGANISM: HIV

<400> SEQUENCE: 169

tataggttga taaattgtgc tacctcaacc attacacagg                            40

<210> SEQ ID NO 170
<211> LENGTH: 40
<212> TYPE: DNA
<213> ORGANISM: HIV

<400> SEQUENCE: 170

tgtgtaatgg ttgaggtagc acaatttatc aacctatagc                            40

<210> SEQ ID NO 171
<211> LENGTH: 32
<212> TYPE: DNA
<213> ORGANISM: HIV

<400> SEQUENCE: 171

tcaactcaac tgctgttagc tggcagtcta gc                                    32
```

<210> SEQ ID NO 172
<211> LENGTH: 35
<212> TYPE: DNA
<213> ORGANISM: HIV

<400> SEQUENCE: 172
ttcttctgct agactgccag ctaacagcag ttgag 35

<210> SEQ ID NO 173
<211> LENGTH: 39
<212> TYPE: DNA
<213> ORGANISM: HIV

<400> SEQUENCE: 173
agaggtagta attagatcta gtgctttcac agacaatgc 39

<210> SEQ ID NO 174
<211> LENGTH: 40
<212> TYPE: DNA
<213> ORGANISM: HIV

<400> SEQUENCE: 174
ttgcattgtc tgtgaaagca ctagatctaa ttactacctc 40

<210> SEQ ID NO 175
<211> LENGTH: 40
<212> TYPE: DNA
<213> ORGANISM: HIV

<400> SEQUENCE: 175
tctagtaatt tcacagccaa tgcaaaaaac ataatagtac 40

<210> SEQ ID NO 176
<211> LENGTH: 44
<212> TYPE: DNA
<213> ORGANISM: HIV

<400> SEQUENCE: 176 atgtttttg cattggctgt gaaattacta gatctaatta ctac 44

<210> SEQ ID NO 177
<211> LENGTH: 38
<212> TYPE: DNA
<213> ORGANISM: HIV

<400> SEQUENCE: 177
atttcacaga caatgcagca aacataatag tacagttg 38

<210> SEQ ID NO 178
<211> LENGTH: 40
<212> TYPE: DNA
<213> ORGANISM: HIV

<400> SEQUENCE: 178
aactgtacta ttatgtttgc tgcattgtct gtgaaattac 40

<210> SEQ ID NO 179
<211> LENGTH: 36
<212> TYPE: DNA
<213> ORGANISM: HIV

<400> SEQUENCE: 179
ttcacagaca atgcaaaagc cataatagta cagttg 36

<210> SEQ ID NO 180
<211> LENGTH: 36
<212> TYPE: DNA
<213> ORGANISM: HIV

<400> SEQUENCE: 180
ttcaactgta ctattatggc ttttgcattg tctgtg 36

<210> SEQ ID NO 181
<211> LENGTH: 35
<212> TYPE: DNA
<213> ORGANISM: HIV

<400> SEQUENCE: 181
agtatacata taggagcagg aagagcattt tatac 35

<210> SEQ ID NO 182
<211> LENGTH: 38
<212> TYPE: DNA
<213> ORGANISM: HIV

<400> SEQUENCE: 182
tgttgtataa aatgctcttc ctgctcctat atgtatac 38

<210> SEQ ID NO 183
<211> LENGTH: 39
<212> TYPE: DNA
<213> ORGANISM: HIV

<400> SEQUENCE: 183
aggagatata agacaaaaac attgcaacat tagtagaac 39

<210> SEQ ID NO 184
<211> LENGTH: 40
<212> TYPE: DNA
<213> ORGANISM: HIV

<400> SEQUENCE: 184
ttgttctact aatgttttaa tgtgcttgtc ttatatctcc 40

<210> SEQ ID NO 185
<211> LENGTH: 37
<212> TYPE: DNA
<213> ORGANISM: HIV

<400> SEQUENCE: 185
aagacaagca cattgcacca ttagtagaac aaaatgg 37

<210> SEQ ID NO 186
<211> LENGTH: 49
<212> TYPE: DNA
<213> ORGANISM: HIV

<400> SEQUENCE: 186
tgttattcca ttttgttcta ctaatggtgc aatgtgcttg tcttatatc 49

<210> SEQ ID NO 187
<211> LENGTH: 41
<212> TYPE: DNA
<213> ORGANISM: HIV

<400> SEQUENCE: 187
aataaaacaa tagtctttaa tgcatcctca ggaggggacc c 41

-continued

<210> SEQ ID NO 188
<211> LENGTH: 56
<212> TYPE: DNA
<213> ORGANISM: HIV

<400> SEQUENCE: 188
acaatttctg ggtcccctcc tgaggatgca ttaaagacta ttgttttatt attccc 56

<210> SEQ ID NO 189
<211> LENGTH: 44
<212> TYPE: DNA
<213> ORGANISM: HIV

<400> SEQUENCE: 189
aacaatagtc tttaatcaag cctcaggagg ggacccagaa attg 44

<210> SEQ ID NO 190
<211> LENGTH: 50
<212> TYPE: DNA
<213> ORGANISM: HIV

<400> SEQUENCE: 190
ttctgggtcc cctcctgagg cttgattaaa gactattgtt ttattattcc 50

<210> SEQ ID NO 191
<211> LENGTH: 47
<212> TYPE: DNA
<213> ORGANISM: HIV

<400> SEQUENCE: 191
aatagtcttt aatcaatccg caggagggga cccagaaatt gtaatgc 47

<210> SEQ ID NO 192
<211> LENGTH: 53
<212> TYPE: DNA
<213> ORGANISM: HIV

<400> SEQUENCE: 192
aatttctggg tcccctcctg cggattgatt aaagactatt gttttattat tcc 53

<210> SEQ ID NO 193
<211> LENGTH: 45
<212> TYPE: DNA
<213> ORGANISM: HIV

<400> SEQUENCE: 193
tagtctttaa tcaatcctca gcaggggacc cagaaattgt aatgc 45

<210> SEQ ID NO 194
<211> LENGTH: 41
<212> TYPE: DNA
<213> ORGANISM: HIV

<400> SEQUENCE: 194
attacaattt ctgggtcccc tgctgaggat tgattaaaga c 41

<210> SEQ ID NO 195
<211> LENGTH: 45
<212> TYPE: DNA
<213> ORGANISM: HIV

<400> SEQUENCE: 195
tagtctttaa tcaatcctca ggagcggacc cagaaattgt aatgc 45

<210> SEQ ID NO 196
<211> LENGTH: 44
<212> TYPE: DNA
<213> ORGANISM: HIV

<400> SEQUENCE: 196
tgcattacaa tttctgggtc cgctcctgag gattgattaa agac 44

<210> SEQ ID NO 197
<211> LENGTH: 41
<212> TYPE: DNA
<213> ORGANISM: HIV

<400> SEQUENCE: 197
ttaatcaatc ctcaggaggg gccccagaaa ttgtaatgca c 41

<210> SEQ ID NO 198
<211> LENGTH: 40
<212> TYPE: DNA
<213> ORGANISM: HIV

<400> SEQUENCE: 198
aactgtgcat tacaatttct ggggcccctc ctgaggattg 40

<210> SEQ ID NO 199
<211> LENGTH: 41
<212> TYPE: DNA
<213> ORGANISM: HIV

<400> SEQUENCE: 199
aatcaatcct caggagggga cgcagaaatt gtaatgcaca g 41

<210> SEQ ID NO 200
<211> LENGTH: 36
<212> TYPE: DNA
<213> ORGANISM: HIV

<400> SEQUENCE: 200
aactgtgcat tacaatttct gcgtcccctc ctgagg 36

<210> SEQ ID NO 201
<211> LENGTH: 41
<212> TYPE: DNA
<213> ORGANISM: HIV

<400> SEQUENCE: 201
aatcaatcct caggagggga cccagcaatt gtaatgcaca g 41

<210> SEQ ID NO 202
<211> LENGTH: 39
<212> TYPE: DNA
<213> ORGANISM: HIV

<400> SEQUENCE: 202
taaaactgtg cattacaatt gctgggtccc ctcctgagg 39

<210> SEQ ID NO 203
<211> LENGTH: 49
<212> TYPE: DNA
<213> ORGANISM: HIV

<400> SEQUENCE: 203
aatcctcagg aggggaccca gaagctgtaa tgcacagttt taattgtgg 49

<210> SEQ ID NO 204
<211> LENGTH: 37
<212> TYPE: DNA
<213> ORGANISM: HIV

<400> SEQUENCE: 204
aattaaaact gtgcattaca gcttctgggt cccctcc 37

<210> SEQ ID NO 205
<211> LENGTH: 52
<212> TYPE: DNA
<213> ORGANISM: HIV

<400> SEQUENCE: 205
atcaatcctc aggaggggac ccagaaattg caatgcacag ttttaattgt gg 52

<210> SEQ ID NO 206
<211> LENGTH: 48
<212> TYPE: DNA
<213> ORGANISM: HIV

<400> SEQUENCE: 206
ttcccctcca caattaaaac tgtgcattgc aatttctggg tcccctcc 48

<210> SEQ ID NO 207
<211> LENGTH: 38
<212> TYPE: DNA
<213> ORGANISM: HIV

<400> SEQUENCE: 207
acccagaaat tgtagcgcac agttttaatt gtggaggg 38

<210> SEQ ID NO 208
<211> LENGTH: 40
<212> TYPE: DNA
<213> ORGANISM: HIV

<400> SEQUENCE: 208
ttcccctcca caattaaaac tgtgcgctac aatttctggg 40

<210> SEQ ID NO 209
<211> LENGTH: 49
<212> TYPE: DNA
<213> ORGANISM: HIV

<400> SEQUENCE: 209
atgacactat cacactccca tgtgcaataa aacaaattat aaacatgtg 49

<210> SEQ ID NO 210
<211> LENGTH: 44
<212> TYPE: DNA
<213> ORGANISM: HIV

<400> SEQUENCE: 210
atgtttataa tttgttttat tgcacatggg agtgtgatag tgtc 44

<210> SEQ ID NO 211
<211> LENGTH: 42
<212> TYPE: DNA
<213> ORGANISM: HIV

<400> SEQUENCE: 211
atattacagg gctgatatta gcaagagatg gtggaaataa cc 42

<210> SEQ ID NO 212
<211> LENGTH: 40
<212> TYPE: DNA
<213> ORGANISM: HIV

<400> SEQUENCE: 212
ttgtggttat ttccaccatc tcttgctaat atcagccctg 40

<210> SEQ ID NO 213
<211> LENGTH: 51
<212> TYPE: DNA
<213> ORGANISM: HIV

<400> SEQUENCE: 213
tacagggctg atattaacaa gagctggtgg aaataaccac aataatgata c 51

<210> SEQ ID NO 214
<211> LENGTH: 40
<212> TYPE: DNA
<213> ORGANISM: HIV

<400> SEQUENCE: 214
ttgtggttat ttccaccagc tcttgttaat atcagccctg 40

<210> SEQ ID NO 215
<211> LENGTH: 40
<212> TYPE: DNA
<213> ORGANISM: HIV

<400> SEQUENCE: 215
taccgagacc tttagacctg caggaggaga tatgagggac 40

<210> SEQ ID NO 216
<211> LENGTH: 40
<212> TYPE: DNA
<213> ORGANISM: HIV

<400> SEQUENCE: 216
ttgtccctca tatctcctcc tgcaggtcta aaggtctcgg 40

<210> SEQ ID NO 217
<211> LENGTH: 41
<212> TYPE: DNA
<213> ORGANISM: HIV

<400> SEQUENCE: 217
agacctttag acctggagca ggagatatga gggacaattg g 41

<210> SEQ ID NO 218
<211> LENGTH: 41
<212> TYPE: DNA
<213> ORGANISM: HIV

<400> SEQUENCE: 218
attgtccctc atatctcctg ctccaggtct aaaggtctcg g 41

<210> SEQ ID NO 219
<211> LENGTH: 41
<212> TYPE: DNA
<213> ORGANISM: HIV

<400> SEQUENCE: 219
acctttagac ctggaggagc agatatgagg gacaattgga g 41

<210> SEQ ID NO 220
<211> LENGTH: 48
<212> TYPE: DNA
<213> ORGANISM: HIV

<400> SEQUENCE: 220
ttctccaatt gtccctcata tctgctcctc caggtctaaa ggtctcgg 48

<210> SEQ ID NO 221
<211> LENGTH: 41
<212> TYPE: DNA
<213> ORGANISM: HIV

<400> SEQUENCE: 221
tagacctgga ggaggagcta tgagggacaa ttggagaagt g 41

<210> SEQ ID NO 222
<211> LENGTH: 42
<212> TYPE: DNA
<213> ORGANISM: HIV

<400> SEQUENCE: 222
ttctccaatt gtccctcata gctcctcctc caggtctaaa gg 42

<210> SEQ ID NO 223
<211> LENGTH: 42
<212> TYPE: DNA
<213> ORGANISM: HIV

<400> SEQUENCE: 223
ttagacctgg aggaggagat gcgagggaca attggagaag tg 42

<210> SEQ ID NO 224
<211> LENGTH: 42
<212> TYPE: DNA
<213> ORGANISM: HIV

<400> SEQUENCE: 224
ttctccaatt gtccctcgca tctcctcctc caggtctaaa gg 42

<210> SEQ ID NO 225
<211> LENGTH: 35
<212> TYPE: DNA
<213> ORGANISM: HIV

<400> SEQUENCE: 225
tggaggagga gatatggcgg acaattggag aagtg 35

<210> SEQ ID NO 226
<211> LENGTH: 44
<212> TYPE: DNA
<213> ORGANISM: HIV

<400> SEQUENCE: 226
acttctccaa ttgtccgcca tatctcctcc tccaggtcta aagg 44

<210> SEQ ID NO 227
<211> LENGTH: 21
<212> TYPE: DNA

-continued

```
<213> ORGANISM: HIV

<400> SEQUENCE: 227

ggtacataat gtttgggcca c                                               21


<210> SEQ ID NO 228
<211> LENGTH: 21
<212> TYPE: DNA
<213> ORGANISM: HIV

<400> SEQUENCE: 228

gctgttaaat ggcagtctag c                                               21


<210> SEQ ID NO 229
<211> LENGTH: 22
<212> TYPE: DNA
<213> ORGANISM: HIV

<400> SEQUENCE: 229

ctactgtaat tcaacacaac tg                                              22
```